US010913958B2

(12) United States Patent
Koepke

(10) Patent No.: US 10,913,958 B2
(45) Date of Patent: Feb. 9, 2021

(54) MICROBIAL FERMENTATION FOR THE PRODUCTION OF TERPENES

(71) Applicant: LanzaTech New Zealand Limited, Skokie, IL (US)

(72) Inventor: Michael Koepke, Skokie, IL (US)

(73) Assignee: LANZATECH NEW ZEALAND LIMITED, Skokie, IL (US)

( * ) Notice: Subject to any disclaimer, the term of this patent is extended or adjusted under 35 U.S.C. 154(b) by 179 days.

(21) Appl. No.: 15/867,306

(22) Filed: Jan. 10, 2018

(65) Prior Publication Data

US 2018/0142265 A1 May 24, 2018

Related U.S. Application Data

(63) Continuation of application No. 14/656,827, filed on Mar. 13, 2015, now abandoned, which is a continuation of application No. 13/909,012, filed on Jun. 3, 2013, now abandoned.

(60) Provisional application No. 61/654,412, filed on Jun. 1, 2012.

(51) Int. Cl.

| | |
|---|---|
| ***C12P 5/02*** | (2006.01) |
| ***C12N 1/21*** | (2006.01) |
| ***C12N 9/04*** | (2006.01) |
| ***C12N 9/10*** | (2006.01) |
| ***C12N 9/12*** | (2006.01) |
| ***C12N 9/88*** | (2006.01) |
| ***C12N 15/53*** | (2006.01) |
| ***C12N 15/54*** | (2006.01) |
| ***C12N 15/60*** | (2006.01) |
| ***C12P 5/00*** | (2006.01) |
| ***C12N 15/74*** | (2006.01) |
| ***C12N 15/52*** | (2006.01) |
| ***C12P 7/42*** | (2006.01) |
| ***C12P 9/00*** | (2006.01) |

(52) U.S. Cl.

CPC ............ *C12P 5/007* (2013.01); *C12N 9/0006* (2013.01); *C12N 9/1022* (2013.01); *C12N 9/1025* (2013.01); *C12N 9/1029* (2013.01); *C12N 9/1085* (2013.01); *C12N 9/1205* (2013.01); *C12N 9/1229* (2013.01); *C12N 9/88* (2013.01); *C12N 15/52* (2013.01); *C12N 15/74* (2013.01); *C12P 7/42* (2013.01); *C12P 9/00* (2013.01); *C12Y 101/01088* (2013.01); *C12Y 101/01267* (2013.01); *C12Y 117/07001* (2013.01); *C12Y 202/01007* (2013.01); *C12Y 203/01009* (2013.01); *C12Y 203/0301* (2013.01); *C12Y 205/0101* (2013.01); *C12Y 205/0109* (2013.01); *C12Y 207/01036* (2013.01); *C12Y 207/01148* (2013.01); *C12Y 207/04002* (2013.01); *C12Y 207/0706* (2013.01); *C12Y 401/01033* (2013.01); *C12Y 402/03027* (2013.01); *C12Y 402/03046* (2013.01); *C12Y 406/01012* (2013.01); *C12Y 503/03002* (2013.01); *Y02E 50/30* (2013.01)

(58) Field of Classification Search

None

See application file for complete search history.

(56) References Cited

U.S. PATENT DOCUMENTS

| | | | | |
|---|---|---|---|---|
| 5,173,429 | A | 12/1992 | Gaddy | |
| 5,593,886 | A | 1/1997 | Gaddy | |
| 6,368,819 | B1 | 4/2002 | Gaddy | |
| 7,803,589 | B2 | 9/2010 | Genomatica | |
| 2010/0055754 | A1 | 3/2010 | Pitera et al. | |
| 2010/0151519 | A1 | 6/2010 | Julien et al. | |
| 2010/0298450 | A1 | 11/2010 | Datta et al. | |
| 2011/0014672 | A1 | 1/2011 | Chotani | |
| 2011/0229947 | A1 | 9/2011 | Coskata | |
| 2011/0236941 | A1 | 9/2011 | Koepke et al. | |
| 2011/0256600 | A1 | 10/2011 | Simpson et al. | |
| 2012/0003652 | A1 | 1/2012 | Coskata | |
| 2012/0157725 | A1* | 6/2012 | McAuliffe | B01J 31/003 585/16 |
| 2013/0273625 | A1 | 10/2013 | Chotani et al. | |
| 2014/0234926 | A1* | 8/2014 | Beck | C12N 1/20 435/146 |

FOREIGN PATENT DOCUMENTS

| | | |
|---|---|---|
| JP | 2010539902 | 12/2010 |
| WO | 2002008438 | 1/2002 |
| WO | 2008028055 | 3/2008 |
| WO | 2008039499 A2 | 4/2008 |

(Continued)

OTHER PUBLICATIONS

Abrini, Arch Microbiol, 161: 345-351, 1994.
Collins, Int J System Bacteriol, 44: 812-826, 1994.
Herbert, FEMS Microbiol Lett, 229: 103-110, 2003.
Jennert, Microbiol,146: 3071-3080, 2000.
Kita, J Biosci Bioeng, 115: 347-352, 2013.
Köpke, PNAS USA, 107: 13087-13092, 2010.

(Continued)

*Primary Examiner* — Robert B Mondesi
*Assistant Examiner* — Todd M Epstein
(74) *Attorney, Agent, or Firm* — Stephen M. Chong

(57) ABSTRACT

The invention provides a method for producing a terpene or a precursor thereof by microbial fermentation. Typically, the method involves culturing a recombinant bacterium in the presence of a gaseous substrate whereby the bacterium produces a terpene or a precursor thereof, such as mevalonic acid, isopentenyl pyrophosphate, dimethylallyl pyrophosphate, isoprene, geranyl pyrophosphate, farnesyl pyrophosphate, and/or farnesene. The bacterium may comprise one or more exogenous enzymes, such as enzymes in mevalonate, DXS, or terpene biosynthesis pathways.

22 Claims, 20 Drawing Sheets

Specification includes a Sequence Listing.

(56) References Cited

FOREIGN PATENT DOCUMENTS

| | | | |
|---|---|---|---|
| WO | 2008137092 | | 11/2008 |
| WO | 2009064200 | | 5/2009 |
| WO | 2009076676 | | 6/2009 |
| WO | 2009094485 | A1 | 7/2009 |
| WO | 2009111513 | | 9/2009 |
| WO | 2010078457 | A2 | 7/2010 |
| WO | 2011160081 | | 12/2011 |
| WO | 2012034023 | A2 | 3/2012 |
| WO | 2012053905 | A1 | 4/2012 |
| WO | 2012115527 | | 8/2012 |
| WO | 2015081331 | | 6/2015 |

OTHER PUBLICATIONS

Köpke, Appl Environ Microbiol, 77: 5467-5475, 2011.
Leang, Appl Environ Microbiol, 79: 1102-1109, 2013.
Mermelstein, Nature Biotechnol, 10: 190-195, 1992.
Perez, Biotechnol Bioeng, 1-30, 2012.
Strätz, Appl Environ Microbiol, 60: 1033-1037, 1994.
Tanner, Int J System Bacteriol, 43: 232-236, 1993.
Tyurin, J Biotechnol Res, 4: 1-12, 2012.
Tyurin, Appl Environ Microbiol, 70: 883-890, 2004.
Williams, J Gen Microbiol, 136: 819-826, 1990.
Tirado-Acevedo, Production of bioethanol from synthesis gas using Clostridium Ijungdahlii, PhD thesis, North Carolina State University, 2010.
Murray, Microbial Molec Biol Rev, 64: 412-434, 2000.
Köpke, Biochemical production of biobutanol, In: Handbook of biofuels production: processes and technologies (Eds.: Luque, Campelo & Clark), Woodhead Publishing Ltd, Cambridge, UK: 221-257, 2011.
Ismail, J Bacteriol, 175: 5079-5105, 1993.
Yang, PLoS One, 7: e33509 (pp. 1-7), 2012.
Balibar, J Bacteriol, 191: 851-861, 2009.
Heap, J Microbiol Methods, 78: 79-85, 2009.
Köpke, Curr Opin Biotechnol, 22: 320-325, 2011.
Lane, On the Mend: Why INEOS Bio isn't producing ethanol in Florida, Biofuels Digest, 2014.
GenBank ABR35218.1, isopentenyl-diphosphate delta-isomerase, type 1 [Clostridium beijerinckii NCIMB 8052], Nov. 21, 2011.
U.S. Appl. No. 61/544,959, filed Oct. 7, 2011.
European Search Report for European Patent Application No. 18156987.2, European Patent Office, dated Sep. 4, 2019.

* cited by examiner

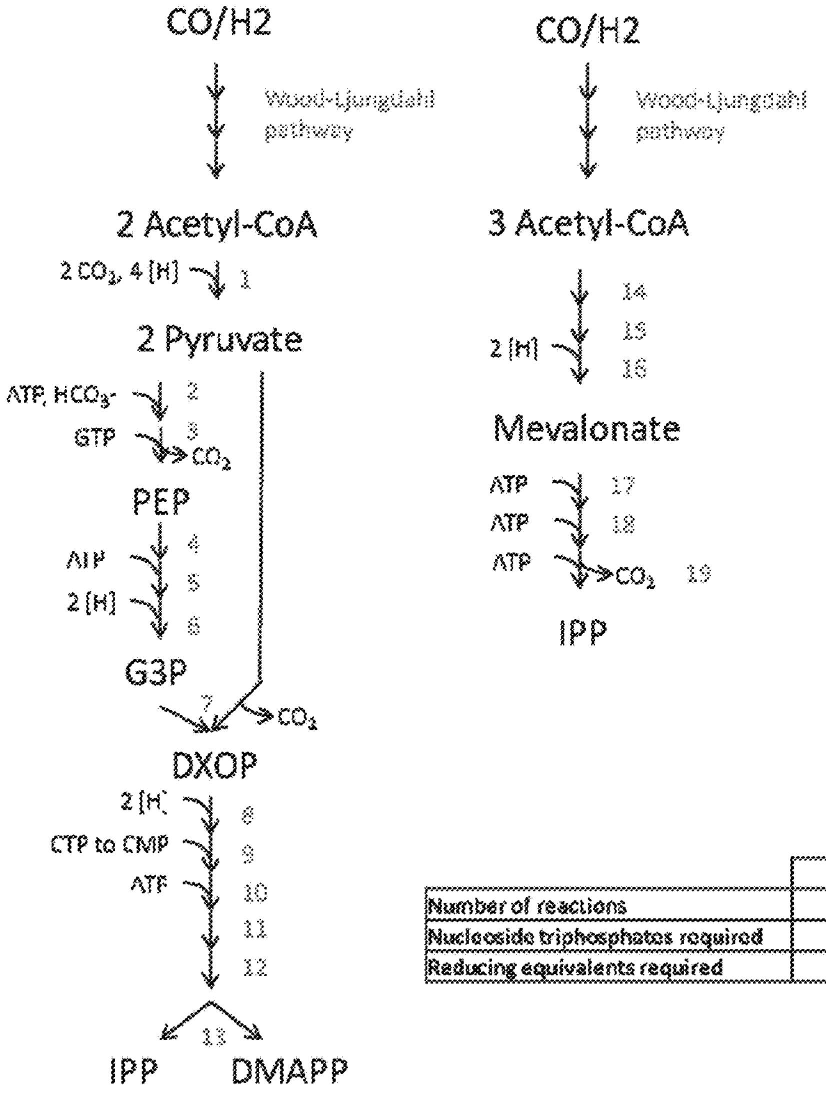

1 Pyruvate:Ferredoxin Oxidoreductase
2 Pyruvate carboxylase
3 PEP carboxykinase
4 Enolase
5 Phosphoglycerate mutase
5 Phosdphoglycerate kinase
7 1-deoxy-D-xylulose-5-phosphate synthase DXS
8 1-deoxy-D-xylulose 5-phosphate reductoisomerase DXR
9 2-C-methyl-D-erythritol 4-phosphate cytidylyltransferase IspD
10 4-diphosphocytidyl-2-C-methyl-D-erythritol kinase IspE
11 2-C-methyl-D-erythritol 2,4-cyclodiphosphate synthase IspF
12 4-hydroxy-3-methylbut-2-en-1-yl diphosphate synthase IspG
13 4-hydroxy-3-methylbut-2-enyl diphosphate reductase
14 thiolase
15 HMG-CoA synthase
16 HMG-CoA reductase
17 Mevalonate kinase
18 Phosphomevalonate kinase
19 Mevalonate Diphosphate decarboxylase PEP Phosphoenolpyruvate
G3P Glyceraldehyde-3-Phosphate
IPP Isopentenyl diphosphate
DMAPP dimethyl allyl pyrophosphate

| | via DXS pathway | via Mevalonate pathway |
|---|---|---|
| Number of reactions | 13 | 6 |
| Nucleoside triphosphates required | 5 | 3 |
| Reducing equivalents required | 8 | 2 |

FIG. 6 pMTL8215-Pptaack-thlA-HMGS-Patp-HMGR

MICROBIAL FERMENTATION FOR THE PRODUCTION OF TERPENES

CROSS REFERENCE TO RELATED APPLICATIONS

This application is a continuation of U.S. patent application Ser. No. 14/656,827 filed Mar. 13, 2015, which is a continuation of U.S. patent application Ser. No. 13/909,012 filed Jun. 3, 2013, which claims the benefit of U.S. Provisional Patent Application 61/654,412 filed Jun. 1, 2012, the entirety of which are incorporated herein by reference.

SEQUENCE LISTING

This application includes a nucleotide/amino acid sequence listing submitted concurrently herewith, the entirety of which is incorporated herein by reference.

FIELD OF THE INVENTION

The present invention relates to recombinant microorganisms and methods for the production of terpenes and/or precursors thereof by microbial fermentation of a substrate comprising CO.

BACKGROUND OF THE INVENTION

Terpenes are a diverse class of naturally occurring chemicals composed of five-carbon isoprene units. Terpene derivatives include terpenoids (also known as isoprenoids) which may be formed by oxidation or rearrangement of the carbon backbone or a number of functional group additions or rearrangements.

Examples of terpenes include: isoprene (C5 hemiterpene), farnesene (C15 Sesquiterpenes), artemisinin (C15 Sesquiterpenes), citral (C10 Monoterpenes), carotenoids (C40 Tetraterpenes), menthol (C10 Monoterpenes), Camphor (C10 Monoterpenes), and cannabinoids.

Terpenes are valuable commercial products used in a diverse number of industries. The highest tonnage uses of terpenes are as resins, solvents, fragrances and vitamins. For example, isoprene is used in the production of synthetic rubber (cis-1,4-polyisoprene) for example in the tyre industry; farnesene is used as an energy dense drop-in fuel used for transportation or as jet-fuel; artemisinin is used as a malaria drug; and citral, carotenoids, menthol, camphor, and cannabinoids are used in the manufacture of pharmaceuticals, butadiene, and as aromatic ingredients.

Terpenes may be produced from petrochemical sources and from terpene feed-stocks, such as turpentine. For example, isoprene is produced petrochemically as a by-product of naphtha or oil cracking in the production of ethylene. Many terpenes are also extracted in relatively small quantities from natural sources. However, these production methods are expensive, unsustainable and often cause environmental problems including contributing to climate change.

Due to the extremely flammable nature of isoprene, known methods of production require extensive safeguards to limit potential for fire and explosions.

It is an object of the invention to overcome one or more of the disadvantages of the prior art, or at least to provide the public with an alternative means for producing terpenes and other related products.

SUMMARY OF THE INVENTION

Microbial fermentation provides an alternative option for the production of terpenes. Terpenes are ubiquitous in nature, for example they are involved in bacterial cell wall biosynthesis, and they are produced by some trees (for example *poplar*) to protect leaves from UV light exposure. However, not all bacteria comprise the necessary cellular machinery to produce terpenes and/or their precursors as metabolic products. For example, carboxydotrophic acetogens, such as *C. autoethanogenum* or *C. ljungdahlii*, which are able to ferment substrates comprising carbon monoxide to produce products such as ethanol, are not known to produce and emit any terpenes and/or their precursors as metabolic products. In addition, most bacteria are not known to produce any terpenes which are of commercial value.

The invention generally provides, inter alia, methods for the production of one or more terpenes and/or precursors thereof by microbial fermentation of a substrate comprising CO, and recombinant microorganisms of use in such methods.

In a first aspect, the invention provides a carboxydotrophic acetogenic recombinant microorganism capable of producing one or more terpenes and/or precursors thereof and optionally one or more other products by fermentation of a substrate comprising CO.

In one particular embodiment, the microorganism is adapted to express one or more enzymes in the mevalonate (MVA) pathway not present in a parental microorganism from which the recombinant microorganism is derived (may be referred to herein as an exogenous enzyme). In another embodiment, the microorganism is adapted to over-express one or more enzymes in the mevalonate (MVA) pathway which are present in a parental microorganism from which the recombinant microorganism is derived (may be referred to herein as an endogenous enzyme).

In a further embodiment, the microorganism is adapted to:

a) express one or more exogenous enzymes in the mevalonate (MVA) pathway and/or overexpress one or more endogenous enzyme in the mevalonate (MVA) pathway; and b) express one or more exogenous enzymes in the DXS pathway and/or overexpress one or more endogenous enzymes in the DXS pathway.

In one embodiment, the one or more enzymes from the mevalonate (MVA) pathway is selected from the group consisting of:

a) thiolase (EC 2.3.1.9), b) HMG-CoA synthase (EC 2.3.3.10), c) HMG-CoA reductase (EC 1.1.1.88), d) Mevalonate kinase (EC 2.7.1.36), e) Phosphomevalonate kinase (EC 2.7.4.2), f) Mevalonate Diphosphate decarboxylase (EC 4.1.1.33), and g) a functionally equivalent variant of any one thereof.

In a further embodiment, the one or more enzymes from the DXS pathway is selected from the group consisting of:

a) 1-deoxy-D-xylulose-5-phosphate synthase DXS (EC:2.2.1.7), b) 1-deoxy-D-xylulose 5-phosphate reductoisomerase DXR (EC:1.1.1.267), c) 2-C-methyl-D-erythritol 4-phosphate cytidylyltransferase IspD (EC:2.7.7.60), d) 4-diphosphocytidyl-2-C-methyl-D-erythritol kinase IspE (EC:2.7.1.148), e) 2-C-methyl-D-erythritol 2,4-cyclodiphosphate synthase IspF (EC:4.6.1.12), f) 4-hydroxy-3-methylbut-2-en-1-yl diphosphate synthase IspG (EC:1.17.7.1), g) 4-hydroxy-3-methylbut-2-enyl diphosphate reductase (EC:1.17.1.2), and h) a functionally equivalent variant of any one thereof.

In a further embodiment, one or more further exogenous or endogenous enzymes are expressed or over-expressed to result in the production of a terpene compound or a precursor thereof wherein the exogenous enzyme that is expressed, or the endogenous enzyme that is overexpressed, is selected from the group consisting of:

a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC 5.3.3.2),
f) farnesene synthase (EC 4.2.3.46/EC 4.2.3.47), and
g) a functionally equivalent variant of any one thereof.

In one embodiment, the parental microorganism is capable of fermenting a substrate comprising CO to produce Acetyl CoA, but not of converting Acetyl CoA to mevalonic acid or isopentenyl pyrophosphate (IPP) and the recombinant microorganism is adapted to express one or more enzymes involved in the mevalonate pathway.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

In one embodiment, the microorganism comprises one or more exogenous nucleic acids adapted to increase expression of one or more endogenous nucleic acids and which one or more endogenous nucleic acids encode one or more of the enzymes referred to herein before.

In one embodiment, the one or more exogenous nucleic acids adapted to increase expression is a regulatory element. In one embodiment, the regulatory element is a promoter. In one embodiment, the promoter is a constitutive promoter. In one embodiment, the promoter is selected from the group comprising Wood-Ljungdahl gene cluster or Phosphotransacetylase/Acetate kinase operon promoters.

In one embodiment, the microorganism comprises one or more exogenous nucleic acids encoding and adapted to express one or more of the enzymes referred to hereinbefore. In one embodiment, the microorganisms comprise one or more exogenous nucleic acids encoding and adapted to express at least two of the enzymes. In other embodiments, the microorganism comprises one or more exogenous nucleic acids encoding and adapted to express at least three, at least four, at least five, at least six, at least seven, at least eight, at least nine or more of the enzymes.

In one embodiment, the one or more exogenous nucleic acid is a nucleic acid construct or vector, in one particular embodiment a plasmid, encoding one or more of the enzymes referred to hereinbefore in any combination.

In one embodiment, the exogenous nucleic acid is an expression plasmid.

In one particular embodiment, the parental microorganism is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii*, and *Thermoanaerobacter kiuvi*.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes in the DXS pathway and/or the mevalonate (MVA) pathway. In one embodiment, the parental microorganism lacks one or more genes encoding an enzyme selected from the group consisting of:

a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33),
g) 1-deoxy-D-xylulose-5-phosphate synthase DXS (EC: 2.2.1.7),
h) 1-deoxy-D-xylulose 5-phosphate reductoisomerase DXR (EC:1.1.1.267),
i) 2-C-methyl-D-erythritol 4-phosphate cytidylyltransferase IspD (EC:2.7.7.60),
j) 4-diphosphocytidyl-2-C-methyl-D-erythritol kinase IspE (EC:2.7.1.148),
k) 2-C-methyl-D-erythritol 2,4-cyclodiphosphate synthase IspF (EC:4.6.1.12),
l) 4-hydroxy-3-methylbut-2-en-1-yl diphosphate synthase IspG (EC:1.17.7.1),
m) 4-hydroxy-3-methylbut-2-enyl diphosphate reductase (EC:1.17.1.2), and
n) a functionally equivalent variant of any one thereof.

In a second aspect, the invention provides a nucleic acid encoding one or more enzymes which when expressed in a microorganism allows the microorganism to produce one or more terpenes and/or precursors thereof by fermentation of a substrate comprising CO.

In one embodiment, the nucleic acid encodes two or more enzymes which when expressed in a microorganism allows the microorganism to produce one or more terpenes and/or precursors thereof by fermentation of a substrate comprising CO. In one embodiment, a nucleic acid of the invention encodes at least three, at least four, at least five, at least six, at least seven, at least eight, at least nine or more of such enzymes.

In one embodiment, the nucleic acid encodes one or more enzymes in the mevalonate (MVA) pathway. In one embodiment, the one or more enzymes is chosen from the group consisting of:

a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a particular embodiment, the nucleic acid encodes thiolase (which may be an acetyl CoA c-acetyltransferase), HMG-CoA synthase and HMG-CoA reductase, In a further embodiment, the nucleic acid encodes one or more enzymes in the mevalonate (MVA) pathway and one or more further nucleic acids in the DXS pathway pathway. In one embodiment, the one or more enzymes from the DXS pathway is selected from the group consisting of:

a) 1-deoxy-D-xylulose-5-phosphate synthase DXS (EC: 2.2.1.7),
b) 1-deoxy-D-xylulose 5-phosphate reductoisomerase DXR (EC:1.1.1.267), c) 2-C-methyl-D-erythritol 4-phosphate cytidylyltransferase IspD (EC:2.7.7.60),
d) 4-diphosphocytidyl-2-C-methyl-D-erythritol kinase IspE (EC:2.7.1.148),
e) 2-C-methyl-D-erythritol 2,4-cyclodiphosphate synthase IspF (EC:4.6.1.12),
f) 4-hydroxy-3-methylbut-2-en-1-yl diphosphate synthase IspG (EC:1.17.7.1),
g) 4-hydroxy-3-methylbut-2-enyl diphosphate reductase (EC:1.17.1.2), and
h) a functionally equivalent variant of any one thereof.

In a further embodiment, the nucleic acid encodes one or more further exogenous or endogenous enzymes are expressed or over-expressed to result in the production of a terpene compound or a precursor thereof wherein the exogenous nucleic acid that is expressed, or the endogenous enzyme that is overexpressed, encodes and enzyme selected from the group consisting of:
a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC 5.3.3.2),
f) farnesene synthase (EC 4.2.3.46/EC 4.2.3.47), and
g) a functionally equivalent variant of any one thereof.

In one embodiment, the nucleic acid encoding thiolase (EC 2.3.1.9) has the sequence SEQ ID NO: 40 or is a functionally equivalent variant thereof.

In one embodiment, the nucleic acid encoding thiolase (EC 2.3.1.9) is acetyl CoA c-acetyl transferase that has the sequence SEQ ID NO: 41 or is a functionally equivalent variant thereof.

In one embodiment, the nucleic acid encoding HMG-CoA synthase (EC 2.3.3.10) has the sequence SEQ ID NO: 42 or is a functionally equivalent variant thereof.

In one embodiment, the nucleic acid encoding HMG-CoA reductase (EC 1.1.1.88) has the sequence SEQ ID NO: 43 or is a functionally equivalent variant thereof.

In one embodiment, the nucleic acid encoding Mevalonate kinase (EC 2.7.1.36) has the sequence SEQ ID NO: 51 or is a functionally equivalent variant thereof.

In one embodiment, the nucleic acid encoding Phosphomevalonate kinase (EC 2.7.4.2) has the sequence SEQ ID NO: 52 or is a functionally equivalent variant thereof.

In one embodiment, the nucleic acid encoding Mevalonate Diphosphate decarboxylase (EC 4.1.1.33) has the sequence SEQ ID NO: 53 or is a functionally equivalent variant thereof.

In one embodiment, the nucleic acid encoding 1-deoxy-D-xylulose-5-phosphate synthase DXS (EC:2.2.1.7) has the sequence SEQ ID NO: 1 or is a functionally equivalent variant thereof.

In one embodiment, the nucleic acid encoding 1-deoxy-D-xylulose 5-phosphate reductoisomerase DXR (EC: 1.1.1.267) has the sequence SEQ ID NO: 3 or is a functionally equivalent variant thereof.

In one embodiment, the nucleic acid encoding 2-C-methyl-D-erythritol 4-phosphate cytidylyltransferase IspD (EC:2.7.7.60) has the sequence SEQ ID NO: 5 or is a functionally equivalent variant thereof.

In one embodiment, the nucleic acid encoding 4-diphosphocytidyl-2-C-methyl-D-erythritol kinase IspE (EC: 2.7.1.148) has the sequence SEQ ID NO: 7 or is a functionally equivalent variant thereof.

In one embodiment, the nucleic acid encoding 2-C-methyl-D-erythritol 2,4-cyclodiphosphate synthase IspF (EC:4.6.1.12) has the sequence SEQ ID NO: 9 or is a functionally equivalent variant thereof.

In one embodiment, the nucleic acid encoding 4-hydroxy-3-methylbut-2-en-1-yl diphosphate synthase IspG (EC: 1.17.7.1) has the sequence SEQ ID NO: 11 or is a functionally equivalent variant thereof.

In one embodiment, the nucleic acid encoding 4-hydroxy-3-methylbut-2-enyl diphosphate reductase (EC:1.17.1.2) has the sequence SEQ ID NO: 13 or is a functionally equivalent variant thereof.

In one embodiment, the nucleic acid encoding geranyltranstransferase Fps has the sequence SEQ ID NO: 15, or it is a functionally equivalent variant thereof.

In one embodiment, the nucleic acid encoding heptaprenyl diphosphate synthase has the sequence SEQ ID NO: 17, or it is a functionally equivalent variant thereof.

In one embodiment, the nucleic acid encoding octaprenyl-diphosphate synthase (EC:2.5.1.90) wherein the octaprenyl-diphosphate synthase is polyprenyl synthetase is encoded by sequence SEQ ID NO: 19, or it is a functionally equivalent variant thereof.

In one embodiment, the nucleic acid encoding isoprene synthase (ispS) has the sequence SEQ ID NO: 21, or it is a functionally equivalent variant thereof.

In one embodiment, the nucleic acid encoding Isopentenyl-diphosphate delta-isomerase (idi) has the sequence SEQ ID NO: 54, or it is a functionally equivalent variant thereof.

In one embodiment, the nucleic acid encoding farnesene synthase has the sequence SEQ ID NO: 57, or it is a functionally equivalent variant thereof.

In one embodiment, the nucleic acid encodes the following enzymes:
a) isoprene synthase;
b) Isopentenyl-diphosphate delta-isomerase (idi); and
c) 1-deoxy-D-xylulose-5-phosphate synthase DXS;
or functionally equivalent variants thereof.

In one embodiment, the nucleic acid encodes the following enzymes:
a) Thiolase;
b) HMG-CoA synthase;
c) HMG-CoA reductase;
d) Mevalonate kinase;
e) Phosphomevalonate kinase;
f) Mevalonate Diphosphate decarboxylase;
g) Isopentenyl-diphosphate delta-isomerase (idi); and
h) isoprene synthase;
or functionally equivalent variants thereof.

In one embodiment, the nucleic acid encodes the following enzymes:
a) geranyltranstransferase Fps; and
b) farnesene synthase
or functionally equivalent variants thereof.

In one embodiment, the nucleic acids of the invention further comprise a promoter. In one embodiment, the promoter allows for constitutive expression of the genes under its control. In a particular embodiment a Wood-Ljungdahl cluster promoter is used. In another particular embodiment, a Phosphotransacetylase/Acetate kinase operon promoter is used. In one particular embodiment, the promoter is from *C. autoethanogenum.*

In a third aspect, the invention provides a nucleic acid construct or vector comprising one or more nucleic acid of the second aspect.

In one particular embodiment, the nucleic acid construct or vector is an expression construct or vector. In one particular embodiment, the expression construct or vector is a plasmid.

In a fourth aspect, the invention provides host organisms comprising any one or more of the nucleic acids of the second aspect or vectors or constructs of the third aspect.

In a fifth aspect, the invention provides a composition comprising an expression construct or vector as referred to in the third aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In a sixth aspect, the invention provides a method for the production of one or more terpenes and/or precursors thereof and optionally one or more other products by microbial fermentation comprising fermenting a substrate comprising CO using a recombinant microorganism of the first aspect of the invention.

In one embodiment the method comprises the steps of:

(a) providing a substrate comprising CO to a bioreactor containing a culture of one or more microorganisms of the first aspect of the invention; and (b) anaerobically fermenting the culture in the bioreactor to produce at least one terpene and/or precursor thereof.

In one embodiment the method comprises the steps of:

(a) capturing CO-containing gas produced as a result of the industrial process;

(b) anaerobic fermentation of the CO-containing gas to produce at least one terpene and/or precursor thereof by a culture containing one or more microorganism of the first aspect of the invention.

In particular embodiments of the method aspects, the microorganism is maintained in an aqueous culture medium.

In particular embodiments of the method aspects, the fermentation of the substrate takes place in a bioreactor.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

Preferably, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering a terpene and/or precursor thereof and optionally one or more other products from the fermentation broth.

In a seventh aspect, the invention provides one or more terpene and/or precursor thereof when produced by the method of the sixth aspect. In one embodiment, the one or more terpene and/or precursor thereof is chosen from the group consisting of mevalonic acid, IPP, dimethylallyl pyrophosphate (DMAPP), isoprene, geranyl pyrophosphate (GPP), farnesyl pyrophosphate (FPP) and farnesene.

In another aspect, the invention provides a method for the production of a microorganism of the first aspect of the invention comprising transforming a carboxydotrophic acetogenic parental microorganism by introduction of one or more nucleic acids such that the microorganism is capable of producing, or increasing the production of, one or more terpenes and/or precursors thereof and optionally one or more other products by fermentation of a substrate comprising CO, wherein the parental microorganism is not capable of producing, or produces at a lower level, the one or more terpene and/or precursor thereof by fermentation of a substrate comprising CO.

In one particular embodiment, a parental microorganism is transformed by introducing one or more exogenous nucleic acids adapted to express one or more enzymes in the mevalonate (MVA) pathway and optionally the DXS pathway. In another embodiment, a parental microorganism is transformed with one or more nucleic acids adapted to over-express one or more enzymes in the mevalonate (MVA) pathway and optionally the DXS pathway which are naturally present in the parental microorganism.

In certain embodiments, the one or more enzymes are as herein before described.

In one embodiment an isolated, genetically engineered, carboxydotrophic, acetogenic bacteria are provided which comprise an exogenous nucleic acid encoding an enzyme in a mevalonate pathway or in a DXS pathway or in a terpene biosynthesis pathway, whereby the bacteria express the enzyme. The enzyme is selected from the group consisting of:

a) thiolase (EC 2.3.1.9);
b) HMG-CoA synthase (EC 2.3.3.10);
c) HMG-CoA reductase (EC 1.1.1.88);
d) Mevalonate kinase (EC 2.7.1.36);
e) Phosphomevalonate kinase (EC 2.7.4.2);
f) Mevalonate Diphosphate decarboxylase (EC 4.1.1.33); 1-deoxy-D-xylulose-5-phosphate synthase DXS (EC: 2.2.1.7);
g) 1-deoxy-D-xylulose 5-phosphate reductoisomerase DXR (EC:1.1.1.267);
h) 2-C-methyl-D-erythritol 4-phosphate cytidylyltransferase IspD (EC:2.7.7.60);
i) 4-diphosphocytidyl-2-C-methyl-D-erythritol kinase IspE (EC:2.7.1.148);
j) 2-C-methyl-D-erythritol 2;4-cyclodiphosphate synthase IspF (EC:4.6.1.12);
k) 4-hydroxy-3-methylbut-2-en-1-yl diphosphate synthase IspG (EC:1.17.7.1);
l) 4-hydroxy-3-methylbut-2-enyl diphosphate reductase (EC:1.17.1.2); geranyltranstransferase Fps (EC: 2.5.1.10);
m) heptaprenyl diphosphate synthase (EC:2.5.1.10);
n) octaprenyl-diphosphate synthase (EC:2.5.1.90);
o) isoprene synthase (EC 4.2.3.27);
p) isopentenyl-diphosphate delta-isomerase (EC 5.3.3.2); and
q) farnesene synthase (EC 4.2.3.46/EC 4.2.3.47).

In some aspects the bacteria do not express the enzyme in the absence of said nucleic acid. In some aspects the bacteria which express the enzyme under anaerobic conditions.

One embodiment provides a plasmid which can replicate in a carboxydotrophic, acetogenic bacteria. The plasmid comprises a nucleic acid encoding an enzyme in a mevalonate pathway or in a DXS pathway or in a terpene biosynthesis pathway, whereby when the plasmid is in the bacteria, the enzyme is expressed by said bacteria. The enzyme is selected from the group consisting of:

a) thiolase (EC 2.3.1.9);
b) HMG-CoA synthase (EC 2.3.3.10);
c) HMG-CoA reductase (EC 1.1.1.88);
d) Mevalonate kinase (EC 2.7.1.36);

e) Phosphomevalonate kinase (EC 2.7.4.2);

f) Mevalonate Diphosphate decarboxylase (EC 4.1.1.33); 1-deoxy-D-xylulose-5-phosphate synthase DXS (EC: 2.2.1.7);

g) 1-deoxy-D-xylulose 5-phosphate reductoisomerase DXR (EC:1.1.1.267);

h) 2-C-methyl-D-erythritol 4-phosphate cytidylyltransferase IspD (EC:2.7.7.60);

i) 4-diphosphocytidyl-2-C-methyl-D-erythritol kinase IspE (EC:2.7.1.148);

j) 2-C-methyl-D-erythritol 2;4-cyclodiphosphate synthase IspF (EC:4.6.1.12);

k) 4-hydroxy-3-methylbut-2-en-1-yl diphosphate synthase IspG (EC:1.17.7.1);

l) 4-hydroxy-3-methylbut-2-enyl diphosphate reductase (EC:1.17.1.2); geranyltranstransferase Fps (EC: 2.5.1.10);

m) heptaprenyl diphosphate synthase (EC:2.5.1.10);

n) octaprenyl-diphosphate synthase (EC:2.5.1.90);

o) isoprene synthase (EC 4.2.3.27);

p) isopentenyl-diphosphate delta-isomerase (EC 5.3.3.2); and q) farnesene synthase (EC 4.2.3.46/EC 4.2.3.47).

A process is provided in another embodiment for converting CO and/or $CO_2$ into isoprene. The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isoprene, and recovering the isoprene from the bioreactor. The carboxydotrophic acetogenic bacteria are genetically engineered to express a isoprene synthase.

Another embodiment provides an isolated, genetically engineered, carboxydotrophic, acetogenic bacteria which comprise a nucleic acid encoding an isoprene synthase. The bacteria express the isoprene synthase and the bacteria are able to convert imethylallyldiphosphate to isoprene. In one aspect the isoprene synthase is a *Populus tremuloides* enzyme. In another aspect the nucleic acid is codon optimized. In still another aspect, expression of the isoprene synthase is under the transcriptional control of a promoter for a pyruvate:ferredoxin oxidoreductase gene from *Clostridium autoethanogenum.*

Another embodiment provides a process for converting CO and/or $CO_2$ into isopentyldiphosphate (IPP). The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isopentyldiphosphate (IPP), and recovering the IPP from the bioreactor. The carboxydotrophic acetogenic bacteria are genetically engineered to express a isopentyldiphosphate delta isomerase.

Still another embodiment provides isolated, genetically engineered, carboxydotrophic, acetogenic bacteria which comprise a nucleic acid encoding an isopentyldiphosphate delta isomerase. The bacteria express the isopentyldiphosphate delta isomerase and the bacteria are able to convert dimethylallyldiphosphate to isopentyldiphosphate. In some aspects the nucleic acid encodes a *Clostridium beijerinckii* isopentyldiphosphate delta isomerase. In other aspects, the nucleic acid is under the transcriptional control of a promoter for a pyruvate:ferredoxin oxidoreductase gene from *Clostridium autoethanogenum*. In still other aspects, the nucleic acid is under the transcriptional control of a promoter for a pyruvate: ferredoxin oxidoreductase gene from *Clostridium autoethanogenum* and downstream of a second nucleic acid encoding an isoprene synthase.

Still another embodiment provides a process for converting CO and/or $CO_2$ into isopentyldiphosphate (IPP) and/or isoprene. The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isopentyldiphosphate (IPP) and/or isoprene, and recovering the IPP and/or isoprene from the bioreactor. The carboxydotrophic acetogenic bacteria are genetically engineered to have an increased copy number of a nucleic acid encoding a deoxyxylulose 5-phosphate synthase (DXS) enzyme, wherein the increased copy number is greater than 1 per genome.

Yet another embodiment provides isolated, genetically engineered, carboxydotrophic, acetogenic bacteria which comprise a copy number of greater than 1 per genome of a nucleic acid encoding a deoxyxylulose 5-phosphate synthase (DXS) enzyme. In some aspects, the isolated, genetically engineered, carboxydotrophic, acetogenic bacteria may further comprise a nucleic acid encoding an isoprene synthase. In other aspects, the isolated, genetically engineered, carboxydotrophic, acetogenic bacteria of may further comprise a nucleic acid encoding an isopentyldiphosphate delta isomerase. In still other aspects the isolated, genetically engineered, carboxydotrophic, acetogenic bacteria may further comprise a nucleic acid encoding an isopentyldiphosphate delta isomerase and a nucleic acid encoding an isoprene synthase.

Another embodiment provides isolated, genetically engineered, carboxydotrophic, acetogenic bacteria which comprise a nucleic acid encoding a phosphomevalonate kinase (PMK). The bacteria express the encoded enzyme and the enzyme is not native to the bacteria. In some aspects the enzymes are *Staphylococcus aureus* enzymes. In some aspects the enzyme is expressed under the control of one or more *C. autoethanogenum* promoters. In some aspects the bacteria further comprise a nucleic acid encoding thiolase (thlA/vraB), a nucleic acid encoding a HMG-CoA synthase (HMGS), and a nucleic acid encoding an HMG-CoA reductase (HMGR). In some aspects the thiolase is *Clostridium acetobutylicum* thiolase. In some aspects the bacteria further comprise a nucleic acid encoding a mevalonate disphosphate decarboxylase (PMD).

Still another embodiment provides isolated, genetically engineered, carboxydotrophic, acetogenic bacteria which comprise an exogenous nucleic acid encoding alpha-farnesene synthase. In some aspects the nucleic acid is codon optimized for expression in *C. autoethanogenum*. In some aspects the alpha-farnesene synthase is a *Malus*× *domestica* alpha-farnesene synthase. In some aspects the bacteria further comprise a nucleic acid segment encoding geranyltranstransferase. In some aspects the gernayltranstransferase is an *E. coli* geranyltranstransferase.

Suitable isolated, genetically engineered, carboxydotrophic, acetogenic bacteria for any of the aspects or embodiments of the invention may be selected from the group consisting of *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa*

*silvacetica, Sporomusa sphaeroides, Oxobacter pfennigii*, and *Thermoanaerobacter kiuvi.*

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures.

FIG. 6: Comparison of energetics for production of terpenes from CO via DXS and mevalonate pathway

DETAILED DESCRIPTION OF THE INVENTION

Figure 1:
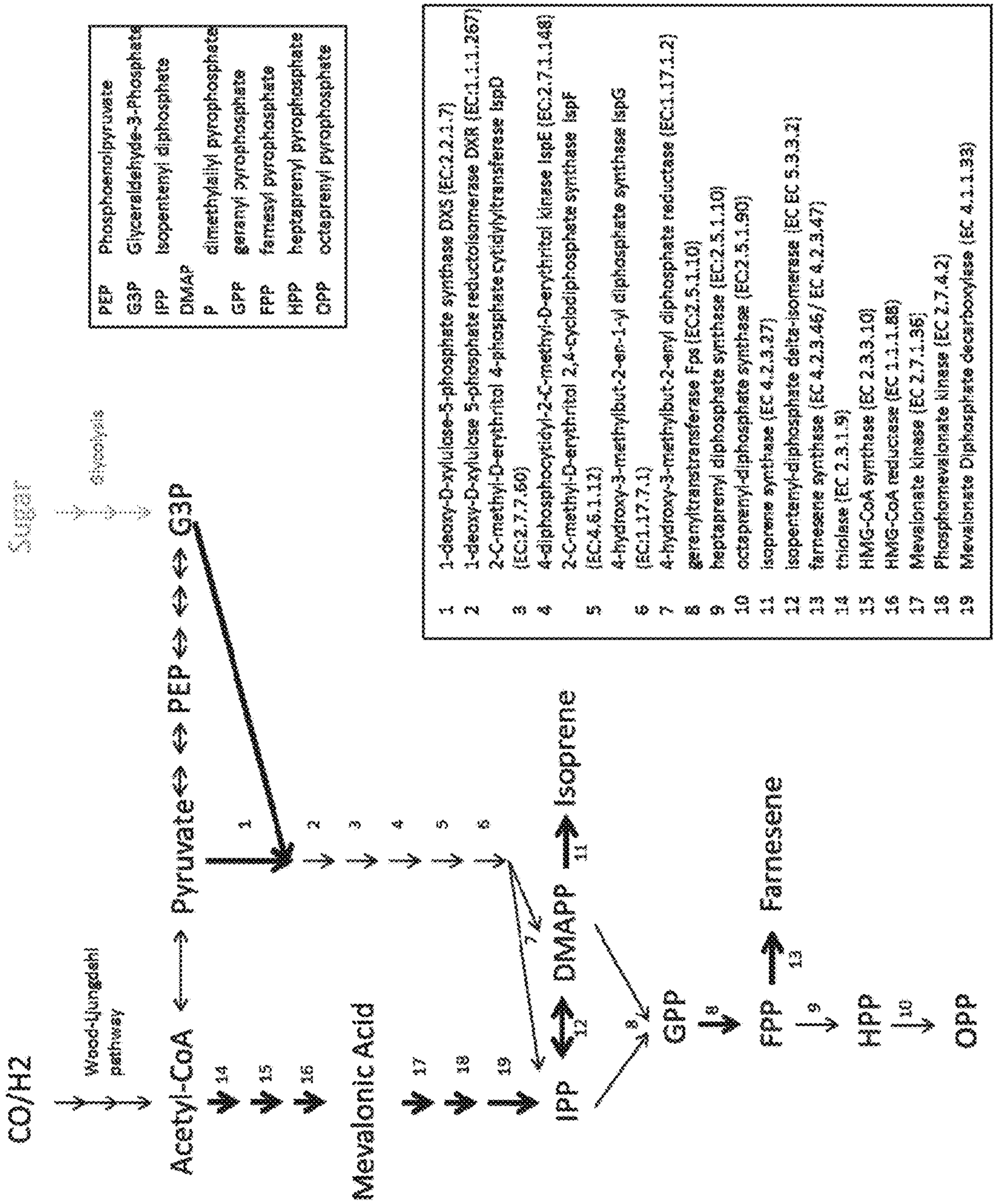
FIG. 1: Pathway diagram for production of terpenes, gene targets described in this application are highlighted with bold arrows.

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The inventors have surprisingly been able to engineer a carboxydotrophic acetogenic microorganism to produce terpene and precursors thereof including isoprene and farnesene by fermentation of a substrate comprising CO. This offers an alternative means for the production of these products which may have benefits over the current methods for their production. In addition, it offers a means of using carbon monoxide from industrial processes which would otherwise be released into the atmosphere and pollute the environment.

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced (for example in a parental microorganism from which the recombinant microorganism is derived), strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

"Exogenous" may also be used to refer to proteins. This refers to a protein that is not present in the parental microorganism from which the recombinant microorganism is derived.

The term "endogenous" as used herein in relation to a recombinant microorganism and a nucleic acid or protein refers to any nucleic acid or protein that is present in a parental microorganism from which the recombinant microorganism is derived.

It should be appreciated that the invention may be practiced using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium acetobutylicum, Clostridium beijerinckii, C. saccharobutylicum* and *C. saccharoperbutylacetonicum*, details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practiced using polypeptides whose sequence varies from the amino acid sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods described by Silver et al. (1991, *Plant Physiol.* 97: 1588-1591) or Zhao et al. (2011, *Appl Microbiol Biotechnol,* 90:1915-1922) for the isoprene synthase enzyme, by Green et al. (2007, *Phytochemistry;* 68:176-188) for the farnesene synthase enzyme, by Kuzuyama et al. (2000, *J. Bacteriol.* 182, 891-897) for the 1-deoxy-D-xylulose 5-phosphate synthase Dxs, by Berndt and Schlegel (1975, *Arch. Microbiol.* 103, 21-30) or by Stim-Herndon et al. (1995, *Gene* 154: 81-85) for the thiolase, by Cabano et al. (1997, *Insect Biochem. Mol. Biol.* 27: 499-505) for the HMG-CoA synthase, by Ma et al. (2011, *Metab. Engin.,* 13:588-597) for the HMG-CoA reductase and mevalonate kinase enzyme, by Herdendorf and Miziorko (2007, *Biochemistry,* 46: 11780-8) for the phosphomevalonate kinase, and by Krepkiy et al. (2004, *Protein Sci.* 13: 1875-1881) for the mevalonate diphosphate decarboxylase. It is also possible to identify genes of DXS and mevalonate pathway using inhibitors like fosmidomycin or mevinoline as described by Trutko et al. (2005, *Microbiology* 74: 153-158).

"Over-express", "over expression" and like terms and phrases when used in relation to the invention should be taken broadly to include any increase in expression of one or more proteins (including expression of one or more nucleic acids encoding same) as compared to the expression level of the protein (including nucleic acids) of a parental microorganism under the same conditions. It should not be taken to mean that the protein (or nucleic acid) is expressed at any particular level.

A "parental microorganism" is a microorganism used to generate a recombinant microorganism of the invention. The parental microorganism may be one that occurs in nature (i.e. a wild type microorganism) or one that has been previously modified but which does not express or over-express one or more of the enzymes that are the subject of the present invention. Accordingly, the recombinant microorganisms of the invention may have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

A "terpene" as referred to herein should be taken broadly to include any compound made up of $C_5$ isoprene units joined together including simple and complex terpenes and oxygen-containing terpene compounds such as alcohols, aldehydes and ketones. Simple terpenes are found in the essential oils and resins of plants such as conifers. More complex terpenes include the terpenoids and vitamin A, carotenoid pigments (such as lycopene), squalene, and rubber. Examples of monoterpenes include, but are not limited to isoprene, pinene, nerol, citral, camphor, menthol, limonene. Examples of sesquiterpenes include but are not limited to nerolidol, farnesol. Examples of diterpenes include but are not limited to phytol, vitamin $A_1$. Squalene is an example of a triterpene, and carotene (provitamin $A_1$) is a tetraterpene.

A "terpene precursor" is a compound or intermediate produced during the reaction to form a terpene starting from Acetyl CoA and optionally pyruvate. The term refers to a precursor compound or intermediate found in the mevalonate (MVA) pathway and optionally the DXS pathway as well as downstream precursors of longer chain terpenes, such as FPP and GPP. In particular embodiments, it includes but is not limited to mevalonic acid, IPP, dimethylallyl pyrophosphate (DMAPP), geranyl pyrophosphate (GPP) and farnesyl pyrophosphate (FPP).

The "DXS pathway" is the enzymatic pathway from pyruvate and D-glyceraldehyde-3-phosphate to DMAPP or IPP. It is also known as the deoxyxylulose 5-phosphate (DXP/DXPS/DOXP or DXS)/methylerythritol phosphate (MEP) pathway.

The "mevalonate (MVA) pathway" is the enzymatic pathway from acetyl-CoA to IPP.

Microorganisms

Two pathways for production of terpenes are known, the deoxyxylulose 5-phosphate (DXP/DXPS/DOXP or DXS)/methylerythritol phosphate (MEP) pathway (Hunter et al., 2007, *J. Biol. chem.* 282: 21573-77) starting from pyruvate and D-glyceraldehyde-3-phosphate (G3P), the two key intermediates in the glycolysis, and the mevalonate (MVA) pathway (Miziorko, 2011, *Arch Biochem Biophys*, 505: 131-143) starting from acetyl-CoA. Many different classes of microorganisms have been investigated for presence of either of these pathways (Lange et al., 2000, *PNAS*, 97: 13172-77; Trutko et al., 2005, *Microbiology*, 74: 153-158; Julsing et al., 2007, *Appl Microbiol Biotechnol*, 75: 1377-84), but not carboxydotrophic acetogens. The DXS pathway for example was found to be present in *E. coli, Bacillus*, or *Mycobacterium*, while the mevalonate pathway is present in yeast *Saccharomyces, Cloroflexus*, or *Myxococcus.*

Genomes of carboxydotrophic acetogens *C. autoethanogenum, C. ljungdahlii* were analysed by the inventors for presence of either of the two pathways. All genes of the DXS pathway were identified in *C. autoethanogenum* and *C. ljungdahlii* (Table 1), while the mevalonate pathway is absent. Additionally, carboxydotrophic acetogens such as *C. autoethanogenum* or *C. ljungdahlii* are not known to produce any terpenes as metabolic end products.

TABLE 1

Terpene biosynthesis genes of the DXS pathway identified in *C. autoethanogenum* and *C. ljungdahlii*:

| Gene/Enzyme | *C. autoethanogenum* | *C. ljungdahlii* |
|---|---|---|
| 1-deoxy-D-xylulose-5-phosphate synthase DXS (EC: 2.2.1.7) | SEQ ID NO: 1-2 | YP_003779286.1; GI: 300854302, CLJU_c11160 |
| 1-deoxy-D-xylulose 5-phosphate reductoisomerase DXR (EC: 1.1.1.267) | SEQ ID NO: 3-4 | YP_003779478.1; GI: 300854494, CLJU_c13080 |
| 2-C-methyl-D-erythritol 4-phosphate cytidylyltransferase IspD (EC: 2.7.7.60) | SEQ ID NO: 5-6 | YP_003782252.1 GI: 300857268, CLJU_c41280 |
| 4-diphosphocytidyl-2-C-methyl-D-erythritol kinase IspE (EC: 2.7.1.148) | SEQ ID NO: 7-8 | YP_003778403.1; GI: 300853419, CLJU_c02110 |
| 2-C-methyl-D-erythritol 2,4-cyclodiphosphate synthase IspF (EC: 4.6.1.12) | SEQ ID NO: 9-10 | YP_003778349.1; GI: 300853365, CLJU_c01570 |
| 4-hydroxy-3-methylbut-2-en-1-yl diphosphate synthase IspG (EC: 1.17.7.1) | SEQ ID NO: 11-12 | YP_003779480.1; GI: 300854496, CLJU_c13100 |
| 4-hydroxy-3-methylbut-2-enyl diphosphate reductase (EC: 1.17.1.2) | SEQ ID NO: 13-14 | YP_003780294.1; GI: 300855310, CLJU_c21320 |

Genes for downstream synthesis of terpenes from isoprene units were also identified in both organisms (Table 2).

| Gene/Enzyme | *C. autoethanogenum* | *C. ljungdahlii* |
|---|---|---|
| geranyltranstransferase Fps (EC: 2.5.1.10) | SEQ ID NO: 15-16 | YP_003779285.1; GI: 300854301, CLJU_c11150 |
| heptaprenyl diphosphate synthase (EC: 2.5.1.10) | SEQ ID NO: 17-18 | YP_003779312.1; GI: 300854328, CLJU_c11420 |
| octaprenyl-diphosphate synthase [EC: 2.5.1.90] | SEQ ID NO: 19-20 | YP_003782157.1; GI: 300857173, CLJU_c40310 |

Terpenes are energy dense compounds, and their synthesis requires the cell to invest energy in the form of nucleoside triphosphates such as ATP. Using sugar as a substrate requires sufficient energy to be supplied from glycolysis to yield several molecules of ATP. The production of terpenes and/or their precursors via the DXS pathway using sugar as a substrate proceeds in a relatively straightforward manner due to the availability of pyruvate and D-glyceraldehyde-3-phosphate (G3P), G3P being derived from C5 pentose and C6 hexose sugars. These C5 and C6 molecules are thus relatively easily converted into C5 isoprene units from which terpenes are composed.

For anaerobic acetogens using a C1 substrate like CO or $CO_2$, it is more difficult to synthesise long molecules such as hemiterpenoids from C1 units. This is especially true for longer chain terpenes like C10 monoterpenes, C15 sesquiterpenes, or C40 tetraterpenes. To date the product with most carbon atoms reported in acetogens (both native and recombinant organisms) are C4 compounds butanol (Köpke et al., 2011, *Curr. Opin. Biotechnol.* 22: 320-325; Schiel-Bengelsdorf and Dürre, 2012, *FEBS Letters:* 10.1016/j.febslet.2012.04.043; Köpke et al., 2011, *Proc. Nat. Sci. U.S.A.* 107: 13087-92; US patent 2011/0236941) and 2,3-butanediol (Köpke et al., 2011, Appl. Environ. Microbiol. 77:5467-75). The inventors have shown that it is surprisingly possible to anaerobically produce these longer chain terpene molecules using the C1 feedstock CO via the acetyl CoA intermediate.

Energetics of the Wood-Ljungdahl pathway of anaerobic acetogens are just emerging, but unlike under aerobic growth conditions or glycolysis of sugar fermenting organisms no ATP is gained in the Wood-Ljungdahl pathway by substrate level phosphorylation, in fact activation of $CO_2$ to formate actually requires one molecule of ATP and a membrane gradient is required. The inventors note that it is important that a pathway for product formation is energy efficient. The inventors note that in acetogens the substrate CO or $CO_2$ is channeled directly into acetyl-CoA, which represents the most direct route to terpenes and/or their precursors, especially when compared to sugar based systems, with only six reactions required (FIG. 1). Though less ATP is available in carboxydotrophic acetogens, the inventors believe that this more direct pathway may sustain a higher metabolic flux (owing to higher chemical motive force of intermediate reactions). A highly effective metabolic flux is important as several intermediates in the terpene biosynthesis pathway, such as key intermediates Mevalonate and FPP, are toxic to most bacteria when not turned over efficiently.

Despite having a higher ATP availability, this problem of intermediate toxicity can be a bottleneck in production of terpenes from sugar.

When comparing the energetics of terpene precursor IPP and DMAPP production from CO (FIG. 6) via the mevalonate pathway versus the DXS pathway, the inventors noted that the mevalonate pathway requires less nucleoside triphosphates as ATP, less reducing equivalents, and is also more direct when compared to the DXS pathway with only six necessary reaction steps from acetyl-CoA. This provides advantages in the speed of the reactions and metabolic fluxes and increases overall energy efficiency. Additionally, the lower number of enzymes required simplifies the recombination method required to produce a recombinant microorganism.

No acetogens with a mevalonate pathway have been identified, but the inventors have shown that it is possible to introduce the mevalonate pathway and optionally the DXS pathway into a carboxydotrophic acetogen such as *Clostridium autoethanogenum* or *C. ljungdahlii* to efficiently produce terpenes and/or precursors thereof from the C1 carbon substrate CO. They contemplate that this is applicable to all carboxydotrophic acetogenic microorganisms.

Additionally, the production of terpenes and/or precursors thereof has never been shown to be possible using recombinant microorganisms under anaerobic conditions. Anaerobic production of isoprene has the advantage of providing a safer operating environment because isoprene is extremely flammable in the presence of oxygen and has a lower flammable limit (LFL) of 1.5-2.0% and an upper flammable (UFL) limit of 2.0-12% at room temperature and atmospheric pressure. As flames cannot occur in the absence of oxygen, the inventors believe that an anaerobic fermentation process is desirable as it would be safer across all product concentrations, gas compositions, temperature and pressure ranges.

As discussed hereinbefore, the invention provides a recombinant microorganism capable of producing one or more terpenes and/or precursors thereof, and optionally one or more other products, by fermentation of a substrate comprising CO.

In a further embodiment, the microorganism is adapted to: express one or more exogenous enzymes from the mevalonate (MVA) pathway and/or overexpress one or more endogenous enzyme from the mevalonate (MVA) pathway; and a) express one or more exogenous enzymes from the DXS pathway and/or overexpress one or more endogenous enzymes from the DXS pathway.

In one embodiment, the parental microorganism from which the recombinant microorganism is derived is capable of fermenting a substrate comprising CO to produce Acetyl CoA, but not of converting Acetyl CoA to mevalonic acid or isopentenyl pyrophosphate (IPP) and the recombinant microorganism is adapted to express one or more enzymes involved in the mevalonate pathway.

The microorganism may be adapted to express or overexpress the one or more enzymes by any number of recombinant methods including, for example, increasing expression of native genes within the microorganism (for example, by introducing a stronger or constitutive promoter to drive expression of a gene), increasing the copy number of a gene encoding a particular enzyme by introducing exogenous nucleic acids encoding and adapted to express the enzyme, introducing an exogenous nucleic acid encoding and adapted to express an enzyme not naturally present within the parental microorganism.

In one embodiment, the one or more enzymes are from the mevalonate (MVA) pathway and are selected from the group consisting of:

a) thiolase (EC 2.3.1.9), b) HMG-CoA synthase (EC 2.3.3.10), c) HMG-CoA reductase (EC 1.1.1.88), d) Mevalonate kinase (EC 2.7.1.36), e) Phosphomevalonate kinase (EC 2.7.4.2), f) Mevalonate Diphosphate decarboxylase (EC 4.1.1.33), and g) a functionally equivalent variant of any one thereof.

In a further embodiment, the optional one or more enzymes are from the DXS pathway is selected from the group consisting of:

a) 1-deoxy-D-xylulose-5-phosphate synthase DXS (EC: 2.2.1.7), b) 1-deoxy-D-xylulose 5-phosphate reductoisomerase DXR (EC:1.1.1.267), c) 2-C-methyl-D-erythritol 4-phosphate cytidylyltransferase IspD (EC:2.7.7.60), d) 4-diphosphocytidyl-2-C-methyl-D-erythritol kinase IspE (EC:2.7.1.148), e) 2-C-methyl-D-erythritol 2,4-cyclodiphosphate synthase IspF (EC:4.6.1.12), f) 4-hydroxy-3-methylbut-2-en-1-yl diphosphate synthase IspG (EC:1.17.7.1), g) 4-hydroxy-3-methylbut-2-enyl diphosphate reductase (EC:1.17.1.2), and h) a functionally equivalent variant of any one thereof.

In a further embodiment, one or more exogenous or endogenous further enzymes are expressed or over-expressed to result in the production of a terpene compound and/or precursor thereof wherein the exogenous enzyme that is expressed, or the endogenous enzyme that is overexpressed is selected from the group consisting of:

a) geranyltranstransferase Fps (EC:2.5.1.10), b) heptaprenyl diphosphate synthase (EC:2.5.1.10), c) octaprenyl-diphosphate synthase (EC:2.5.1.90), d) isoprene synthase (EC 4.2.3.27), e) isopentenyl-diphosphate delta-isomerase (EC EC 5.3.3.2), f) farnesene synthase (EC 4.2.3.46/EC 4.2.3.47), and g) a functionally equivalent variant of any one thereof.

By way of example only, sequence information for each of the enzymes is listed in the figures herein.

The enzymes of use in the microorganisms of the invention may be derived from any appropriate source, including different genera and species of bacteria, or other organisms. However, in one embodiment, the enzymes are derived from *Staphylococcus aureus*.

In one embodiment, the enzyme isoprene synthase (ispS) is derived from *Poplar tremuloides*. In a further embodiment, it has the nucleic acid sequence exemplified in SEQ ID NO: 21 hereinafter, or it is a functionally equivalent variant thereof.

In one embodiment, the enzyme deoxyxylulose 5-phosphate synthase is derived from *C. autoethanogenum*, encoded by the nucleic acid sequence exemplified in SEQ ID NO: 1 and/or with the amino acid sequence exemplified in SEQ ID NO: 2 hereinafter, or it is a functionally equivalent variant thereof.

In one embodiment, the enzyme 1-deoxy-D-xylulose 5-phosphate reductoisomerase DXR is derived from *C. autoethanogenum* and is encoded by the nucleic acid sequence exemplified in SEQ ID NO: 3 or is a functionally equivalent variant thereof.

In one embodiment, the enzyme 2-C-methyl-D-erythritol 4-phosphate cytidylyltransferase IspD is derived from *C. autoethanogenum* and is encoded by the nucleic acid sequence exemplified in SEQ ID NO: 5 or is a functionally equivalent variant thereof.

In one embodiment, the enzyme 4-diphosphocytidyl-2-C-methyl-D-erythritol kinase IspE is derived from *C. autoethanogenum* and is encoded by the nucleic acid sequence exemplified in SEQ ID NO: 7 or is a functionally equivalent variant thereof.

In one embodiment, the enzyme 2-C-methyl-D-erythritol 2,4-cyclodiphosphate synthase IspF is derived from *C. autoethanogenum* and is encoded by the nucleic acid sequence exemplified in SEQ ID NO: 9 or is a functionally equivalent variant thereof.

In one embodiment, the enzyme 4-hydroxy-3-methylbut-2-en-1-yl diphosphate synthase IspG is derived from *C. autoethanogenum* and is encoded by the nucleic acid sequence exemplified in SEQ ID NO: 11 or is a functionally equivalent variant thereof.

In one embodiment, the enzyme 4-hydroxy-3-methylbut-2-enyl diphosphate reductase is derived from *C. autoethanogenum* and is encoded by the nucleic acid sequence exemplified in SEQ ID NO: 13 or is a functionally equivalent variant thereof.

In one embodiment, the enzyme mevalonate kinase (MK) is derived from *Staphylococcus aureus* subsp. *aureus* Mu50 and is encoded by the nucleic acid sequence exemplified in SEQ ID NO: 51 hereinafter, or it is a functionally equivalent variant thereof.

In one embodiment, the enzyme phosphomevalonate kinase (PMK) is derived from *Staphylococcus aureus* subsp. *aureus* Mu50 and is encoded by the nucleic acid sequence exemplified in SEQ ID NO: 52 hereinafter, or it is a functionally equivalent variant thereof.

In one embodiment, the enzyme mevalonate diphosphate decarboxylase (PMD) is derived from *Staphylococcus aureus* subsp. *aureus* Mu50 and is encoded by the nucleic acid sequence exemplified in SEQ ID NO: 53 hereinafter, or it is a functionally equivalent variant thereof.

In one embodiment, the enzyme Isopentenyl-diphosphate delta-isomerase (idi) is derived from *Clostridium beijerinckii* and is encoded by the nucleic acid sequence exemplified in SEQ ID NO: 54 hereinafter, or it is a functionally equivalent variant thereof.

In one embodiment, the enzyme thiolase (thlA) is derived from *Clostridium acetobutylicum* ATCC824 and is encoded by the nucleic acid sequence exemplified in SEQ ID NO: 40 hereinafter, or it is a functionally equivalent variant thereof.

In one embodiment, the enzyme is a thiolase enzyme, and is an acetyl-CoA c-acetyltransferase (vraB) derived from *Staphylococcus aureus* subsp. *aureus* Mu50 and is encoded by the nucleic acid sequence exemplified in SEQ ID NO: 41 hereinafter, or it is a functionally equivalent variant thereof.

In one embodiment, the enzyme 3-hydroxy-3-methylglutaryl-CoA synthase (HMGS) is derived from *Staphylococcus aureus* subsp. *aureus* Mu50 and is encoded by the nucleic acid sequence exemplified in SEQ ID NO: 42 hereinafter, or it is a functionally equivalent variant thereof.

In one embodiment, the enzyme Hydroxymethylglutaryl-CoA reductase (HMGR) is derived from *Staphylococcus aureus* subsp. *aureus* Mu50 and is encoded by the nucleic acid sequence exemplified in SEQ ID NO: 43 hereinafter, or it is a functionally equivalent variant thereof.

In one embodiment, the enzyme Geranyltranstransferase (ispA) is derived from *Escherichia coli* str. K-12 substr. MG1655 is encoded by the nucleic acid sequence exemplified in SEQ ID NO: 56 hereinafter, or it is a functionally equivalent variant thereof.

In one embodiment, the enzyme heptaprenyl diphosphate synthase is derived from *C. autoethanogenum* and is encoded by the nucleic acid sequence exemplified in SEQ ID NO: 17 or is a functionally equivalent variant thereof.

In one embodiment, the enzyme polyprenyl synthetase is derived from *C. autoethanogenum* and is encoded by the nucleic acid sequence exemplified in SEQ ID NO: 19 or is a functionally equivalent variant thereof.

In one embodiment, the enzyme Alpha-farnesene synthase (FS) is derived from *Malus×domestica* and is encoded by the nucleic acid sequence exemplified in SEQ ID NO: 57 hereinafter, or it is a functionally equivalent variant thereof.

The enzymes and functional variants of use in the microorganisms may be identified by assays known to one of skill in the art. In particular embodiments, the enzyme isoprene synthase may be identified by the method outlined Silver et al. (1991, *Plant Physiol.* 97: 1588-1591) or Zhao et al. (2011, *Appl Microbiol Biotechnol,* 90:1915-1922). In a further particular embodiment, the enzyme farnesene synthase may be identified by the method outlined in Green et al., 2007, Phytochemistry; 68:176-188. In further particular embodiments, enzymes from the mevalonate pathway may be identified by the method outlined in Cabano et al. (1997, *Insect Biochem. Mol. Biol.* 27: 499-505) for the HMG-CoA synthase, Ma et al. (2011, *Metab. Engin.,* 13:588-597) for the HMG-CoA reductase and mevalonate kinase enzyme, Herdendorf and Miziorko (2007, *Biochemistry,* 46: 11780-8) for the phosphomevalonate kinase, and Krepkiy et al. (2004, *Protein Sci.* 13: 1875-1881) for the mevalonate diphosphate decarboxylase. Ma et al., 2011, *Metab. Engin.,* 13:588-597. The 1-deoxy-D-xylulose 5-phosphate synthase of the DXS pathway can be assayed using the method outlined in Kuzuyama et al. (2000, *J. Bacteriol.* 182, 891-897). It is also possible to identify genes of DXS and mevalonate pathway using inhibitors like fosmidomycin or mevinoline as described by Trutko et al. (2005, *Microbiology* 74: 153-158).

In one embodiment, the microorganism comprises one or more exogenous nucleic acids adapted to increase expression of one or more endogenous nucleic acids and which one or more endogenous nucleic acids encode one or more of the enzymes referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or Phosphotransacetylase/Acetate kinase operon promoters. It will be appreciated by those of skill in the art that other promoters which can direct expression, preferably a high level of expression under appropriate fermentation conditions, would be effective as alternatives to the exemplified embodiments.

In one embodiment, the microorganism comprises one or more exogenous nucleic acids encoding and adapted to express one or more of the enzymes referred to herein before. In one embodiment, the microorganisms comprise one or more exogenous nucleic acid encoding and adapted to express at least two, at least of the enzymes. In other embodiments, the microorganism comprises one or more exogenous nucleic acid encoding and adapted to express at least three, at least four, at least five, at least six, at least seven, at least eight, at least nine or more of the enzymes.

In one particular embodiment, the microorganism comprises one or more exogenous nucleic acid encoding an enzyme of the invention or a functionally equivalent variant thereof.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acid is a nucleic acid construct or vector, in one particular embodiment a plasmid, encoding one or more of the enzymes referred to hereinbefore in any combination.

The exogenous nucleic acids may remain extra-chromosomal upon transformation of the parental microorganism or may integrate into the genome of the parental microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or enzymes as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster and Phosphotransacetylase/Acetate kinase promoters. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid.

In one particular embodiment, the parental microorganism is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii*, and *Thermoanaerobacter kiuvi.*

In one particular embodiment, the parental microorganism is selected from the cluster of ethanologenic, acetogenic Clostridia comprising the species *C. autoethanogenum, C. ljungdahlii*, and *C. ragsdalei* and related isolates. These include but are not limited to strains *C. autoethanogenum* JAI-1T (DSM10061) [Abrini J, Naveau H, Nyns E-J: *Clostridium autoethanogenum*, sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* PETC$^T$ (DSM13528=ATCC 55383) [Tanner R S, Miller L M, Yang D: *Clostridium ljungdahlii* sp. nov., an Acetogenic Species in Clostridial rRNA Homology Group I. Int J Syst Bacteriol 1993, 43: 232-236], *C. ljungdahlii* ERI-2 (ATCC 55380) [Gaddy J L: *Clostridium* stain which produces acetic acid from waste gases. US patent 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. US patent, 2002, U.S. Pat. No. 6,368,819], *C. ljungdahlii* O-52 (ATCC 55989) [Gaddy J L, Clausen E C, Ko C-W: Microbial process for the preparation of acetic acid as well as solvent for its extraction from the fermentation broth. US patent, 2002, U.S. Pat. No. 6,368,819], *C. ragsdalei* P11$^T$ (ATCC BAA-622) [Huhnke R L, Lewis R S, Tanner R S: Isolation and Characterization of novel Clostridial Species. International patent 2008, WO 2008/028055], related isolates such as "*C. coskatii*" [Zahn et al—Novel ethanologenic species *Clostridium coskatii* (US Patent Application number US20110229947)] and "*Clostridium* sp." (Tyurin et al., 2012, *J. Biotech Res.* 4: 1-12), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel Clostridial Species. International patent 2008, WO 2008/028055].

All species of this cluster have a similar morphology and size (logarithmic growing cells are between 0.5-0.7×3-5 μm), are mesophilic (optimal growth temperature between 30-37° C.) and strictly anaerobe [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not.

In one embodiment, the parental carboxydotrophic acetogenic microorganism is selected from the group consisting of *Clostridium autoethanogenum, Clostridium ljungdahlii, Clostridium ragsdalei, Clostridium carboxidivorans, Clostridium drakei, Clostridium scatologenes, Butyribacte-*

*rium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii*, and *Thermoanaerobacter kiuvi.*

In one particular embodiment of the first or second aspects, the parental microorganism is selected from the group of carboxydotrophic Clostridia comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum.*

In a one embodiment, the microorganism is selected from a cluster of carboxydotrophic Clostridia comprising the species *C. autoethanogenum, C. ljungdahlii*, and "*C. ragsdalei*" and related isolates. These include but are not limited to strains *C. autoethanogenum* JAI-$1^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* $PETC^T$ (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), or "*C. ragsdalei* $P11^T$" (ATCC BAA-622) (WO 2008/028055), and related isolates such as "*C. coskatii*" (US patent 2011/0229947), "*Clostridium* sp. MT351" (Michael Tyurin & Kiriukhin, 2012) and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010).

These strains form a subcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Köpke et al., 2010) and a GC composition of around 32% mol (Abrini et al., 1994; Köpke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde:ferredoxin oxidoreductase (Köpke et al., 2010, 2011). The organization and number of Wood-Ljungdahl pathway genes, responsible for gas uptake, has been found to be the same in all species, despite differences in nucleic and amino acid sequences (Köpke et al., 2011).

The strains all have a similar morphology and size (logarithmic growing cells are between 0.5-0.7×3-5 μm), are mesophilic (optimal growth temperature between 30-37° C.) and strictly anaerobe (Abrini et al., 1994; Tanner et al., 1993)(WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Köpke et al., 2011; Tanner et al., 1993) However, the species differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not. Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

The recombinant carboxydotrophic acetogenic microorganisms of the invention may be prepared from a parental carboxydotrophic acetogenic microorganism and one or more exogenous nucleic acids using any number of techniques known in the art for producing recombinant microorganisms. By way of example only, transformation (including transduction or transfection) may be achieved by electroporation, electrofusion, ultrasonication, polyethylene glycol-mediated transformation, conjugation, or chemical and natural competence. Suitable transformation techniques are described for example in Sambrook J, Fritsch E F, Maniatis T: Molecular Cloning: A laboratory Manual, Cold Spring Harbour Laboratory Press, Cold Spring Harbour, 1989.

Electroporation has been described for several carboxydotrophic acetogens as *C. ljungdahlii* (Köpke et al., 2010; Leang, Ueki, Nevin, & Lovley, 2012) (PCT/NZ2011/000203; WO2012/053905), *C. autoethanogenum* (PCTNZ2011/000203; WO2012/053905), *Acetobacterium woodii* (Strätz, Sauer, Kuhn, & Dürre, 1994) or *Moorella thermoacetica* (Kita et al., 2012) and is a standard method used in many Clostridia such as *C. acetobutylicum* (Mermelstein, Welker, Bennett, & Papoutsakis, 1992), *C. cellulolyticum* (Jennert, Tardif, Young, & Young, 2000) or *C. thermocellum* (MV Tyurin, Desai, & Lynd, 2004).

Electrofusion has been described for acetogenic *Clostridium* sp. MT351 (Tyurin and Kiriukhin, 2012).

Prophage induction has been described for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University).

Conjugation has been described as method of choice for acetogen *Clostridium difficile* (Herbert, O'Keeffe, Purdy, Elmore, & Minton, 2003) and many other Clostridia including *C. acetobutylicum* (Williams, Young, & Young, 1990).

In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

Nucleic Acids

The invention also provides one or more nucleic acids or nucleic acid constructs of use in generating a recombinant microorganism of the invention.

In one embodiment, the nucleic acid comprises sequences encoding one or more of the enzymes in the mevalonate (MVA) pathway and optionally the DXS pathway which when expressed in a microorganism allows the microorganism to produce one or more terpenes and/or precursors thereof by fermentation of a substrate comprising CO. In one particular embodiment, the invention provides a nucleic acid encoding two or more enzymes which when expressed in a microorganism allows the microorganism to produce one or more terpene and/or precursor thereof by fermentation of substrate comprising CO. In one embodiment, a nucleic acid of the invention encodes three, four, five or more of such enzymes.

In one embodiment, the one or more enzymes encoded by the nucleic acid are from the mevalonate (MVA) pathway and are selected from the group consisting of:

a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a further embodiment, the one or more optional enzymes encoded by the nucleic acid are from the DXS pathway are selected from the group consisting of:

a) 1-deoxy-D-xylulose-5-phosphate synthase DXS (EC: 2.2.1.7),
b) 1-deoxy-D-xylulose 5-phosphate reductoisomerase DXR (EC:1.1.1.267),
c) 2-C-methyl-D-erythritol 4-phosphate cytidylyltransferase IspD (EC:2.7.7.60),
d) 4-diphosphocytidyl-2-C-methyl-D-erythritol kinase IspE (EC:2.7.1.148),
e) 2-C-methyl-D-erythritol 2,4-cyclodiphosphate synthase IspF (EC:4.6.1.12),
f) 4-hydroxy-3-methylbut-2-en-1-yl diphosphate synthase IspG (EC:1.17.7.1),
g) 4-hydroxy-3-methylbut-2-enyl diphosphate reductase (EC:1.17.1.2), and
h) a functionally equivalent variant of any one thereof.

In a further embodiment, the nucleic acid encodes one or more further enzymes that are expressed or over-expressed to result in the production of a terpene compound and/or precursor thereof wherein the exogenous enzyme that is expressed, or the endogenous enzyme that is overexpressed is selected from the group consisting of:

a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC EC 5.3.3.2),
f) farnesene synthase (EC 4.2.3.46/EC 4.2.3.47), and
g) a functionally equivalent variant of any one thereof.

Exemplary amino acid sequences and nucleic acid sequences encoding each of the above enzymes are provided herein or can be obtained from GenBank as mentioned hereinbefore. However, skilled persons will readily appreciate alternative nucleic acid sequences encoding the enzymes or functionally equivalent variants thereof, having regard to the information contained herein, in GenBank and other databases, and the genetic code.

In a further embodiment, the nucleic acid encoding thiolase (thlA) derived from *Clostridium acetobutylicum* ATCC824 is encoded by the nucleic acid sequence exemplified in SEQ ID NO: 40 hereinafter, or it is a functionally equivalent variant thereof.

In a further embodiment, the nucleic acid encoding thiolase wherein the thiolase is acetyl-CoA c-acetyltransferase (vraB) derived from *Staphylococcus aureus* subsp. *aureus* Mu50 is encoded by the nucleic acid sequence exemplified in SEQ ID NO: 41 hereinafter, or it is a functionally equivalent variant thereof.

In a further embodiment, the nucleic acid encoding 3-hydroxy-3-methylglutaryl-CoA synthase (HMGS) derived from *Staphylococcus aureus* subsp. *aureus* Mu50 is encoded by the nucleic acid sequence exemplified in SEQ ID NO: 42 hereinafter, or it is a functionally equivalent variant thereof.

In a further embodiment, the nucleic acid encoding Hydroxymethylglutaryl-CoA reductase (HMGR) derived from *Staphylococcus aureus* subsp. *aureus* Mu50 is encoded by the nucleic acid sequence exemplified in SEQ ID NO: 43 hereinafter, or it is a functionally equivalent variant thereof.

In a further embodiment, the nucleic acid encoding mevalonate kinase (MK) derived from *Staphylococcus aureus* subsp. *aureus* Mu50 is encoded by the nucleic acid sequence exemplified in SEQ ID NO: 51 hereinafter, or it is a functionally equivalent variant thereof.

In a further embodiment, the nucleic acid encoding phosphomevalonate kinase (PMK) derived from *Staphylococcus aureus* subsp. *aureus* Mu50 is encoded by the nucleic acid sequence exemplified in SEQ ID NO: 52 hereinafter, or it is a functionally equivalent variant thereof.

In a further embodiment, the nucleic acid encoding mevalonate diphosphate decarboxylase (PMD) derived from *Staphylococcus aureus* subsp. *aureus* Mu50 is encoded by the nucleic acid sequence exemplified in SEQ ID NO: 53 hereinafter, or it is a functionally equivalent variant thereof.

In a further embodiment, the nucleic acid encoding deoxyxylulose 5-phosphate synthase derived from *C. autoethanogenum*, is encoded by the nucleic acid sequence exemplified in SEQ ID NO: 1 and/or with the amino acid sequence exemplified in SEQ ID NO: 2 hereinafter, or it is a functionally equivalent variant thereof.

In one embodiment, the nucleic acid encoding 1-deoxy-D-xylulose 5-phosphate reductoisomerase DXR (EC: 1.1.1.267) has the sequence SEQ ID NO: 3 or is a functionally equivalent variant thereof.

In one embodiment, the nucleic acid encoding 2-C-methyl-D-erythritol 4-phosphate cytidylyltransferase IspD (EC:2.7.7.60) has the sequence SEQ ID NO: 5 or is a functionally equivalent variant thereof.

In one embodiment, the nucleic acid encoding 4-diphosphocytidyl-2-C-methyl-D-erythritol kinase IspE (EC: 2.7.1.148) has the sequence SEQ ID NO: 7 or is a functionally equivalent variant thereof.

In one embodiment, the nucleic acid encoding 2-C-methyl-D-erythritol 2,4-cyclodiphosphate synthase IspF (EC:4.6.1.12) has the sequence SEQ ID NO: 9 or is a functionally equivalent variant thereof.

In one embodiment, the nucleic acid encoding 4-hydroxy-3-methylbut-2-en-1-yl diphosphate synthase IspG (EC: 1.17.7.1) has the sequence SEQ ID NO: 11 or is a functionally equivalent variant thereof.

In one embodiment, the nucleic acid encoding 4-hydroxy-3-methylbut-2-enyl diphosphate reductase (EC:1.17.1.2) has the sequence SEQ ID NO: 13 or is a functionally equivalent variant thereof.

In a further embodiment, the nucleic acid encoding Geranyltranstransferase (ispA) derived from *Escherichia coli* str. K-12 substr. MG1655 is encoded by the nucleic acid sequence exemplified in SEQ ID NO: 56 hereinafter, or it is a functionally equivalent variant thereof.

In one embodiment, the nucleic acid encoding heptaprenyl diphosphate synthase has the sequence SEQ ID NO: 17, or it is a functionally equivalent variant thereof.

In one embodiment, the nucleic acid encoding octaprenyl-diphosphate synthase (EC:2.5.1.90) wherein the octaprenyl-diphosphate synthase is polyprenyl synthetase is encoded by sequence SEQ ID NO: 19, or it is a functionally equivalent variant thereof.

In one embodiment, the nucleic acid encoding isoprene synthase (ispS) derived from *Poplar tremuloides* is exemplified in SEQ ID NO: 21 hereinafter, or it is a functionally equivalent variant thereof.

In a further embodiment, the nucleic acid encoding Isopentenyl-diphosphate delta-isomerase (idi) derived from *Clostridium beijerinckii* is encoded by the nucleic acid sequence exemplified in SEQ ID NO: 54 hereinafter, or it is a functionally equivalent variant thereof.

In a further embodiment, the nucleic acid encoding Alpha-farnesene synthase (FS) derived from *Malus×domestica* is encoded by the nucleic acid sequence exemplified in SEQ ID NO: 57 hereinafter, or it is a functionally equivalent variant thereof.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kinase promoter is used. In another embodiment a pyruvate:ferredoxin oxidoreductase promoter, an Rnf complex operon promoter or an ATP synthase operon promoter. In one particular embodiment, the promoter is from *C. autoethanogenum.*

The nucleic acids of the invention may remain extra-chromosomal upon transformation of a parental microorganism or may be adapted for intergration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

Methods of Producing Organisms

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:

b) introduction into a shuttle microorganism of (i) of an expression construct/vector as described herein and (ii) a methylation construct/vector comprising a methyltransferase gene;
c) expression of the methyltransferase gene;
d) isolation of one or more constructs/vectors from the shuttle microorganism; and,
e) introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli, Bacillus subtillis*, or *Lactococcus lactis.*

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of SEQ ID NO: 60 or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase is as described in the Examples herein after (for example the nucleic acid of SEQ ID NO: 63, or it is a functionally equivalent variant thereof).

Any number of constructs/vectors adapted to allow expression of a methyltransferase gene may be used to generate the methylation construct/vector. However, by way of example, the plasmid described in the Examples section hereinafter may be used.

Methods of Production

The invention provides a method for the production of one or more terpenes and/or precursors thereof, and optionally one or more other products, by microbial fermentation comprising fermenting a substrate comprising CO using a recombinant microorganism of the invention. Preferably, the one or more terpene and/or precursor thereof is the main fermentation product. The methods of the invention may be used to reduce the total atmospheric carbon emissions from an industrial process.

Preferably, the fermentation comprises the steps of anaerobically fermenting a substrate in a bioreactor to produce at least one or more terpenes and/or a precursor thereof using a recombinant microorganism of the invention.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

Instead of producing isoprene directly from terpenoid key intermediates IPP and DMAPP then using this to synthesise longer chain terpenes, it is also possible to synthesise longer chain terpenes, such as C10 Monoterpenoids or C15 Sesquiterpenoids, directly via a geranyltransferase (see Table 6). From C15 Sesquiterpenoid building block farnesyl-PP it is possible to produce farnesene, which, similarly to ethanol, can be used as a transportation fuel.

In one embodiment the method comprises the steps of:

(a) providing a substrate comprising CO to a bioreactor containing a culture of one or more microorganism of the invention; and (b) anaerobically fermenting the culture in the bioreactor to produce at least one or more terpene and/or precursor thereof.

In one embodiment the method comprises the steps of:

a) capturing CO-containing gas produced as a result of the industrial process;

b) anaerobic fermentation of the CO-containing gas to produce the at least one or more terpene and/or precursor thereof by a culture containing one or more microorganism of the invention.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing a terpene for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and CO-to-at least one or more terpene and/or precursor thereof to occur, in addition to the CO-containing substrate gas, a suitable liquid nutrient medium will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce a terpene and/or a precursor thereof using CO are known in the art. For example, suitable media are described Biebel (2001). In one embodiment of the invention the media is as described in the Examples section herein after.

The fermentation should desirably be carried out under appropriate conditions for the CO-to-the at least one or more terpene and/or precursor thereof fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of at least one or more terpene and/or precursor thereof. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO-to-at least one or more terpene and/or precursor thereof conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that one or more product is consumed by the culture.

The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Terpenes and/or precursors thereof, or a mixed stream containing one or more terpenes, precursors thereof and/or one or more other products, may be recovered from the fermentation broth by methods known in the art, such as fractional distillation or evaporation, pervaporation, gas stripping and extractive fermentation, including for example, liquid-liquid extraction.

In certain preferred embodiments of the invention, the one or more terpene and/or precursor thereof and one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

The invention will now be described in more detail with reference to the following non-limiting examples.

Example 1—Expression of Isoprene Synthase in *C. autoethanogenum* for Production of Isoprene from CO The inventors have identified terpene biosynthesis genes in carboxydotrophic acetogens such as *C. autoethanogenum* and *C. ljungdahlii*. A recombinant organism was engineered to produce isoprene. Isoprene is naturally emitted by some plant such as *poplar* to protect its leave from UV radiation. Isoprene synthase (EC 4.2.3.27) gene of *Poplar* was codon optimized and introduced into a carboxydotrophic acetogen *C. autoethanogenum* to produce isoprene from CO. The enzyme takes key intermediate DMAPP (Dimethylallyl diphosphate) of terpenoid biosynthesis to isoprene in an irreversible reaction (FIG. 1).

Strains and Growth Conditions:

All subcloning steps were performed in *E. coli* using standard strains and growth conditions as described earlier (Sambrook et al, Molecular Cloning: A laboratory Manual, Cold Spring Harbour Laboratory Press, Cold Spring Harbour, 1989; Ausubel et al, Current protocols in molecular biology, John Wiley & Sons, Ltd., Hoboken, 1987).

*C. autoethanogenum* DSM10061 and DSM23693 (a derivative of DSM10061) were obtained from DSMZ (The German Collection of Microorganisms and Cell Cultures, Inhoffenstraße 7 B, 38124 Braunschweig, Germany). Growth was carried out at 37° C. using strictly anaerobic conditions and techniques (Hungate, 1969, Methods in Microbiology, vol. 3B. Academic Press, New York: 117-132; Wolfe, 1971, *Adv. Microb. Physiol.,* 6: 107-146). Chemically defined PETC media without yeast extract (Table 1) and 30 psi carbon monoxide containing steel mill waste gas (collected from New Zealand Steel site in Glenbrook, NZ; composition: 44% CO, 32% $N_2$, 22% $CO_2$, 2% $H_2$) as sole carbon and energy source was used.

TABLE 1

| Media component | Concentration per 1.0 L of media |
|---|---|
| $NH_4Cl$ | 1 g |
| KCl | 0.1 g |
| $MgSO_4$•$7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Resazurin (2 g/L stock) | 0.5 ml |
| $NaHCO_3$ | 2 g |
| Reducing agent | 0.006-0.008% (v/v) |
| Distilled water | Up to 1 L, pH 5.5 (adjusted with HCl) |

TABLE 1-continued

| Wolfe's vitamin solution | per L of Stock |
|---|---|
| Biotin | 2 mg |
| Folic acid | 2 mg |
| Pyridoxine hydrochloride | 10 mg |
| Riboflavin | 5 mg |
| Nicotinic acid | 5 mg |
| Calcium D-(+)-pantothenate | 5 mg |
| Vitamin $B_{12}$ | 0.1 mg |
| p-Aminobenzoic acid | 5 mg |
| Lipoic acid | 5 mg |
| Thiamine | 5 mg |
| Distilled water | To 1 L |

| Trace metal solution | per L of stock |
|---|---|
| Nitrilotriacetic Acid | 2 g |
| $MnSO_4$•$H_2O$ | 1 g |
| Fe $(SO_4)_2(NH_4)_2$•$6H_2O$ | 0.8 g |
| $CoCl_2$•$6H_2O$ | 0.2 g |
| $ZnSO_4$•$7H_2O$ | 0.2 mg |
| $CuCl_2$•$2H_2O$ | 0.02 g |
| $NaMoO_4$•$2H_2O$ | 0.02 g |
| $Na_2SeO_3$ | 0.02 g |
| $NiCl_2$•$6H_2O$ | 0.02 g |
| $Na_2WO_4$•$2H_2O$ | 0.02 g |
| Distilled water | To 1 L |

| Reducing agent stock | per 100 mL of stock |
|---|---|
| NaOH | 0.9 g |
| Cystein•HCl | 4 g |
| $Na_2S$ | 4 g |
| Distilled water | To 100 mL |

Construction of Expression Plasmid:

Standard Recombinant DNA and molecular cloning techniques were used in this invention (Sambrook J, Fritsch E F, Maniatis T: Molecular Cloning: A laboratory Manual, Cold Spring Harbour Laboratory Press, Cold Spring Harbour, 1989; Ausubel F M, Brent R, Kingston R E, Moore D D, Seidman J G, Smith J A, Struhl K: Current protocols in molecular biology. John Wiley & Sons, Ltd., Hoboken, 1987). The isoprene synthase of *Poplar tremuloides* (AAQ16588.1; GI:33358229) was codon-optimized (SEQ ID NO: 21) and synthesized. A promoter region of the Pyruvate:ferredoxin oxidoreductase of *C. autoethanogenum* (SEQ ID NO: 22) was used to express the gene.

Genomic DNA from *Clostridium autoethanogenum* DSM23693 was isolated using a modified method by Bertram and Dürre (1989). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 μl lysozyme (~100,000 U) was added and the mixture was incubated at 37° C. for 30 min, followed by addition of 280 μl of a 10% (w/v) SDS solution and another incubation for 10 min. RNA was digested at room temperature by addition of 240 μl of an EDTA solution (0.5 M, pH 8), 20 μl Tris-HCl (1 M, pH 7.5), and 10 μl RNase A (Fermentas Life Sciences). Then, 100 μl Proteinase K (0.5

U) was added and proteolysis took place for 1-3 h at 37° C. Finally, 600 μl of sodium perchlorate (5 M) was added, followed by a phenol-chloroform extraction and an isopropanol precipitation. DNA quantity and quality was inspected spectrophotometrically. The Pyruvate:ferredoxin oxidoreductase promoter sequence was amplified by PCR using oligonucleotides Ppfor-NotI-F (SEQ ID NO: 23: AAGCGGCCGCAAAATAGTTGATAATAATGC) and Ppfor-NdeI-R (SEQ ID NO: 24: TACGCATATGAATTCCTCTCCTTTTCAAGC) using iProof High Fidelity DNA Polymerase (Bio-Rad Laboratories) and the following program: initial denaturation at 98° C. for 30 seconds, followed by 32 cycles of denaturation (98° C. for 10 seconds), annealing (50-62° C. for 30-120 seconds) and elongation (72° C. for 30-90 seconds), before a final extension step (72° C. for 10 minutes).

Figure 2:
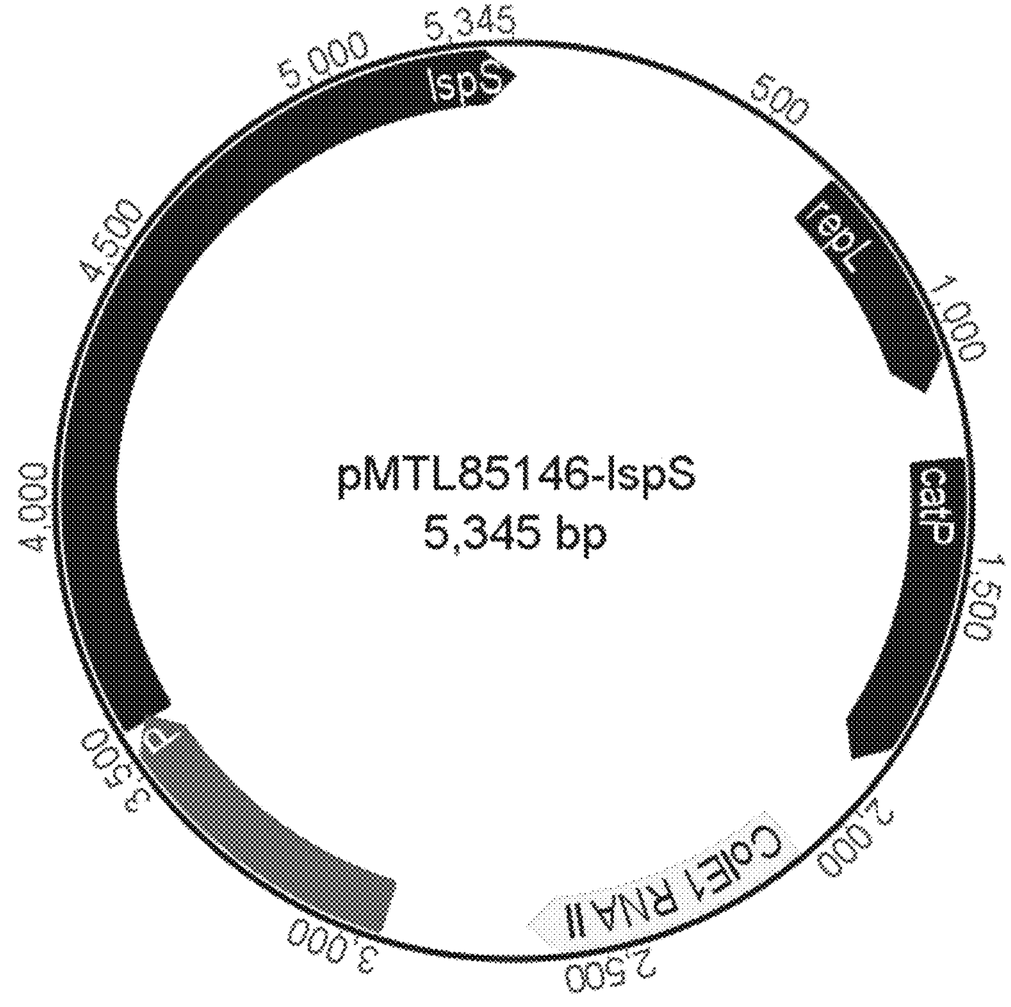
FIG. 2: Genetic map of plasmid pMTL 85146-ispS

Construction of Isoprene Synthase Expression Plasmid:

Construction of an expression plasmid was performed in *E. coli* DH5α-T1$^R$ (Invitrogen) and XL1-Blue MRF' Kan (Stratagene). In a first step, the amplified Ppfor promoter region was cloned into the *E. coli-Clostridium* shuttle vector pMTL85141 (FJ797651.1; Nigel Minton, University of Nottingham; Heap et al., 2009) using NotI and NdeI restriction sites, generating plasmid pMTL85146. As a second step, ispS was cloned into pMTL85146 using restriction sites NdeI and EcoRI, resulting in plasmid pMTL 85146-ispS (FIG. 2, SEQ ID NO: 25).

Transformation and Expression in *C. autoethanogenum*

Prior to transformation, DNA was methylated in vivo in *E. coli* using a synthesized hybrid Type II methyltransferase (SEQ ID NO: 63) co-expressed on a methylation plasmid (SEQ ID NO: 64) designed from methyltransferase genes from *C. autoethanogenum, C. ragsdalei* and *C. ljungdahlii* as described in US patent 2011/0236941.

Both expression plasmid and methylation plasmid were transformed into same cells of restriction negative *E. coli* XL1-Blue MRF' Kan (Stratagene), which is possible due to their compatible Gram-(−) origins of replication (high copy ColE1 in expression plasmid and low copy p15A in methylation plasmid). In vivo methylation was induced by addition of 1 mM IPTG, and methylated plasmids were isolated using QIAGEN Plasmid Midi Kit (QIAGEN). The resulting mixture was used for transformation experiments with *C. autoethanogenum* DSM23693, but only the abundant (high-copy) expression plasmid has a Gram-(+) replication origin (repL) allowing it to replicate in Clostridia.

Transformation into *C. autoethanogenum:*

During the complete transformation experiment, *C. autoethanogenum* DSM23693 was grown in PETC media (Table 1) supplemented with 1 g/L yeast extract and 10 g/l fructose as well as 30 psi steel mill waste gas (collected from New Zealand Steel site in Glenbrook, NZ; composition: 44% CO, 32% $N_2$, 22% $CO_2$, 2% $H_2$) as carbon source.

To make competent cells, a 50 ml culture of *C. autoethanogenum* DSM23693 was subcultured to fresh media for 3 consecutive days. These cells were used to inoculate 50 ml PETC media containing 40 mM DL-threonine at an $OD_{600nm}$ of 0.05. When the culture reached an $OD_{600nm}$ of 0.4, the cells were transferred into an anaerobic chamber and harvested at 4,700×g and 4° C. The culture was twice washed with ice-cold electroporation buffer (270 mM sucrose, 1 mM MgCl2, 7 mM sodium phosphate, pH 7.4) and finally suspended in a volume of 600 μl fresh electroporation buffer. This mixture was transferred into a pre-cooled electroporation cuvette with a 0.4 cm electrode gap containing 1 μg of the methylated plasmid mixture and immediately pulsed using the Gene pulser Xcell electroporation system (Bio-Rad) with the following settings: 2.5 kV, 600Ω, and 25 μF. Time constants of 3.7-4.0 ms were achieved. The culture was transferred into 5 ml fresh media. Regeneration of the cells was monitored at a wavelength of 600 nm using a Spectronic Helios Epsilon Spectrophotometer (Thermo) equipped with a tube holder. After an initial drop in biomass, the cells started growing again. Once the biomass has doubled from that point, the cells were harvested, suspended in 200 μl fresh media and plated on selective PETC plates (containing 1.2% Bacto™ Agar (BD)) with appropriate antibiotics 4 μg/ml Clarithromycin or 15 μg/ml thiamphenicol. After 4-5 days of inoculation with 30 psi steel mill gas at 37° C., colonies were visible.

The colonies were used to inoculate 2 ml PETC media with antibiotics. When growth occurred, the culture was scaled up into a volume of 5 ml and later 50 ml with 30 psi steel mill gas as sole carbon source.

Confirmation of the Successful Transformation:

To verify the DNA transfer, a plasmid mini prep was performed from 10 ml culture volume using Zyppy plasmid miniprep kit (Zymo). Since the quality of the isolated plasmid was not sufficient for a restriction digest due to Clostridial exonuclease activity [Burchhardt and Dürre, 1990], a PCR was performed with the isolated plasmid with oligonucleotide pairs colE1-F (SEQ ID NO: 65: CGTCAGACCCCGTAGAAA) plus colE1-R (SEQ ID NO: 66: CTCTCCTGTTCCGACCCT). PCR was carried out using iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes).

To confirm the identity of the clones, genomic DNA was isolated (see above) from 50 ml cultures of *C. autoethanogenum* DSM23693. A PCR was performed against the 16s rRNA gene using oligonucleotides fD1 (SEQ ID NO: 67: CCGAATTCGTCGACAACAGAGTTTGATCCTGGCTCAG) and rP2 (SEQ ID NO: 68: CCCGGGATCCAAGCTTACGGCTACCTTGTTACGACTT) [Weisberg et al., 1991] and iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes). Sequencing results were at least 99.9% identity against the 16s rRNA gene (rrsA) of *C. autoethanogenum* (Y18178, GI:7271109).

Expression of Isoprene Synthase Gene qRT-PCR experiments were performed to confirm successful expression of introduced isoprene synthase gene in *C. autoethanogenum.*

A culture harboring isoprene synthase plasmid pMTL 85146-ispS and a control culture without plasmid was grown in 50 mL serum bottles and PETC media (Table 1) with 30 psi steel mill waste gas (collected from New Zealand Steel site in Glenbrook, NZ; composition: 44% CO, 32% $N_2$, 22% $CO_2$, 2% $H_2$) as sole energy and carbon source. 0.8 mL samples were taken during logarithmic growth phase at an $OD_{600nm}$ of around 0.5 and mixed with 1.6 mL RNA protect reagent (Qiagen). The mixture was centrifuged (6,000×g, 5 min, 4° C.), and the cell sediment snap frozen in liquid nitrogen and stored at −80° C. until RNA extraction. Total RNA was isolated using RNeasy Mini Kit (Qiagen) according to protocol 5 of the manual. Disruption of the cells was carried out by passing the mixture through a syringe 10 times, and eluted in 50 µL of RNase/DNase-free water. After DNase I treatment using DNA-Free™ Kit (Ambion), the reverse transcription step was then carried out using Super-Script III Reverse Transcriptase Kit (Invitrogen, Carlsbad, Calif., USA). RNA was checked using an Agilent Bioanalyzer 2100 (Agilent Technologies, Santa Clara, Calif., USA), Qubit Fluorometer (Invitrogen, Carlsbad, Calif., USA) and by gel electrophoresis. A non-RT control was performed for every oligonucleotide pair. All qRT-PCR reactions were performed in duplicate using a MyiQ™ Single Colour Detection System (Bio-Rad Laboratories, Carlsbad, Calif., USA) in a total reaction volume of 15 µL with 25 ng of cDNA template, 67 nM of each oligonucleotide (Table 2), and 1×iQ™ SYBR® Green Supermix (Bio-Rad Laboratories, Carlsbad, Calif., USA). The reaction conditions were 95° C. for 3 min, followed by 40 cycles of 95° C. for 15 s, 55° C. for 15 s and 72° C. for 30 s. For detection of oligonucleotide dimerisation or other artifacts of amplification, a melting-curve analysis was performed immediately after completion of the qPCR (38 cycles of 58° C. to 95° C. at 1° C./s). Two housekeeping genes (guanylate kinase and formate tetrahydrofolate ligase) were included for each cDNA sample for normalization. Determination of relative gene expression was conducted using Relative Expression Software Tool (REST©) 2008 V2.0.7 (38). Dilution series of cDNA spanning 4 log units were used to generate standard curves and the resulting amplification efficiencies to calculate concentration of mRNA.

Figure 3:
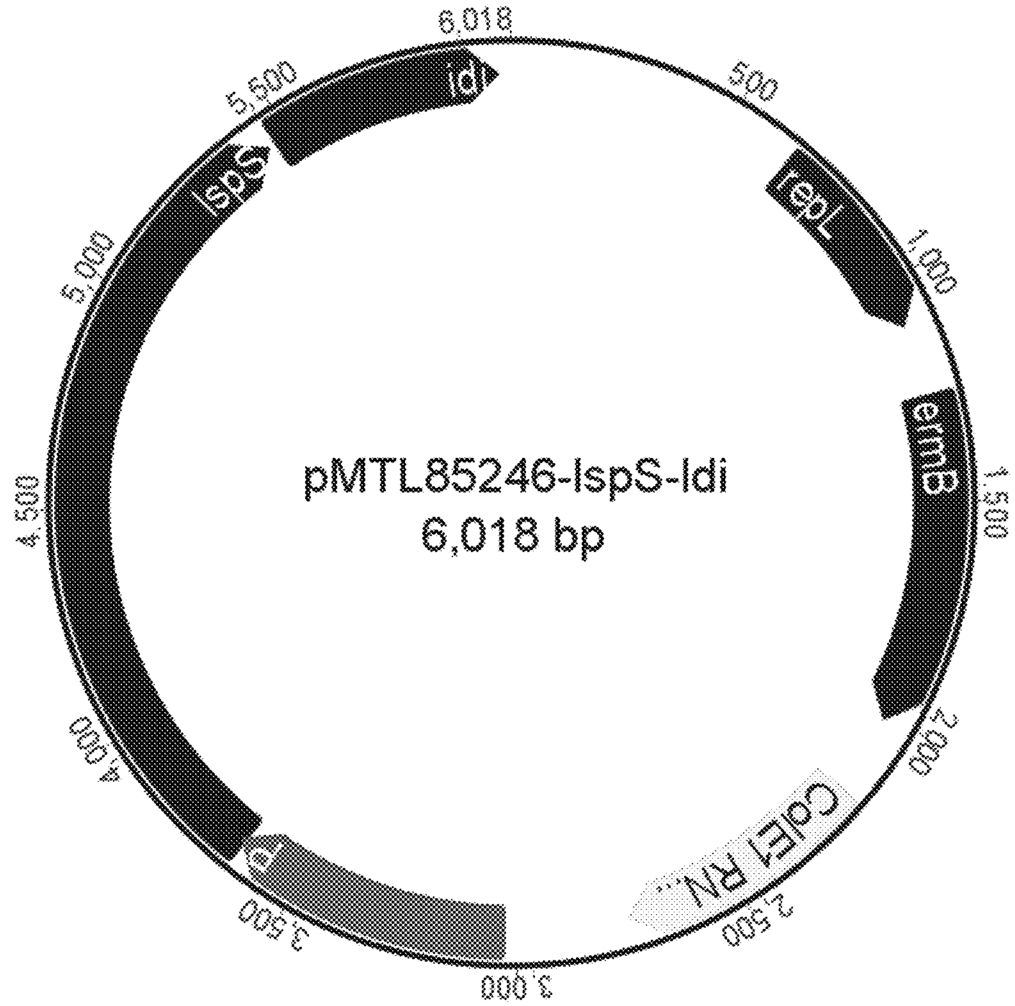
FIG. 3: Genetic map of plasmid pMTL 85246-ispS-idi

Construction of Isopentenyl-Diphosphate Delta-Isomerase Expression Plasmid:

An Isopentenyl-diphosphate delta-isomerase gene idi from *C. beijerinckii* (Gene ID:5294264), encoding an Isopentenyl-diphosphate delta-isomerase (YP_001310174.1), was cloned downstream of ispS. The gene was amplified using oligonucleotide Idi-Cbei-SacI-F (SEQ ID NO: 26: GTGAGCTCGAAAGGGGAAATTAAATG) and Idi-Cbei-KpnI-R (SEQ ID NO: 27: ATGGTACCCCAAATCTTTATTTAGACG) from genomic DNA of *C. beijerinckii* NCIMB8052, obtained using the same method as described above for *C. autoethanogenum*. The PCR product was cloned into vector pMTL 85146-ispS using SacI and KpnI restriction sites to yield plasmid pMTL85146-ispS-idi (SEQ ID NO: 28). The antibiotic resistance marker was exchanged from catP to ermB (released from vector pMTL82254 (FJ797646.1; Nigel Minton, University of Nottingham; Heap et al., 2009) using restriction enzymes PmeI and FseI to form plasmid pMTL85246-ispS-idi (FIG. 3).

Figure 8:
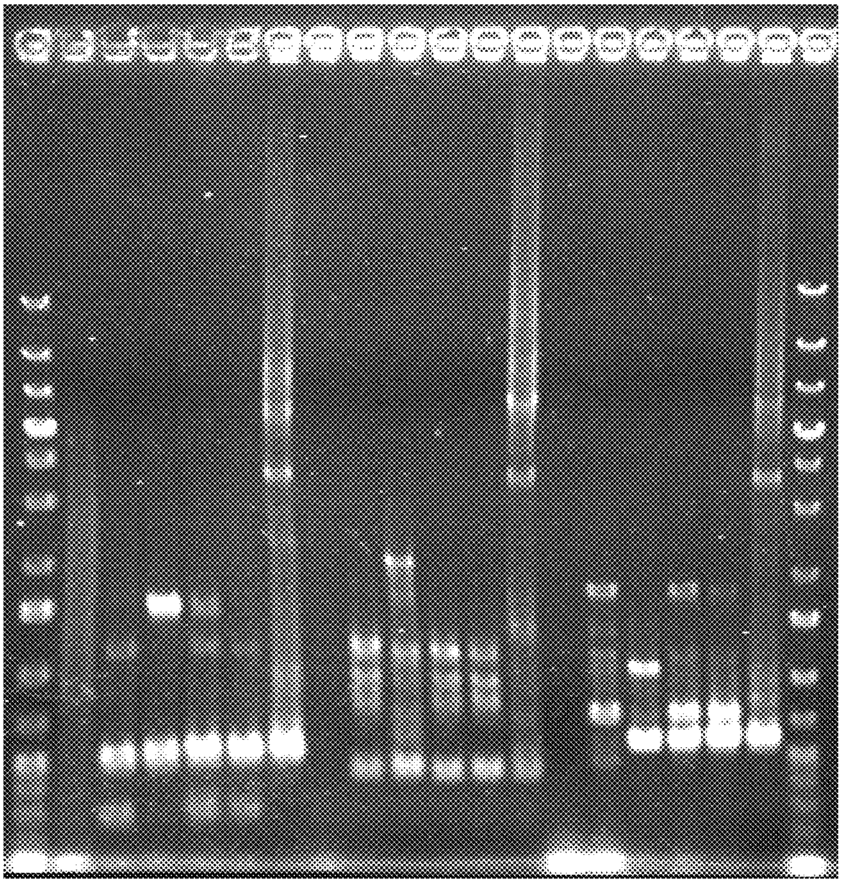
FIG. 8: Agarose gel electrophoresis image confirming presence of isoprene expression plasmid pMTL 85246-ispS-idi in *C. autoethanogenum* transformants. Lanes 1, and 20 show 100 bp Plus DNA Ladder. Lane 3-6, 9-12, 15-18 show PCR with isolated plasmids from 4 different clones as template, each in the following order: colE1, ermB, and idi. Lanes 2, 8, and 14 show PCR without template as negative control, each in the following order: colE1, ermB, and idi. Lanes 7, 13, and 19 show PCR with pMTL 85246-ispS-idi from *E. coli* as positive control, each in the following order: colE1, ermB, and idi.
Figure 9:
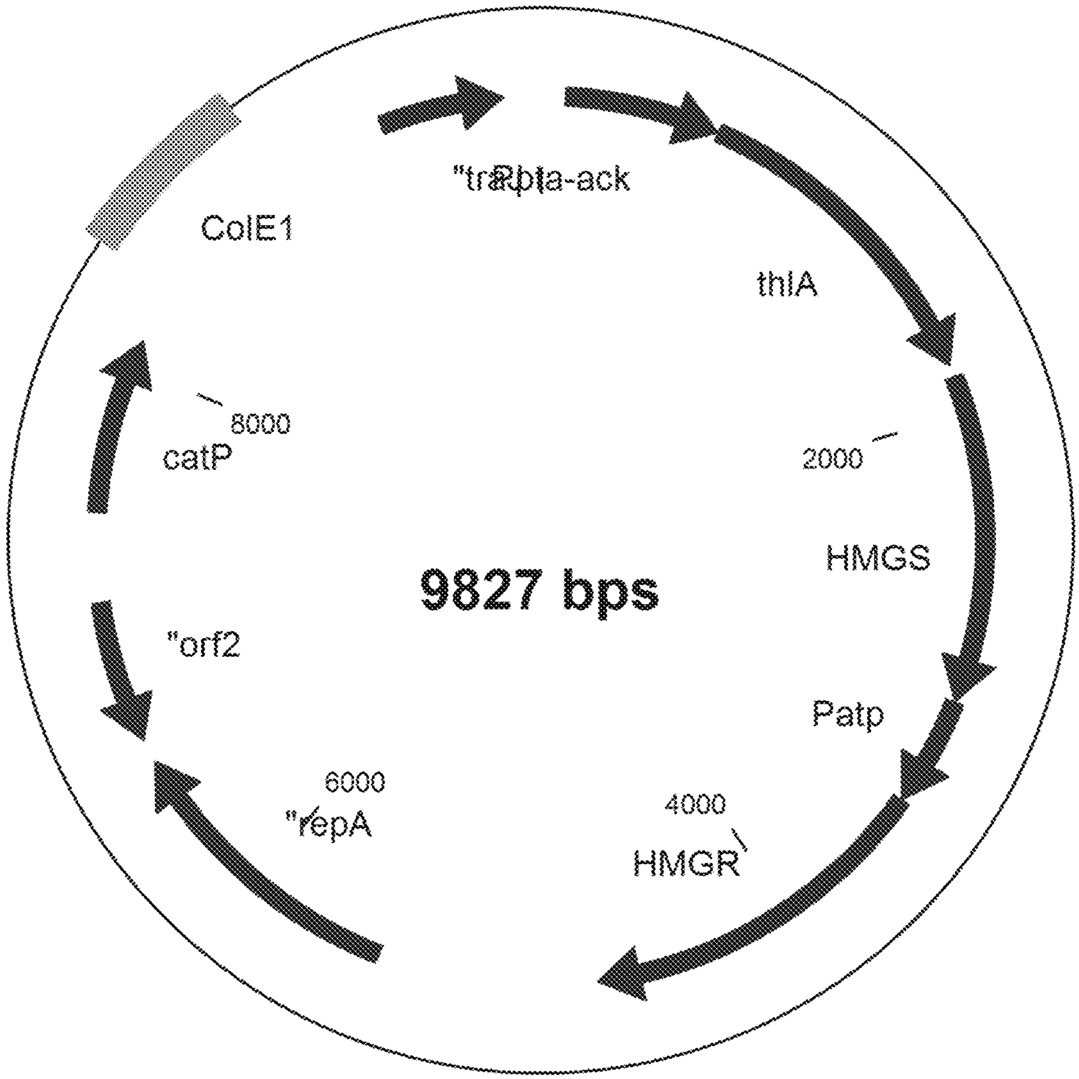
FIG. 9—Mevalonate expression plasmid pMTL8215-Pptaack-thlA-HMGS-Patp-HMGR

Transformation and expression in *C. autoethanogenum* was carried out as described for plasmid pMTL 85146-ispS. After successful transformation, growth experiment was carried out in 50 mL 50 mL serum bottles and PETC media (Table 1) with 30 psi steel mill waste gas (collected from New Zealand Steel site in Glenbrook, NZ; composition: 44% CO, 32% $N_2$, 22% $CO_2$, 2% $H_2$) as sole energy and carbon source. To confirm that the plasmid has been successfully introduced, plasmid mini prep DNA was carried out from transformants as described previously. PCR against the isolated plasmid using oligonucleotide pairs that target colE1 (colE1-F: SEQ ID NO: 65: CGTCAGACCCCGTAGAAA and colE1-R: SEQ ID NO: 66: CTCTCCTGTTCCGACCCT), ermB (ermB-F: SEQ ID NO: 106: TTTGTAATTAAGAAGGAG and ermB-R: SEQ ID NO: 107: GTAGAATCCTTCTTCAAC) and idi (Idi-Cbei-SacI-F: SEQ ID NO: 26: GTGAGCTCGAAAGGGGAAATTAAATG and Idi-Cbei-KpnI-R: SEQ ID NO: 27: ATGGTACCCCAAATCTTTATTTAGACG) confirmed transformation success (FIG. 8). Similarly, genomic DNA from these transformants were extracted, and the resulting 16s rRNA amplicon using oligonucleotides fD1 and rP2 (see above) confirmed 99.9% identity against the 16S rRNA gene of *C. autoethanogenum* (Y18178, GI:7271109).

Successful confirmation of gene expression was carried out as described above using a oligonucleotide pair against Isopentenyl-diphosphate delta-isomerase gene idi (idi-F, SEQ ID NO: 71: ATA CGT GCT GTA GTC ATC CAA GAT A and idiR, SEQ ID NO: 72: TCT TCA AGT TCA CAT GTA

TABLE 2

Oligonucleotides for qRT-PCR

| Target | Oligonucleotide Name | DNA Sequence (5' to 3') | SEQ ID NO: |
|---|---|---|---|
| Guanylate kinase (gnk) | GnK-F | TCAGGACCTTCTGGAACTGG | 108 |
| | GnK-R | ACCTCCCCTTTTCTTGGAGA | 109 |
| Formate tetrahydrofolate ligase (FoT4L) | FoT4L-F | CAGGTTTCGGTGCTGACCTA | 110 |
| | FoT4L-F | AACTCCGCCGTTGTATTTCA | 111 |
| Isoprene Synthase | ispS-F | AGG CTG AAT TTC TTA CAC TTC TTG A | 69 |
| | ispS-R | GTA ACT CCA TCA AAT CCT CCA CTA C | 70 |

While no amplification was observed with the wild-type strain using oligonucleotide pair ispS, a signal with the ispS oligonucleotide pair was measured for the strain carrying plasmid pMTL 85146-ispS, confirming successful expression of the ispS gene.

Example 2—Expression of Isopentenyl-Diphosphate Delta-Isomerase to Convert Between Key Terpene Precursors DMAPP (Dimethylallyl Diphosphate) and IPP (Isopentenyl Diphosphate)

Availability and balance of precursors DMAPP (Dimethylallyl diphosphate) and IPP (Isopentenyl diphosphate) is crucial for production of terpenes. While the DXS pathway synthesizes both IPP and DMAPP equally, in the mevalonate pathway the only product is IPP. Production of isoprene requires only the precursor DMAPP to be present in conjunction with an isoprene synthase, while for production of higher terpenes and terpenoids, it is required to have equal amounts of IPP and DMAPP available to produce Geranyl-PP by a geranyltransferase.

Figure 14:
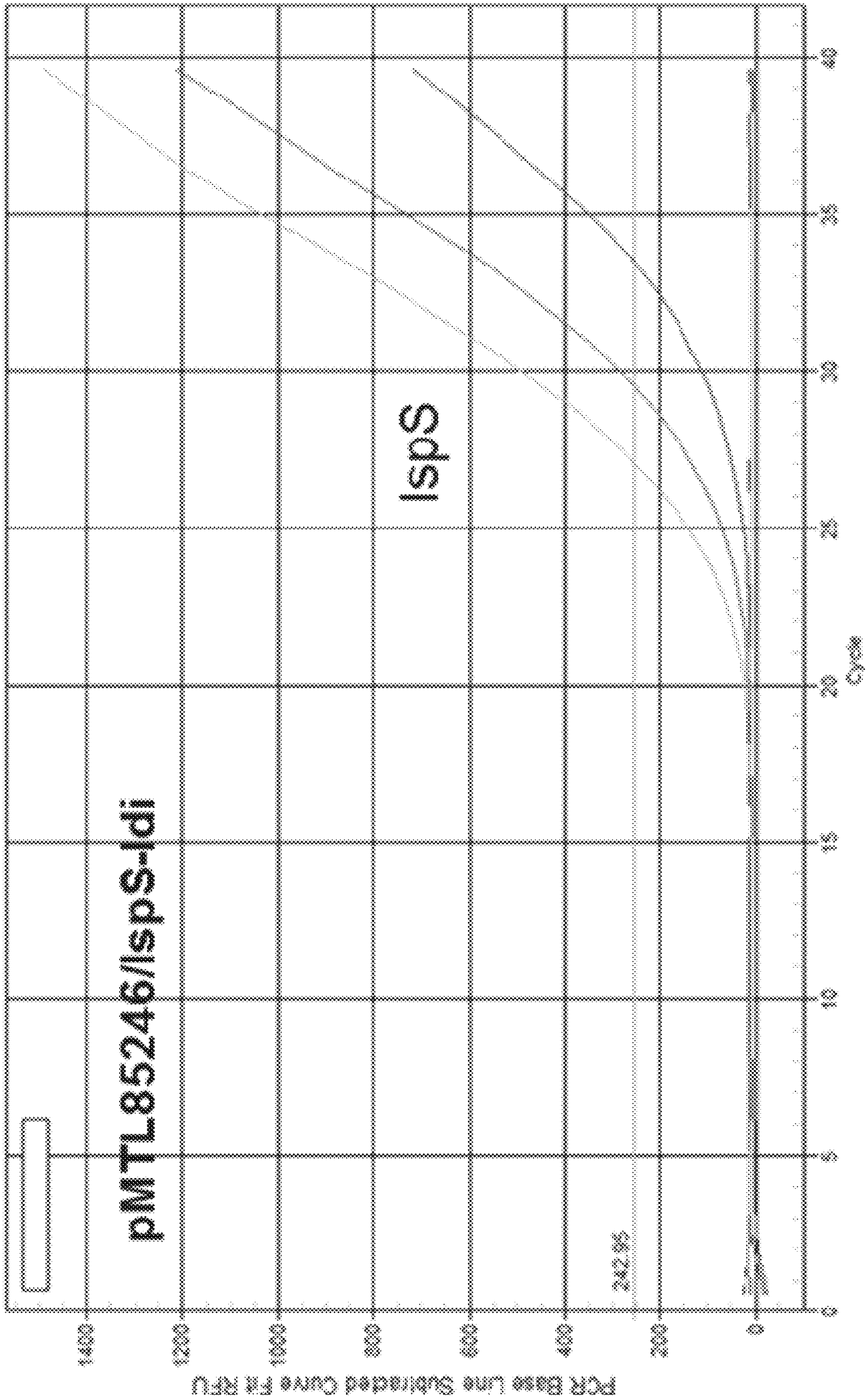

AAA CCC A) and a sample from a serum bottle growth experiment with *C. autoethanogenum* carrying plasmid pMTL 85146-ispS-idi. A signal for the isoprene synthase gene ispS was also observed (FIG. 14).

Example 3—Overexpression of DXS Pathway

To improve flow through the DXS pathway, genes of the pathway were overexpressed. The initial step of the pathway, converting pyruvate and D-glyceraldehyde-3-phosphate (G3P) into deoxyxylulose 5-phosphate (DXP/DXPS/DOXP), is catalyzed by an deoxyxylulose 5-phosphate synthase (DXS).

Figure 4:
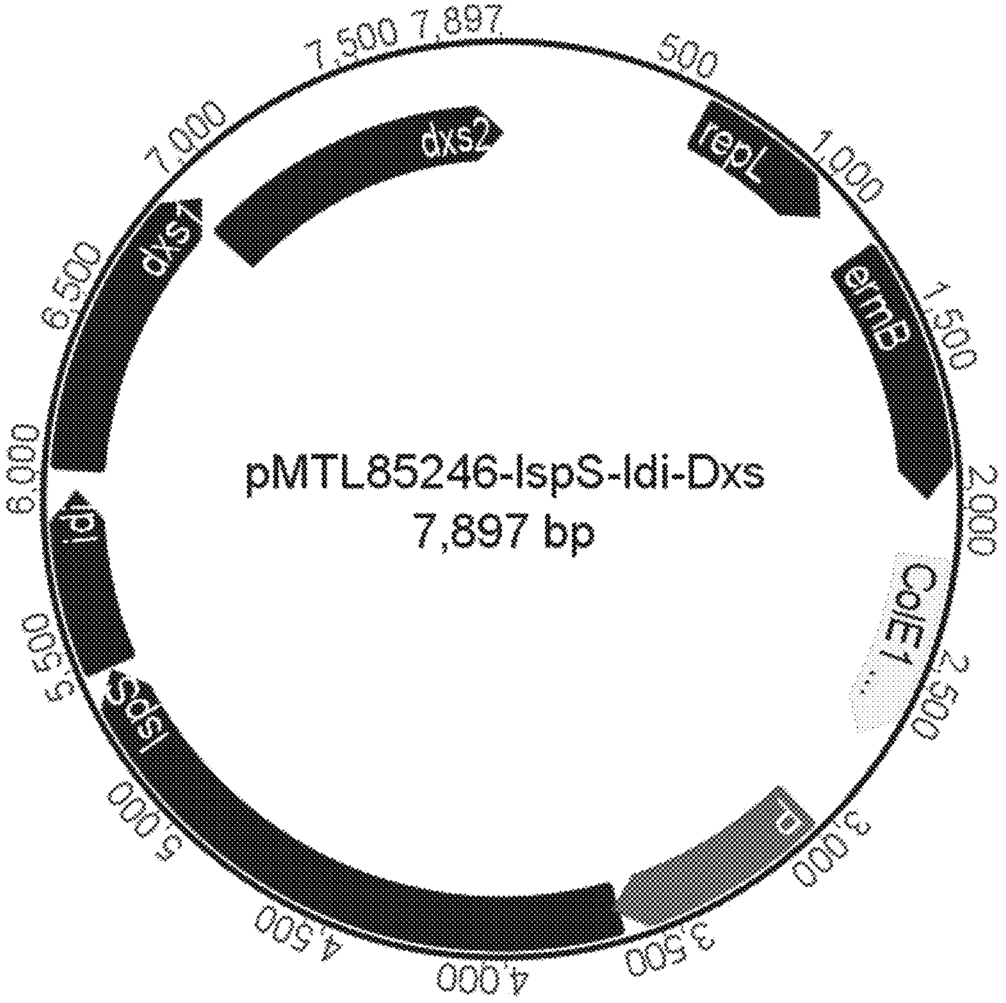
FIG. 4: Genetic map of plasmid pMTL 85246-ispS-idi-dxs
Figure 5:
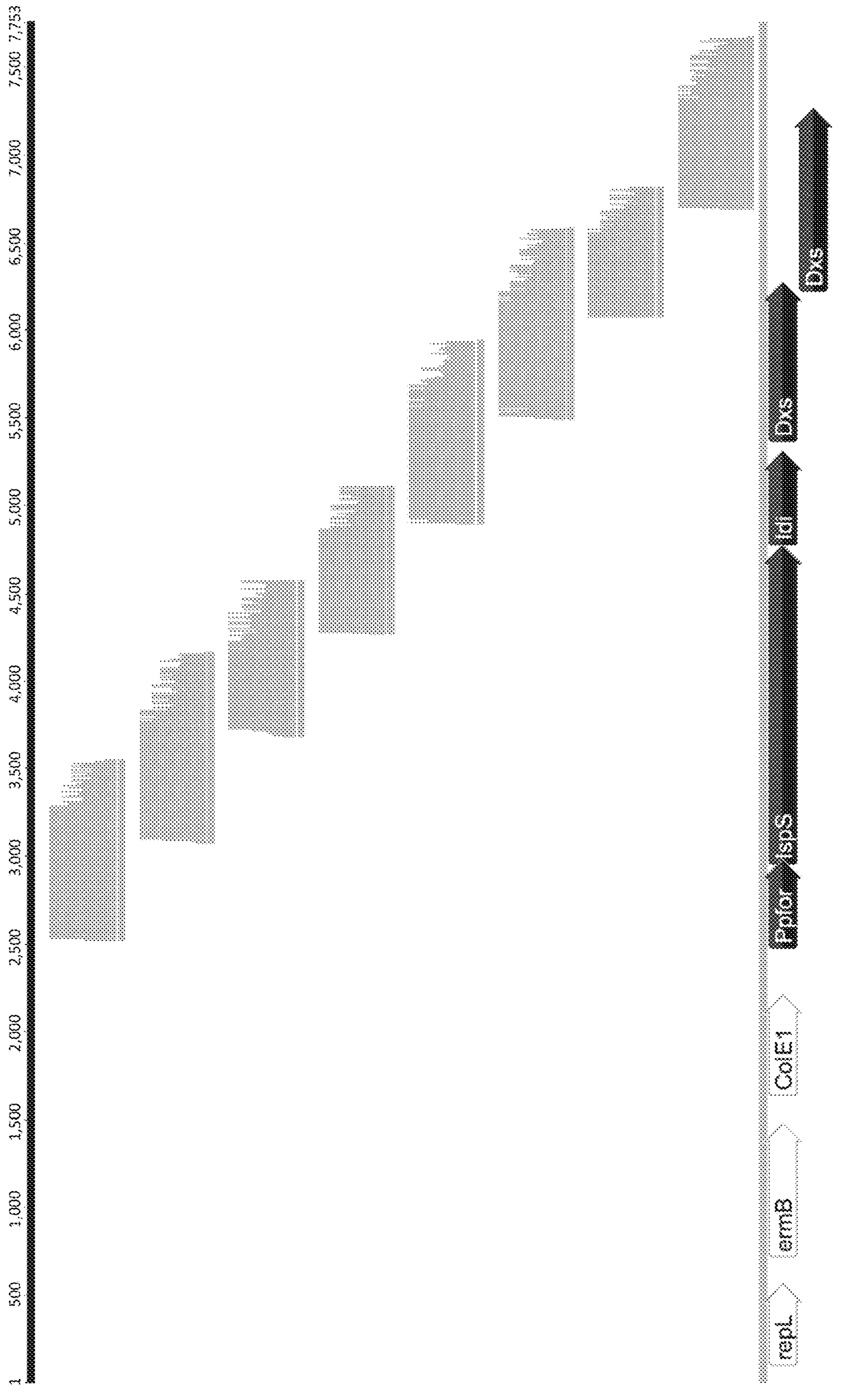
FIG. 5: Sequencing results for plasmid pMTL 85246-ispS-idi-dxs

Construction of DXS Overexpression Expression Plasmid:

The dxs gene of *C. autoethanogenum* was amplified from genomic DNA with oligonucleotides Dxs-SalI-F (SEQ ID NO: 29: GCAGTCGACTTTATTAAAGGGATAGATAA) and Dxs-XhoI-R (SEQ ID NO: 30: TGCTCGAGTTAAAATATATGACTTACCTCTG) as described for other genes above. The amplified gene was then cloned into plasmid pMTL85246-ispS-idi with SalI and XhoI to produce plasmid pMTL85246-ispS-idi-dxs (SEQ ID NO: 31 and FIG. 4). DNA sequencing using oligonucleotides given in Table 3 confirmed successful cloning of ispS, idi, and dxs without mutations (FIG. 5). The ispS and idi genes are as described in example 1 and 2 respectively.

TABLE 3

| Oligonucleotides for sequencing | | |
|---|---|---|
| Oligonucleotide Name | DNA Sequence (5' to 3') | SEQ ID NO: |
| M13R | CAGGAAACAGCTATGAC | 32 |
| Isoprene-seq1 | GTTATTCAAGCTACACCTTT | 33 |
| Isoprene-seq2 | GATTGGTAAAGAATTAGCTG | 34 |
| Isoprene-seq3 | TCAAGAAGCTAAGTGGCT | 35 |
| Isoprene-seq4 | CTCACCGTAAAGGAACA | 36 |
| Isoprene-seq5 | GCTAGCTAGAGAAATTAGAA | 37 |
| Isoprene-seq6 | GGAATGGCAAAATATCTTGA | 38 |
| Isoprene-seq7 | GAAACACATCAGGGAATATT | 39 |

Transformation and Expression in *C. autoethanogenum*

Figure 15:
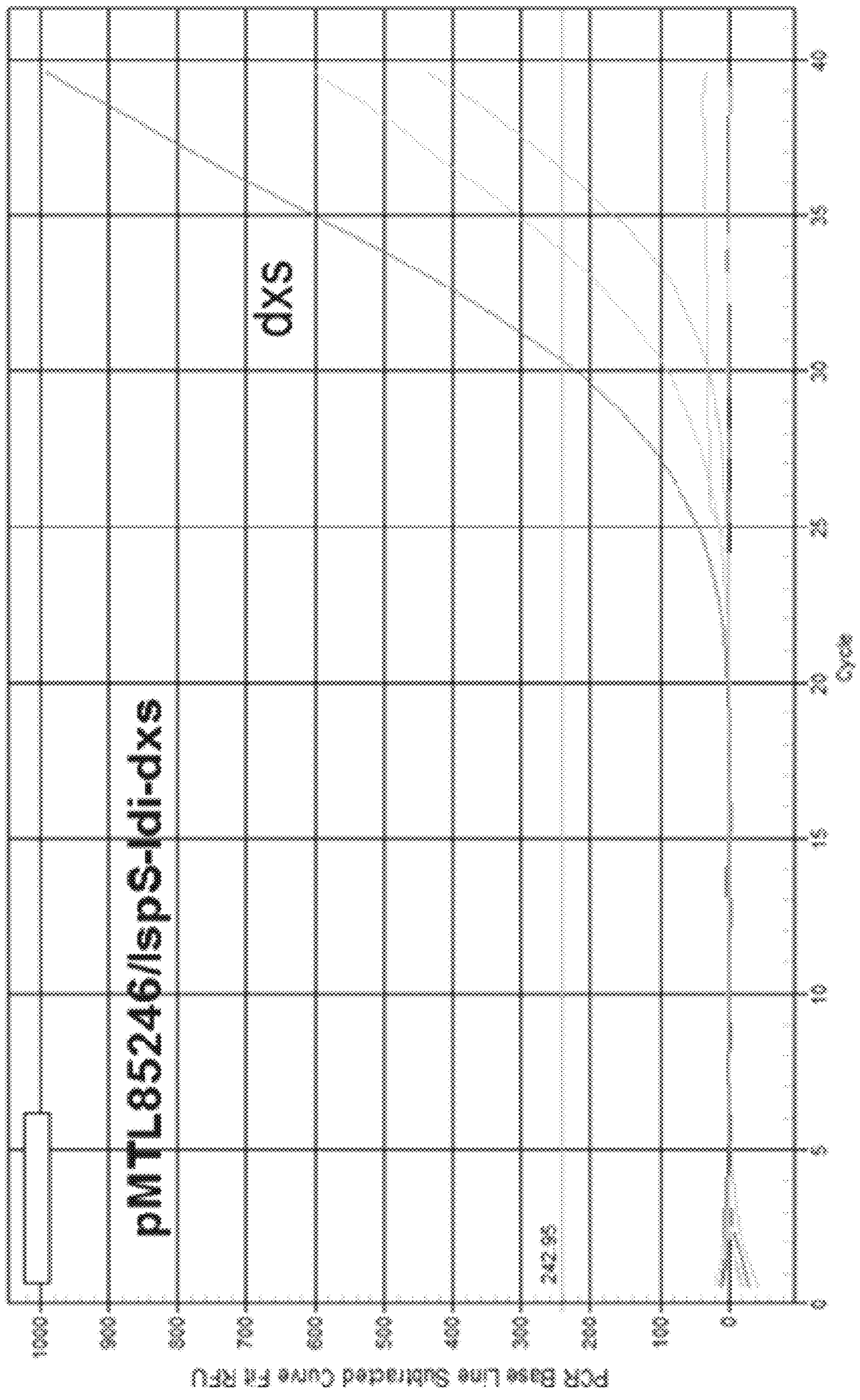

Transformation and expression in *C. autoethanogenum* was carried out as described for plasmid pMTL 85146-ispS. After successful transformation, a growth experiment was carried out in 50 mL 50 mL serum bottles and PETC media (Table 1) with 30 psi steel mill waste gas (collected from New Zealand Steel site in Glenbrook, NZ; composition: 44% CO, 32% $N_2$, 22% $CO_2$, 2% $H_2$) as sole energy and carbon source. Confirmation of gene expression was carried out as described above from a sample collected at $OD_{600nm}$=0.75. Oligonucleotide pair dxs-F (SEQ ID NO: 73: ACAAAGTATCTAAGACAGGAGGTCA) and dxs-R (SEQ ID NO: 74: GATGTCCCACATCCCATATAAGTTT) was used to measure expression of gene dxs in both wild-type strain and strain carrying plasmid pMTL 85146-ispS-idi-dxs. mRNA levels in the strain carrying the plasmid were found to be over 3 times increased compared to the wild-type (FIG. 15). Biomass was normalized before RNA extraction.

Example 4—Introduction and Expression of Mevalonate Pathway

Figure 7:
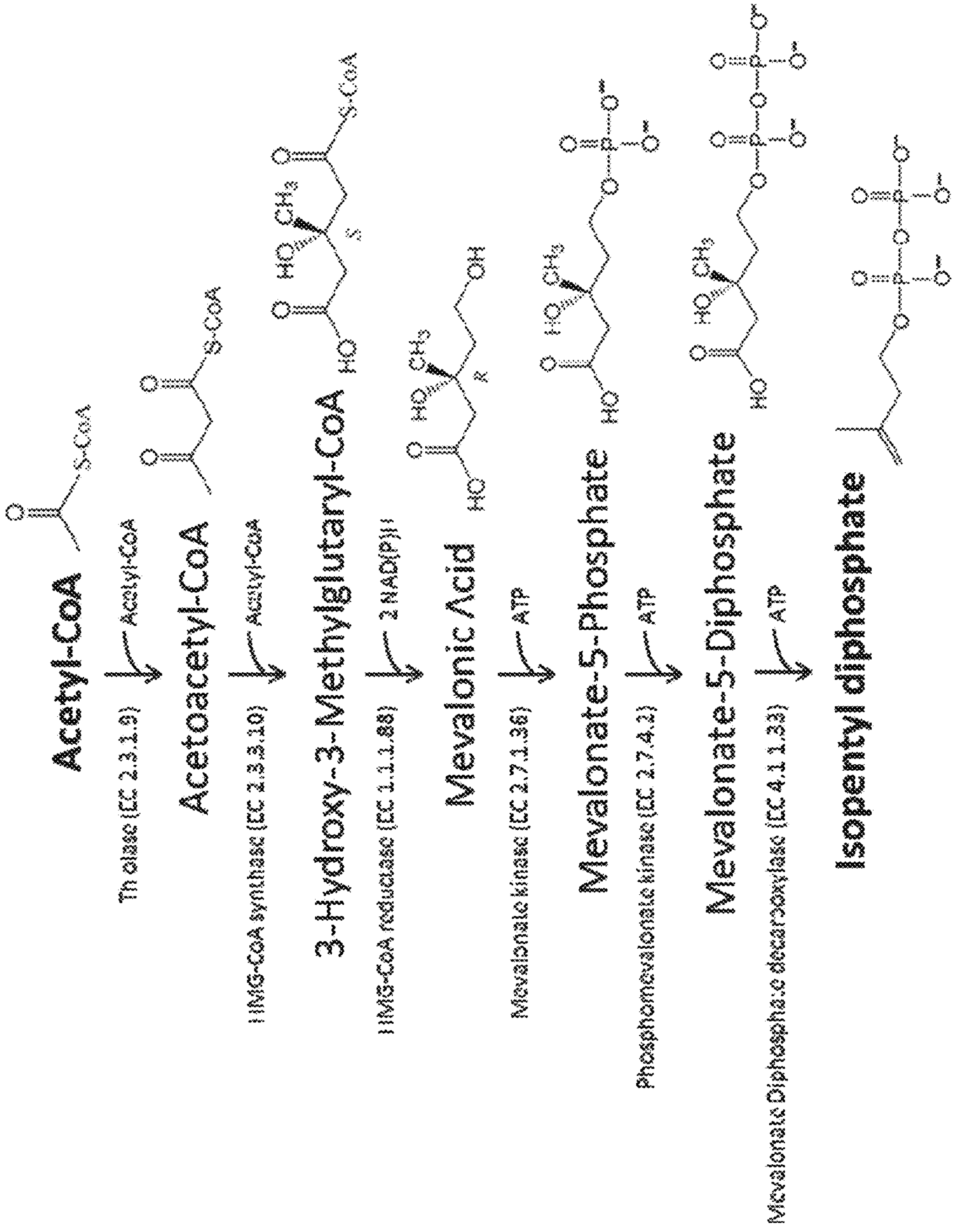
FIG. 7: Mevalonate pathway

The first step of the mevalonate pathway (FIG. 7) is catalyzed by a thiolase that converts two molecules of acetyl-CoA into acetoacetyl-CoA (and HS-CoA). This enzyme has been successfully expressed in carboxydotrophic acetogens *Clostridium autoethanogenum* and *C. ljungdahlii* by the same inventors (US patent 2011/0236941). Constructs for the remaining genes of the mevalonate pathway have been designed.

Construction of Mevalonate Expression Plasmid:

Standard recombinant DNA and molecular cloning techniques were used (Sambrook, J., and Russell, D., Molecular cloning: A Laboratory Manual 3rd Ed., Cold Spring Harbour Lab Press, Cold Spring Harbour, N Y, 2001). The three genes required for mevalonate synthesis via the upper part of the mevalonate pathway, i.e., thiolase (thlA/vraB), HMG-CoA synthase (HMGS) and HMG-CoA reductase (HMGR), were codon-optimised as an operon ($P_{ptaack}$-thlA/vraB-HMGS-$P_{atp}$-HMGR).

The Phosphotransacetylase/Acetate kinase operon promoter ($P_{pta-ack}$) of *C. autoethanogenum* (SEQ ID NO: 61) was used for expression of the thiolase and HMG-CoA synthase while a promoter region of the ATP synthase ($P_{atp}$) of *C. autoethanogenum* was used for expression of the HMG-CoA reductase. Two variants of thiolase, thlA from *Clostridium acetobutylicum* and vraB from *Staphylococcus aureus*, were synthesised and flanked by NdeI and EcoRI restriction sites for further sub-cloning. Both HMG-CoA synthase (HMGS) and HMG-CoA reductase (HMGR) were synthesised from *Staphylococcus aureus* and flanked by EcoRI-SacI and KpnI-XbaI restriction sites respectively for further sub-cloning. All optimized DNA sequences used are given in Table 4.

TABLE 4

| Sequences of mevalonate expression plasmid | | |
|---|---|---|
| Description | Source | SEQ NO: |
| Thiolase (thlA) | *Clostridium Acetobutylicum* ATCC 824; NC_003030.1; GI: 1119056 | 40 |
| Acetyl-CoA c-acetyltransferase (vraB) | *Staphylococcus aureus* subsp. *aureus* Mu50; NC_002758.2; region: 652965 . . . 654104; including GI: 15923566 | 41 |
| 3-hydroxy-3-methylglutaryl-CoA synthase (HMGS) | *Staphylococcus aureus* subsp. *aureus* Mu50; NC_002758.2; region: 2689180 . . . 2690346; including GI: 15925536 | 42 |

TABLE 4-continued

Sequences of mevalonate expression plasmid

| Description | Source | SEQ NO: |
|---|---|---|
| Hydroxymethylglutaryl-CoA reductase (HMGR) | *Staphylococcus aureus* subsp. *aureus* Mu50; NC_002758.2; region: complement(2687648 . . . 2688925); including GI: 15925535 | 43 |
| Phosphotransacetylase-acetate kinase operon ($P_{pta-ack}$) | *Clostridium autoethanogenum* DSM10061 | 44 |
| ATP synthase promoter ($P_{atp}$) | *Clostridium autoethanogenum* DSM10061 | 45 |

The ATP synthase promoter ($P_{atp}$) together with the hydroxymethylglutaryl-CoA reductase (HMGR) was amplified using oligonucleotides pUC57-F (SEQ ID NO: 46: AGCAGATTGTACTGAGAGTGC) and pUC57-R (SEQ ID NO: 47: ACAGCTATGACCATGATTACG) and pUC57-Patp-HMGR as a template. The 2033 bp amplified fragment was digested with SacI and XbaI and ligated into the *E. coli-Clostridium* shuttle vector pMTL 82151 (FJ7976; Nigel Minton, University of Nottingham, UK; Heap et al., 2009, *J Microbiol Methods.* 78: 79-85) resulting in plasmid pMTL 82151-Patp-HMGR (SEQ ID NO: 76).

3-hydroxy-3-methylglutaryl-CoA synthase (HMGS) was amplified from the codon-synthesised plasmid pGH-seq3.2 using oligonucleotides EcoRI-HMGS_F (SEQ ID NO: 77: AGCCGTGAATTCGAGGCTTTTACTAAAAACA) and EcoRI-HMGS_R (SEQ ID NO: 78: AGGCGTCTAGATGTTCGTCTCTACAAATAATT). The 1391 bp amplified fragment was digested with SacI and EcoRI and ligated into the previously created plasmid pMTL 82151-Patp-HMGR to give pMTL 82151-HMGS-Patp-HMGR (SEQ ID NO: 79). The created plasmid pMTL 82151-HMGS-Patp-HMGR (SEQ ID NO: 79) and the 1768 bp codon-optimised operon of $P_{ptaack}$-thlA/vraB were both cut with NotI and EcoRI. A ligation was performed and subsequently transformed into *E. coli* XL1-Blue MRF' Kan resulting in plasmid pMTL8215-$P_{ptaack}$-thlA/vraB-HMGS-$P_{atp}$-HMGR (SEQ ID NO: 50).

The five genes required for synthesis of terpenoid key intermediates from mevalonate via the bottom part of the mevalonate pathway, i.e., mevalonate kinase (MK), phosphomevalonate kinase (PMK), mevalonate diphosphate decarboxylase (PMD), isopentenyl-diphosphate delta-isomerase (idi) and isoprene synthase (ispS) were codon-optimised by ATG: Biosynthetics GmbH (Merzhausen, Germany). Mevalonate kinase (MK), phosphomevalonate kinase (PMK) and mevalonate diphosphate decarboxylase (PMD) were obtained from *Staphylococcus aureus*.

The promoter region of the RNF Complex ($P_{rnf}$) of *C. autoethanogenum* (SEQ ID NO: 62) was used for expression of mevalonate kinase (MK), phosphomevalonate kinase (PMK) and mevalonate diphosphate decarboxylase (PMD), while the promoter region of the Pyruvate:ferredoxin oxidoreductase ($P_{for}$) of *C. autoethanogenum* (SEQ ID NO: 22) was used for expression of isopentenyl-diphosphate delta-isomerase (idi) and isoprene synthase (ispS). All DNA sequences used are given in Table 5. The codon-optimised Prnf-MK was amplified from the synthesised plasmid pGH-Prnf-MK-PMK-PMD with oligonucleotides NotI-XbaI-Prnf-MK_F (SEQ ID NO: 80: ATGCGCGGCCGCTAGGTCTAGAATATCGATACAGATAAAAAAATATATAATACA G) and SalI-Prnf-MK_R (SEQ ID NO: 81: TGGTTCTGTAACAGCGTATTCACCTGC). The amplified gene was then cloned into plasmid pMTL83145 (SEQ ID NO: 49) with NotI and SalI to produce plasmid pMTL8314-Prnf-MK (SEQ ID NO: 82). This resulting plasmid and the 2165 bp codon optimised fragment PMK-PMD was subsequently digested with SalI and HindIII. A ligation was performed resulting in plasmid pMTL 8314-Prnf-MK-PMK-PMD (SEQ ID NO: 83).

Figure 10:
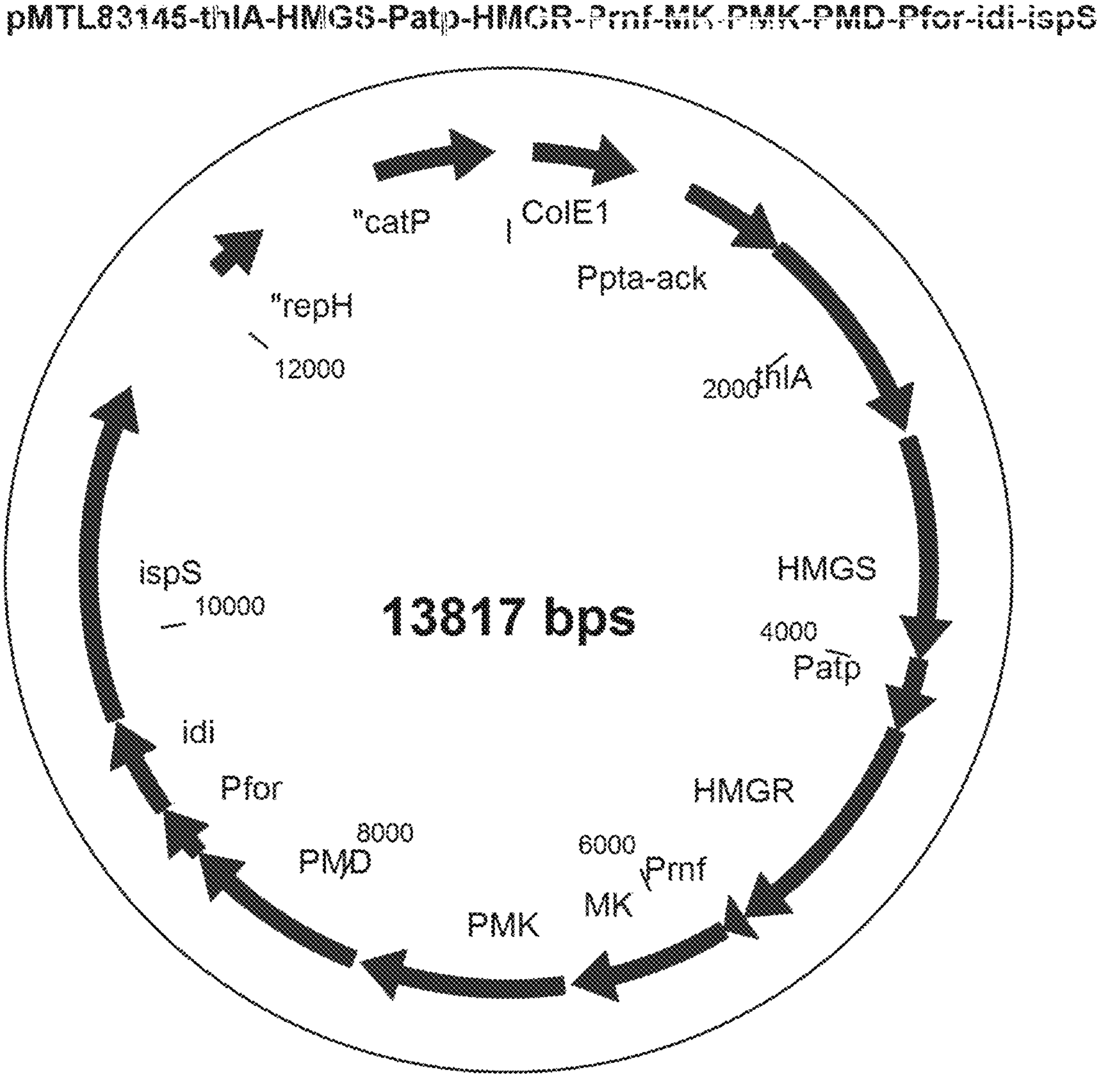
FIG. 10—Isoprene expression plasmid pMTL 8314-Pptaack-thlA-HMGS-Patp-HMGR-Prnf-MK-PMK-PMD-Pfor-idi-ispS FIG. 11—Farnesene expression plasmid pMTL8314-Pptaack-thlA-HMGS-Patp-HMGR-Prnf-MK-PMK-PMD-Pfor-idi-ispA-FS FIG. 12—Genetic map of plasmid pMTL 85246-ispS-idi-dxs FIG. 13—Amplification chart for gene expression experiment with *C. autoethanogenum* carrying plasmid pMTL 85146-ispS FIG. 14—Amplification chart for gene expression experiment with *C. autoethanogenum* carrying plasmid pMTL 85246-ispS-idi FIG. 15—Amplification chart for gene expression experiment with *C. autoethanogenum* carrying plasmid pMTL 85246-ispS-idi-dxs FIG. 16—PCR check for the presence of the plasmid pMTL8314Prnf-MK-PMK-PMD-Pfor-idi-ispA-FS.
Expected band size 1584 bp. The DNA marker Fermentas 1 kb DNA ladder.
Figure 11:
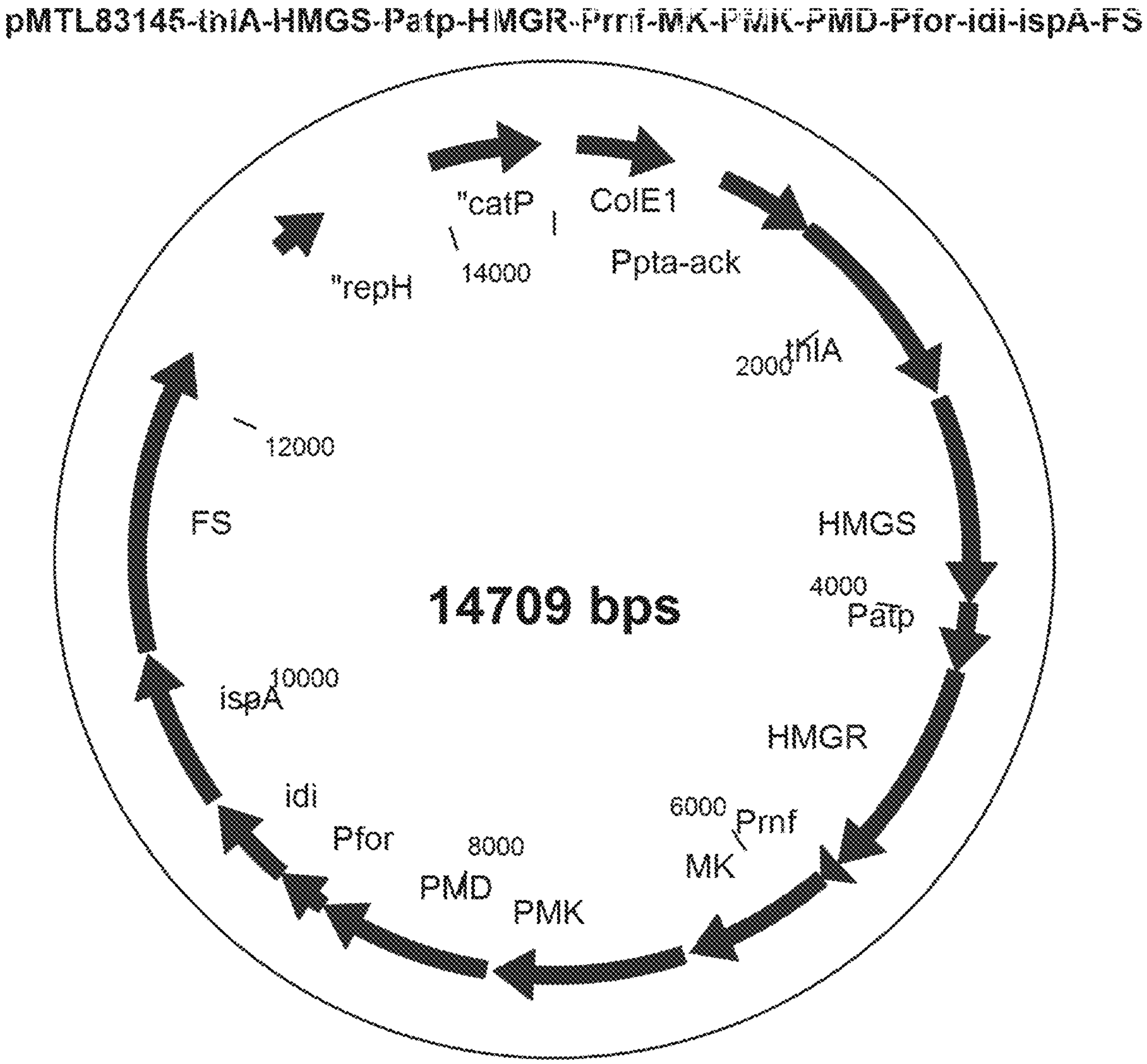
Figure 12:
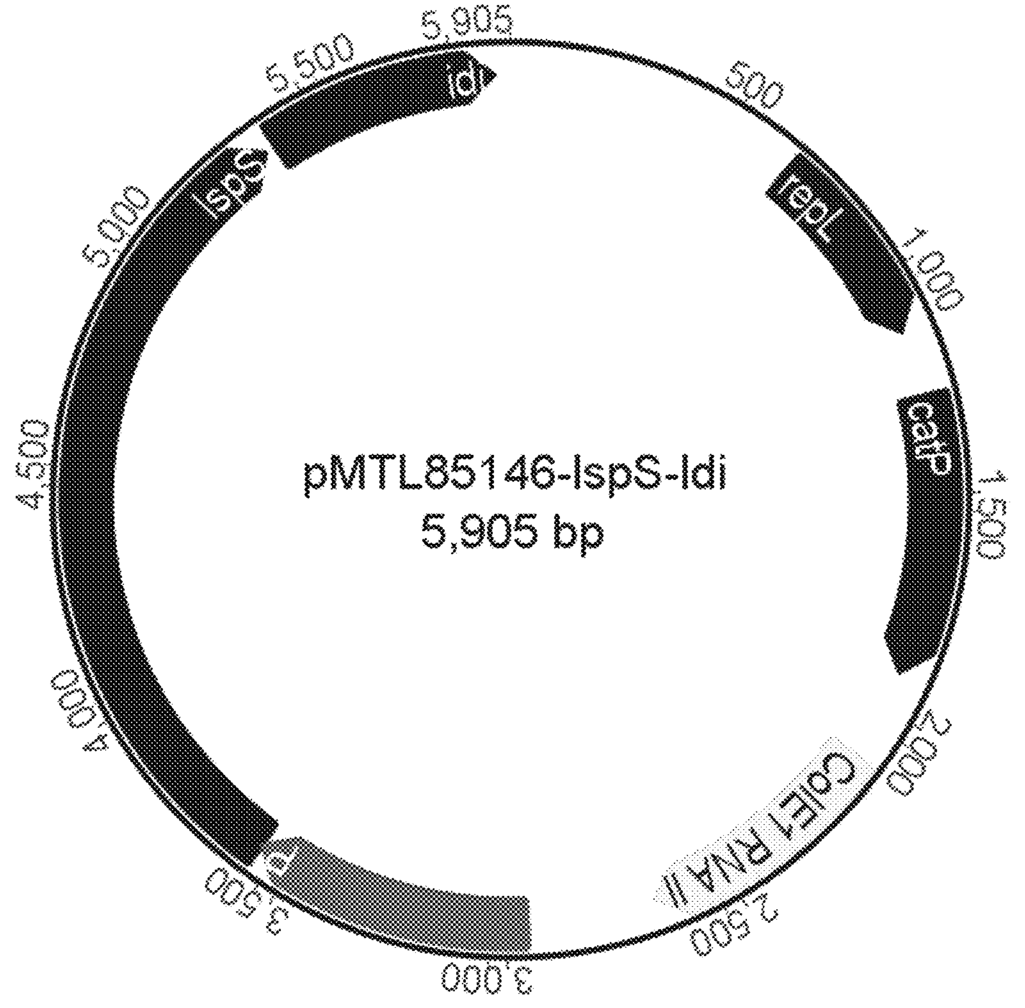
Figure 13:
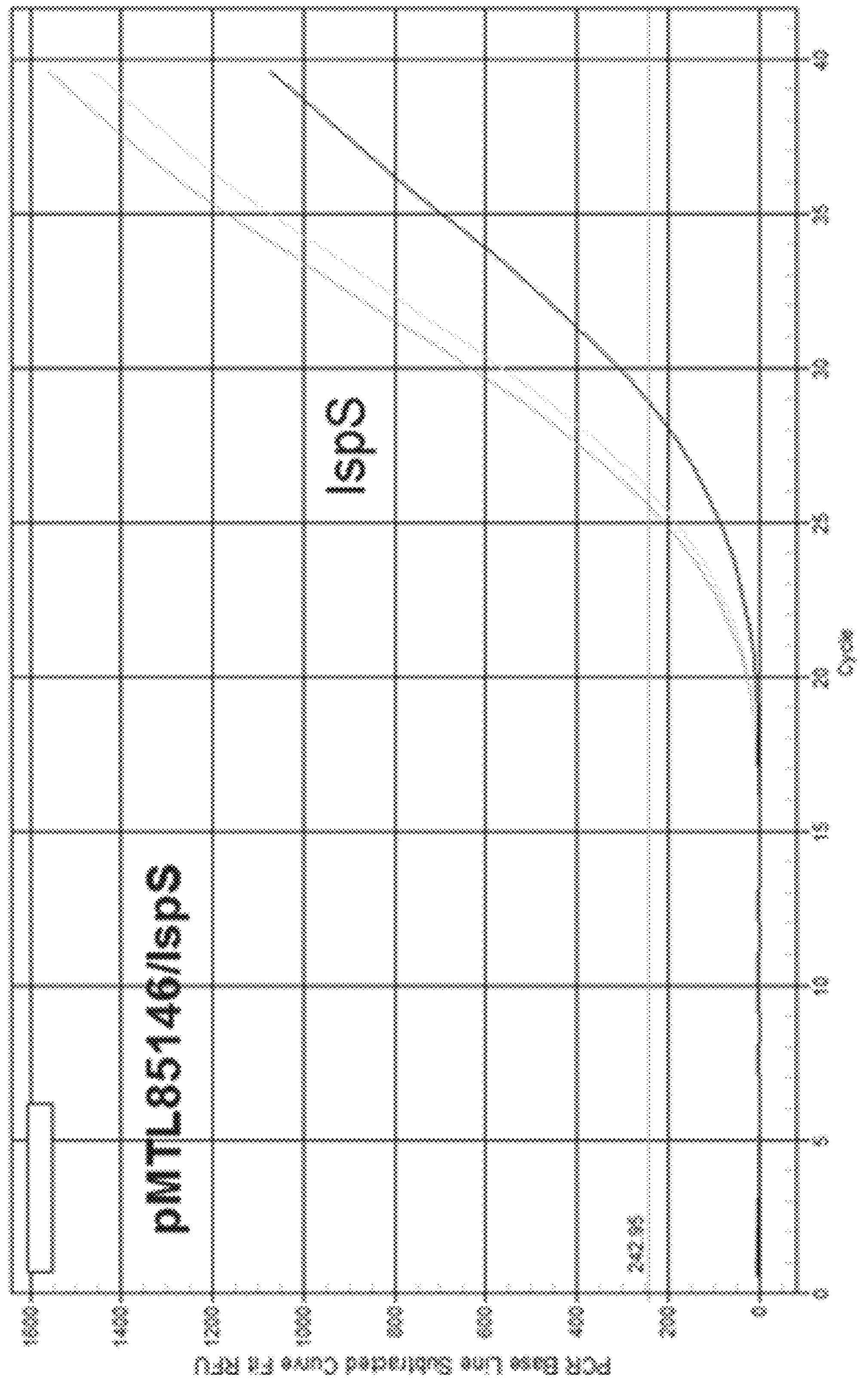

The isoprene expression plasmid without the mevalonate pathway was created by ligating the isoprene synthase (ispS) flanked by restriction sites AgeI and NheI to the previously created farnesene plasmid, pMTL 8314-Prnf-MK-PMK-PMD-Pfor-idi-ispA-FS (SEQ ID NO:91) to result in plasmid pMTL8314-Prnf-MK-PMK-PMD-Pfor-idi-ispS (SEQ ID NO:84). The final isoprene expression plasmid, pMTL 8314-Pptaack-thlA-HMGS-Patp-HMGR-Prnf-MK-PMK-PMD-Pfor-idi-ispS (SEQ ID NO: 58, FIG. 10) is created by ligating the 4630 bp fragment of Pptaack-thlA-HMGS-Patp-HMGR from pMTL8215-Pptaack-thlA-HMGS-Patp-HMGR (SEQ ID NO: 50) with pMTL 8314-Prnf-MK-PMK-PMD-Pfor-idi-ispS (SEQ ID NO: 84) using restriction sites NotI and XbaI.

TABLE 5

Sequences of isoprene expression plasmid from mevalonate pathway

| Description | Source | SEQ ID NO: |
|---|---|---|
| Mevalonate kinase (MK) | *Staphylococcus aureus* subsp. *aureus* Mu50; NC_002758.2; region: 665080 . . . 665919; including GI: 15923580 | 51 |
| Phosphomevalonate kinase (PMK) | *Staphylococcus aureus* subsp. *aureus* Mu50; NC_002758.2; region: 666920 . . . 667996; including GI: 15923582 | 52 |
| Mevalonate diphosphate decarboxylase (PMD) | *Staphylococcus aureus* subsp. *aureus* Mu50; NC_002758.2; region: 665924 . . . 666907; including GI: 15923581 | 53 |

TABLE 5-continued

| Sequences of isoprene expression plasmid from mevalonate pathway | | |
|---|---|---|
| Description | Source | SEQ ID NO: |
| Isoprene synthase (isIS) | isoprene synthase of *Poplar tremuloides* (AAQ16588.1; GI: 33358229) | 21 |
| Isopentenyl-diphosphate delta-isomerase (idi) | *Clostridium beijerinckii* NCIMB 8052; YP_001310174.1; region: complement(3597793 . . . 3598308); including GI: 150017920 | 54 |
| RNF Complex promoter ($P_{rnf}$) | *Clostridium autoethanogenum* DSM10061 | 55 |

Example 5—Introduction of Farnesene Synthase in *C. autoethanogenum* for Production of Farnesene from CO Via the Mevalonate Pathway Instead of producing isoprene directly from terpenoid key intermediates IPP and DMAPP then using this to synthesise longer chain terpenes, it is also possible to synthesise longer chain terpenes, such as C10 Monoterpenoids or C15 Sesquiterpenoids, directly via a geranyltransferase (see Table 6). From C15 Sesquiterpenoid building block farnesyl-PP it is possible to produce farnesene, which, similarly to ethanol, can be used as a transportation fuel.

Construction of Farnesene Expression Plasmid

The two genes required for farnesene synthesis from IPP and DMAPP via the mevalonate pathway, i.e., geranyltranstransferase (ispA) and alpha-farnesene synthase (FS) were codon-optimised. Geranyltranstransferase (ispA) was obtained from *Escherichia coli* str. K-12 substr. MG1655 and alpha-farnesene synthase (FS) was obtained from *Malus×domestica*. All DNA sequences used are given in Table 6. The codon-optimised idi was amplified from the synthesised plasmid pMTL83245-Pfor-FS-idi (SEQ ID NO: 85) with via the mevalonate pathways idi_F (SEQ ID NO: 86: AGGCACTCGAGATGGCAGAGTATATAATAGCAGTAG) and idi_R2 (SEQ ID NO:87: AGGCGCAAGCTTGGCGCACCGGTTTATT-TAAATATCTTATTTTCAGC). The amplified gene was then cloned into plasmid pMTL83245-Pfor with XhoI and HindIII to produce plasmid pMTL83245-Pfor-idi (SEQ ID NO: 88). This resulting plasmid and the 1754 bp codon optimised fragment of farnesene synthase (FS) was subsequently digested with HindIII and NheI. A ligation was performed resulting in plasmid pMTL83245-Pfor-idi-FS (SEQ ID NO: 89). The 946 bp fragment of ispA and pMTL83245-Pfor-idi-FS was subsequently digested with AgeI and HindIII and ligated to create the resulting plasmid pMTL83245-Pfor-idi-ispA-FS (SEQ ID NO: 90). The farnesene expression plasmid without the upper mevalonate pathway was created by ligating the 2516 bp fragment of Pfor-idi-ispA-FS from pMTL83245-Pfor-idi-ispA-FS to pMTL 8314-Prnf-MK-PMK-PMD to result in plasmid pMTL 8314-Prnf-MK-PMK-PMD-Pfor-idi-ispA-FS (SEQ ID NO: 91). The final farnesene expression plasmid pMTL83145-thlA-HMGS-Patp-HMGR-Prnf-MK-PMK-PMD-Pfor-idi-ispA-FS (SEQ ID NO: 59 and FIG. 18) is created by ligating the 4630 bp fragment of Pptaack-thlA-HMGS-Patp-HMGR from pMTL8215-Pptaack-thlA-HMGS-Patp-HMGR (SEQ ID NO: 50) with pMTL 8314-Prnf-MK-PMK-PMD-Pfor-idi-ispA-FS (SEQ ID NO: 91) using restriction sites NotI and XbaI.

TABLE 6

| Sequences of farnesene expression plasmid from mevalonate pathway | | |
|---|---|---|
| Description | Source | SEQ ID NO: |
| Geranyltranstransferase (ispA) | *Escherichia coli* str. K-12 substr. MG1655; NC_000913.2; region: complement(439426 . . . 440325); including GI: 16128406 | 56 |
| Alpha-farnesene synthase (FS) | *Malus × domestica*; AY787633.1; GI: 60418690 | 57 |

Transformation into *C. autoethanogenum*

Transformation and expression in *C. autoethanogenum* was carried out as described in example 1.

Confirmation of Successful Transformation

Figure 16:
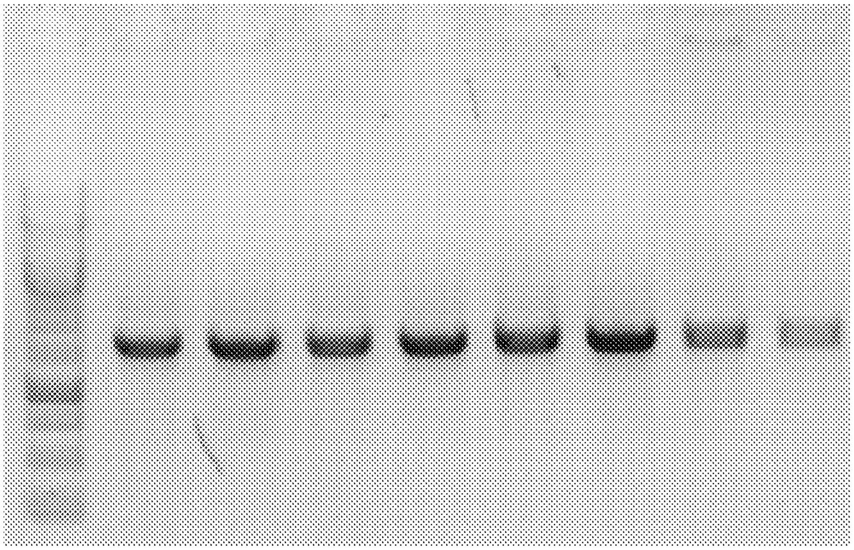

The presence of pMTL8314-Prnf-MK-PMK-PMD-Pfor-idi-ispA-FS (SEQ ID NO: 59) was confirmed by colony PCR using oligonucleotides repHF (SEQ ID NO: 92: AAGAAGGGCGTATATGAAAACTTGT) andcatR (SEQ ID NO: 93: TTCGTTTACAAAACGGCAAATGTGA) which selectively amplifies a portion of the garm +ve perplicon and most of the cat gene on the pMTL831xxx series plasmids. Yielding a band of 1584 bp (FIG. 16).

Expression of Lower Mevalonate Pathway in *C. autoethanogenum*

Confirmation of expression of the lower mevalonate pathway genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi; SEQ ID NO: 54), Geranyltranstransferase (ispA; SEQ ID NO: 56) and Farnesene synthase (FS SEQ ID NO: 57) was done as described above in example 1. Using oligonucleotides listed in table 7.

TABLE 7

List of oligonucleotides used for the detection of expression of the genes in the lower mevalonate pathway carried on plasmid pMTL8314Prnf-MK-PMK-PMD-Pfor-idi-ispA-FS (SEQ ID NO: 91)

| Target | Oligonucleotide Name | DNA Sequence (5' to 3') | SEQ ID NO: |
|---|---|---|---|
| Mevalonate kinase | MK-RTPCR-F | GTGCTGGTAGAGGTGGTTCA | 94 |
| | MK-RTPCR-R | CCAAGTATGTGCTGCACCAG | 95 |
| Phosphomevalonate Kinase | PMK-RTPCR-F | ATATCAGACCCACACGCAGC | 96 |
| | PMK-RTPCR-R | AATGCTTCATTGCTATGTCACATG | 97 |
| Mevalonate Diphosphate Decarboxylase | PMD-RTPCR-F | GCAGAAGCAAAGGCAGCAAT | 98 |
| | PMD-RTPCR-R | TTGATCCAAGATTTGTAGCATGC | 99 |
| Isopentyl-diphosphate Delta-isomerase | idi-RTPCR-F | GGACAAACACTTGTTGTAGTCACC | 100 |
| | idi-RTPCR-R | TCAAGTTCGCAAGTAAATCCCA | 101 |
| Geranyltranstransferase | ispA-RTPCR-F | ACCAGCAATGGATGACGATG | 102 |
| | ispA-RTPCR-R | AGTTTGTAAAGCGTCACCTGC | 103 |
| Farnesene synthase | FS-RTPCR-F | AAGCTAGTAGATGGTGGGCT | 104 |
| | FS-RTPCR-R | AATGCTACACCTACTGCGCA | 105 |

Figure 18:
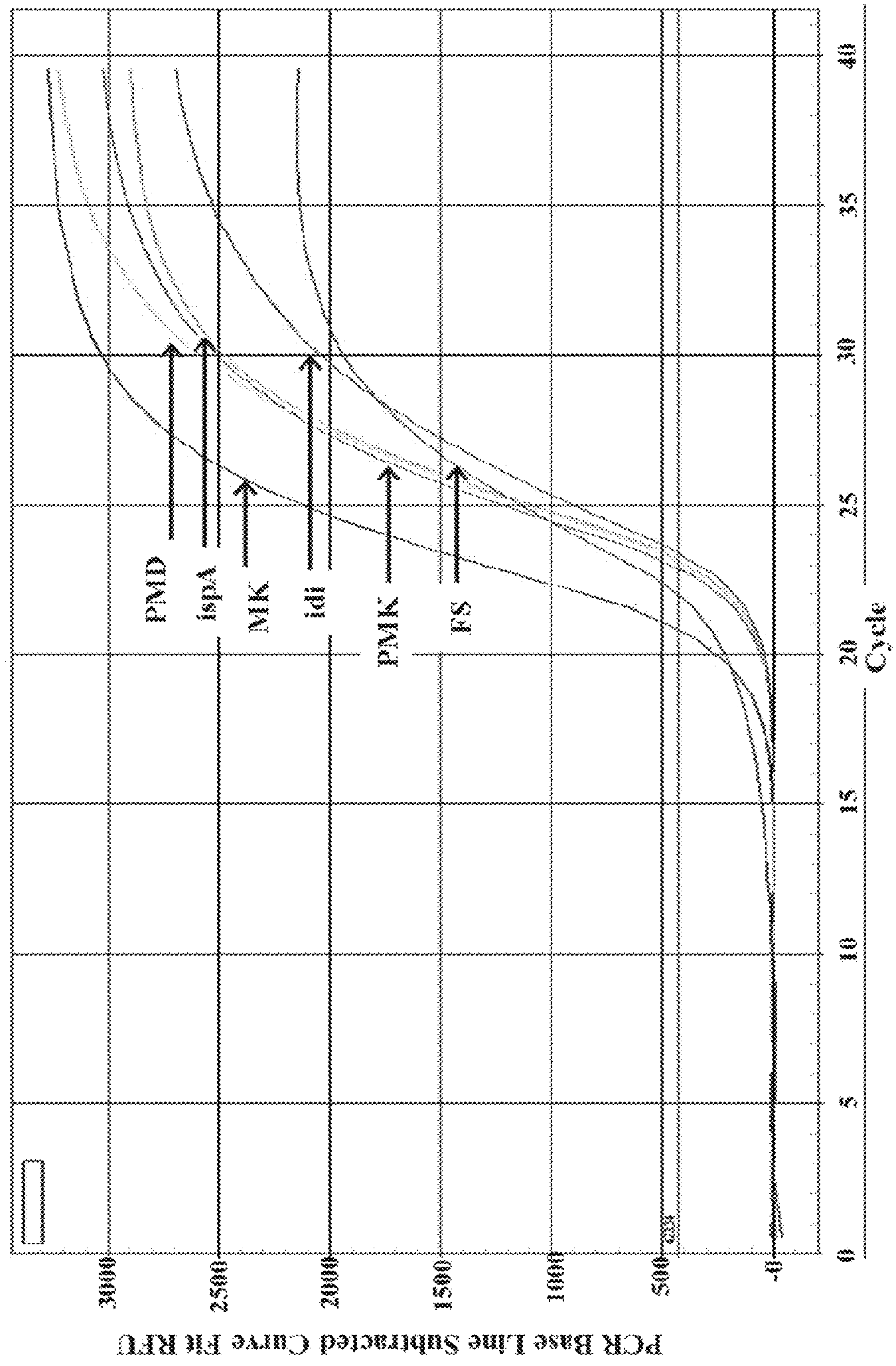

Rt-PCR data confirming expression of all genes in the lower mevalonate pathway is shown in FIG. 18, this data is also summarised in Table 8.

TABLE 8

Avarage CT values for the genes genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi SEQ ID NO: 54), Geranyltranstransferase (ispA SEQ ID NO: 56) and Farnesene synthase (FS SEQ ID NO: 57). for two independent samples taken from the two starter cultures for the mevalonate feeding experiment (see below).

| Gene | Sample 1 (Ct Mean) | Sample 2 (Ct Mean) |
|---|---|---|
| MK | 21.9 | 20.82 |
| PMK | 23.64 | 22.81 |
| PMD | 24 | 22.83 |
| Idi | 24.23 | 27.54 |
| ispA | 23.92 | 23.22 |
| FS | 21.28 (single Ct) | 21.95 (single Ct) |
| HK (rho) | 31.5 | 28.88 |

Production of Alpha-Farnesene from Mevalonate

Figure 17:
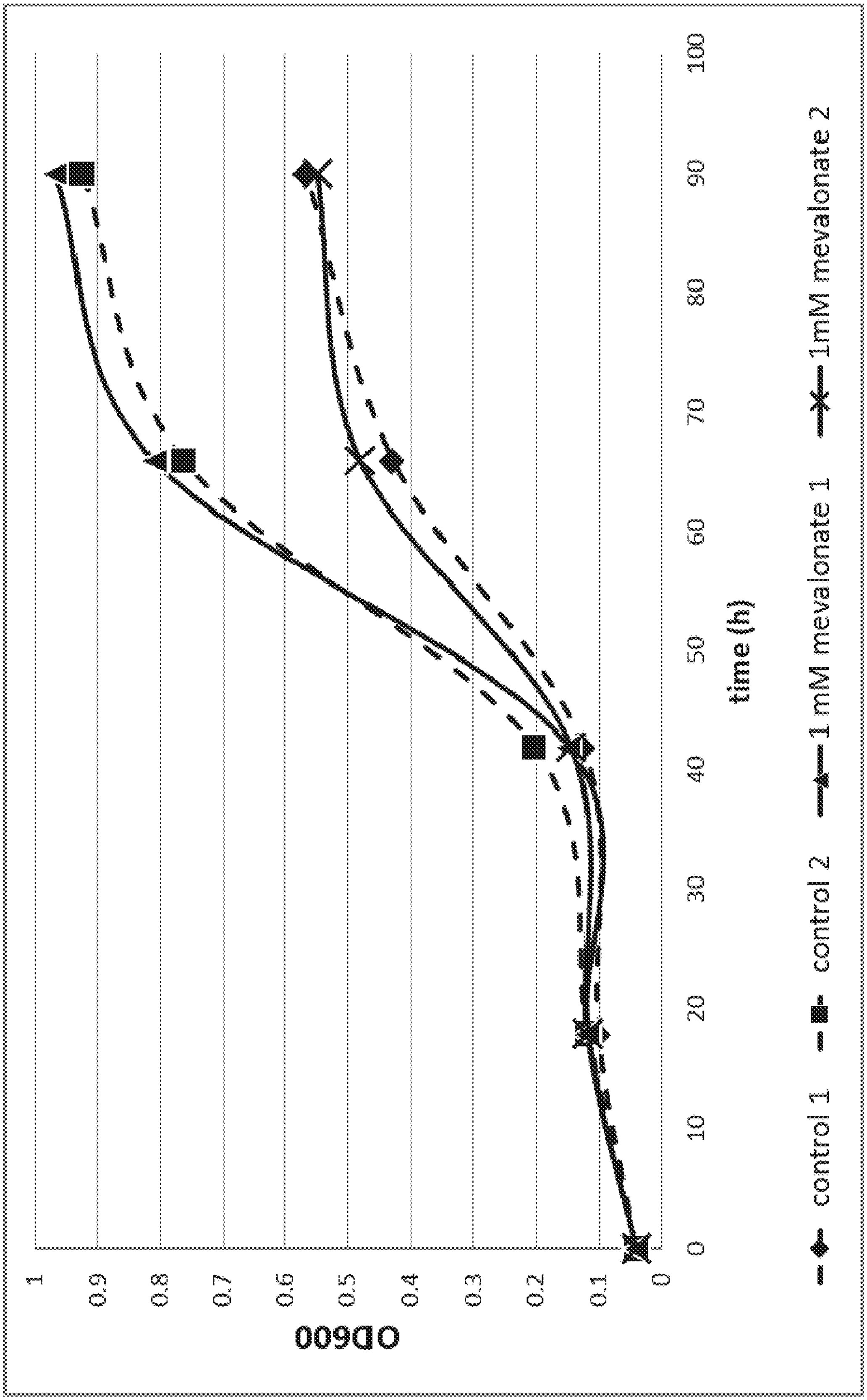
FIG. 17—Growth curve for transformed *C. autoethanogemun* carrying plasmid pMTL8314Prnf-MK-PMK-PMD-Pfor-idi-ispA-F S FIG. 18—RT-PRC data showing the expression of the genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi SEQ ID NO: 54), Geranyltranstransferase (ispA SEQ ID NO: 56) and Farnesene synthase (FS SEQ ID NO: 57).
Figure 19:
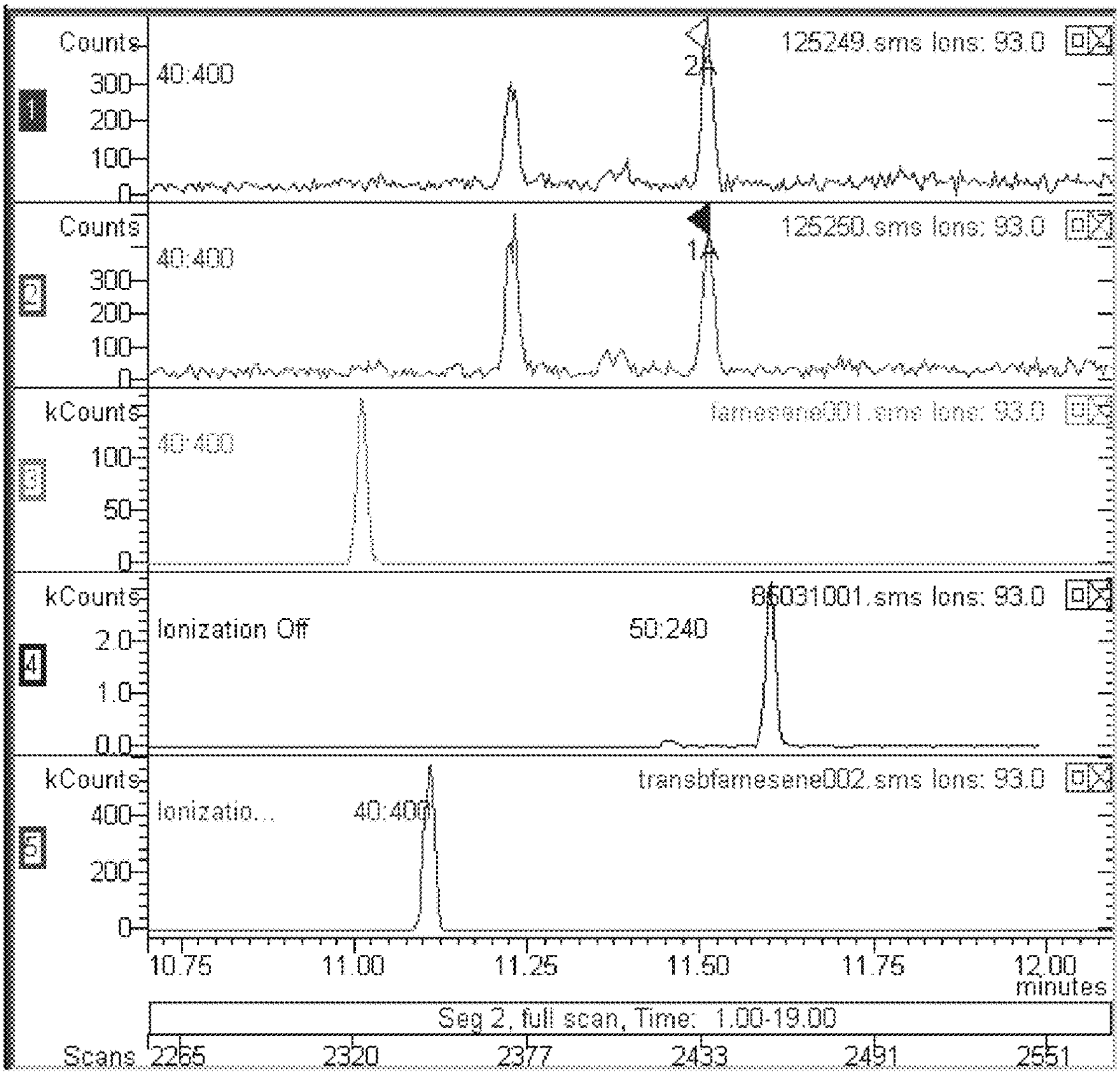
FIG. 19—GC-MS detection and conformation of the presence of farnesene in 1 mM mevalonate spiked cultures carrying pMTL8314Prnf-MK-PMK-PMD-Pfor-idi-ispA-FS. GC-MS chromatogram scanned for peaks containing ions with a mass of 93. Chromatogram 1 and 2 are transformed *C. autoethanogenum,* 3 is beta-farnesene standard run at the same time as the *C. autoethanogenum* samples. 4 is *E. coli* carrying the plasmids pMTL8314Prnf-MK-PMK-PMD-Pfor-idi-ispA-FS grown on M9 Glucose showing alpha-farnesene production and 5 is beta-farnesene standard run at the time of the *E. coli* samples. The difference in retention time between the *E. coli* and the *C. autoethanogenum* samples are due to minor changes to the instrument. However the difference in retention time between the beta-farnesene standard and the produced alpha-farnesene are the exact same in both cases, which together with the match in mass spectra's confirm the production of alpha-farnesene in *C. autoethanogenum.*
Figure 20:
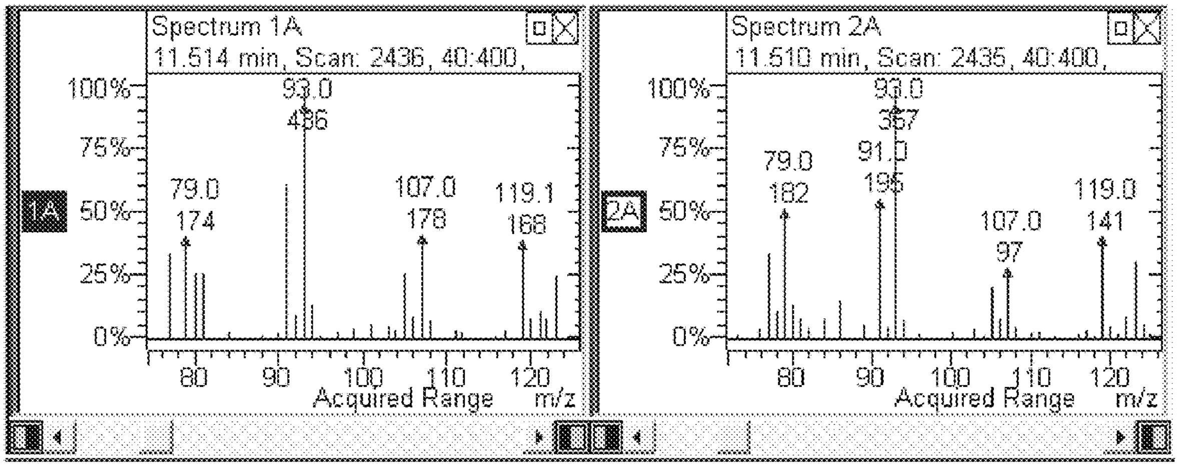
FIG. 20—MS spectrums for peaks labeled 1A and 2A in FIG. 19. The MS spectra's matches up with the NIST database spectra (FIG. 21) confirming the peak is alpha-farnesene.
Figure 21:
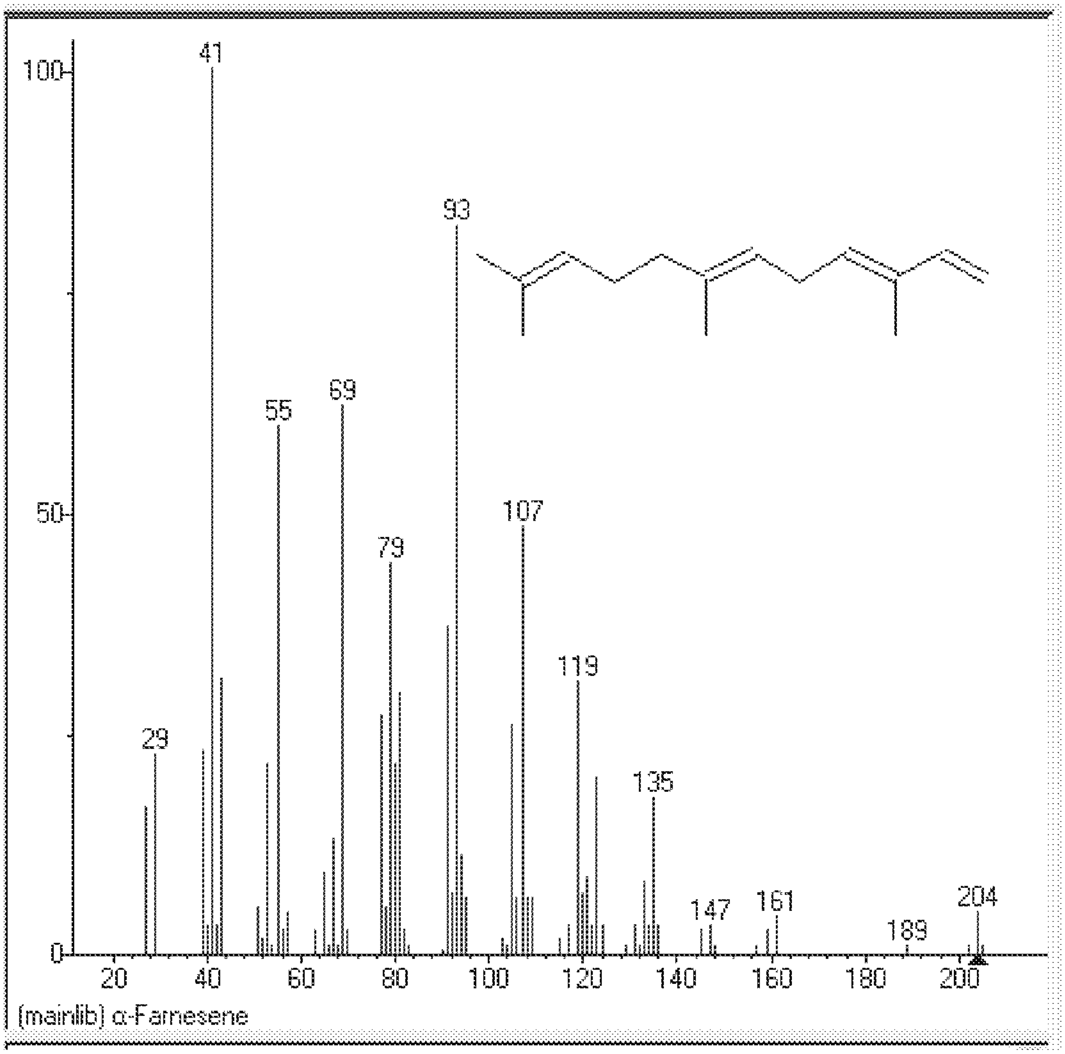
FIG. 21—MS spectrum for alpha-farnesene from the NIST Mass Spectral Database.

After conformation of successfully transformed of the plasmid pMTL8314-Prnf-MK-PMK-PMD-Pfor-idi-ispA-FS, a growth experiment was carried out in 50 ml PETC media (Table 1) in 250 ml serum bottles with 30 psi Real Mill Gas (collected from New Zealand Steel site in Glenbrook, NZ; composition: 44% CO, 32% $N_2$, 22% $CO_2$, 2% $H_2$) as sole energy and carbon source. All cultures were incubated at 37° C. on an orbital shaker adapted to hold serum bottles. Transformants were first grown up to an OD600 of ~0.4 before being subcultured into fresh media supplemented with 1 mM mevalonic acid. Controls without mevalonic acid were set up at the same time from the same culture. Samples for GC-MS (Gas Chromatography-Mass Spectroscopy) were taken at each time point. FIG. 17 shows a representative growth curve for 2 control cultures and two cultures fed 1 mM mevalonate. Farnesene was detected in the samples taken at 66 h and 90 h after start of experiment (FIG. 19-21).

Detection of Alpha-Farnesene by Gas Chromatography-Mass Spectroscopy

For GC-MS detection of alpha-farnesene hexane extraction was performed on 5 ml of culture by adding 2 ml hexane and shaking vigorously to mix in a sealed glass balch tube. The tubes were then incubated in a sonicating water bath for 5 min to encourage phase separation. 400 μl hexane extract were transferred to a GC vail and loaded on to the auto loader. The samples was analysed on a VARIAN GC3800 MS4000 iontrap GC/MS (Varian Inc, CA, USA. Now Agilent Technologies) with a EC-1000 column 0.25 μm film thickness (Grace Davidson, OR, USA) Varian MS workstation (Varian Inc, Ca. Now Agilent Technologies, CA, USA) and NIST MS Search 2.0 (Agilent Technologies, CA, USA). Injection volume of 1 μl with Helium carrier gas flow rate of 1 ml per min.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to."

The invention claimed is:

1. A recombinant cell prepared by introducing a nucleic acid encoding isoprene synthase into a host cell wherein the host cell is a *Clostridium* bacterium or a *Moorella* bacterium, wherein the nucleic acid is expressed in the host cell, and the recombinant cell is capable of producing isoprene from at least one Cl compound selected from the group consisting of carbon monoxide and carbon dioxide, wherein a nucleic acid encoding a group of exogenous enzymes acting in a mevalonate pathway is further introduced so that an isopentenyl diphosphate synthesis ability by a mevalonate pathway is further imparted, and wherein the group of exogenous enzymes acting in a mevalonate pathway comprises mevalonate kinase, mevalonate diphosphate decarboxylase, phosphomevalonate kinase, isopentenyl diphosphate (IPP) isomerase, 3-hydroxy-3-methylglutaryl coenzyme A (HMG-CoA) reductase, and HMG-CoA synthase.

2. The recombinant cell according to claim 1, having carbon monoxide dehydrogenase.

3. The recombinant cell according to claim 1, wherein the mevalonate pathway is that of yeast or bacterium.

4. The recombinant cell according to claim 2, wherein a nucleic acid encoding at least one enzyme acting in a DXS pathway is further introduced, and the nucleic acid is expressed in the host cell.

5. The recombinant cell according to claim 4, wherein the DXS pathway is that of a different organism than the host cell.

6. The recombinant cell according to claim 1, wherein the isoprene synthase is derived from a plant.

7. The recombinant cell according to claim 1, wherein the nucleic acid encoding isoprene synthase comprises SEQ ID NO: 21.

8. The recombinant cell according to claim 1, wherein the nucleic acid encoding isoprene synthase introduced into the host cell is codon optimized.

9. The recombinant cell according to claim 1, wherein the nucleic acid encoding isoprene synthase introduced into the host cell is incorporated in a genome of the host cell.

10. The recombinant cell according to claim 1, wherein the nucleic acid encoding isoprene synthase introduced into the host cell is incorporated in a plasmid.

11. The recombinant cell according to claim 1, wherein the nucleic acid encoding isoprene synthase and the nucleic acid encoding a group of exogenous enzymes acting in a mevalonate pathway are regulated by a constitutive promoter.

12. The recombinant cell according to claim 1, wherein the nucleic acid encoding isopentenyl diphosphate synthesis ability by a mevalonate pathway introduced into the host cell is codon optimized.

13. The recombinant cell according to claim 1, wherein the nucleic acid encoding isopentenyl diphosphate synthesis ability by a mevalonate pathway introduced into the host cell is incorporated in a genome of the host cell.

14. The recombinant cell according to claim 1, wherein the nucleic acid encoding isopentenyl diphosphate synthesis ability by a mevalonate pathway introduced into the host cell is incorporated in a plasmid.

15. A method for producing isoprene by culturing the recombinant cell according to claim 1 using at least one Cl compound selected from the group consisting of carbon monoxide and carbon dioxide as a carbon source, to allow the recombinant cell to produce isoprene.

16. The method according to claim 15, wherein the recombinant cell is provided with a gas comprising hydrogen.

17. The method according to claim 15, wherein the isoprene is recovered.

18. The method of claim 15, wherein the Cl compound is derived from an industrial process selected from the group consisting of ferrous metal products manufacturing, non-ferrous products manufacturing, petroleum refining, coal gasification, electric power production, carbon black production, ammonia production, methanol production, and coke manufacturing.

19. The method of claim 15, wherein the Cl compound is syngas.

20. A method for producing isoprene by bringing at least one Cl compound selected from the group consisting of carbon monoxide and carbon dioxide into contact with the recombinant cell according to claim 1, to allow the recombinant cell to produce isoprene from the Cl compound.

21. The method according to claim 20, wherein the recombinant cell is provided with a gas comprising hydrogen.

22. The method according to claim 20, wherein the isoprene is recovered.

* * * * *

SEQUENCE LISTING

<160> NUMBER OF SEQ ID NOS: 111

<210> SEQ ID NO 1
<211> LENGTH: 1875
<212> TYPE: DNA
<213> ORGANISM: Clostridium autoethanogenum

<400> SEQUENCE: 1

```
atgagtaatt tattagataa ttataaagat ataaatgacg taaagaagat gtcgttaaat      60

gataaaaaaa agctagctag agaaattaga aaatttttaa tagacaaagt atctaagaca     120

ggaggtcatt tggcgtctaa cttaggggtt gtggagctca ctttgagttt atttagtgta     180

tttgatctaa attatgataa acttatatgg gatgtgggac atcaggctta tgtgcataaa     240

atcctcacgg gaagaaagga taaatttgat actttaaggc aatttggagg attaagtgga     300

tttcctaaaa ggtgcgaaag tatatatgat tttttcgaaa cagggcatag tagtacttca     360

atatctgcag cacttggaat ggctagggct agagatttaa agcatgagaa atataatgtt     420

gttgcagtta taggagatgg agcacttact ggaggtatgg cactagaggc cctaaatgat     480

gtaggttata gaaaaactaa gcttataata atattaaatg ataatcaaat gtctatagga     540

aaaaatgtag gtggagtatc taaatattta aataaactta gagtggaccc taagtataat     600

aaatttaaag cggatgtaga agctaaatta aaaaagatac ctaatatagg aaaaggaatg     660

gcaaaatatc ttgaaaaggt aaaaaatgga ataaaacaaa tggtagttcc tggaatgttt     720

tttgaagata tgggaattaa atatttagga ccaatagatg gtcataatat aaaagaactt     780

acagacgtac tcgcttctgc aaaagacata caaggtccag ttattataca tataataact     840

aagaaaggaa aaggatatga atttgcagaa aaaaatccag gtaaattcca tggaataggg     900

ccttttaatt gcgccaatgg tgaactggat gctggatctt caaatactta ttccaaggcc     960

tttggaaatg aaatggtaaa gctagcagaa aaagacgata gaatagtggc tataactgca    1020

gccatgaggg atggaacagg tcttaaaagt ttttctcaaa agtttcctga aaggtttttt    1080

gatgtgggaa tagcagaaca gcatgctgta accctggcag ctggaatggc acaggcaaat    1140

ttaaaacctg tatttgcagt ttactctact tttcttcaaa gagcttatga tcaacttatt    1200

catgatgtat gtatgcaaaa acttccagta gtttttgctg tagatagggc cggcattgta    1260

ggagaagatg gtgaaacaca tcagggaata tttgatttat cttacttaac ggaaatgcca    1320

catatgacgc ttatgtctcc taaatgtata gatgaacttc catatatgtt aaaatgggca    1380

ttaggccaga gttttcctgt agctataagg tatccaaggg gaggagatag tgtatgtctc    1440

aatcccgtag aaaattttaa acttggaaag tgggactgta tttcaaatga aggcagtgta    1500

gcaataattg ctcagggtaa aatggtacaa aatgcagtgt tagcaggaaa aaaacttaaa    1560

gaaaagggta tagatgtaag gattataagt gcatgtttta ttaagccgct ggacaaggaa    1620

atgttaaaca ggttagttga agaaagtgta actatcgtta ctgttgaaga caatgtaata    1680

agaggaggat taggatccta tatattagaa tatgtaaata aattaaataa aaaagtaaaa    1740

ataataaact tagggtttga tgataagttt gtacagcatg gaaaatccga tattttgtat    1800

aagctgtatg gtttggatcc taaaggtatc gtaaatagtg tacttgaagc agcagaggta    1860

agtcatatat tttaa                                                     1875
```

<210> SEQ ID NO 2
<211> LENGTH: 627
<212> TYPE: PRT
<213> ORGANISM: Clostridium autoethanogenum -continued

<400> SEQUENCE: 2

Met Ser Asn Leu Leu Asp Asn Tyr Lys Asp Ile Asn Asp Val Lys Lys
1 5 10 15

Met Ser Leu Asn Asp Lys Lys Lys Leu Ala Arg Glu Ile Arg Lys Phe
20 25 30

Leu Ile Asp Lys Val Ser Lys Thr Gly Gly His Leu Ala Ser Asn Leu
35 40 45

Gly Val Val Glu Leu Thr Leu Ser Leu Phe Ser Val Phe Asp Leu Asn
50 55 60

Tyr Asp Lys Leu Ile Trp Asp Val Gly His Gln Ala Tyr Val His Lys
65 70 75 80

Ile Leu Thr Gly Arg Lys Asp Lys Phe Asp Thr Leu Arg Gln Phe Gly
85 90 95

Gly Leu Ser Gly Phe Pro Lys Arg Cys Glu Ser Ile Tyr Asp Phe Phe
100 105 110

Glu Thr Gly His Ser Ser Thr Ser Ile Ser Ala Ala Leu Gly Met Ala
115 120 125

Arg Ala Arg Asp Leu Lys His Glu Lys Tyr Asn Val Val Ala Val Ile
130 135 140

Gly Asp Gly Ala Leu Thr Gly Gly Met Ala Leu Glu Ala Leu Asn Asp
145 150 155 160

Val Gly Tyr Arg Lys Thr Lys Leu Ile Ile Ile Leu Asn Asp Asn Gln
165 170 175

Met Ser Ile Gly Lys Asn Val Gly Gly Val Ser Lys Tyr Leu Asn Lys
180 185 190

Leu Arg Val Asp Pro Lys Tyr Asn Lys Phe Lys Ala Asp Val Glu Ala
195 200 205

Lys Leu Lys Lys Ile Pro Asn Ile Gly Lys Gly Met Ala Lys Tyr Leu
210 215 220

Glu Lys Val Lys Asn Gly Ile Lys Gln Met Val Val Pro Gly Met Phe
225 230 235 240

Phe Glu Asp Met Gly Ile Lys Tyr Leu Gly Pro Ile Asp Gly His Asn
245 250 255

Ile Lys Glu Leu Thr Asp Val Leu Ala Ser Ala Lys Asp Ile Gln Gly
260 265 270

Pro Val Ile Ile His Ile Ile Thr Lys Lys Gly Lys Gly Tyr Glu Phe
275 280 285

Ala Glu Lys Asn Pro Gly Lys Phe His Gly Ile Gly Pro Phe Asn Cys
290 295 300

Ala Asn Gly Glu Leu Asp Ala Gly Ser Ser Asn Thr Tyr Ser Lys Ala
305 310 315 320

Phe Gly Asn Glu Met Val Lys Leu Ala Glu Lys Asp Asp Arg Ile Val
325 330 335

Ala Ile Thr Ala Ala Met Arg Asp Gly Thr Gly Leu Lys Ser Phe Ser
340 345 350

Gln Lys Phe Pro Glu Arg Phe Phe Asp Val Gly Ile Ala Glu Gln His
355 360 365

Ala Val Thr Leu Ala Ala Gly Met Ala Gln Ala Asn Leu Lys Pro Val
370 375 380

Phe Ala Val Tyr Ser Thr Phe Leu Gln Arg Ala Tyr Asp Gln Leu Ile
385 390 395 400

His Asp Val Cys Met Gln Lys Leu Pro Val Val Phe Ala Val Asp Arg

-continued

```
            405                 410                 415

Ala Gly Ile Val Gly Glu Asp Gly Glu Thr His Gln Gly Ile Phe Asp
        420                 425                 430

Leu Ser Tyr Leu Thr Glu Met Pro His Met Thr Leu Met Ser Pro Lys
    435                 440                 445

Cys Ile Asp Glu Leu Pro Tyr Met Leu Lys Trp Ala Leu Gly Gln Ser
    450                 455                 460

Phe Pro Val Ala Ile Arg Tyr Pro Arg Gly Gly Asp Ser Val Cys Leu
465                 470                 475                 480

Asn Pro Val Glu Asn Phe Lys Leu Gly Lys Trp Asp Cys Ile Ser Asn
            485                 490                 495

Glu Gly Ser Val Ala Ile Ile Ala Gln Gly Lys Met Val Gln Asn Ala
        500                 505                 510

Val Leu Ala Gly Lys Lys Leu Lys Glu Lys Gly Ile Asp Val Arg Ile
    515                 520                 525

Ile Ser Ala Cys Phe Ile Lys Pro Leu Asp Lys Glu Met Leu Asn Arg
    530                 535                 540

Leu Val Glu Glu Ser Val Thr Ile Val Thr Val Glu Asp Asn Val Ile
545                 550                 555                 560

Arg Gly Gly Leu Gly Ser Tyr Ile Leu Glu Tyr Val Asn Lys Leu Asn
            565                 570                 575

Lys Lys Val Lys Ile Ile Asn Leu Gly Phe Asp Asp Lys Phe Val Gln
        580                 585                 590

His Gly Lys Ser Asp Ile Leu Tyr Lys Leu Tyr Gly Leu Asp Pro Lys
    595                 600                 605

Gly Ile Val Asn Ser Val Leu Glu Ala Ala Glu Val Ser His Ile Phe
    610                 615                 620

Arg Glu Phe
625


<210> SEQ ID NO 3
<211> LENGTH: 1158
<212> TYPE: DNA
<213> ORGANISM: Clostridium autoethanogenum

<400> SEQUENCE: 3

atgaagagaa tttcaataat tggagccaca ggttctatag gaacccaaac tcttgatgta      60

cttagaaaac aaaaaggaga ttttcagctt ataggtgtat ctgcaaatag tagtgtagat     120

aaacttttac atataataga tgaatttaac cccaaatatg cggtgctaac cgaaaaagaa     180

tcttatttaa agataaaaga tatttttagt aataaaaaat caaatacaaa aatattattt     240

ggagtagatg gattaaatac tatagctagt cttcctgaag ttgatatggt tgtaacatct     300

gtagttggaa tgatagggct tgtaccaact ataaaagcaa ttaaagcgaa gaaagacata     360

gctttagcta ataaggagac attagttgta ggaggagaac tggttacaaa attatcgaaa     420

gaaaataata taaaaatatt tcctgtagat tcagagcata gtgctgtttt tcaatgcctt     480

cagggaaata attttgacga agttgctaat ttgattttaa ccgcttcagg tggacctttt     540

aggggaaaaa caaaagatca actctcaaaa gtaactgtaa aagaggcgtt gaatcatcca     600

aattggagta tgggaaaaaa gctcacaata gattctgcta ctcttatgaa taagggactt     660

gaagttatag aagctcactt cttatttaac ttaccttatg aaaatataaa ggttgtagtt     720

catccacaaa gtatagtaca ttctatggtg gaatataggg atggaagtgt tatggcacag     780

cttgccactg cagatatgag attacctata caatatgcac tgaattatcc gaaaagaaag     840
```

-continued

```
gaagctgtaa tagataaatt ggacttctat agcgtaggaa atttaagttt tgaaaagcct    900

gatacagata cattcagacc acttaaatta gcttatgaag cagggaggat aggaggcaca    960

atgccagcta tactaaattg tgcaaatgag gaagcagtaa gtttattcct tgctaataaa   1020

ataaattttt tggatatagg caacatatta gaagagtgta tgaataaatt tacttcacaa   1080

agtacgtata ctctggatga tttacttgac ctagaaataa aagttaagaa atatgtaaaa   1140

gataaattta tcaaataa                                                 1158
```

```
<210> SEQ ID NO 4
<211> LENGTH: 385
<212> TYPE: PRT
<213> ORGANISM: Clostridium autoethanogenum

<400> SEQUENCE: 4

Met Lys Arg Ile Ser Ile Ile Gly Ala Thr Gly Ser Ile Gly Thr Gln
1               5                   10                  15

Thr Leu Asp Val Leu Arg Lys Gln Lys Gly Asp Phe Gln Leu Ile Gly
            20                  25                  30

Val Ser Ala Asn Ser Ser Val Asp Lys Leu Leu His Ile Ile Asp Glu
        35                  40                  45

Phe Asn Pro Lys Tyr Ala Val Leu Thr Glu Lys Glu Ser Tyr Leu Lys
    50                  55                  60

Ile Lys Asp Ile Phe Ser Asn Lys Lys Ser Asn Thr Lys Ile Leu Phe
65                  70                  75                  80

Gly Val Asp Gly Leu Asn Thr Ile Ala Ser Leu Pro Glu Val Asp Met
                85                  90                  95

Val Val Thr Ser Val Val Gly Met Ile Gly Leu Val Pro Thr Ile Lys
            100                 105                 110

Ala Ile Lys Ala Lys Lys Asp Ile Ala Leu Ala Asn Lys Glu Thr Leu
        115                 120                 125

Val Val Gly Gly Glu Leu Val Thr Lys Leu Ser Lys Glu Asn Asn Ile
    130                 135                 140

Lys Ile Phe Pro Val Asp Ser Glu His Ser Ala Val Phe Gln Cys Leu
145                 150                 155                 160

Gln Gly Asn Asn Phe Asp Glu Val Ala Asn Leu Ile Leu Thr Ala Ser
                165                 170                 175

Gly Gly Pro Phe Arg Gly Lys Thr Lys Asp Gln Leu Ser Lys Val Thr
            180                 185                 190

Val Lys Glu Ala Leu Asn His Pro Asn Trp Ser Met Gly Lys Lys Leu
        195                 200                 205

Thr Ile Asp Ser Ala Thr Leu Met Asn Lys Gly Leu Glu Val Ile Glu
    210                 215                 220

Ala His Phe Leu Phe Asn Leu Pro Tyr Glu Asn Ile Lys Val Val Val
225                 230                 235                 240

His Pro Gln Ser Ile Val His Ser Met Val Glu Tyr Arg Asp Gly Ser
                245                 250                 255

Val Met Ala Gln Leu Ala Thr Ala Asp Met Arg Leu Pro Ile Gln Tyr
            260                 265                 270

Ala Leu Asn Tyr Pro Lys Arg Lys Glu Ala Val Ile Asp Lys Leu Asp
        275                 280                 285

Phe Tyr Ser Val Gly Asn Leu Ser Phe Glu Lys Pro Asp Thr Asp Thr
    290                 295                 300

Phe Arg Pro Leu Lys Leu Ala Tyr Glu Ala Gly Arg Ile Gly Gly Thr
```

```
305                 310                 315                 320

Met Pro Ala Ile Leu Asn Cys Ala Asn Glu Glu Ala Val Ser Leu Phe
                325                 330                 335

Leu Ala Asn Lys Ile Asn Phe Leu Asp Ile Gly Asn Ile Leu Glu Glu
            340                 345                 350

Cys Met Asn Lys Phe Thr Ser Gln Ser Thr Tyr Thr Leu Asp Asp Leu
        355                 360                 365

Leu Asp Leu Glu Ile Lys Val Lys Lys Tyr Val Lys Asp Lys Phe Ile
    370                 375                 380

Lys
385


<210> SEQ ID NO 5
<211> LENGTH: 693
<212> TYPE: DNA
<213> ORGANISM: Clostridium autoethanogenum

<400> SEQUENCE: 5

atgaatggta attatgctat tattgtagct gccggcaagg gaaaaagaat gggaactact     60

attaataagc aatttattaa aattaagggt aagcctatat tatattattc cataagggca    120

ttttccataa atcctcttat agatggaatt atactggtat gtgcagaaac tgagatagaa    180

tattgtaaaa gagaagtagt agataaatat gggcttcaga aggtaattaa attagttgct    240

gggggtaaag aacgtcagga ttcggtattt aatggactag gagttttaga aaaagaaaac    300

tgtagtgttg ttctaattca cgatggggct agaccttttg tcactagtaa aattattgat    360

gatggaataa aatattctaa taggtatggg gcttgtgctt gtggagttag gcctaaggat    420

acactaaaag ttagggaaga aagtggattt tcttcttcta cattagagag aaaaagttta    480

tttgcagttc aaactccgca gtgttttaaa tatgatttaa tttatgactg tcataaaaaa    540

ttaatgaatg aaaaaatgtg tgttactgat gatactatgg tagtagagcg ttatggaaat    600

aaggtttatt tgtatgaagg taactatgaa aacataaaag tgaccacacc agaagattta    660

aatatagctg aaagtatagt tgaaaaatat taa                                 693


<210> SEQ ID NO 6
<211> LENGTH: 230
<212> TYPE: PRT
<213> ORGANISM: Clostridium autoethanogenum

<400> SEQUENCE: 6

Met Asn Gly Asn Tyr Ala Ile Ile Val Ala Ala Gly Lys Gly Lys Arg
1               5                   10                  15

Met Gly Thr Thr Ile Asn Lys Gln Phe Ile Lys Ile Lys Gly Lys Pro
            20                  25                  30

Ile Leu Tyr Tyr Ser Ile Arg Ala Phe Ser Ile Asn Pro Leu Ile Asp
        35                  40                  45

Gly Ile Ile Leu Val Cys Ala Glu Thr Glu Ile Glu Tyr Cys Lys Arg
    50                  55                  60

Glu Val Val Asp Lys Tyr Gly Leu Gln Lys Val Ile Lys Leu Val Ala
65                  70                  75                  80

Gly Gly Lys Glu Arg Gln Asp Ser Val Phe Asn Gly Leu Gly Val Leu
                85                  90                  95

Glu Lys Glu Asn Cys Ser Val Val Leu Ile His Asp Gly Ala Arg Pro
            100                 105                 110

Phe Val Thr Ser Lys Ile Ile Asp Asp Gly Ile Lys Tyr Ser Asn Arg
```

-continued

```
        115                 120                 125

Tyr Gly Ala Cys Ala Cys Gly Val Arg Pro Lys Asp Thr Leu Lys Val
    130                 135                 140

Arg Glu Glu Ser Gly Phe Ser Ser Ser Thr Leu Glu Arg Lys Ser Leu
145                 150                 155                 160

Phe Ala Val Gln Thr Pro Gln Cys Phe Lys Tyr Asp Leu Ile Tyr Asp
                165                 170                 175

Cys His Lys Lys Leu Met Asn Glu Lys Met Cys Val Thr Asp Asp Thr
            180                 185                 190

Met Val Val Glu Arg Tyr Gly Asn Lys Val Tyr Leu Tyr Glu Gly Asn
        195                 200                 205

Tyr Glu Asn Ile Lys Val Thr Thr Pro Glu Asp Leu Asn Ile Ala Glu
    210                 215                 220

Ser Ile Val Glu Lys Tyr
225                 230


<210> SEQ ID NO 7
<211> LENGTH: 798
<212> TYPE: DNA
<213> ORGANISM: Clostridium autoethanogenum

<400> SEQUENCE: 7

gtgggaaaaa gaaaagatgg gtatcatctt ttgaaaatga taatgcagaa tatagactta      60

tatgatgttt taaaaataga tgagatcaaa actggaatac agatatgctc taataataga     120

tatattccct gtgacaggag aaatttggtt tacagagcag caaaattatt tattgataaa     180

tataatataa agaatggaat tagtataaac ataggtaaaa atatacctgt atcagctgga     240

cttgctggtg gaagtgcgga tgctgcagct atactaaaga ctatgagaaa tatttatact     300

cctgaagtaa gtgataaaga attgagcgaa ttaggcttaa atataggggc agatgttcct     360

tattgtataa taggaggtac agccttgtgc gaggggatag gagagaaggt tacaccactc     420

atgccgttta gaaaccatat actcatatta attaaaccac cttttggagt gagcacagca     480

gaggtatata agagtttaga cataagtaaa ataaaaaggc atcctaatac agaaatttta     540

atagatgcgg ttaatgaatc aaaattggag atgctgagta aaaacatgaa aaatgttttg     600

gaaaatgtaa ctttaaaaaa atatcccgtg cttagaaaaa taaaaactga tttgatagat     660

tttggagcag ttggttcact tatgagtgga agcggtccaa gcatttttgc ttttttttgat     720

gatatgctaa aagcacagaa atgttatgat aatatgaaaa ctaggtatag agaggtgttt     780

attacaagaa ccatttaa                                                   798


<210> SEQ ID NO 8
<211> LENGTH: 265
<212> TYPE: PRT
<213> ORGANISM: Clostridium autoethanogenum

<400> SEQUENCE: 8

Met Gly Lys Arg Lys Asp Gly Tyr His Leu Leu Lys Met Ile Met Gln
1               5                   10                  15

Asn Ile Asp Leu Tyr Asp Val Leu Lys Ile Asp Glu Ile Lys Thr Gly
            20                  25                  30

Ile Gln Ile Cys Ser Asn Asn Arg Tyr Ile Pro Cys Asp Arg Arg Asn
        35                  40                  45

Leu Val Tyr Arg Ala Ala Lys Leu Phe Ile Asp Lys Tyr Asn Ile Lys
    50                  55                  60
```

```
Asn Gly Ile Ser Ile Asn Ile Gly Lys Asn Ile Pro Val Ser Ala Gly
65                  70                  75                  80

Leu Ala Gly Gly Ser Ala Asp Ala Ala Ala Ile Leu Lys Thr Met Arg
                85                  90                  95

Asn Ile Tyr Thr Pro Glu Val Ser Asp Lys Glu Leu Ser Glu Leu Gly
            100                 105                 110

Leu Asn Ile Gly Ala Asp Val Pro Tyr Cys Ile Ile Gly Gly Thr Ala
        115                 120                 125

Leu Cys Glu Gly Ile Gly Glu Lys Val Thr Pro Leu Met Pro Phe Arg
    130                 135                 140

Asn His Ile Leu Ile Leu Ile Lys Pro Pro Phe Gly Val Ser Thr Ala
145                 150                 155                 160

Glu Val Tyr Lys Ser Leu Asp Ile Ser Lys Ile Lys Arg His Pro Asn
                165                 170                 175

Thr Glu Ile Leu Ile Asp Ala Val Asn Glu Ser Lys Leu Glu Met Leu
            180                 185                 190

Ser Lys Asn Met Lys Asn Val Leu Glu Asn Val Thr Leu Lys Lys Tyr
        195                 200                 205

Pro Val Leu Arg Lys Ile Lys Thr Asp Leu Ile Asp Phe Gly Ala Val
    210                 215                 220

Gly Ser Leu Met Ser Gly Ser Gly Pro Ser Ile Phe Ala Phe Phe Asp
225                 230                 235                 240

Asp Met Leu Lys Ala Gln Lys Cys Tyr Asp Asn Met Lys Thr Arg Tyr
                245                 250                 255

Arg Glu Val Phe Ile Thr Arg Thr Ile
            260                 265


<210> SEQ ID NO 9
<211> LENGTH: 480
<212> TYPE: DNA
<213> ORGANISM: Clostridium autoethanogenum

<400> SEQUENCE: 9

gtgaaaatcg ggcttggtta tgatgtccat aaattagttt ataatagacc tcttatttta      60

ggaggcgtaa atatcccttt tgaaaaaggt cttatgggac attcagatgc agatgtactt     120

cttcatgcaa taatggatag tctccttgga gccttgtgtc taggtgatat cggcaagcat     180

ttccctgata atgataataa atataagaac atatgtagtc ttaaattgct gtcacatgta     240

tcagctttga ttaatgaaaa aggatatact atagggaaca tagattctat tataatagcc     300

gaaaagccta aactttcttc atacatacaa gatatgaggg taaatatagc taaaactcta     360

aatgtaacta cagccgtaat aagtgtaaaa gccactacag aggaaggtct tggctttacc     420

ggcaaaggag aaggcatagc cgctcaaagc atctgtttgt taacagctaa ttcaaaataa     480


<210> SEQ ID NO 10
<211> LENGTH: 159
<212> TYPE: PRT
<213> ORGANISM: Clostridium autoethanogenum

<400> SEQUENCE: 10

Met Lys Ile Gly Leu Gly Tyr Asp Val His Lys Leu Val Tyr Asn Arg
1               5                   10                  15

Pro Leu Ile Leu Gly Gly Val Asn Ile Pro Phe Glu Lys Gly Leu Met
            20                  25                  30

Gly His Ser Asp Ala Asp Val Leu Leu His Ala Ile Met Asp Ser Leu
        35                  40                  45
```

-continued

```
Leu Gly Ala Leu Cys Leu Gly Asp Ile Gly Lys His Phe Pro Asp Asn
    50                  55                  60

Asp Asn Lys Tyr Lys Asn Ile Cys Ser Leu Lys Leu Leu Ser His Val
65                  70                  75                  80

Ser Ala Leu Ile Asn Glu Lys Gly Tyr Thr Ile Gly Asn Ile Asp Ser
                85                  90                  95

Ile Ile Ile Ala Glu Lys Pro Lys Leu Ser Ser Tyr Ile Gln Asp Met
            100                 105                 110

Arg Val Asn Ile Ala Lys Thr Leu Asn Val Thr Thr Ala Val Ile Ser
        115                 120                 125

Val Lys Ala Thr Thr Glu Glu Gly Leu Gly Phe Thr Gly Lys Gly Glu
    130                 135                 140

Gly Ile Ala Ala Gln Ser Ile Cys Leu Leu Thr Ala Asn Ser Lys
145                 150                 155


<210> SEQ ID NO 11
<211> LENGTH: 1051
<212> TYPE: DNA
<213> ORGANISM: Clostridium autoethanogenum

<400> SEQUENCE: 11

ttgaatagag taaaaaagaa aacagtaaag gtaggcaata tatttttagg tggagatttt      60

ccagtagccg tacaatctat gacaaatacg gatactaggg atgtagaagc cactacagct     120

cagatatttc agctaaaaga agcaggttgt gatatcgtca gatgtgcggt gcctgatgat     180

atagcttgca attccatgaa aaaaatcata gaaagagtag atattccact tgtagcagat     240

atacattttg attataagtt ggcgcttaaa tctatagaaa atgggatatc tgcacttaga     300

ataaatcctg gaaatattgg aagcatagaa agagtacgag aagtggcaag agcagcaaaa     360

gaagctaata ttccaattag aataggggta aactctggat cattaaaaaa agatatttta     420

aataaatatg gtagagtttg ttcggatgca ctagtagaga gtgctctaga acatgtaaaa     480

attttggaaa acgtaggatt ttatgatata gttatatcca taaaatcttc aaatgtaaat     540

cagatgatag aaagttatag aaaaatatct gaaattgtag attatccact tcaccttgga     600

gtaacagaag caggaactat ttggcgagga actataaaat caagcatagg cataggtact     660

cttttgatgg aaggtatagg agacactata agagtatctc ttacaggaaa tccagtggaa     720

gaagtaagag tgggaaaaga aatattaaaa tcctgtggaa ttataaaaga aggtgtggaa     780

tttatatcat gtcccacctg tggtagaact gaaattgatt taattaaaat agctgagcaa     840

gtggaaaaaa gacttttaaa tatgcataaa aacataaagg ttgctgttat gggatgtgta     900

gtaaatggac caggtgaggc tcgggaagca gatattggta tagcaggcgg caaaggtgaa     960

ggcattatat ttaaaaaagg aaaaatagta aaaaaggtaa gtgaagaaag tttagtagaa    1020

tcacttatag aagaaataga aaacatttga r                                  1051


<210> SEQ ID NO 12
<211> LENGTH: 349
<212> TYPE: PRT
<213> ORGANISM: Clostridium autoethanogenum

<400> SEQUENCE: 12

Met Asn Arg Val Lys Lys Lys Thr Val Lys Val Gly Asn Ile Phe Leu
1               5                   10                  15

Gly Gly Asp Phe Pro Val Ala Val Gln Ser Met Thr Asn Thr Asp Thr
            20                  25                  30
```

-continued

```
Arg Asp Val Glu Ala Thr Thr Ala Gln Ile Phe Gln Leu Lys Glu Ala
        35                  40                  45

Gly Cys Asp Ile Val Arg Cys Ala Val Pro Asp Asp Ile Ala Cys Asn
    50                  55                  60

Ser Met Lys Lys Ile Ile Glu Arg Val Asp Ile Pro Leu Val Ala Asp
65                  70                  75                  80

Ile His Phe Asp Tyr Lys Leu Ala Leu Lys Ser Ile Glu Asn Gly Ile
                85                  90                  95

Ser Ala Leu Arg Ile Asn Pro Gly Asn Ile Gly Ser Ile Glu Arg Val
            100                 105                 110

Arg Glu Val Ala Arg Ala Ala Lys Glu Ala Asn Ile Pro Ile Arg Ile
        115                 120                 125

Gly Val Asn Ser Gly Ser Leu Lys Lys Asp Ile Leu Asn Lys Tyr Gly
    130                 135                 140

Arg Val Cys Ser Asp Ala Leu Val Glu Ser Ala Leu Glu His Val Lys
145                 150                 155                 160

Ile Leu Glu Asn Val Gly Phe Tyr Asp Ile Val Ile Ser Ile Lys Ser
                165                 170                 175

Ser Asn Val Asn Gln Met Ile Glu Ser Tyr Arg Lys Ile Ser Glu Ile
            180                 185                 190

Val Asp Tyr Pro Leu His Leu Gly Val Thr Glu Ala Gly Thr Ile Trp
        195                 200                 205

Arg Gly Thr Ile Lys Ser Ser Ile Gly Ile Gly Thr Leu Leu Met Glu
    210                 215                 220

Gly Ile Gly Asp Thr Ile Arg Val Ser Leu Thr Gly Asn Pro Val Glu
225                 230                 235                 240

Glu Val Arg Val Gly Lys Glu Ile Leu Lys Ser Cys Gly Ile Ile Lys
                245                 250                 255

Glu Gly Val Glu Phe Ile Ser Cys Pro Thr Cys Gly Arg Thr Glu Ile
            260                 265                 270

Asp Leu Ile Lys Ile Ala Glu Gln Val Glu Lys Arg Leu Leu Asn Met
        275                 280                 285

His Lys Asn Ile Lys Val Ala Val Met Gly Cys Val Val Asn Gly Pro
    290                 295                 300

Gly Glu Ala Arg Glu Ala Asp Ile Gly Ile Ala Gly Gly Lys Gly Glu
305                 310                 315                 320

Gly Ile Ile Phe Lys Lys Gly Lys Ile Val Lys Lys Val Ser Glu Glu
                325                 330                 335

Ser Leu Val Glu Ser Leu Ile Glu Glu Ile Glu Asn Ile
            340                 345
```

<210> SEQ ID NO 13
<211> LENGTH: 1923
<212> TYPE: DNA
<213> ORGANISM: Clostridium autoethanogenum

<400> SEQUENCE: 13

```
gtgataaaat tgaacattat tttagcagac aaatccggat tttgctttgg agtaaaaaga      60

gctgtagacg aatctttaaa ggttcaaaaa aaatttaata aaaaaatata tactttaggt     120

cctttgattc ataatagtga tgtagtaaat aaattaaagg aaaaaggtat atatcctata     180

gaaatagata atatagataa tctaagggaa gatgatgtgg ttataatacg ttctcatggt     240

gttcccgaaa aaatattttt tactttaaaa aataaaaaaa taaacatagt aaatgcaact     300
```

-continued tgcccatatg ttttaaatat acaaagaaaa gtacaagaat attataaatt agggtattct 360
atattaatag taggagataa aaatcatcct gaagtaattg gaataaatgg atggtgtgaa 420
aataaagctt taatatctaa agatggcacc aatttagaaa agttaccatc aaaactgtgt 480
atagtttctc aaactacaga aaaacaatct aactgggaaa aagtgcttag tatagtggct 540
aaaaattgta aagaatttat tgcttttaat actatatgca gtgccacaga atttcgtcag 600
aaggcagcag cagatatttc taaagaagta gatatgatgg tagtaatagg tggtaaaaac 660
agctctaata ctactaaact ttatgaaata tgtaaagata actgcaataa tactatttat 720
gttgaaaatt caggagaaat acctgatgat ataagtaatt gtaataaaat taaaactata 780
ggtgttacag caggagcttc aacaccagat tggataataa aggaggcaat tttaaaaatg 840
agtgatgaca aaaatttaga actaaatgag caactatctt atatggacaa aaatgatacc 900
caaataatat taggtgaaaa aattaagggt acagtaatat ctgtaaatcc aaaagaggtt 960
tttttaaata taggatataa atcagaaggt gtacttccaa aacgtgaaat aacaaaaaat 1020
gaaagtgaca acttagaaga attaattcat tgtggagatg aattatatgt taaagtaata 1080
agaagacaaa atgaagatgg atatgtggta ttatctaaga tagaattaga aagagaaaat 1140
gcttataaag aattaaagga agctaatgga aatagtcagg tattaaaggt tattgtaaaa 1200
gaagctgtaa atggaggtct tgttgccaat tacaaaggtg ctagggtatt tatacctgct 1260
tctcatgtag aattatatca tgtagatgat ctttcacaat atgtagataa agagcttgat 1320
gtaactataa ttgaatttaa agaagaaaag aaaggtacca gaatagtagc ttcaagaaga 1380
gaccttttga gaatggaaag agaaaaaatg gaagaacaga cttggaatgt gcttgaaaaa 1440
gatactgtag tagatggtga agttagaaga ttgactgatt ttggcgcatt tgttgatgta 1500
caaggagttg acgggcttct acatgtatct gaactttcct ggggaagagt tggaaaacca 1560
agtgatgttt taaaaatcgg agatacgatt aaggtttata tcttagacat tgataaagaa 1620
aaaaagaagt tatctttatc tttaaaaaag ctcatggaag atccatggat caacgtagac 1680
ataaaatatc ctgttggcaa tgtagttctt ggtaaagtag ttaggtttgc aaattttggt 1740
gcatttgttg aattagagcc aggtgtagat gcattagttc atatatcaca aataagccat 1800
aagagaatag ataaaccaga agatgtactt aaaataggtc aggaaataaa ggctaagatc 1860
cttgaagtaa acaaagatag cgaaaaaata gctttaagta taaaagaagt agatgaaatc 1920
taa 1923

<210> SEQ ID NO 14
<211> LENGTH: 640
<212> TYPE: PRT
<213> ORGANISM: Clostridium autoethanogenum

<400> SEQUENCE: 14

Met Ile Lys Leu Asn Ile Ile Leu Ala Asp Lys Ser Gly Phe Cys Phe
1               5                   10                  15

Gly Val Lys Arg Ala Val Asp Glu Ser Leu Lys Val Gln Lys Lys Phe
            20                  25                  30

Asn Lys Lys Ile Tyr Thr Leu Gly Pro Leu Ile His Asn Ser Asp Val
        35                  40                  45

Val Asn Lys Leu Lys Glu Lys Gly Ile Tyr Pro Ile Glu Ile Asp Asn
    50                  55                  60

Ile Asp Asn Leu Arg Glu Asp Asp Val Val Ile Ile Arg Ser His Gly
65                  70                  75                  80

-continued

```
Val Pro Glu Lys Ile Phe Phe Thr Leu Lys Asn Lys Lys Ile Asn Ile
                85                  90                  95

Val Asn Ala Thr Cys Pro Tyr Val Leu Asn Ile Gln Arg Lys Val Gln
            100                 105                 110

Glu Tyr Tyr Lys Leu Gly Tyr Ser Ile Leu Ile Val Gly Asp Lys Asn
        115                 120                 125

His Pro Glu Val Ile Gly Ile Asn Gly Trp Cys Glu Asn Lys Ala Leu
    130                 135                 140

Ile Ser Lys Asp Gly Thr Asn Leu Glu Lys Leu Pro Ser Lys Leu Cys
145                 150                 155                 160

Ile Val Ser Gln Thr Thr Glu Lys Gln Ser Asn Trp Glu Lys Val Leu
                165                 170                 175

Ser Ile Val Ala Lys Asn Cys Lys Glu Phe Ile Ala Phe Asn Thr Ile
            180                 185                 190

Cys Ser Ala Thr Glu Phe Arg Gln Lys Ala Ala Ala Asp Ile Ser Lys
        195                 200                 205

Glu Val Asp Met Met Val Val Ile Gly Gly Lys Asn Ser Ser Asn Thr
    210                 215                 220

Thr Lys Leu Tyr Glu Ile Cys Lys Asp Asn Cys Asn Asn Thr Ile Tyr
225                 230                 235                 240

Val Glu Asn Ser Gly Glu Ile Pro Asp Asp Ile Ser Asn Cys Asn Lys
                245                 250                 255

Ile Lys Thr Ile Gly Val Thr Ala Gly Ala Ser Thr Pro Asp Trp Ile
            260                 265                 270

Ile Lys Glu Ala Ile Leu Lys Met Ser Asp Asp Lys Asn Leu Glu Leu
        275                 280                 285

Asn Glu Gln Leu Ser Tyr Met Asp Lys Asn Asp Thr Gln Ile Ile Leu
    290                 295                 300

Gly Glu Lys Ile Lys Gly Thr Val Ile Ser Val Asn Pro Lys Glu Val
305                 310                 315                 320

Phe Leu Asn Ile Gly Tyr Lys Ser Glu Gly Val Leu Pro Lys Arg Glu
                325                 330                 335

Ile Thr Lys Asn Glu Ser Asp Asn Leu Glu Glu Leu Ile His Cys Gly
            340                 345                 350

Asp Glu Leu Tyr Val Lys Val Ile Arg Arg Gln Asn Glu Asp Gly Tyr
        355                 360                 365

Val Val Leu Ser Lys Ile Glu Leu Glu Arg Glu Asn Ala Tyr Lys Glu
    370                 375                 380

Leu Lys Glu Ala Asn Gly Asn Ser Gln Val Leu Lys Val Ile Val Lys
385                 390                 395                 400

Glu Ala Val Asn Gly Gly Leu Val Ala Asn Tyr Lys Gly Ala Arg Val
                405                 410                 415

Phe Ile Pro Ala Ser His Val Glu Leu Tyr His Val Asp Asp Leu Ser
            420                 425                 430

Gln Tyr Val Asp Lys Glu Leu Asp Val Thr Ile Ile Glu Phe Lys Glu
        435                 440                 445

Glu Lys Lys Gly Thr Arg Ile Val Ala Ser Arg Arg Asp Leu Leu Arg
    450                 455                 460

Met Glu Arg Glu Lys Met Glu Glu Gln Thr Trp Asn Val Leu Glu Lys
465                 470                 475                 480

Asp Thr Val Val Asp Gly Glu Val Arg Arg Leu Thr Asp Phe Gly Ala
                485                 490                 495

Phe Val Asp Val Gln Gly Val Asp Gly Leu Leu His Val Ser Glu Leu
```

```
            500                 505                 510

Ser Trp Gly Arg Val Gly Lys Pro Ser Asp Val Leu Lys Ile Gly Asp
        515                 520                 525

Thr Ile Lys Val Tyr Ile Leu Asp Ile Asp Lys Glu Lys Lys Lys Leu
    530                 535                 540

Ser Leu Ser Leu Lys Lys Leu Met Glu Asp Pro Trp Ile Asn Val Asp
545                 550                 555                 560

Ile Lys Tyr Pro Val Gly Asn Val Val Leu Gly Lys Val Val Arg Phe
                565                 570                 575

Ala Asn Phe Gly Ala Phe Val Glu Leu Glu Pro Gly Val Asp Ala Leu
            580                 585                 590

Val His Ile Ser Gln Ile Ser His Lys Arg Ile Asp Lys Pro Glu Asp
        595                 600                 605

Val Leu Lys Ile Gly Gln Glu Ile Lys Ala Lys Ile Leu Glu Val Asn
    610                 615                 620

Lys Asp Ser Glu Lys Ile Ala Leu Ser Ile Lys Glu Val Asp Glu Ile
625                 630                 635                 640


<210> SEQ ID NO 15
<211> LENGTH: 882
<212> TYPE: DNA
<213> ORGANISM: Clostridium autoethanogenum

<400> SEQUENCE: 15

atggaaatta aaggtgtaat tgaaacatta agagaggaat tgaataaata cctctatgac      60

tatatggagg gaaaaggatc ttataataag agagtatatg aagctatgca gtatagctta     120

gatgcaggag gaaagagaat aagacctcta ctatttcttt tgacatataa actttataag     180

acagattgca atgaggttat ggatatagca gcagctatag aaatgataca cacttattcc     240

ttaattcatg atgatttacc tgctatggac aatgatgatt taagaagggg caaacctaca     300

aatcataagg tatttggaga agctattgct gtacttgcgg gagatggact tttaaatgaa     360

gcaatgagtc tgatgtttag acactgtatt gggaaaaagg ataacgctat aagggcttgt     420

agcattattt ctgaaagtgc aggagctgat gggatggttg gcggacagac agtggatatt     480

ttaagtgaaa acactaagat acctatagat cagctctatt acatgcacag taaaaaaacg     540

ggagcgctca taaaaggatc tataatatct gcagcagtat atgcgggagc aagtaaagct     600

gaaatagata aattaagcta ttatggagaa aagttaggat tggcatttca aataaaggat     660

gatatattgg atttaacagg agatactgct cttttaggta aaaagataaa aagtgatcta     720

aataataaca aaactacatt tataagtact tatggaataa ataaatgcaa agaaatgtgc     780

aattcaatta caagtgaatg tataggagta ctgaatggga tgagtgtaga tacttcttat     840

ctaaaagatt taacatcatt tttattaaat agagaaaagt ga                        882


<210> SEQ ID NO 16
<211> LENGTH: 293
<212> TYPE: PRT
<213> ORGANISM: Clostridium autoethanogenum

<400> SEQUENCE: 16

Met Glu Ile Lys Gly Val Ile Glu Thr Leu Arg Glu Glu Leu Asn Lys
1               5                   10                  15

Tyr Leu Tyr Asp Tyr Met Glu Gly Lys Gly Ser Tyr Asn Lys Arg Val
            20                  25                  30

Tyr Glu Ala Met Gln Tyr Ser Leu Asp Ala Gly Gly Lys Arg Ile Arg
```

```
        35                  40                  45

Pro Leu Leu Phe Leu Leu Thr Tyr Lys Leu Tyr Lys Thr Asp Cys Asn
    50                  55                  60

Glu Val Met Asp Ile Ala Ala Ala Ile Glu Met Ile His Thr Tyr Ser
65                  70                  75                  80

Leu Ile His Asp Asp Leu Pro Ala Met Asp Asn Asp Asp Leu Arg Arg
                85                  90                  95

Gly Lys Pro Thr Asn His Lys Val Phe Gly Glu Ala Ile Ala Val Leu
            100                 105                 110

Ala Gly Asp Gly Leu Leu Asn Glu Ala Met Ser Leu Met Phe Arg His
        115                 120                 125

Cys Ile Gly Lys Lys Asp Asn Ala Ile Arg Ala Cys Ser Ile Ile Ser
    130                 135                 140

Glu Ser Ala Gly Ala Asp Gly Met Val Gly Gly Gln Thr Val Asp Ile
145                 150                 155                 160

Leu Ser Glu Asn Thr Lys Ile Pro Ile Asp Gln Leu Tyr Tyr Met His
                165                 170                 175

Ser Lys Lys Thr Gly Ala Leu Ile Lys Gly Ser Ile Ile Ser Ala Ala
            180                 185                 190

Val Tyr Ala Gly Ala Ser Lys Ala Glu Ile Asp Lys Leu Ser Tyr Tyr
        195                 200                 205

Gly Glu Lys Leu Gly Leu Ala Phe Gln Ile Lys Asp Asp Ile Leu Asp
    210                 215                 220

Leu Thr Gly Asp Thr Ala Leu Leu Gly Lys Lys Ile Lys Ser Asp Leu
225                 230                 235                 240

Asn Asn Asn Lys Thr Thr Phe Ile Ser Thr Tyr Gly Ile Asn Lys Cys
                245                 250                 255

Lys Glu Met Cys Asn Ser Ile Thr Ser Glu Cys Ile Gly Val Leu Asn
            260                 265                 270

Gly Met Ser Val Asp Thr Ser Tyr Leu Lys Asp Leu Thr Ser Phe Leu
        275                 280                 285

Leu Asn Arg Glu Lys
    290
```

<210> SEQ ID NO 17
<211> LENGTH: 519
<212> TYPE: DNA
<213> ORGANISM: Clostridium autoethanogenum

<400> SEQUENCE: 17

```
atgaataaaa caaggaaaat ggttttttta agctttctaa caagtatggc tttagtcata      60

tacataatag aaactcaagt tccggtttta tttcccggaa taaaattagg acttgcaaat     120

acaatttccc tagctgcact tatacttata ggatggaaag aagccttact aattatgttt     180

ttaaggacgc ttctaggatc tatgtttggt gggacaatgt ctacctttat gttcagcata     240

gccggaggaa ttttaagtaa cattgttatg atccttctat acaaatattt taaaaattcc     300

ttaagtctat ggactataag catatgcggg gcaatatttc acaacatagg ccaactttta     360

gtagcttcta tagtaattca agattttagg atatacatat atctaccggt gcttttaatc     420

tctgctataa tcacaggata ctttataggt tggtgcgtga aattcctaac taataactta     480

tataaaattc ctatgtttaa agaattaaaa aataagtaa                            519
```

<210> SEQ ID NO 18
<211> LENGTH: 172

<212> TYPE: PRT
<213> ORGANISM: Clostridium autoethanogenum

<400> SEQUENCE: 18

```
Met Asn Lys Thr Arg Lys Met Val Phe Leu Ser Phe Leu Thr Ser Met
1               5                   10                  15

Ala Leu Val Ile Tyr Ile Ile Glu Thr Gln Val Pro Val Leu Phe Pro
            20                  25                  30

Gly Ile Lys Leu Gly Leu Ala Asn Thr Ile Ser Leu Ala Ala Leu Ile
        35                  40                  45

Leu Ile Gly Trp Lys Glu Ala Leu Leu Ile Met Phe Leu Arg Thr Leu
    50                  55                  60

Leu Gly Ser Met Phe Gly Gly Thr Met Ser Thr Phe Met Phe Ser Ile
65                  70                  75                  80

Ala Gly Gly Ile Leu Ser Asn Ile Val Met Ile Leu Leu Tyr Lys Tyr
                85                  90                  95

Phe Lys Asn Ser Leu Ser Leu Trp Thr Ile Ser Ile Cys Gly Ala Ile
            100                 105                 110

Phe His Asn Ile Gly Gln Leu Leu Val Ala Ser Ile Val Ile Gln Asp
        115                 120                 125

Phe Arg Ile Tyr Ile Tyr Leu Pro Val Leu Leu Ile Ser Ala Ile Ile
    130                 135                 140

Thr Gly Tyr Phe Ile Gly Trp Cys Val Lys Phe Leu Thr Asn Asn Leu
145                 150                 155                 160

Tyr Lys Ile Pro Met Phe Lys Glu Leu Lys Asn Lys
                165                 170
```

<210> SEQ ID NO 19
<211> LENGTH: 825
<212> TYPE: DNA
<213> ORGANISM: Clostridium autoethanogenum

<400> SEQUENCE: 19

```
atgaacttcg atggaatttc aattccaata ataaaagaac ttaatcaact tgagttagag      60

ttaaaaaata ttgcatcaaa attagattct actgttacac aagatatttt tacctacttt     120

ttttcaattc caggtaaaag actaagacct acattaacat ttttatctgc aggtgctatt     180

agtagcgagc ttacttcatc tgcaaaacac aacttaattc agttgtcaat aagcttagag     240

cttattcaca gcgctagtct aattcatgat gatatcatag atggtgactt actaagacgt     300

ggtcagaaaa ccttaaataa gacctttgga aataaaatag cagtacttgc cggtgatgct     360

ttgtactcaa gggcctttac tattttctca gatactctgc caagagaatt tgcgcaggta     420

atgggcagag ttactgaatc aatgtctgta gctgaaatat taaatgctaa caatccctct     480

cccgatcgtg aaacctattt taaaatcatc ttaggaaaaa cagcatcttt catgagcgct     540

tgttgtaggc ttggtggcag catagcttat gccccttacg aagagtctaa tatgctttct     600

aaatacggtg aaaaccttgg tatggcatat caaatactgg atgattatat cgatgaggat     660

cccgttgcaa tgaaaaatgt aactattgaa gagggatttg aatttgcata taatgccaaa     720

gcttctattg aaaatttaaa agactcagca tacaaacaaa gcttaataat gttagtagac     780

tatgttttag atttttatag tcctaaggta gagaatacat tatag                     825
```

<210> SEQ ID NO 20
<211> LENGTH: 274
<212> TYPE: PRT
<213> ORGANISM: Clostridium autoethanogenum

<400> SEQUENCE: 20

Met Asn Phe Asp Gly Ile Ser Ile Pro Ile Ile Lys Glu Leu Asn Gln
1 5 10 15

Leu Glu Leu Glu Leu Lys Asn Ile Ala Ser Lys Leu Asp Ser Thr Val
20 25 30

Thr Gln Asp Ile Phe Thr Tyr Phe Phe Ser Ile Pro Gly Lys Arg Leu
35 40 45

Arg Pro Thr Leu Thr Phe Leu Ser Ala Gly Ala Ile Ser Ser Glu Leu
50 55 60

Thr Ser Ser Ala Lys His Asn Leu Ile Gln Leu Ser Ile Ser Leu Glu
65 70 75 80

Leu Ile His Ser Ala Ser Leu Ile His Asp Asp Ile Ile Asp Gly Asp
85 90 95

Leu Leu Arg Arg Gly Gln Lys Thr Leu Asn Lys Thr Phe Gly Asn Lys
100 105 110

Ile Ala Val Leu Ala Gly Asp Ala Leu Tyr Ser Arg Ala Phe Thr Ile
115 120 125

Phe Ser Asp Thr Leu Pro Arg Glu Phe Ala Gln Val Met Gly Arg Val
130 135 140

Thr Glu Ser Met Ser Val Ala Glu Ile Leu Asn Ala Asn Asn Pro Ser
145 150 155 160

Pro Asp Arg Glu Thr Tyr Phe Lys Ile Ile Leu Gly Lys Thr Ala Ser
165 170 175

Phe Met Ser Ala Cys Cys Arg Leu Gly Gly Ser Ile Ala Tyr Ala Pro
180 185 190

Tyr Glu Glu Ser Asn Met Leu Ser Lys Tyr Gly Glu Asn Leu Gly Met
195 200 205

Ala Tyr Gln Ile Leu Asp Asp Tyr Ile Asp Glu Asp Pro Val Ala Met
210 215 220

Lys Asn Val Thr Ile Glu Glu Gly Phe Glu Phe Ala Tyr Asn Ala Lys
225 230 235 240

Ala Ser Ile Glu Asn Leu Lys Asp Ser Ala Tyr Lys Gln Ser Leu Ile
245 250 255

Met Leu Val Asp Tyr Val Leu Asp Phe Tyr Ser Pro Lys Val Glu Asn
260 265 270

Thr Leu

<210> SEQ ID NO 21
<211> LENGTH: 1797
<212> TYPE: DNA
<213> ORGANISM: Populus tremuloides

<400> SEQUENCE: 21
catatggcaa cagaattatt atgtttacac agacctatat cacttactca caaacttttt 60
aggaatccat tacctaaagt tattcaagct acacctttaa cattaaaact taggtgtagt 120
gtttctacag aaaatgtatc atttagtgag acagaaactg aaacaagaag atcagcaaat 180
tatgaaccaa attcttggga ttatgattat cttctttctt ctgatactga tgagtcaata 240
gaagtacata aagataaggc taagaaatta gaagctgaag ttaggagaga aataaataat 300
gagaaggctg aatttcttac acttcttgaa cttattgata atgtacaaag acttggatta 360
ggatatagat ttgagtctga tataagaaga gcattagata gatttgtaag tagtggagga 420
tttgatggag ttactaaaac ttcattacat ggaacagcat tatcatttag gttattaagg 480
caacatggtt ttgaagtatc tcaagaagct tttagtggat ttaaagatca gaatggaaac 540
tttcttgaga atttaaagga agacataaaa gcaattcttt ctctttatga agcatcattt 600
ttagcattag aaggtgagaa tatattagat gaggctaaag tatttgcaat atctcatctt 660
aaagaactta gtgaagaaaa gattggtaaa gaattagctg aacaagtttc acatgcttta 720
gaattaccat tacatagaag aacacaaaga ttagaagcag tttggtcaat agaagcatat 780
agaaagaaag aagacgcaaa tcaagtactt ttagaacttg caatacttga ctacaatatg 840
attcaaagtg tatatcagag ggatttaaga gaaacatcaa gatggtggag aagagtagga 900
ttagcaacta aattacattt tgctagagat aggcttattg aaagttttta ttgggctgtt 960
ggagttgctt ttgaaccaca atattctgat tgcagaaata gtgtagcaaa gatgttttca 1020
tttgttacta taattgacga tatttacgat gtatatggaa ctttagatga acttgaactt 1080
tttactgatg cagttgaaag atgggatgta aatgctatta atgatcttcc tgattatatg 1140
aagttatgtt ttcttgcact ttacaatact attaacgaga tagcttacga taacttaaaa 1200
gataaaggtg agaacatact tccttattta acaaaagcat gggcagattt atgtaatgca 1260
tttcttcaag aagctaagtg gctttataat aaatcaacac ctacatttga tgattatttt 1320
ggaaatgcat ggaaaagttc tagtggacct ttacagctta tttttgctta ttttgctgta 1380
gtacagaaca ttaaaaagga agagattgag aatcttcaga aatatcatga cataatatca 1440
agacctagtc acatttttag gctttgtaat gatttagcat ctgcttcagc agaaatagca 1500
agaggtgaaa ctgctaattc tgtaagttgt tatatgagaa caaaaggtat atctgaagaa 1560
ttagctactg aaagtgttat gaatcttata gacgaaactt ggaagaaaat gaacaaagaa 1620
aaacttggtg gatctttatt tgcaaaacct tttgttgaga ctgctataaa tttagctaga 1680
cagtctcatt gcacatatca taatggtgat gcacatacta gtccagatga attaactagg 1740
aaaagagtac ttagtgtaat aactgaacca atattaccat ttgaaagata agaattc 1797

<210> SEQ ID NO 22
<211> LENGTH: 617
<212> TYPE: DNA
<213> ORGANISM: Clostridium autoethanogenum

<400> SEQUENCE: 22
ggttaatgtt aaaaatttat agtataactt taaaaaactg tcttaaaaag ttgttatata 60
aaaaatgttg acaattaaac agctatttag tgcaaaacaa ccataaaaat ttaaaaaata 120
ccataaatta cttgaaaaat agttgataat aatgtagagt tataaacaaa ggtgaaaagc 180
attacttgta ttcttttta tatattatta taaattaaaa tgaagctgta ttagaaaaaa 240
tacacacctg taatataaaa ttttaaatta atttttaatt ttttcaaaat gtattttaca 300
tgtttagaat tttgatgtat attaaaatag tagaatacat aagatactta atttaattaa 360
agatagttaa gtacttttca atgtgctttt ttagatgttt aatacaaatc tttaattgta 420
aaagaaatgc tgtactattt actgtactag tgacgggatt aaactgtatt aattataaat 480
aaaaaataag tacagttgtt taaaattata ttttgtatta aatctaatag tacgatgtaa 540
gttattttat actattgcta gtttaataaa aagatttaat tatatacttg aaaaggagag 600
gaatttttat gcgtaaa 617

<210> SEQ ID NO 23
<211> LENGTH: 30
<212> TYPE: DNA

<213> ORGANISM: Artificial Sequence
<220> FEATURE:
<223> OTHER INFORMATION: oligonucleotide Ppfor-NotI-F

<400> SEQUENCE: 23
aagcggccgc aaaatagttg ataataatgc 30

<210> SEQ ID NO 24
<211> LENGTH: 30
<212> TYPE: DNA
<213> ORGANISM: Artificial Sequence
<220> FEATURE:
<223> OTHER INFORMATION: oligonucleotide Ppfor-NdeI-R

<400> SEQUENCE: 24
tacgcatatg aattcctctc cttttcaagc 30

<210> SEQ ID NO 25
<211> LENGTH: 5345
<212> TYPE: DNA
<213> ORGANISM: Artificial Sequence
<220> FEATURE:
<223> OTHER INFORMATION: plasmid pMTL 85146-ispS

<400> SEQUENCE: 25
aattcgagct cggtacccgg ggatcctcta gagtcgacgt cacgcgtcca tggagatctc 60
gaggcctgca gacatgcaag cttggcactg gccgtcgttt tacaacgtcg tgactgggaa 120
aaccctggcg ttacccaact taatcgcctt gcagcacatc ccccttcgc cagctggcgt 180 aatagcgaag aggcccgcac cgatcgccct tcccaacagt tgcgcagcct gaatggcgaa 240
tggcgctagc ataaaaataa gaagcctgca tttgcaggct tcttattttt atggcgcgcc 300
gcattcactt cttttctata taaatatgag cgaagcgaat aagcgtcgga aaagcagcaa 360
aaagtttcct ttttgctgtt ggagcatggg ggttcagggg gtgcagtatc tgacgtcaat 420
gccgagcgaa agcgagccga agggtagcat ttacgttaga taaccccctg atatgctccg 480
acgctttata tagaaaagaa gattcaacta ggtaaaatct taatataggt tgagatgata 540
aggtttataa ggaatttgtt tgttctaatt tttcactcat tttgttctaa tttcttttaa 600
caaatgttct ttttttttta gaacagttat gatatagtta gaatagttta aaataaggag 660
tgagaaaaag atgaaagaaa gatatggaac agtctataaa ggctctcaga ggctcataga 720
cgaagaaagt ggagaagtca tagaggtaga caagttatac cgtaaacaaa cgtctggtaa 780
cttcgtaaag gcatatatag tgcaattaat aagtatgtta gatatgattg gcggaaaaaa 840
acttaaaatc gttaactata tcctagataa tgtccactta agtaacaata caatgatagc 900
tacaacaaga gaaatagcaa aagctacagg aacaagtcta caaacagtaa taacaacact 960
taaaatctta gaagaaggaa atattataaa aagaaaaact ggagtattaa tgttaaaccc 1020
tgaactacta atgagaggcg acgaccaaaa acaaaaatac ctcttactcg aatttgggaa 1080
ctttgagcaa gaggcaaatg aaatagattg acctcccaat aacaccacgt agttattggg 1140
aggtcaatct atgaaatgcg attaagggcc ggccagtggg caagttgaaa aattcacaaa 1200
aatgtggtat aatatctttg ttcattagag cgataaactt gaatttgaga gggaacttag 1260
atggtatttg aaaaaattga taaaaatagt tggaacagaa aagagtattt tgaccactac 1320
tttgcaagtg taccttgtac ctacagcatg accgttaaag tggatatcac acaaataaag 1380
gaaaagggaa tgaaactata tcctgcaatg ctttattata ttgcaatgat tgtaaaccgc 1440
cattcagagt ttaggacggc aatcaatcaa gatggtgaat tggggatata tgatgagatg 1500

```
ataccaagct atacaatatt tcacaatgat actgaaacat tttccagcct ttggactgag   1560
tgtaagtctg actttaaatc atttttagca gattatgaaa gtgatacgca acggtatgga   1620
aacaatcata gaatggaagg aaagccaaat gctccggaaa acatttttaa tgtatctatg   1680
ataccgtggt caaccttcga tggctttaat ctgaatttgc agaaaggata tgattatttg   1740
attcctattt ttactatggg gaaatattat aaagaagata acaaaattat acttcctttg   1800
gcaattcaag ttcatcacgc agtatgtgac ggatttcaca tttgccgttt tgtaaacgaa   1860
ttgcaggaat tgataaatag ttaacttcag gtttgtctgt aactaaaaac aagtatttaa   1920
gcaaaaacat cgtagaaata cggtgttttt tgttacccta agtttaaact cctttttgat   1980
aatctcatga ccaaaatccc ttaacgtgag ttttcgttcc actgagcgtc agaccccgta   2040
gaaaagatca aaggatcttc ttgagatcct ttttttctgc gcgtaatctg ctgcttgcaa   2100
acaaaaaaac caccgctacc agcggtggtt tgtttgccgg atcaagagct accaactctt   2160
tttccgaagg taactggctt cagcagagcg cagataccaa atactgttct tctagtgtag   2220
ccgtagttag gccaccactt caagaactct gtagcaccgc ctacatacct cgctctgcta   2280
atcctgttac cagtggctgc tgccagtggc gataagtcgt gtcttaccgg gttggactca   2340
agacgatagt taccggataa ggcgcagcgg tcgggctgaa cggggggttc gtgcacacag   2400
cccagcttgg agcgaacgac ctacaccgaa ctgagatacc tacagcgtga gctatgagaa   2460
agcgccacgc ttcccgaagg gagaaaggcg gacaggtatc cggtaagcgg cagggtcgga   2520
acaggagagc gcacgaggga gcttccaggg ggaaacgcct ggtatcttta tagtcctgtc   2580
gggtttcgcc acctctgact tgagcgtcga tttttgtgat gctcgtcagg ggggcggagc   2640
ctatggaaaa acgccagcaa cgcggccttt ttacggttcc tggccttttg ctggcctttt   2700
gctcacatgt tctttcctgc gttatcccct gattctgtgg ataaccgtat taccgccttt   2760
gagtgagctg ataccgctcg ccgcagccga acgaccgagc gcagcgagtc agtgagcgag   2820
gaagcggaag agcgcccaat acgcagggcc ccctgcagga taaaaaaatt gtagataaat   2880
tttataaaat agttttatct acaatttttt tatcaggaaa cagctatgac cgcggccgcg   2940
gttaatgtta aaaatttata gtataacttt aaaaaactgt cttaaaaagt tgttatataa   3000
aaaatgttga caattaaaca gctatttagt gcaaaacaac cataaaaatt taaaaaatac   3060
cataaattac ttgaaaaata gttgataata atgtagagtt ataaacaaag gtgaaaagca   3120
ttacttgtat tctttttat atattattat aaattaaaat gaagctgtat tagaaaaaat   3180
acacacctgt aatataaaat tttaaattaa tttttaattt tttcaaaatg tattttacat   3240
gtttagaatt ttgatgtata ttaaaatagt agaatacata agatacttaa tttaattaaa   3300
gatagttaag tacttttcaa tgtgcttttt tagatgttta atacaaatct ttaattgtaa   3360
aagaaatgct gtactattta ctgtactagt gacgggatta aactgtatta attataaata   3420
aaaaataagt acagttgttt aaaattatat tttgtattaa atctaatagt acgatgtaag   3480
ttattttata ctattgctag tttaataaaa agatttaatt atatacttga aaaggagagg   3540
aatttttatg cgtcatatgg caacagaatt attatgttta cacagaccta tatcacttac   3600
tcacaaactt tttaggaatc cattacctaa agttattcaa gctacacctt taacattaaa   3660
acttaggtgt agtgtttcta cagaaaatgt atcatttagt gagacagaaa ctgaaacaag   3720
aagatcagca aattatgaac caaattcttg ggattatgat tatcttcttt cttctgatac   3780
tgatgagtca atagaagtac ataaagataa ggctaagaaa ttagaagctg aagttaggag   3840
```

-continued

```
agaaataaat aatgagaagg ctgaatttct tacacttctt gaacttattg ataatgtaca   3900

aagacttgga ttaggatata gatttgagtc tgatataaga agagcattag atagatttgt   3960

aagtagtgga ggatttgatg gagttactaa aacttcatta catggaacag cattatcatt   4020

taggttatta aggcaacatg gttttgaagt atctcaagaa gcttttagtg gatttaaaga   4080

tcagaatgga aactttcttg agaatttaaa ggaagacata aaagcaattc tttctcttta   4140

tgaagcatca tttttagcat tagaaggtga gaatatatta gatgaggcta aagtatttgc   4200

aatatctcat cttaaagaac ttagtgaaga aaagattggt aaagaattag ctgaacaagt   4260

ttcacatgct ttagaattac cattacatag aagaacacaa agattagaag cagtttggtc   4320

aatagaagca tatagaaaga aagaagacgc aaatcaagta cttttagaac ttgcaatact   4380

tgactacaat atgattcaaa gtgtatatca gagggattta agagaaacat caagatggtg   4440

gagaagagta ggattagcaa ctaaattaca ttttgctaga gataggctta ttgaaagttt   4500

ttattgggct gttggagttg cttttgaacc acaatattct gattgcagaa atagtgtagc   4560

aaagatgttt tcatttgtta ctataattga cgatatttac gatgtatatg gaactttaga   4620

tgaacttgaa ctttttactg atgcagttga aagatgggat gtaaatgcta ttaatgatct   4680

tcctgattat atgaagttat gttttcttgc actttacaat actattaacg agatagctta   4740

cgataactta aaagataaag gtgagaacat acttccttat ttaacaaaag catgggcaga   4800

tttatgtaat gcatttcttc aagaagctaa gtggctttat aataaatcaa cacctacatt   4860

tgatgattat tttggaaatg catggaaaag ttctagtgga cctttacagc ttatttttgc   4920

ttattttgct gtagtacaga acattaaaaa ggaagagatt gagaatcttc agaaatatca   4980

tgacataata tcaagaccta gtcacatttt taggctttgt aatgatttag catctgcttc   5040

agcagaaata gcaagaggtg aaactgctaa ttctgtaagt tgttatatga gaacaaaagg   5100

tatatctgaa gaattagcta ctgaaagtgt tatgaatctt atagacgaaa cttggaagaa   5160

aatgaacaaa gaaaaacttg gtggatcttt atttgcaaaa ccttttgttg agactgctat   5220

aaatttagct agacagtctc attgcacata tcataatggt gatgcacata ctagtccaga   5280

tgaattaact aggaaaagag tacttagtgt aataactgaa ccaatattac catttgaaag   5340

ataag                                                               5345
```

<210> SEQ ID NO 26
<211> LENGTH: 26
<212> TYPE: DNA
<213> ORGANISM: Artificial Sequence
<220> FEATURE:
<223> OTHER INFORMATION: Oligonucleotide Idi-Cbei-SacI-F

<400> SEQUENCE: 26

```
gtgagctcga aaggggaaat taaatg                                          26
```

<210> SEQ ID NO 27
<211> LENGTH: 27
<212> TYPE: DNA
<213> ORGANISM: Artificial Sequence
<220> FEATURE:
<223> OTHER INFORMATION: Oligonucleotide Idi-Cbei-KpnI-R

<400> SEQUENCE: 27

```
atggtacccc aaatctttat ttagacg                                         27
```

<210> SEQ ID NO 28
<211> LENGTH: 5905

-continued

<212> TYPE: DNA
<213> ORGANISM: Artificial Sequence
<220> FEATURE:
<223> OTHER INFORMATION: plasmid pMTL85246-ispS-idi

<400> SEQUENCE: 28

```
ccggggatcc tctagagtcg acgtcacgcg tccatggaga tctcgaggcc tgcagacatg     60

caagcttggc actggccgtc gttttacaac gtcgtgactg ggaaaaccct ggcgttaccc    120

aacttaatcg ccttgcagca catccccctt tcgccagctg gcgtaatagc gaagaggccc    180

gcaccgatcg cccttcccaa cagttgcgca gcctgaatgg cgaatggcgc tagcataaaa    240

ataagaagcc tgcatttgca ggcttcttat ttttatggcg cgccgcattc acttcttttc    300

tatataaata tgagcgaagc gaataagcgt cggaaaagca gcaaaaagtt tcctttttgc    360

tgttggagca tgggggttca gggggtgcag tatctgacgt caatgccgag cgaaagcgag    420

ccgaagggta gcatttacgt tagataaccc cctgatatgc tccgacgctt tatatagaaa    480

agaagattca actaggtaaa atcttaatat aggttgagat gataaggttt ataaggaatt    540

tgtttgttct aatttttcac tcattttgtt ctaatttctt ttaacaaatg ttcttttttt    600

tttagaacag ttatgatata gttagaatag tttaaaataa ggagtgagaa aaagatgaaa    660

gaaagatatg gaacagtcta taaaggctct cagaggctca tagacgaaga aagtggagaa    720

gtcatagagg tagacaagtt ataccgtaaa caaacgtctg gtaacttcgt aaaggcatat    780

atagtgcaat taataagtat gttagatatg attggcggaa aaaaacttaa aatcgttaac    840

tatatcctag ataatgtcca cttaagtaac aatacaatga tagctacaac aagagaaata    900

gcaaaagcta caggaacaag tctacaaaca gtaataacaa cacttaaaat cttagaagaa    960

ggaaatatta taaaaagaaa aactggagta ttaatgttaa accctgaact actaatgaga   1020

ggcgacgacc aaaaacaaaa atacctctta ctcgaatttg ggaactttga gcaagaggca   1080

aatgaaatag attgacctcc caataacacc acgtagttat tgggaggtca atctatgaaa   1140

tgcgattaag ggccggccag tgggcaagtt gaaaaattca caaaaatgtg gtataatatc   1200

tttgttcatt agagcgataa acttgaattt gagagggaac ttagatggta tttgaaaaaa   1260

ttgataaaaa tagttggaac agaaaagagt attttgacca ctactttgca agtgtacctt   1320

gtacctacag catgaccgtt aaagtggata tcacacaaat aaaggaaaag ggaatgaaac   1380

tatatcctgc aatgctttat tatattgcaa tgattgtaaa ccgccattca gagtttagga   1440

cggcaatcaa tcaagatggt gaattgggga tatatgatga gatgatacca agctatacaa   1500

tatttcacaa tgatactgaa acattttcca gcctttggac tgagtgtaag tctgacttta   1560

aatcattttt agcagattat gaaagtgata cgcaacggta tggaaacaat catagaatgg   1620

aaggaaagcc aaatgctccg gaaaacattt ttaatgtatc tatgataccg tggtcaacct   1680

tcgatggctt taatctgaat ttgcagaaag gatatgatta tttgattcct atttttacta   1740

tggggaaata ttataaagaa gataacaaaa ttatacttcc tttggcaatt caagttcatc   1800

acgcagtatg tgacggattt cacatttgcc gttttgtaaa cgaattgcag gaattgataa   1860

atagttaact tcaggtttgt ctgtaactaa aaacaagtat ttaagcaaaa acatcgtaga   1920

aatacggtgt tttttgttac cctaagttta aactcctttt tgataatctc atgaccaaaa   1980

tcccttaacg tgagttttcg ttccactgag cgtcagaccc cgtagaaaag atcaaaggat   2040

cttcttgaga tccttttttt ctgcgcgtaa tctgctgctt gcaaacaaaa aaaccaccgc   2100

taccagcggt ggtttgtttg ccggatcaag agctaccaac tctttttccg aaggtaactg   2160
```

-continued

```
gcttcagcag agcgcagata ccaaatactg ttcttctagt gtagccgtag ttaggccacc   2220
acttcaagaa ctctgtagca ccgcctacat acctcgctct gctaatcctg ttaccagtgg   2280
ctgctgccag tggcgataag tcgtgtctta ccgggttgga ctcaagacga tagttaccgg   2340
ataaggcgca gcggtcgggc tgaacggggg gttcgtgcac acagcccagc ttggagcgaa   2400
cgacctacac cgaactgaga tacctacagc gtgagctatg agaaagcgcc acgcttcccg   2460
aagggagaaa ggcggacagg tatccggtaa gcggcagggt cggaacagga gagcgcacga   2520
gggagcttcc agggggaaac gcctggtatc tttatagtcc tgtcgggttt cgccacctct   2580
gacttgagcg tcgatttttg tgatgctcgt caggggggcg gagcctatgg aaaaacgcca   2640
gcaacgcggc ctttttacgg ttcctggcct tttgctggcc ttttgctcac atgttctttc   2700
ctgcgttatc ccctgattct gtggataacc gtattaccgc ctttgagtga gctgataccg   2760
ctcgccgcag ccgaacgacc gagcgcagcg agtcagtgag cgaggaagcg gaagagcgcc   2820
caatacgcag ggcccccctgc aggataaaaa aattgtagat aaattttata aaatagtttt   2880
atctacaatt tttttatcag gaaacagcta tgaccgcggc cgcggttaat gttaaaaatt   2940
tatagtataa ctttaaaaaa ctgtcttaaa aagttgttat ataaaaaatg ttgacaatta   3000
aacagctatt tagtgcaaaa caaccataaa aatttaaaaa ataccataaa ttacttgaaa   3060
aatagttgat aataatgtag agttataaac aaaggtgaaa agcattactt gtattctttt   3120
ttatatatta ttataaatta aaatgaagct gtattagaaa aaatacacac ctgtaatata   3180
aaattttaaa ttaattttta attttttcaa aatgtatttt acatgtttag aattttgatg   3240
tatattaaaa tagtagaata cataagatac ttaatttaat taaagatagt taagtacttt   3300
tcaatgtgct tttttagatg tttaatacaa atctttaatt gtaaaagaaa tgctgtacta   3360
tttactgtac tagtgacggg attaaactgt attaattata aataaaaaat aagtacagtt   3420
gtttaaaatt atattttgta ttaaatctaa tagtacgatg taagttattt tatactattg   3480
ctagtttaat aaaaagattt aattatatac ttgaaaagga gaggaatttt tatgcgtcat   3540
atggcaacag aattattatg tttacacaga cctatatcac ttactcacaa actttttagg   3600
aatccattac ctaaagttat tcaagctaca cctttaacat taaaacttag gtgtagtgtt   3660
tctacagaaa atgtatcatt tagtgagaca gaaactgaaa caagaagatc agcaaattat   3720
gaaccaaatt cttgggatta tgattatctt ctttcttctg atactgatga gtcaatagaa   3780
gtacataaag ataaggctaa gaaattagaa gctgaagtta ggagagaaat aaataatgag   3840
aaggctgaat ttcttacact tcttgaactt attgataatg tacaaagact tggattagga   3900
tatagatttg agtctgatat aagaagagca ttagatagat ttgtaagtag tggaggattt   3960
gatggagtta ctaaaacttc attacatgga acagcattat catttaggtt attaaggcaa   4020
catggttttg aagtatctca agaagctttt agtggattta aagatcagaa tggaaacttt   4080
cttgagaatt taaaggaaga cataaaagca attctttctc tttatgaagc atcattttta   4140
gcattagaag gtgagaatat attagatgag gctaaagtat ttgcaatatc tcatcttaaa   4200
gaacttagtg aagaaaagat tggtaaagaa ttagctgaac aagtttcaca tgctttagaa   4260
ttaccattac atagaagaac acaaagatta gaagcagttt ggtcaataga agcatataga   4320
aagaaagaag acgcaaatca agtactttta gaacttgcaa tacttgacta caatatgatt   4380
caaagtgtat atcagaggga tttaagagaa acatcaagat ggtggagaag agtaggatta   4440
gcaactaaat tacattttgc tagagatagg cttattgaaa gtttttattg ggctgttgga   4500
gttgcttttg aaccacaata ttctgattgc agaaatagtg tagcaaagat gttttcattt   4560
```

gttactataa ttgacgatat ttacgatgta tatggaactt tagatgaact tgaacttttt 4620
actgatgcag ttgaaagatg ggatgtaaat gctattaatg atcttcctga ttatatgaag 4680
ttatgttttc ttgcacttta caatactatt aacgagatag cttacgataa cttaaaagat 4740
aaaggtgaga acatacttcc ttatttaaca aaagcatggg cagatttatg taatgcattt 4800
cttcaagaag ctaagtggct ttataataaa tcaacaccta catttgatga ttattttgga 4860
aatgcatgga aaagttctag tggaccttta cagcttattt ttgcttattt tgctgtagta 4920
cagaacatta aaaaggaaga gattgagaat cttcagaaat atcatgacat aatatcaaga 4980
cctagtcaca tttttaggct ttgtaatgat ttagcatctg cttcagcaga aatagcaaga 5040
ggtgaaactg ctaattctgt aagttgttat atgagaacaa aaggtatatc tgaagaatta 5100
gctactgaaa gtgttatgaa tcttatagac gaaacttgga agaaaatgaa caaagaaaaa 5160
cttggtggat ctttatttgc aaaacctttt gttgagactg ctataaattt agctagacag 5220
tctcattgca catatcataa tggtgatgca catactagtc cagatgaatt aactaggaaa 5280
agagtactta gtgtaataac tgaaccaata ttaccatttg aaagataaga attcgagctc 5340
gaaaggggaa attaaatggc agaatatata atagctgtag atgaatttga taacgaaata 5400
ggttcaattg aaaaaatgga ggctcaccgt aaaggaacat tacatagagc tttttctata 5460
ttagtattta attctaaaaa tcaattgtta ttacagaaaa gaaatgtaaa aaaatatcat 5520
tcgcctggtc tctggacaaa tacgtgctgt agtcatccaa gatacggtga aagtttacat 5580
gatgcgattt atagaaggct taaggaagaa atgggtttta catgtgaact tgaagaagta 5640
tttagtttta tttataaagt aaaacttgaa gataatcttt ttgaaaatga atatgatcat 5700
gtattcattg ggaaatatga tggagaaata attgtaaaca aagatgaagt agatgatttt 5760
aagtgggttg atattaatga ggttaagaag gatattatag aaaggccaga agcatacact 5820
tattggttca agtatttagt taataaggca gaaaacaaaa tatttaaata agtaagaatt 5880
tcgtctaaat aaagatttgg ggtac 5905

<210> SEQ ID NO 29
<211> LENGTH: 29
<212> TYPE: DNA
<213> ORGANISM: Artificial Sequence
<220> FEATURE:
<223> OTHER INFORMATION: Oligonucleotide Dxs-SalI-F

<400> SEQUENCE: 29
gcagtcgact ttattaaagg gatagataa 29

<210> SEQ ID NO 30
<211> LENGTH: 31
<212> TYPE: DNA
<213> ORGANISM: Artificial Sequence
<220> FEATURE:
<223> OTHER INFORMATION: Oligonucleotide Dxs-XhoI-R

<400> SEQUENCE: 30
tgctcgagtt aaaatatatg acttacctct g 31

<210> SEQ ID NO 31
<211> LENGTH: 7784
<212> TYPE: DNA
<213> ORGANISM: Artificial Sequence
<220> FEATURE:
<223> OTHER INFORMATION: plasmid pMTL85246-ispS-idi-dxs

<400> SEQUENCE: 31
tcgaggcctg cagacatgca agcttggcac tggccgtcgt tttacaacgt cgtgactggg 60
aaaaccctgg cgttacccaa cttaatcgcc ttgcagcaca tccccctttc gccagctggc 120
gtaatagcga agaggcccgc accgatcgcc cttcccaaca gttgcgcagc ctgaatggcg 180
aatggcgcta gcataaaaat aagaagcctg catttgcagg cttcttattt ttatggcgcg 240
ccgcattcac ttcttttcta tataaatatg agcgaagcga ataagcgtcg gaaaagcagc 300
aaaaagtttc ctttttgctg ttggagcatg ggggttcagg gggtgcagta tctgacgtca 360
atgccgagcg aaagcgagcc gaagggtagc atttacgtta gataaccccc tgatatgctc 420
cgacgcttta tatagaaaag aagattcaac taggtaaaat cttaatatag gttgagatga 480
taaggtttat aaggaatttg tttgttctaa tttttcactc attttgttct aatttctttt 540
aacaaatgtt cttttttttt tagaacagtt atgatatagt tagaatagtt taaaataagg 600
agtgagaaaa agatgaaaga aagatatgga acagtctata aaggctctca gaggctcata 660
gacgaagaaa gtggagaagt catagaggta gacaagttat accgtaaaca aacgtctggt 720
aacttcgtaa aggcatatat agtgcaatta ataagtatgt tagatatgat tggcggaaaa 780
aaacttaaaa tcgttaacta tatcctagat aatgtccact taagtaacaa tacaatgata 840
gctacaacaa gagaaatagc aaaagctaca ggaacaagtc tacaaacagt aataacaaca 900
cttaaaatct tagaagaagg aaatattata aaaagaaaaa ctggagtatt aatgttaaac 960
cctgaactac taatgagagg cgacgaccaa aaacaaaaat acctcttact cgaatttggg 1020
aactttgagc aagaggcaaa tgaaatagat tgacctccca ataacaccac gtagttattg 1080
ggaggtcaat ctatgaaatg cgattaaggg ccggccagtg ggcaagttga aaaattcaca 1140
aaaatgtggt ataatatctt tgttcattag agcgataaac ttgaatttga gagggaactt 1200
agatggtatt tgaaaaaatt gataaaaata gttggaacag aaaagagtat tttgaccact 1260
actttgcaag tgtaccttgt acctacagca tgaccgttaa agtggatatc acacaaataa 1320
aggaaaaggg aatgaaacta tatcctgcaa tgctttatta tattgcaatg attgtaaacc 1380
gccattcaga gtttaggacg gcaatcaatc aagatggtga attggggata tatgatgaga 1440
tgataccaag ctatacaata tttcacaatg atactgaaac attttccagc ctttggactg 1500
agtgtaagtc tgactttaaa tcatttttag cagattatga aagtgatacg caacggtatg 1560
gaaacaatca tagaatggaa ggaaagccaa atgctccgga aaacattttt aatgtatcta 1620
tgataccgtg gtcaaccttc gatggcttta atctgaattt gcagaaagga tatgattatt 1680
tgattcctat ttttactatg ggaaatattt ataaagaaga taacaaaatt atacttcctt 1740
tggcaattca agttcatcac gcagtatgtg acggatttca catttgccgt tttgtaaacg 1800
aattgcagga attgataaat agttaacttc aggtttgtct gtaactaaaa acaagtattt 1860
aagcaaaaac atcgtagaaa tacggtgttt tttgttaccc taagtttaaa ctccttttg 1920
ataatctcat gaccaaaatc ccttaacgtg agttttcgtt ccactgagcg tcagaccccg 1980
tagaaaagat caaaggatct tcttgagatc cttttttct gcgcgtaatc tgctgcttgc 2040
aaacaaaaaa accaccgcta ccagcggtgg tttgtttgcc ggatcaagag ctaccaactc 2100
tttttccgaa ggtaactggc ttcagcagag cgcagatacc aaatactgtt cttctagtgt 2160
agccgtagtt aggccaccac ttcaagaact ctgtagcacc gcctacatac ctcgctctgc 2220
taatcctgtt accagtggct gctgccagtg gcgataagtc gtgtcttacc gggttggact 2280
caagacgata gttaccggat aaggcgcagc ggtcgggctg aacgggggt tcgtgcacac 2340

-continued

```
agcccagctt ggagcgaacg acctacaccg aactgagata cctacagcgt gagctatgag   2400
aaagcgccac gcttcccgaa gggagaaagg cggacaggta tccggtaagc ggcagggtcg   2460
gaacaggaga gcgcacgagg gagcttccag gggaaacgc ctggtatctt tatagtcctg   2520
tcgggtttcg ccacctctga cttgagcgtc gatttttgtg atgctcgtca ggggggcgga   2580
gcctatggaa aaacgccagc aacgcggcct ttttacggtt cctggccttt tgctggcctt   2640
ttgctcacat gttctttcct gcgttatccc ctgattctgt ggataaccgt attaccgcct   2700
ttgagtgagc tgataccgct cgccgcagcc gaacgaccga gcgcagcgag tcagtgagcg   2760
aggaagcgga agagcgccca atacgcaggg cccccctgcag gataaaaaaa ttgtagataa   2820
attttataaa atagttttat ctacaatttt tttatcagga aacagctatg accgcggccg   2880
cggttaatgt taaaaattta tagtataact ttaaaaaact gtcttaaaaa gttgttatat   2940
aaaaaatgtt gacaattaaa cagctattta gtgcaaaaca accataaaaa tttaaaaaat   3000
accataaatt acttgaaaaa tagttgataa taatgtagag ttataaacaa aggtgaaaag   3060
cattacttgt attctttttt atatattatt ataaattaaa atgaagctgt attagaaaaa   3120
atacacacct gtaatataaa attttaaatt aatttttaat tttttcaaaa tgtattttac   3180
atgtttagaa ttttgatgta tattaaaata gtagaataca taagatactt aatttaatta   3240
aagatagtta agtacttttc aatgtgcttt tttagatgtt taatacaaat ctttaattgt   3300
aaaagaaatg ctgtactatt tactgtacta gtgacgggat taaactgtat taattataaa   3360
taaaaaataa gtacagttgt ttaaaattat attttgtatt aaatctaata gtacgatgta   3420
agttatttta tactattgct agtttaataa aaagatttaa ttatatactt gaaaaggaga   3480
ggaattttta tgcgtcatat ggcaacagaa ttattatgtt tacacagacc tatatcactt   3540
actcacaaac tttttaggaa tccattacct aaagttattc aagctacacc tttaacatta   3600
aaacttaggt gtagtgtttc tacagaaaat gtatcattta gtgagacaga aactgaaaca   3660
agaagatcag caaattatga accaaattct tgggattatg attatcttct ttcttctgat   3720
actgatgagt caatagaagt acataaagat aaggctaaga aattagaagc tgaagttagg   3780
agagaaataa ataatgagaa ggctgaattt cttacacttc ttgaacttat tgataatgta   3840
caaagacttg gattaggata tagatttgag tctgatataa gaagagcatt agatagattt   3900
gtaagtagtg gaggatttga tggagttact aaaacttcat tacatggaac agcattatca   3960
tttaggttat taaggcaaca tggttttgaa gtatctcaag aagcttttag tggatttaaa   4020
gatcagaatg gaaactttct tgagaattta aaggaagaca taaaagcaat tctttctctt   4080
tatgaagcat catttttagc attagaaggt gagaatatat tagatgaggc taaagtattt   4140
gcaatatctc atcttaaaga acttagtgaa gaaaagattg gtaaagaatt agctgaacaa   4200
gtttcacatg ctttagaatt accattacat agaagaacac aaagattaga agcagtttgg   4260
tcaatagaag catatagaaa gaaagaagac gcaaatcaag tacttttaga acttgcaata   4320
cttgactaca atatgattca aagtgtatat cagagggatt taagagaaac atcaagatgg   4380
tggagaagag taggattagc aactaaatta cattttgcta gagataggct tattgaaagt   4440
ttttattggg ctgttggagt tgcttttgaa ccacaatatt ctgattgcag aaatagtgta   4500
gcaaagatgt tttcatttgt tactataatt gacgatattt acgatgtata tggaacttta   4560
gatgaacttg aactttttac tgatgcagtt gaaagatggg atgtaaatgc tattaatgat   4620
cttcctgatt atatgaagtt atgttttctt gcactttaca atactattaa cgagatagct   4680
```

-continued

```
tacgataact taaaagataa aggtgagaac atacttcctt atttaacaaa agcatgggca   4740
gatttatgta atgcatttct tcaagaagct aagtggcttt ataataaatc aacacctaca   4800
tttgatgatt attttggaaa tgcatggaaa agttctagtg gacctttaca gcttattttt   4860
gcttattttg ctgtagtaca gaacattaaa aaggaagaga ttgagaatct tcagaaatat   4920
catgacataa tatcaagacc tagtcacatt tttaggcttt gtaatgattt agcatctgct   4980
tcagcagaaa tagcaagagg tgaaactgct aattctgtaa gttgttatat gagaacaaaa   5040
ggtatatctg aagaattagc tactgaaagt gttatgaatc ttatagacga aacttggaag   5100
aaaatgaaca aagaaaaact tggtggatct ttatttgcaa aacctttttgt tgagactgct   5160
ataaatttag ctagacagtc tcattgcaca tatcataatg gtgatgcaca tactagtcca   5220
gatgaattaa ctaggaaaag agtacttagt gtaataactg aaccaatatt accatttgaa   5280
agataagaat tcgagctcga aaggggaaat taaatggcag aatatataat agctgtagat   5340
gaatttgata acgaaatagg ttcaattgaa aaaatggagg ctcaccgtaa aggaacatta   5400
catagagctt tttctatatt agtatttaat tctaaaaatc aattgttatt acagaaaaga   5460
aatgtaaaaa aatatcattc gcctggtctc tggacaaata cgtgctgtag tcatccaaga   5520
tacggtgaaa gtttacatga tgcgatttat agaaggctta aggaagaaat gggttttaca   5580
tgtgaacttg aagaagtatt tagttttatt tataaagtaa aacttgaaga taatcttttt   5640
gaaaatgaat atgatcatgt attcattggg aaatatgatg gagaaataat tgtaaacaaa   5700
gatgaagtag atgattttaa gtgggttgat attaatgagg ttaagaagga tattatagaa   5760
aggccagaag catacactta ttggttcaag tatttagtta ataaggcaga aaacaaaata   5820
tttaaataag taagaatttc gtctaaataa agatttgggg tacccgggga tcctctagag   5880
tcgactttat taaagggata gataaggatg agtaatttat tagataatta taaagatata   5940
aatgacgtaa agaagatgtc gttaaatgat aaaaaaaagc tagctagaga aattagaaaa   6000
tttttaatag acaaagtatc taagacagga ggtcatttgg cgtctaactt aggggttgtg   6060
gagctcactt tgagtttatt tagtgtattt gatctaaatt atgataaact tatatgggat   6120
gtgggacatc aggcttatgt gcataaaatc ctcacgggaa gaaaggataa atttgatact   6180
ttaaggcaat ttggaggatt aagtggattt cctaaaaggt gcgaaagtat atatgatttt   6240
ttcgaaacag ggcatagtag tacttcaata tctgcagcac ttggaatggc tagggctaga   6300
gatttaaagc atgagaaata taatgttgtt gcagttatag gagatggagc acttactgga   6360
ggtatggcac tagaggccct aaatgatgta ggttatagaa aaactaagct tataataata   6420
ttaaatgata atcaaatgtc tataggaaaa aatgtaggtg gagtatctaa atatttaaat   6480
aaacttagag tggaccctaa gtataataaa tttaaagcgg atgtagaagc taaattaaaa   6540
aagataccta atataggaaa aggaatggca aaatatcttg aaaaggtaaa aaatggaata   6600
aaacaaatgg tagttcctgg aatgtttttt gaagatatgg gaattaaata tttaggacca   6660
atagatggtc ataatataaa agaacttaca gacgtactcg cttctgcaaa agacatacaa   6720
ggtccagtta ttatacatat aataactaag aaaggaaaag gatatgaatt tgcaagaaaa   6780
aaatccaggt aaattccatg gaatagggcc ttttaattgc gccaatggtg aactggatgc   6840
tggatcttca aatacttatt ccaaggcctt tggaaatgaa atggtaaagc tagcagaaaa   6900
agacgataga atagtggcta taactgcagc catgagggat ggaacaggtc ttaaaagttt   6960
ttctcaaaag tttcctgaaa ggtttttttga tgtgggaata gcagaacagc atgctgtaac   7020
cctggcagct ggaatggcac aggcaaattt aaaacctgta tttgcagttt actctacttt   7080
```

-continued tcttcaaaga gcttatgatc aacttattca tgatgtatgt atgcaaaaac ttccagtagt 7140
ttttgctgta gatagggccg gcattgtagg agaagatggt gaaacacatc agggaatatt 7200
tgatttatct tacttaacgg aaatgccaca tatgacgctt atgtctccta aatgtataga 7260
tgaacttcca tatatgttaa aatgggcatt aggccagagt tttcctgtag ctataaggta 7320
tccaagggga ggagatagtg tatgtctcaa tcccgtagaa aattttaaac ttggaaagtg 7380
ggactgtatt tcaaatgaag gcagtgtagc aataattgct cagggtaaaa tggtacaaaa 7440
tgcagtgtta gcaggaaaaa aacttaaaga aaagggtata gatgtaagga ttataagtgc 7500
atgttttatt aagccgctgg acaaggaaat gttaaacagg ttagttgaag aaagtgtaac 7560
tatcgttact gttgaagaca atgtaataag aggaggatta ggatcctata tattagaata 7620
tgtaaataaa ttaaataaaa aagtaaaaat aataaactta gggtttgatg ataagtttgt 7680
acagcatgga aaatccgata ttttgtataa gctgtatggt ttggatccta aaggtatcgt 7740
aaatagtgta cttgaagcag cagaggtaag tcatatattt taac 7784

<210> SEQ ID NO 32
<211> LENGTH: 17
<212> TYPE: DNA
<213> ORGANISM: Artificial Sequence
<220> FEATURE:
<223> OTHER INFORMATION: Oligonucleotide M13R

<400> SEQUENCE: 32
caggaaacag ctatgac 17

<210> SEQ ID NO 33
<211> LENGTH: 20
<212> TYPE: DNA
<213> ORGANISM: Artificial Sequence
<220> FEATURE:
<223> OTHER INFORMATION: Oligonucleotides Isoprene-seq1

<400> SEQUENCE: 33
gttattcaag ctacaccttt 20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide Isoprene-seq2

<400> SEQUENCE: 34
gattggtaaa gaattagctg 20

<210> SEQ ID NO 35
<211> LENGTH: 18
<212> TYPE: DNA
<213> ORGANISM: Artificial Sequence
<220> FEATURE:
<223> OTHER INFORMATION: Oligonucleotide Isoprene-seq3

<400> SEQUENCE: 35
tcaagaagct aagtggct 18

<210> SEQ ID NO 36
<211> LENGTH: 17
<212> TYPE: DNA
<213> ORGANISM: Artificial Sequence
<220> FEATURE:

<223> OTHER INFORMATION: Oligonucleotide Isoprene-seq4

<400> SEQUENCE: 36
ctcaccgtaa aggaaca 17

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide Isoprene-seq5

<400> SEQUENCE: 37
gctagctaga gaaattagaa 20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide Isoprene-seq6

<400> SEQUENCE: 38
ggaatggcaa aatatcttga 20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide Isoprene-seq7

<400> SEQUENCE: 39
gaaacacatc agggaatatt 20

<210> SEQ ID NO 40
<211> LENGTH: 1179
<212> TYPE: DNA
<213> ORGANISM: Clostridium acetobutylicum

<400> SEQUENCE: 40
atgaaagagg ttgttattgc atcagctgtt agaactgcaa taggatctta tggaaaaagt 60
cttaaagatg taccagcagt agacttaggt gcaactgcaa taaaggaagc agtaaagaaa 120
gcaggtataa aacctgaaga tgttaatgaa gttattttag gaaacgtatt acaagctgga 180
cttggacaga atccagctag acaggcatca ttcaaagcag gattaccagt agagatacct 240
gctatgacta ttaataaagt ttgtggttca ggattaagaa cagtttcttt agctgctcaa 300
attataaaag ctggtgacgc agatgtaata atagcaggtg gtatggaaaa tatgtcaaga 360
gcaccatacc ttgctaataa tgctagatgg ggttatagaa tgggaaacgc taaatttgta 420
gacgaaatga taactgatgg actttgggat gcatttaacg attatcacat gggaattact 480
gctgaaaata tagctgagag atggaatata agtagagaag aacaagatga gtttgcactt 540
gcatctcaga aaaaggcaga agaagctatt aaatcaggac aatttaaaga tgaaattgtt 600
ccagtagtaa ttaaaggtag aaaaggtgaa acagttgtag acactgatga acatcctaga 660
tttggatcta caatagaagg tttagctaaa ttaaagcctg cttttaagaa agacggaaca 720
gtaactgctg gaaacgcatc aggtttaaat gattgtgcag ctgttttagt tattatgtct 780
gctgaaaagg caaaggaatt aggtgttaaa ccacttgcta agatagttag ttatggttca 840
gcaggtgtag atcctgctat tatgggatat ggaccttttt atgctacaaa ggcagctatt 900
gaaaaggctg gttggacagt tgatgaactt gatcttatag agtcaaatga ggcatttgca 960
gcacaaagtc ttgctgttgc taaggatctt aaattcgata tgaataaagt aaatgtaaac 1020
ggtggtgcta tagcacttgg tcatccaata ggtgctagtg gtgctagaat tttagttaca 1080
ttagttcatg caatgcaaaa gagagacgct aaaaagggac ttgcaacttt atgcataggt 1140
ggtggtcaag gaacagcaat acttcttgaa aaatgttaa 1179

<210> SEQ ID NO 41
<211> LENGTH: 1140
<212> TYPE: DNA
<213> ORGANISM: Staphylococcus aureus subsp. aureus

<400> SEQUENCE: 41
atgaatcagg ctgttatagt tgctgcaaag agaactgcat ttggaaaata tggtggtact 60
ttaaaacacc ttgaaccaga acaattactt aagccattat ttcagcactt taaagaaaaa 120
tatcctgaag ttatatctaa aatagatgat gtagttttag gaaacgtagt tggaaatggt 180
ggtaatattg ctagaaaagc acttcttgaa gcaggattaa aagatagtat accaggtgta 240
actatagaca gacaatgcgg atctggatta gaatcagtac aatacgcatg tagaatgata 300
caagcaggtg ctggaaaagt ttatattgca ggtggtgttg aatctacatc aagagcacct 360
tggaaaataa agagaccaca ttctgtttat gaaactgcat taccagagtt ctatgaaaga 420
gcatcattcg cacctgaaat gtcagatcca agtatgatac aaggtgctga gaatgtagct 480
aaaatgtatg atgttagtag agaacttcaa gatgagtttg catacagatc acatcaactt 540
acagctgaaa atgtaaagaa tggaaatatt tcacaagaaa ttcttccaat aacagtaaag 600
ggtgaaatat tcaatactga tgaaagttta aaatctcata ttccaaaaga taatttcggt 660
agatttaaac ctgtaataaa aggtggtact gtaacagctg ctaatagttg tatgaagaac 720
gatggtgcag tattattact tattatggaa aaggatatgg cttatgaact tggatttgag 780
catggattat tatttaaaga cggtgtaact gtaggtgtag atagtaactt tccaggaata 840
ggacctgttc ctgctatatc aaatctttta aagagaaacc aacttacaat agaaaatatt 900
gaagtaattg agataaatga agcattttct gctcaggtag ttgcttgtca gcaagctctt 960
aatataagta atactcagtt aaacatttgg ggtggtgcat tagcaagtgg tcatccttat 1020
ggtgcatcag gtgcacagtt agttacaaga ttattttata tgttcgataa agagacaatg 1080
attgcttcta tgggaatagg tggtggttta ggaaatgcag ctctttttac tagattttaa 1140

<210> SEQ ID NO 42
<211> LENGTH: 1167
<212> TYPE: DNA
<213> ORGANISM: Staphylococcus aureus subsp. aureus

<400> SEQUENCE: 42
atgactatag gaattgacaa aataaacttt tacgtaccaa aatattatgt agatatggca 60
aaattagcag aagcaagaca agtagaccca aataaatttc ttattggaat aggacagact 120
gaaatggcag ttagtccagt aaaccaagat atagtatcaa tgggtgctaa tgctgctaaa 180
gatataataa ctgatgaaga caaaaagaaa ataggaatgg taatagtagc aactgagtca 240
gcagtagatg cagcaaaggc agcagcagta cagattcata atttattagg tattcaacca 300
tttgcaagat gtttcgaaat gaaagaagca tgttatgctg ctactcctgc aattcagtta 360
gctaaggatt atttagctac aagaccaaat gagaaagttt tagttatagc tacagataca 420

```
gctagatatg gacttaattc aggtggtgaa cctactcaag gtgctggtgc tgttgctatg    480
gttatagctc ataatcctag tatacttgca ttaaatgaag acgctgttgc ttatacagaa    540
gatgtttatg atttctggag accaacagga cataagtatc cattagtaga tggtgcttta    600
tcaaaagacg catatattag atcttttcaa caatcttgga atgaatatgc taagagacaa    660
ggaaagagtt tagctgattt tgctagtctt tgctttcatg ttccttttac taaaatgggt    720
aaaaaggctt tagaatctat aatagataac gcagatgaaa caactcaaga gagattaaga    780
tctggatatg aagatgcagt tgattacaat agatatgttg gaaatatata cacaggaagt    840
ctttatcttt ctcttataag tcttcttgaa aatagagatt tacaggctgg tgaaactatt    900
ggattatttt catacggatc aggttctgtt ggtgaatttt attcagctac acttgtagaa    960
ggatataaag atcaccttga tcaggcagca cacaaagcac ttttaaacaa tagaactgaa   1020
gtatcagtag atgcatacga aacatttttc aagagatttg atgatgtaga atttgatgaa   1080
gagcaggatg cagttcatga agatagacat atattctatc tttcaaacat agagaataat   1140
gtaagagaat atcatagacc tgaataa                                       1167
```

<210> SEQ ID NO 43
<211> LENGTH: 1278
<212> TYPE: DNA
<213> ORGANISM: Staphylococcus aureus subsp. aureus

<400> SEQUENCE: 43

```
atgcaatcat tagacaaaaa tttcagacat ttatcaagac aacaaaagtt acaacaatta     60
gttgataaac agtggctttc agaagatcag tttgatattt tacttaatca tcctcttata    120
gatgaagaag ttgctaatag tcttatagaa aatgtaattg cacagggtgc attaccagtt    180
ggacttcttc ctaatataat agttgatgat aaggcttatg ttgtaccaat gatggttgaa    240
gaacctagtg ttgttgcagc tgcatcttat ggtgctaaat tagtaaatca gacaggtgga    300
tttaaaactg tatcatcaga aagaataatg attggacaga tagtatttga tggtgtagat    360
gacactgaaa aattaagtgc agatattaaa gcattagaaa aacaaataca taagattgca    420
gatgaagcat atcctagtat aaaagcaaga ggtggtggtt atcaaagaat agcaatagat    480
acatttccag agcaacaact tttaagtctt aaggtatttg tagatacaaa agatgctatg    540
ggtgctaata tgcttaatac tatacttgag gcaataactg cattccttaa aaatgaatct    600
cctcaatcag atatattaat gtctatactt tcaaaccatg caactgctag tgtagtaaaa    660
gtacaaggtg agatagatgt aaaagatctt gctagaggtg aaagaacagg tgaagaagta    720
gctaagagaa tggaaagagc ttctgtatta gctcaggttg atattcatag agctgcaaca    780
cataacaaag gtgttatgaa tggaatacat gctgttgttt tagctacagg aaatgatact    840
agaggtgctg aagcatctgc acatgcatac gcatcaagag acggacaata tagaggtata    900
gcaacttgga gatatgatca gaagagacaa agacttattg gaactattga agttccaatg    960
acacttgcta tagtaggtgg tggtactaaa gtattaccaa tagctaaggc atcattagag   1020
ttattaaatg ttgattctgc acaagaactt ggacacgtag ttgctgctgt tggattagca   1080
caaaactttg ctgcttgtag agcacttgtt tctgaaggta ttcaacaagg acacatgtca   1140
ttacaatata aaagtttagc aatagtagta ggtgcaaaag gtgacgagat agcacaagta   1200
gcagaagctc ttaaacagga accaagagct aatacacagg ttgctgaaag aattttacag   1260
gaaattagac agcaataa                                                 1278
```

<210> SEQ ID NO 44
<211> LENGTH: 552
<212> TYPE: DNA
<213> ORGANISM: Clostridium autoethanogenum

<400> SEQUENCE: 44
agatagtcat aatagttcca gaatagttca atttagaaat tagactaaac ttcaaaatgt 60
ttgttaaata tataccaatc tagtatagat attttttaaa tactggactt aaacagtagt 120
aatttgccta aaaaattttt tcaatttttt ttaaaaaatc cttttcaagt tgtacattgt 180
tatggtaata tgtaattgaa gaagttatgt agtaatattg taaacgtttc ttgatttttt 240
tacatccatg tagtgcttaa aaaaccaaaa tatgtcacat gcacttgtat atttcaaata 300
acaatattta ttttctcgtt aaattcacaa ataatttatt aataatatca ataaccaaga 360
ttatacttaa atggatgttt attttttaac acttttatag taaatatatt tattttatgt 420
agtaaaaagg ttataattat aattgtattt attacaatta attaaaataa aaaatagggt 480
tttaggtaaa attaagttat tttaagaagt aattacaata aaaattgaag ttatttcttt 540
aaggaggaaa tt 552

<210> SEQ ID NO 45
<211> LENGTH: 386
<212> TYPE: DNA
<213> ORGANISM: Clostridium autoethanogenum

<400> SEQUENCE: 45
gttataattt tcaattttca ttctttttaa aggagattag catacatttt atcataatta 60
tacagacaat atagtaatat atgatgttaa aatatcaata tatggttaaa aatctgtata 120
ttttttccca ttttaattat ttgtactata atattacact gagtgtattg catatttaaa 180
aaatatttgg tacaattagt tagttaaata aattctaaat tgtaaattat cagaatcctt 240
attaaggaaa tacatagatt taaggagaaa tcataaaaag gtgtaatata aactggctaa 300
aattgagcaa aaattgagca attaagactt tttgattgta tctttttata tatttaaggt 360
atataatctt atttatattg ggggaa 386

<210> SEQ ID NO 46
<211> LENGTH: 21
<212> TYPE: DNA
<213> ORGANISM: Artificial Sequence
<220> FEATURE:
<223> OTHER INFORMATION: oligonucleotide pUC57-F

<400> SEQUENCE: 46
agcagattgt actgagagtg c 21

<210> SEQ ID NO 47
<211> LENGTH: 21
<212> TYPE: DNA
<213> ORGANISM: Artificial Sequence
<220> FEATURE:
<223> OTHER INFORMATION: oligonucleotide pUC57-R

<400> SEQUENCE: 47
acagctatga ccatgattac g 21

<210> SEQ ID NO 48
<211> LENGTH: 3552
<212> TYPE: DNA
<213> ORGANISM: Artificial Sequence
<220> FEATURE:

<223> OTHER INFORMATION: plasmid pMTL 85245

<400> SEQUENCE: 48
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc cagggggaaa cgcctggtat 600
ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720
ttttgctggc cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggccccctg caggataaaa 900
aaattgtaga taaattttat aaaatagttt tatctacaat ttttttatca ggaaacagct 960
atgaccgcgg ccgcaatatg atatttatgt ccattgtgaa agggattata ttcaactatt 1020
attccagtta cgttcataga aattttcctt tctaaaatat tttattccat gtcaagaact 1080
ctgtttattt cattaaagaa ctataagtac aaagtataag gcatttgaaa aaataggcta 1140
gtatattgat tgattattta ttttaaaatg cctaagtgaa atatatacat attataacaa 1200
taaaataagt attagtgtag gatttttaaa tagagtatct attttcagat taaatttttg 1260
attatttgat ttacattata taatattgag taaagtattg actagcaaaa tttttttgata 1320 ctttaatttg tgaaatttct tatcaaaagt tatatttttg aataattttt attgaaaaat 1380
acaactaaaa aggattatag tataagtgtg tgtaattttg tgttaaattt aaagggagga 1440
aatgaacatg aaacatatgg tgaccatgat tacgaattcg agctcggtac ccggggatcc 1500
tctagagtcg acgtcacgcg tccatggaga tctcgaggcc tgcagacatg caagcttggc 1560
actggccgtc gttttacaac gtcgtgactg ggaaaaccct ggcgttaccc aacttaatcg 1620
ccttgcagca catccccctt tcgccagctg gcgtaatagc gaagaggccc gcaccgatcg 1680
cccttcccaa cagttgcgca gcctgaatgg cgaatggcgc tagcataaaa ataagaagcc 1740
tgcatttgca ggcttcttat ttttatggcg cgccgcattc acttcttttc tatataaata 1800
tgagcgaagc gaataagcgt cggaaaagca gcaaaaagtt tccttttttgc tgttggagca 1860 tgggggttca gggggtgcag tatctgacgt caatgccgag cgaaagcgag ccgaagggta 1920
gcatttacgt tagataaccc cctgatatgc tccgacgctt tatatagaaa agaagattca 1980
actaggtaaa atcttaatat aggttgagat gataaggttt ataaggaatt tgtttgttct 2040
aatttttcac tcattttgtt ctaatttctt ttaacaaatg ttcttttttt tttagaacag 2100
ttatgatata gttagaatag tttaaaataa ggagtgagaa aaagatgaaa gaaagatatg 2160
gaacagtcta taaaggctct cagaggctca tagacgaaga aagtggagaa gtcatagagg 2220
tagacaagtt ataccgtaaa caaacgtctg gtaacttcgt aaaggcatat atagtgcaat 2280
taataagtat gttagatatg attggcggaa aaaaacttaa aatcgttaac tatatcctag 2340
ataatgtcca cttaagtaac aatacaatga tagctacaac aagagaaata gcaaaagcta 2400
caggaacaag tctacaaaca gtaataacaa cacttaaaat cttagaagaa ggaaatatta 2460
taaaaagaaa aactggagta ttaatgttaa accctgaact actaatgaga ggcgacgacc 2520
aaaaacaaaa atacctctta ctcgaatttg ggaactttga gcaagaggca aatgaaatag 2580
attgacctcc caataacacc acgtagttat tgggaggtca atctatgaaa tgcgattaag 2640
ggccggccga agcaaactta agagtgtgtt gatagtgcag tatcttaaaa ttttgtataa 2700
taggaattga agttaaatta gatgctaaaa atttgtaatt aagaaggagt gattacatga 2760
acaaaaatat aaaatattct caaaactttt taacgagtga aaaagtactc aaccaaataa 2820
taaaacaatt gaatttaaaa gaaaccgata ccgtttacga aattggaaca ggtaaagggc 2880
atttaacgac gaaactggct aaaataagta aacaggtaac gtctattgaa ttagacagtc 2940
atctattcaa cttatcgtca gaaaaattaa aactgaatac tcgtgtcact ttaattcacc 3000
aagatattct acagtttcaa ttccctaaca aacagaggta taaaattgtt gggagtattc 3060
cttaccattt aagcacacaa attattaaaa aagtggtttt tgaaagccat gcgtctgaca 3120
tctatctgat tgttgaagaa ggattctaca agcgtacctt ggatattcac cgaacactag 3180
ggttgctctt gcacactcaa gtctcgattc agcaattgct taagctgcca gcggaatgct 3240
ttcatcctaa accaaaagta aacagtgtct taataaaact tacccgccat accacagatg 3300
ttccagataa atattggaag ctatatacgt actttgtttc aaaatgggtc aatcgagaat 3360
atcgtcaact gtttactaaa aatcagtttc atcaagcaat gaaacacgcc aaagtaaaca 3420
atttaagtac cgttacttat gagcaagtat tgtctatttt taatagttat ctattattta 3480
acgggaggaa ataattctat gagtcgcttt tgtaaatttg gaaagttaca cgttactaaa 3540
gggaatgtgt tt 3552

<210> SEQ ID NO 49
<211> LENGTH: 4186
<212> TYPE: DNA
<213> ORGANISM: Artificial Sequence
<220> FEATURE:
<223> OTHER INFORMATION: plasmid pMTL 83145

<400> SEQUENCE: 49
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc caggggggaaa cgcctggtat 600 ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720

-continued

```
ttttgctggc cttttgctca catgttcttt cctgcgttat cccctgattc tgtggataac    780

cgtattaccg cctttgagtg agctgatacc gctcgccgca gccgaacgac cgagcgcagc    840

gagtcagtga gcgaggaagc ggaagagcgc ccaatacgca gggcccccctg caggataaaa    900

aaattgtaga taaattttat aaaatagttt tatctacaat ttttttatca ggaaacagct    960

atgaccgcgg ccgcaatatg atatttatgt ccattgtgaa agggattata ttcaactatt   1020

attccagtta cgttcataga aattttcctt tctaaaatat tttattccat gtcaagaact   1080

ctgtttattt cattaaagaa ctataagtac aaagtataag gcatttgaaa aaataggcta   1140

gtatattgat tgattattta ttttaaaatg cctaagtgaa atatatacat attataacaa   1200

taaaataagt attagtgtag gatttttaaa tagagtatct attttcagat taaattttg   1260

attatttgat ttacattata taatattgag taaagtattg actagcaaaa tttttgata   1320

ctttaatttg tgaaatttct tatcaaaagt tatatttttg aataattttt attgaaaaat   1380

acaactaaaa aggattatag tataagtgtg tgtaattttg tgttaaattt aaagggagga   1440

aatgaacatg aaacatatgg tgaccatgat tacgaattcg agctcggtac ccggggatcc   1500

tctagagtcg acgtcacgcg tccatggaga tctcgaggcc tgcagacatg caagcttggc   1560

actggccgtc gttttacaac gtcgtgactg ggaaaaccct ggcgttaccc aacttaatcg   1620

ccttgcagca catcccccttt tcgccagctg gcgtaatagc gaagaggccc gcaccgatcg   1680

cccttcccaa cagttgcgca gcctgaatgg cgaatggcgc tagcataaaa ataagaagcc   1740

tgcatttgca ggcttcttat ttttatggcg cgccgccatt attttttga acaattgaca   1800

attcatttct tattttttat taagtgatag tcaaaaggca taacagtgct gaatagaaag   1860

aaatttacag aaaagaaaat tatagaattt agtatgatta attatactca tttatgaatg   1920

tttaattgaa tacaaaaaaa aatacttgtt atgtattcaa ttacgggtta aaatatagac   1980

aagttgaaaa atttaataaa aaaataagtc ctcagctctt atatattaag ctaccaactt   2040

agtatataag ccaaaactta aatgtgctac caacacatca agccgttaga gaactctatc   2100

tatagcaata tttcaaatgt accgacatac aagagaaaca ttaactatat atattcaatt   2160

tatgagatta tcttaacaga tataaatgta aattgcaata agtaagattt agaagtttat   2220

agcctttgtg tattggaagc agtacgcaaa ggcttttta tttgataaaa attagaagta   2280

tatttatttt ttcataatta atttatgaaa atgaaagggg gtgagcaaag tgacagagga   2340

aagcagtatc ttatcaaata acaaggtatt agcaatatca ttattgactt tagcagtaaa   2400

cattatgact tttatagtgc ttgtagctaa gtagtacgaa agggggagct ttaaaaagct   2460

ccttggaata catagaattc ataaattaat ttatgaaaag aagggcgtat atgaaaactt   2520

gtaaaaattg caaagagttt attaaagata ctgaaatatg caaaatacat tcgttgatga   2580

ttcatgataa aacagtagca acctattgca gtaaatacaa tgagtcaaga tgtttacata   2640

aagggaaagt ccaatgtatt aattgttcaa agatgaaccg atatggatgg tgtgccataa   2700

aaatgagatg ttttacagag gaagaacaga aaaaagaacg tacatgcatt aaatattatg   2760

caaggagctt taaaaaagct catgtaaaga agagtaaaaa gaaaaaataa tttatttatt   2820

aatttaatat tgagagtgcc gacacagtat gcactaaaaa atatatctgt ggtgtagtga   2880

gccgatacaa aaggatagtc actcgcattt tcataataca tcttatgtta tgattatgtg   2940

tcggtgggac ttcacgacga aaacccacaa taaaaaaaga gttcggggta gggttaagca   3000

tagttgaggc aactaaacaa tcaagctagg atatgcagta gcagaccgta aggtcgttgt   3060

ttaggtgtgt tgtaatacat acgctattaa gatgtaaaaa tacggatacc aatgaaggga   3120
```

aaagtataat ttttggatgt agtttgtttg ttcatctatg ggcaaactac gtccaaagcc 3180
gtttccaaat ctgctaaaaa gtatatcctt tctaaaatca aagtcaagta tgaaatcata 3240
aataaagttt aattttgaag ttattatgat attatgtttt tctattaaaa taaattaagt 3300
atatagaata gtttaataat agtatatact taatgtgata agtgtctgac agtgtcacag 3360
aaaggatgat tgttatggat tataagcggc cggccagtgg gcaagttgaa aaattcacaa 3420
aaatgtggta taatatcttt gttcattaga gcgataaact tgaatttgag agggaactta 3480
gatggtattt gaaaaaattg ataaaaatag ttggaacaga aaagagtatt ttgaccacta 3540
ctttgcaagt gtaccttgta cctacagcat gaccgttaaa gtggatatca cacaaataaa 3600
ggaaaaggga atgaaactat atcctgcaat gctttattat attgcaatga ttgtaaaccg 3660
ccattcagag tttaggacgg caatcaatca agatggtgaa ttggggatat atgatgagat 3720
gataccaagc tatacaatat ttcacaatga tactgaaaca ttttccagcc tttggactga 3780
gtgtaagtct gactttaaat catttttagc agattatgaa agtgatacgc aacggtatgg 3840
aaacaatcat agaatggaag gaaagccaaa tgctccggaa aacattttta atgtatctat 3900
gataccgtgg tcaaccttcg atggctttaa tctgaatttg cagaaaggat atgattattt 3960
gattcctatt tttactatgg ggaaatatta taaagaagat aacaaaatta tacttccttt 4020
ggcaattcaa gttcatcacg cagtatgtga cggatttcac atttgccgtt ttgtaaacga 4080
attgcaggaa ttgataaata gttaacttca ggtttgtctg taactaaaaa caagtattta 4140
agcaaaaaca tcgtagaaat acggtgtttt ttgttaccct aagttt 4186

<210> SEQ ID NO 50
<211> LENGTH: 9827
<212> TYPE: DNA
<213> ORGANISM: Artificial Sequence
<220> FEATURE:
<223> OTHER INFORMATION: plasmid pMTL8215-Pptaack-thlA-HMGS-Patp-HMGR

<400> SEQUENCE: 50
cctgcaggat aaaaaaattg tagataaatt ttataaaata gttttatcta caattttttt 60
atcaggaaac agctatgacc gcggccgcag atagtcataa tagttccaga atagttcaat 120
ttagaaatta gactaaactt caaaatgttt gttaaatata taccaatcta gtatagatat 180
tttttaaata ctggacttaa acagtagtaa tttgcctaaa aaattttttc aatttttttt 240
aaaaaatcct tttcaagttg tacattgtta tggtaatatg taattgaaga agttatgtag 300
taatattgta aacgtttctt gatttttttta catccatgta gtgcttaaaa aaccaaaata 360
tgtcacatgc acttgtatat ttcaaataac aatatttatt ttctcgttaa attcacaaat 420
aatttattaa taatatcaat aaccaagatt atacttaaat ggatgtttat tttttaacac 480
ttttatagta aatatattta ttttatgtag taaaaaggtt ataattataa ttgtatttat 540
tacaattaat taaaataaaa aatagggttt taggtaaaat taagttattt taagaagtaa 600
ttacaataaa aattgaagtt atttctttaa ggaggaaatt catatgaaag aggttgttat 660
tgcatcagct gttagaactg caataggatc ttatggaaaa agtcttaaag atgtaccagc 720
agtagactta ggtgcaactg caataaagga agcagtaaag aaagcaggta taaaacctga 780
agatgttaat gaagttattt taggaaacgt attacaagct ggacttggac agaatccagc 840
tagacaggca tcattcaaag caggattacc agtagagata cctgctatga ctattaataa 900
agtttgtggt tcaggattaa gaacagtttc tttagctgct caaattataa aagctggtga 960

-continued

```
cgcagatgta ataatagcag gtggtatgga aaatatgtca agagcaccat accttgctaa   1020
taatgctaga tggggttata gaatgggaaa cgctaaattt gtagacgaaa tgataactga   1080
tggactttgg gatgcattta acgattatca catgggaatt actgctgaaa atatagctga   1140
gagatggaat ataagtagag aagaacaaga tgagtttgca cttgcatctc agaaaaaggc   1200
agaagaagct attaaatcag gacaatttaa agatgaaatt gttccagtag taattaaagg   1260
tagaaaaggt gaaacagttg tagacactga tgaacatcct agatttggat ctacaataga   1320
aggtttagct aaattaaagc ctgcttttaa gaaagacgga acagtaactg ctggaaacgc   1380
atcaggttta aatgattgtg cagctgtttt agttattatg tctgctgaaa aggcaaagga   1440
attaggtgtt aaaccacttg ctaagatagt tagttatggt tcagcaggtg tagatcctgc   1500
tattatggga tatggacctt tttatgctac aaaggcagct attgaaaagg ctggttggac   1560
agttgatgaa cttgatctta tagagtcaaa tgaggcattt gcagcacaaa gtcttgctgt   1620
tgctaaggat cttaaattcg atatgaataa agtaaatgta aacggtggtg ctatagcact   1680
tggtcatcca ataggtgcta gtggtgctag aattttagtt acattagttc atgcaatgca   1740
aaagagagac gctaaaaagg gacttgcaac tttatgcata ggtggtggtc aaggaacagc   1800
aatacttctt gaaaaatgtt aagaattcga ggcttttact aaaaacaata aaaacaggag   1860
gaaataatat gactatagga attgacaaaa taaactttta cgtaccaaaa tattatgtag   1920
atatggcaaa attagcagaa gcaagacaag tagacccaaa taaatttctt attggaatag   1980
gacagactga aatggcagtt agtccagtaa accaagatat agtatcaatg ggtgctaatg   2040
ctgctaaaga tataataact gatgaagaca aaaagaaaat aggaatggta atagtagcaa   2100
ctgagtcagc agtagatgca gcaaaggcag cagcagtaca gattcataat ttattaggta   2160
ttcaaccatt tgcaagatgt ttcgaaatga aagaagcatg ttatgctgct actcctgcaa   2220
ttcagttagc taaggattat ttagctacaa gaccaaatga gaaagtttta gttatagcta   2280
cagatacagc tagatatgga cttaattcag gtggtgaacc tactcaaggt gctggtgctg   2340
ttgctatggt tatagctcat aatcctagta tacttgcatt aaatgaagac gctgttgctt   2400
atacagaaga tgtttatgat ttctggagac caacaggaca taagtatcca ttagtagatg   2460
gtgctttatc aaaagacgca tatattagat cttttcaaca atcttggaat gaatatgcta   2520
agagacaagg aaagagttta gctgattttg ctagtctttg ctttcatgtt ccttttacta   2580
aaatgggtaa aaaggcttta gaatctataa tagataacgc agatgaaaca actcaagaga   2640
gattaagatc tggatatgaa gatgcagttg attacaatag atatgttgga aatatataca   2700
caggaagtct ttatctttct cttataagtc ttcttgaaaa tagagattta caggctggtg   2760
aaactattgg attattttca tacggatcag gttctgttgg tgaattttat tcagctacac   2820
ttgtagaagg atataaagat caccttgatc aggcagcaca caaagcactt ttaaacaata   2880
gaactgaagt atcagtagat gcatacgaaa catttttcaa gagatttgat gatgtagaat   2940
ttgatgaaga gcaggatgca gttcatgaag atagacatat attctatctt tcaaacatag   3000
agaataatgt aagagaatat catagacctg aataagagct cgttataatt ttcaattttc   3060
attcttttta aaggagatta gcatacattt tatcataatt atacagacaa tatagtaata   3120
tatgatgtta aaatatcaat atatggttaa aaatctgtat attttttccc attttaatta   3180
tttgtactat aatattacac tgagtgtatt gcatatttaa aaaatatttg gtacaattag   3240
ttagttaaat aaattctaaa ttgtaaatta tcagaatcct tattaaggaa atacatagat   3300
ttaaggagaa atcataaaaa ggtgtaatat aaactggcta aaattgagca aaaattgagc   3360
```

-continued aattaagact ttttgattgt atctttttat atatttaagg tatataatct tatttatatt 3420
gggggaaggt accatgcaat cattagacaa aaatttcaga catttatcaa gacaacaaaa 3480
gttacaacaa ttagttgata aacagtggct ttcagaagat cagtttgata ttttacttaa 3540
tcatcctctt atagatgaag aagttgctaa tagtcttata gaaaatgtaa ttgcacaggg 3600
tgcattacca gttggacttc ttcctaatat aatagttgat gataaggctt atgttgtacc 3660
aatgatggtt gaagaaccta gtgttgttgc agctgcatct tatggtgcta aattagtaaa 3720
tcagacaggt ggatttaaaa ctgtatcatc agaaagaata atgattggac agatagtatt 3780
tgatggtgta gatgacactg aaaaattaag tgcagatatt aaagcattag aaaaacaaat 3840
acataagatt gcagatgaag catatcctag tataaaagca agaggtggtg gttatcaaag 3900
aatagcaata gatacatttc cagagcaaca acttttaagt cttaaggtat ttgtagatac 3960
aaaagatgct atgggtgcta atatgcttaa tactatactt gaggcaataa ctgcattcct 4020
taaaaatgaa tctcctcaat cagatatatt aatgtctata ctttcaaacc atgcaactgc 4080
tagtgtagta aaagtacaag gtgagataga tgtaaaagat cttgctagag gtgaaagaac 4140
aggtgaagaa gtagctaaga gaatggaaag agcttctgta ttagctcagg ttgatattca 4200
tagagctgca acacataaca aaggtgttat gaatggaata catgctgttg ttttagctac 4260
aggaaatgat actagaggtg ctgaagcatc tgcacatgca tacgcatcaa gagacggaca 4320
atatagaggt atagcaactt ggagatatga tcagaagaga caaagactta ttggaactat 4380
tgaagttcca atgacacttg ctatagtagg tggtggtact aaagtattac caatagctaa 4440
ggcatcatta gagttattaa atgttgattc tgcacaagaa cttggacacg tagttgctgc 4500
tgttggatta gcacaaaact ttgctgcttg tagagcactt gtttctgaag gtattcaaca 4560
aggacacatg tcattacaat ataaaagttt agcaatagta gtaggtgcaa aaggtgacga 4620
gatagcacaa gtagcagaag ctcttaaaca ggaaccaaga gctaatacac aggttgctga 4680
aagaatttta caggaaatta gacagcaata atctagagtc gacgtcacgc gtccatggag 4740
atctcgaggc ctgcagacat gcaagcttgg cactggccgt cgttttacaa cgtcgtgact 4800
gggaaaaccc tggcgttacc caacttaatc gccttgcagc acatccccct ttcgccagct 4860
ggcgtaatag cgaagaggcc cgcaccgatc gcccttccca acagttgcgc agcctgaatg 4920
gcgaatggcg ctagcataaa aataagaagc ctgcatttgc aggcttctta tttttatggc 4980
gcgccgttct gaatccttag ctaatggttc aacaggtaac tatgacgaag atagcaccct 5040
ggataagtct gtaatggatt ctaaggcatt taatgaagac gtgtatataa aatgtgctaa 5100
tgaaaaagaa aatgcgttaa aagagcctaa aatgagttca aatggttttg aaattgattg 5160
gtagtttaat ttaatatatt ttttctattg gctatctcga tacctataga atcttctgtt 5220
cacttttgtt tttgaaatat aaaaaggggc tttttagccc cttttttta aaactccgga 5280
ggagtttctt cattcttgat actatacgta actattttcg atttgacttc attgtcaatt 5340
aagctagtaa aatcaatggt taaaaaacaa aaaacttgca tttttctacc tagtaattta 5400
taattttaag tgtcgagttt aaaagtataa tttaccagga aaggagcaag ttttttaata 5460
aggaaaaatt tttccttta aaattctatt tcgttatatg actaattata atcaaaaaaa 5520
tgaaaataaa caagaggtaa aaactgcttt agagaaatgt actgataaaa aaagaaaaaa 5580
tcctagattt acgtcataca tagcaccttt aactactaag aaaaatattg aaaggacttc 5640
cacttgtgga gattatttgt ttatgttgag tgatgcagac ttagaacatt ttaaattaca 5700
taaaggtaat ttttgcggta atagattttg tccaatgtgt agttggcgac ttgcttgtaa 5760
ggatagttta gaaatatcta ttcttatgga gcatttaaga aaagaagaaa ataaagagtt 5820
tatattttta actcttacaa ctccaaatgt aaaaagttat gatcttaatt attctattaa 5880
acaatataat aaatctttta aaaaattaat ggagcgtaag gaagttaagg atataactaa 5940
aggttatata agaaaattag aagtaactta ccaaaaggaa aaatacataa caaaggattt 6000
atggaaaata aaaaaagatt attatcaaaa aaaaggactt gaaattggtg atttagaacc 6060
taattttgat acttataatc ctcattttca tgtagttatt gcagttaata aaagttattt 6120
tacagataaa aattattata taaatcgaga aagatggttg gaattatgga agtttgctac 6180
taaggatgat tctataactc aagttgatgt tagaaaagca aaaattaatg attataaaga 6240
ggtttacgaa cttgcgaaat attcagctaa agacactgat tatttaatat cgaggccagt 6300
atttgaaatt ttttataaag cattaaaagg caagcaggta ttagtttttta gtggattttt 6360 taaagatgca cacaaattgt acaagcaagg aaaacttgat gtttataaaa agaaagatga 6420
aattaaatat gtctatatag tttattataa ttggtgcaaa aacaatatg aaaaaactag 6480 aataagggaa cttacggaag atgaaaaaga agaattaaat caagatttaa tagatgaaat 6540
agaaatagat taaagtgtaa ctatacttta tatatatatg attaaaaaaa taaaaaacaa 6600
cagcctatta ggttgttgtt ttttattttc tttattaatt tttttaattt ttagttttta 6660
gttctttttt aaaataagtt tcagcctctt tttcaatatt ttttaaagaa ggagtatttg 6720
catgaattgc cttttttcta acagacttag gaaatatttt aacagtatct tcttgcgccg 6780
gtgattttgg aacttcataa cttactaatt tataattatt attttctttt ttaattgtaa 6840
cagttgcaaa agaagctgaa cctgttcctt caactagttt atcatcttca atataatatt 6900
cttgacctat atagtataaa tatattttta ttatattttt acttttttct gaatctatta 6960
ttttataatc ataaaaagtt ttaccaccaa aagaaggttg tactccttct ggtccaacat 7020 attttttttac tatattatct aaataatttt tgggaactgg tgttgtaatt tgattaatcg 7080
aacaaccagt tatacttaaa ggaattataa ctataaaaat atataggatt atctttttaa 7140
atttcattat tggcctcctt tttattaaat ttatgttacc ataaaaagga cataacggga 7200
atatgtagaa tatttttaat gtagacaaaa ttttacataa atataaagaa aggaagtgtt 7260
tgtttaaatt ttatagcaaa ctatcaaaaa ttagggggat aaaaatttat gaaaaaaagg 7320
ttttcgatgt tatttttatg tttaacttta atagtttgtg gtttatttac aaattcggcc 7380
ggccagtggg caagttgaaa aattcacaaa aatgtggtat aatatctttg ttcattagag 7440
cgataaactt gaatttgaga gggaacttag atggtatttg aaaaaattga taaaaatagt 7500
tggaacagaa aagagtattt tgaccactac tttgcaagtg taccttgtac ctacagcatg 7560
accgttaaag tggatatcac acaaataaag gaaaagggaa tgaaactata tcctgcaatg 7620
ctttattata ttgcaatgat tgtaaaccgc cattcagagt ttaggacggc aatcaatcaa 7680
gatggtgaat tggggatata tgatgagatg ataccaagct atacaatatt tcacaatgat 7740
actgaaacat tttccagcct ttggactgag tgtaagtctg actttaaatc atttttagca 7800
gattatgaaa gtgatacgca acggtatgga aacaatcata gaatggaagg aaagccaaat 7860
gctccggaaa acatttttaa tgtatctatg ataccgtggt caaccttcga tggctttaat 7920
ctgaatttgc agaaaggata tgattatttg attcctattt ttactatggg gaaatattat 7980
aaagaagata acaaaattat acttcctttg gcaattcaag ttcatcacgc agtatgtgac 8040
ggatttcaca tttgccgttt tgtaaacgaa ttgcaggaat tgataaatag ttaacttcag 8100

```
gtttgtctgt aactaaaaac aagtatttaa gcaaaaacat cgtagaaata cggtgttttt   8160
tgttacccta agtttaaact ccttttttgat aatctcatga ccaaaatccc ttaacgtgag   8220
ttttcgttcc actgagcgtc agaccccgta gaaaagatca aaggatcttc ttgagatcct   8280
tttttctgc gcgtaatctg ctgcttgcaa acaaaaaaac caccgctacc agcggtggtt   8340
tgtttgccgg atcaagagct accaactctt tttccgaagg taactggctt cagcagagcg   8400
cagataccaa atactgttct tctagtgtag ccgtagttag gccaccactt caagaactct   8460
gtagcaccgc ctacatacct cgctctgcta atcctgttac cagtggctgc tgccagtggc   8520
gataagtcgt gtcttaccgg gttggactca agacgatagt taccggataa ggcgcagcgg   8580
tcgggctgaa cggggggttc gtgcacacag cccagcttgg agcgaacgac ctacaccgaa   8640
ctgagatacc tacagcgtga gctatgagaa agcgccacgc ttcccgaagg gagaaaggcg   8700
gacaggtatc cggtaagcgg cagggtcgga acaggagagc gcacgaggga gcttccaggg   8760
ggaaacgcct ggtatcttta tagtcctgtc gggtttcgcc acctctgact tgagcgtcga   8820
tttttgtgat gctcgtcagg ggggcggagc ctatggaaaa acgccagcaa cgcggccttt   8880
ttacggttcc tggccttttg ctggcctttt gctcacatgt tctttcctgc gttatcccct   8940
gattctgtgg ataaccgtat taccgccttt gagtgagctg ataccgctcg ccgcagccga   9000
acgaccgagc gcagcgagtc agtgagcgag gaagcggaag agcgcccaat acgcagggcc   9060
ccctgcttcg ggtcattat agcgattttt tcggtatatc catccttttt cgcacgatat   9120
acaggatttt gccaaagggt tcgtgtagac tttccttggt gtatccaacg gcgtcagccg   9180
ggcaggatag gtgaagtagg cccacccgcg agcgggtgtt ccttcttcac tgtcccttat   9240
tcgcacctgg cggtgctcaa cgggaatcct gctctgcgag gctggccggc taccgccggc   9300
gtaacagatg agggcaagcg gatggctgat gaaaccaagc caaccaggaa gggcagccca   9360
cctatcaagg tgtactgcct tccagacgaa cgaagagcga ttgaggaaaa ggcggcggcg   9420
gccggcatga gcctgtcggc ctacctgctg gccgtcggcc agggctacaa aatcacgggc   9480
gtcgtggact atgagcacgt ccgcgagctg gcccgcatca atggcgacct gggccgcctg   9540
ggcggcctgc tgaaactctg gctcaccgac gacccgcgca cggcgcggtt cggtgatgcc   9600
acgatcctcg ccctgctggc gaagatcgaa gagaagcagg acgagcttgg caaggtcatg   9660
atgggcgtgg tccgcccgag ggcagagcca tgactttttt agccgctaaa acggccgggg   9720
ggtgcgcgtg attgccaagc acgtccccat gcgctccatc aagaagagcg acttcgcgga   9780
gctggtgaag tacatcaccg acgagcaagg caagaccgat cgggccc                 9827
```

```
<210> SEQ ID NO 51
<211> LENGTH: 843
<212> TYPE: DNA
<213> ORGANISM: Staphylococcus aureus subsp. aureus

<400> SEQUENCE: 51

atgatagctg ttccatttaa cgctggaaaa ataaaagttt taattgaggc attagaatct     60
ggaaattatt catcaataaa atcagatgta tatgacggaa tgttatatga tgcaccagat    120
caccttaaat cattagtaaa cagatttgta gaacttaata atataactga gccattagca    180
gtaactatac agacaaatct tcctccttca agaggtcttg gatctagtgc agctgttgct    240
gttgcttttg taagagcaag ttatgatttc ttaggaaaaa gtttaactaa agaagagctt    300
atagaaaagg ctaattgggc tgaacaaata gctcatggaa agccatctgg aatagataca    360
```

```
caaacaatag tatctggaaa gcctgtttgg tttcaaaagg gacatgcaga aacacttaaa    420

actctttcac ttgatggata catggtagta attgatacag gtgttaaagg aagtacaaga    480

caggctgtag aagatgttca taaactttgc gaagatcctc aatatatgag tcacgtaaaa    540

cacataggaa aacttgtact tagagcatct gatgttattg aacatcataa ctttgaagca    600

cttgctgata tattcaatga atgtcatgct gatttaaagg ctcttacagt aagtcatgac    660

aaaatagaac agttaatgaa gataggaaaa gaaaatggtg ctatagctgg taaattaact    720

ggtgctggta gaggtggttc aatgttatta cttgcaaaag acttaccaac tgcaaagaat    780

atagttaaag cagtagagaa agctggtgca gcacatactt ggattgaaaa tttaggtggt    840

taa                                                                  843
```

<210> SEQ ID NO 52
<211> LENGTH: 1077
<212> TYPE: DNA
<213> ORGANISM: Staphylococcus aureus subsp. aureus

<400> SEQUENCE: 52

```
atgatacaag taaaggcacc aggaaaatta tatatagcag gtgaatacgc tgttacagaa     60

ccaggatata aatctgttct tatagctctt gatagatttg ttacagctac tattgaggaa    120

gctgatcaat acaaaggaac aatacattca aaggcattac atcacaatcc agtaactttt    180

agtagagatg aagattctat tgttatatca gacccacacg cagcaaaaca acttaattat    240

gtagtaactg ctatagaaat atttgagcaa tatgcaaaat catgtgacat agcaatgaag    300

cattttcatt taactataga ttctaactta gatgatagta atggacataa gtatggactt    360

ggatcttctg ctgctgtttt agtttcagta attaaagtac ttaacgaatt ttatgatatg    420

aaactttcaa acctttatat atataagtta gcagtaattg ctaatatgaa attacagagt    480

ttatcttcat gcggtgatat agcagtaagt gtttattcag gttggttagc ttattctaca    540

tttgaccatg aatgggtaaa acaccagata gaagatacaa cagttgaaga agtacttatt    600

aaaaattggc ctggattaca catagagcca cttcaagctc ctgaaaatat ggaagttctt    660

ataggttgga caggtagtcc agctagtagt cctcattttg tttctgaagt taaaagactt    720

aagtcagatc cttcatttta cggtgatttc ttagaagatt cacatagatg tgtagaaaaa    780

ttaattcatg cattcaaaac taataatatt aagggtgttc agaaaatggt aagacagaat    840

agaactatta tacaaagaat ggataaggaa gcaacagttg atatagagac tgagaagtta    900

aaatatttat gtgatattgc tgaaaaatat catggtgcaa gtaaaacttc aggtgctggt    960

ggtggtgatt gcggaataac tataataaat aaggatgtag acaaagagaa aatatatgat   1020

gaatggacta aacatggaat aaagcctctt aagtttaata tttatcatgg acaataa      1077
```

<210> SEQ ID NO 53
<211> LENGTH: 984
<212> TYPE: DNA
<213> ORGANISM: Staphylococcus aureus subsp. aureus

<400> SEQUENCE: 53

```
atgataaaat ctggaaaagc aagagcacac actaatatag cacttataaa atattggggt     60

aagaaagatg aggcattaat aataccaatg aataactcaa tatcagtaac tttagaaaag    120

ttttatactg aaacaaaagt tacatttaac gatcagctta ctcaagatca attttggctt    180

aatggtgaaa aagtttctgg aaaagaatta gaaaagattt caaagtatat ggatattgtt    240

agaaatagag ctggaataga ttggtatgct gagatagaat ctgataattt tgttcctaca    300
```

-continued

```
gctgctggtc ttgctagttc tgctagtgct tatgcagcat tagctgctgc atgtaaccaa    360

gcacttgatt tacagttaag tgataaagac ttaagtagat tagctagaat tggatcagga    420

tcagcatcaa gatcaatata cggtggtttt gcagaatggg aaaaaggata taatgacgaa    480

acttcttatg ctgttccatt agaaagtaat cactttgaag atgatcttgc tatgattttt    540

gtagtaataa accaacattc taaaaaggtt ccttcaagat atggaatgtc tcttacaaga    600

aatacaagta gattctatca atattggtta gaccatattg atgaagatct tgcagaagca    660

aaggcagcaa tacaagataa ggattttaag agattaggtg aagttattga agagaatgga    720

cttagaatgc atgctacaaa tcttggatca actccacctt ttacttactt agtacaagag    780

tcatacgatg taatggcatt agtacatgag tgtagagaag caggatatcc atgctatttc    840

actatggatg ctggacctaa tgtaaaaata cttgtagaga agaaaaacaa acaacagata    900

atagataaac ttttaactca gttcgataat aatcagataa tagatagtga tattatagct    960

acaggtattg aaattataga ataa                                           984
```

<210> SEQ ID NO 54
<211> LENGTH: 516
<212> TYPE: DNA
<213> ORGANISM: Clostridium beijerinckii

<400> SEQUENCE: 54

```
atggcagagt atataatagc agtagatgag ttcgataacg aaataggatc aatagaaaag     60

atggaagctc atagaaaagg aacacttcat agagcattca gtattttagt ttttaactca    120

aagaatcaac ttttattaca gaaaagaaat gtaaagaaat atcactctcc aggattatgg    180

acaaacactt gttgtagtca cccaagatat ggtgaatctc ttcatgatgc tatatacaga    240

agattaaaag aagagatggg atttacttgc gaacttgaag aagtattctc attcatatat    300

aaggtaaaac ttgaagataa tttatttgag aatgaatatg accatgtatt tattggtaaa    360

tatgatggtg agataattgt taataaagat gaagttgatg attttaaatg ggtagacatt    420

aatgaagtta aaaaggacat aatagaaaga cctgaggcat atacttactg gtttaagtat    480

cttgtaaata aagctgaaaa taagatattt aaataa                               516
```

<210> SEQ ID NO 55
<211> LENGTH: 120
<212> TYPE: DNA
<213> ORGANISM: Clostridium autoethanogenum

<400> SEQUENCE: 55

```
atatcgatac agataaaaaa atatataata cagaagaaaa aattataaat ttgtggtata     60

atataaagta tagtaattta agtttaaacc tcgtgaaaac gctaacaaat aataggaggt    120
```

<210> SEQ ID NO 56
<211> LENGTH: 900
<212> TYPE: DNA
<213> ORGANISM: Escherichia coli

<400> SEQUENCE: 56

```
atggatttcc cacaacaatt agaagcatgt gtaaaacagg ctaatcaggc acttagtaga     60

tttattgctc ctcttccttt tcaaaataca ccagtagtag aaactatgca atacggtgca    120

cttttaggtg gtaaaagatt aagaccattc ttagtatatg ctacaggaca tatgtttggt    180

gtatcaacta atactttaga cgctccagct gctgctgttg aatgtattca tgcatattct    240
```

-continued ttaatacatg atgacttacc agcaatggat gacgatgatt taagaagagg tttacctaca 300
tgtcatgtta aatttggtga agctaatgca attttagcag gtgacgcttt acaaacttta 360
gctttttcta tactttcaga tgcagacatg cctgaagttt cagatagaga tagaatttct 420
atgatatcag agcttgcatc tgcatcagga atagctggaa tgtgcggtgg tcaagcactt 480
gatttagatg cagaaggtaa acacgtacca cttgatgcat tagagagaat tcatagacat 540
aaaacaggtg ctcttataag agcagcagta agattaggtg ctttaagtgc tggtgacaag 600
ggtagaagag cacttccagt acttgataag tatgcagaaa gtataggatt agcttttcaa 660
gttcaagatg acatacttga cgttgttggt gatactgcta ctttaggaaa aagacagggt 720
gcagatcagc aattaggaaa atctacatac cctgctttac ttggattaga acaggctaga 780
aagaaagcaa gagacttaat agatgacgca agacaaagtc ttaaacagtt agctgaacaa 840
tcacttgaca caagtgcact tgaagcactt gcagattata ttatacagag aaacaagtaa 900

<210> SEQ ID NO 57
<211> LENGTH: 975
<212> TYPE: DNA
<213> ORGANISM: Malus x domestica

<400> SEQUENCE: 57
atggaattta gagtacattt acaggcagac aacgaacaga aaatatttca aaatcaaatg 60
aaaccagagc cagaagcatc atatcttata aatcaaagaa gaagtgctaa ttataaacca 120
aacatttgga aaaacgattt tcttgatcag tctttaatat caaaatatga tggtgatgaa 180
tatagaaaac tttcagaaaa gttaatagaa gaagtaaaga tatacatatc agcagagact 240
atggatttag ttgctaaatt agaacttata gattctgtta gaaaacttgg acttgctaat 300
ctttttgaga aagaaataaa ggaagcatta gacagtatag cagcaataga atcagataat 360
ttaggaacta gagacgatct ttatggaaca gctcttcatt ttaagattct tagacagcat 420
ggatataagg taagtcaaga tatatttggt agatttatgg atgagaaagg aacattagaa 480
aatcatcact ttgcacactt aaaaggaatg ttagaattat ttgaggcaag taatcttgga 540
tttgaaggtg aagacatatt agatgaagct aaagcatctc ttacacttgc tcttagagat 600
tcaggacata tttgttatcc agactcaaac ttaagtagag atgtagttca tagtttagaa 660
ttacctagtc atagaagagt tcaatggttc gatgtaaaat ggcagattaa tgcatacgaa 720
aaagatattt gtagagtaaa tgcaacttta ttagagttag caaagttaaa ttttaatgtt 780
gttcaagctc agcttcagaa gaatcttaga gaagctagta gatggtgggc taatcttggt 840
ttcgcagata atttaaagtt tgctagagat agacttgtag agtgtttttc atgcgcagta 900
ggtgtagcat ttgaaccaga gcattcatct tttagaatat gtttaactaa ggtaattaat 960
cttgttctta ttata 975

<210> SEQ ID NO 58
<211> LENGTH: 13817
<212> TYPE: DNA
<213> ORGANISM: Artificial Sequence
<220> FEATURE:
<223> OTHER INFORMATION:
pMTL8314-Pptaack-thlA-HMGS-Patp-HMGR-Prnf-MK-PMK-PMD-Pfor-idi-isp
S

<400> SEQUENCE: 58
aaactccttt ttgataatct catgaccaaa atcccttaac gtgagttttc gttccactga 60
gcgtcagacc ccgtagaaaa gatcaaagga tcttcttgag atcctttttt tctgcgcgta 120

```
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc cagggggaaa cgcctggtat    600
ctttatagtc ctgtcgggtt tcgccacctc tgacttgagc gtcgattttt gtgatgctcg    660
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat ttttttatca ggaaacagct    960
atgaccgcgg ccgcagatag tcataatagt tccagaatag ttcaatttag aaattagact   1020
aaacttcaaa atgtttgtta aatatatacc aatctagtat agatattttt taaatactgg   1080
acttaaacag tagtaatttg cctaaaaaat tttttcaatt ttttttaaaa aatccttttc   1140
aagttgtaca ttgttatggt aatatgtaat tgaagaagtt atgtagtaat attgtaaacg   1200
tttcttgatt tttttacatc catgtagtgc ttaaaaaacc aaaatatgtc acatgcactt   1260
gtatatttca aataacaata tttattttct cgttaaattc acaaataatt tattaataat   1320
atcaataacc aagattatac ttaaatggat gtttattttt taacactttt atagtaaata   1380
tatttatttt atgtagtaaa aaggttataa ttataattgt atttattaca attaattaaa   1440
ataaaaaata gggttttagg taaaattaag ttattttaag aagtaattac aataaaaatt   1500
gaagttattt ctttaaggag gaaattcata tgaaagaggt tgttattgca tcagctgtta   1560
gaactgcaat aggatcttat ggaaaaagtc ttaaagatgt accagcagta gacttaggtg   1620
caactgcaat aaaggaagca gtaaagaaag caggtataaa acctgaagat gttaatgaag   1680
ttattttagg aaacgtatta caagctggac ttggacagaa tccagctaga caggcatcat   1740
tcaaagcagg attaccagta gagatacctg ctatgactat taataaagtt tgtggttcag   1800
gattaagaac agtttcttta gctgctcaaa ttataaaagc tggtgacgca gatgtaataa   1860
tagcaggtgg tatggaaaat atgtcaagag caccatacct tgctaataat gctagatggg   1920
gttatagaat gggaaacgct aaatttgtag acgaaatgat aactgatgga ctttgggatg   1980
catttaacga ttatcacatg ggaattactg ctgaaaatat agctgagaga tggaatataa   2040
gtagagaaga acaagatgag tttgcacttg catctcagaa aaaggcagaa gaagctatta   2100
aatcaggaca atttaaagat gaaattgttc cagtagtaat taaaggtaga aaaggtgaaa   2160
cagttgtaga cactgatgaa catcctagat ttggatctac aatagaaggt ttagctaaat   2220
taaagcctgc ttttaagaaa gacggaacag taactgctgg aaacgcatca ggtttaaatg   2280
attgtgcagc tgttttagtt attatgtctg ctgaaaaggc aaaggaatta ggtgttaaac   2340
cacttgctaa gatagttagt tatggttcag caggtgtaga tcctgctatt atgggatatg   2400
gaccttttta tgctacaaag gcagctattg aaaaggctgg ttggacagtt gatgaacttg   2460
```

```
atcttataga gtcaaatgag gcatttgcag cacaaagtct tgctgttgct aaggatctta   2520
aattcgatat gaataaagta aatgtaaacg gtggtgctat agcacttggt catccaatag   2580
gtgctagtgg tgctagaatt ttagttacat tagttcatgc aatgcaaaag agagacgcta   2640
aaaagggact tgcaacttta tgcataggtg gtggtcaagg aacagcaata cttcttgaaa   2700
aatgttaaga attcgaggct tttactaaaa acaataaaaa caggaggaaa taatatgact   2760
ataggaattg acaaaataaa cttttacgta ccaaaatatt atgtagatat ggcaaaatta   2820
gcagaagcaa gacaagtaga cccaaataaa tttcttattg gaataggaca gactgaaatg   2880
gcagttagtc cagtaaacca agatatagta tcaatgggtg ctaatgctgc taaagatata   2940
ataactgatg aagacaaaaa gaaaatagga atggtaatag tagcaactga gtcagcagta   3000
gatgcagcaa aggcagcagc agtacagatt cataatttat taggtattca accatttgca   3060
agatgtttcg aaatgaaaga agcatgttat gctgctactc ctgcaattca gttagctaag   3120
gattatttag ctacaagacc aaatgagaaa gttttagtta tagctacaga tacagctaga   3180
tatggactta attcaggtgg tgaacctact caaggtgctg gtgctgttgc tatggttata   3240
gctcataatc ctagtatact tgcattaaat gaagacgctg ttgcttatac agaagatgtt   3300
tatgatttct ggagaccaac aggacataag tatccattag tagatggtgc tttatcaaaa   3360
gacgcatata ttagatcttt tcaacaatct tggaatgaat atgctaagag acaaggaaag   3420
agtttagctg attttgctag tctttgcttt catgttcctt ttactaaaat gggtaaaaag   3480
gctttagaat ctataataga taacgcagat gaaacaactc aagagagatt aagatctgga   3540
tatgaagatg cagttgatta caatagatat gttggaaata tatacacagg aagtctttat   3600
ctttctctta taagtcttct tgaaaataga gatttacagg ctggtgaaac tattggatta   3660
ttttcatacg gatcaggttc tgttggtgaa ttttattcag ctacacttgt agaaggatat   3720
aaagatcacc ttgatcaggc agcacacaaa gcacttttaa acaatagaac tgaagtatca   3780
gtagatgcat acgaaacatt tttcaagaga tttgatgatg tagaatttga tgaagagcag   3840
gatgcagttc atgaagatag acatatattc tatctttcaa acatagagaa taatgtaaga   3900
gaatatcata gacctgaata agagctcgtt ataattttca attttcattc tttttaaagg   3960
agattagcat acattttatc ataattatac agacaatata gtaatatatg atgttaaaat   4020
atcaatatat ggttaaaaat ctgtatattt tttcccattt taattatttg tactataata   4080
ttacactgag tgtattgcat atttaaaaaa tatttggtac aattagttag ttaaataaat   4140
tctaaattgt aaattatcag aatccttatt aaggaaatac atagatttaa ggagaaatca   4200
taaaaaggtg taatataaac tggctaaaat tgagcaaaaa ttgagcaatt aagacttttt   4260
gattgtatct tttatatat ttaaggtata taatcttatt tatattgggg gaaggtacca   4320
tgcaatcatt agacaaaaat ttcagacatt tatcaagaca acaaaagtta caacaattag   4380
ttgataaaca gtggctttca gaagatcagt ttgatatttt acttaatcat cctcttatag   4440
atgaagaagt tgctaatagt cttatagaaa atgtaattgc acagggtgca ttaccagttg   4500
gacttcttcc taatataata gttgatgata aggcttatgt tgtaccaatg atggttgaag   4560
aacctagtgt tgttgcagct gcatcttatg gtgctaaatt agtaaatcag acaggtggat   4620
ttaaaactgt atcatcagaa agaataatga ttggacagat agtatttgat ggtgtagatg   4680
acactgaaaa attaagtgca gatattaaag cattagaaaa acaaatacat aagattgcag   4740
atgaagcata tcctagtata aaagcaagag gtggtggtta tcaaagaata gcaatagata   4800
catttccaga gcaacaactt ttaagtctta aggtatttgt agatacaaaa gatgctatgg   4860
```

```
gtgctaatat gcttaatact atacttgagg caataactgc attccttaaa aatgaatctc   4920
ctcaatcaga tatattaatg tctatacttt caaaccatgc aactgctagt gtagtaaaag   4980
tacaaggtga gatagatgta aaagatcttg ctagaggtga aagaacaggt gaagaagtag   5040
ctaagagaat ggaaagagct tctgtattag ctcaggttga tattcataga gctgcaacac   5100
ataacaaagg tgttatgaat ggaatacatg ctgttgtttt agctacagga aatgatacta   5160
gaggtgctga agcatctgca catgcatacg catcaagaga cggacaatat agaggtatag   5220
caacttggag atatgatcag aagagacaaa gacttattgg aactattgaa gttccaatga   5280
cacttgctat agtaggtggt ggtactaaag tattaccaat agctaaggca tcattagagt   5340
tattaaatgt tgattctgca caagaacttg gacacgtagt tgctgctgtt ggattagcac   5400
aaaactttgc tgcttgtaga gcacttgttt ctgaaggtat tcaacaagga cacatgtcat   5460
tacaatataa aagtttagca atagtagtag gtgcaaaagg tgacgagata gcacaagtag   5520
cagaagctct taaacaggaa ccaagagcta atacacaggt tgctgaaaga attttacagg   5580
aaattagaca gcaataatct agaatatcga tacagataaa aaaatatata atacagaaga   5640
aaaaattata aatttgtggt ataatataaa gtatagtaat ttaagtttaa acctcgtgaa   5700
aacgctaaca aataatagga ggtcaattga tgatagctgt tccatttaac gctggaaaaa   5760
taaaagtttt aattgaggca ttagaatctg gaaattattc atcaataaaa tcagatgtat   5820
atgacggaat gttatatgat gcaccagatc accttaaatc attagtaaac agatttgtag   5880
aacttaataa tataactgag ccattagcag taactataca gacaaatctt cctccttcaa   5940
gaggtcttgg atctagtgca gctgttgctg ttgcttttgt aagagcaagt tatgatttct   6000
taggaaaaag tttaactaaa gaagagctta tagaaaaggc taattgggct gaacaaatag   6060
ctcatggaaa gccatctgga atagatacac aaacaatagt atctggaaag cctgtttggt   6120
ttcaaaaggg acatgcagaa acacttaaaa ctctttcact tgatggatac atggtagtaa   6180
ttgatacagg tgttaaagga agtacaagac aggctgtaga agatgttcat aaactttgcg   6240
aagatcctca atatatgagt cacgtaaaac acataggaaa acttgtactt agagcatctg   6300
atgttattga acatcataac tttgaagcac ttgctgatat attcaatgaa tgtcatgctg   6360
atttaaaggc tcttacagta agtcatgaca aaatagaaca gttaatgaag atagaaaaag   6420
aaaatggtgc tatagctggt aaattaactg gtgctggtag aggtggttca atgttattac   6480
ttgcaaaaga cttaccaact gcaaagaata tagttaaagc agtagagaaa gctggtgcag   6540
cacatacttg gattgaaaat ttaggtggtt aagtcgacaa agacactaaa aaattataaa   6600
agtaaaggag gacattaaat gatacaagta aaggcaccag gaaaattata tatagcaggt   6660
gaatacgctg ttacagaacc aggatataaa tctgttctta tagctcttga tagatttgtt   6720
acagctacta ttgaggaagc tgatcaatac aaaggaacaa tacattcaaa ggcattacat   6780
cacaatccag taacttttag tagagatgaa gattctattg ttatatcaga cccacacgca   6840
gcaaaacaac ttaattatgt agtaactgct atagaaatat ttgagcaata tgcaaaatca   6900
tgtgacatag caatgaagca ttttcattta actatagatt ctaacttaga tgatagtaat   6960
ggacataagt atggacttgg atcttctgct gctgttttag tttcagtaat taaagtactt   7020
aacgaatttt atgatatgaa actttcaaac ctttatatat ataagttagc agtaattgct   7080
aatatgaaat tacagagttt atcttcatgc ggtgatatag cagtaagtgt ttattcaggt   7140
tggttagctt attctacatt tgaccatgaa tgggtaaaac accagataga agatacaaca   7200
```

gttgaagaag tacttattaa aaattggcct ggattacaca tagagccact tcaagctcct 7260
gaaaatatgg aagttcttat aggttggaca ggtagtccag ctagtagtcc tcattttgtt 7320
tctgaagtta aaagacttaa gtcagatcct tcattttacg gtgatttctt agaagattca 7380
catagatgtg tagaaaaatt aattcatgca ttcaaaacta ataatattaa gggtgttcag 7440
aaaatggtaa gacagaatag aactattata caaagaatgg ataaggaagc aacagttgat 7500
atagagactg agaagttaaa atatttatgt gatattgctg aaaaatatca tggtgcaagt 7560
aaaacttcag gtgctggtgg tggtgattgc ggaataacta taataaataa ggatgtagac 7620
aaagagaaaa tatatgatga atggactaaa catggaataa agcctcttaa gtttaatatt 7680
tatcatggac aataaccatg gtcaataatc ttacaataaa taaaagaaag gaggcaaaaa 7740
tatgataaaa tctggaaaag caagagcaca cactaatata gcacttataa aatattgggg 7800
taagaaagat gaggcattaa taataccaat gaataactca atatcagtaa ctttagaaaa 7860
gttttatact gaaacaaaag ttacatttaa cgatcagctt actcaagatc aattttggct 7920
taatggtgaa aaagtttctg gaaaagaatt agaaaagatt tcaaagtata tggatattgt 7980
tagaaataga gctggaatag attggtatgc tgagatagaa tctgataatt ttgttcctac 8040
agctgctggt cttgctagtt ctgctagtgc ttatgcagca ttagctgctg catgtaacca 8100
agcacttgat ttacagttaa gtgataaaga cttaagtaga ttagctagaa ttggatcagg 8160
atcagcatca agatcaatat acggtggttt tgcagaatgg gaaaaaggat ataatgacga 8220
aacttcttat gctgttccat tagaaagtaa tcactttgaa gatgatcttg ctatgatttt 8280
tgtagtaata aaccaacatt ctaaaaaggt tccttcaaga tatggaatgt ctcttacaag 8340
aaatacaagt agattctatc aatattggtt agaccatatt gatgaagatc ttgcagaagc 8400
aaaggcagca atacaagata aggattttaa gagattaggt gaagttattg aagagaatgg 8460
acttagaatg catgctacaa atcttggatc aactccacct tttacttact tagtacaaga 8520
gtcatacgat gtaatggcat tagtacatga gtgtagagaa gcaggatatc catgctattt 8580
cactatggat gctggaccta atgtaaaaat acttgtagag aagaaaaaca aacaacagat 8640
aatagataaa cttttaactc agttcgataa taatcagata atagatagtg atattatagc 8700
tacaggtatt gaaattatag aataaactag ttgtatatta aaatagtaga atacataaga 8760
tacttaattt aattaaagat agttaagtac ttttcaatgt gctttttag atgtttaata 8820 caaatcttta attgtaaaag aaatgctgta ctatttactg ttctagtgac gggattaaac 8880
tgtattaatt ataaataaaa aataagtaca gttgtttaaa attatatttt gtattaaatc 8940
taatagtacg atgtaagtta ttttatacta ttgctagttt aataaaaaga tttaattata 9000
tacttgaaaa ggagaggaac tcgagatggc agagtatata atagcagtag atgagttcga 9060
taacgaaata ggatcaatag aaaagatgga agctcataga aaaggaacac ttcatagagc 9120
attcagtatt ttagttttta actcaaagaa tcaactttta ttacagaaaa gaaatgtaaa 9180
gaaatatcac tctccaggat tatggacaaa cacttgttgt agtcacccaa gatatggtga 9240
atctcttcat gatgctatat acagaagatt aaaagaagag atgggattta cttgcgaact 9300
tgaagaagta ttctcattca tatataaggt aaaacttgaa gataatttat ttgagaatga 9360
atatgaccat gtatttattg gtaaatatga tggtgagata attgttaata aagatgaagt 9420
tgatgatttt aaatgggtag acattaatga agttaaaaag gacataatag aaagacctga 9480
ggcatatact tactggttta agtatcttgt aaataaagct gaaaataaga tatttaaata 9540
aaccggtggg aggaaatgaa catggcaaca gaattattat gtttacacag acctatatca 9600

-continued

```
cttactcaca aactttttag gaatccatta cctaaagtta ttcaagctac acctttaaca   9660
ttaaaactta ggtgtagtgt ttctacagaa aatgtatcat ttagtgagac agaaactgaa   9720
acaagaagat cagcaaatta tgaaccaaat tcttgggatt atgattatct tctttcttct   9780
gatactgatg agtcaataga agtacataaa gataaggcta agaaattaga agctgaagtt   9840
aggagagaaa taaataatga gaaggctgaa tttcttacac ttcttgaact tattgataat   9900
gtacaaagac ttggattagg atatagattt gagtctgata taagaagagc attagataga   9960
tttgtaagta gtggaggatt tgatggagtt actaaaactt cattacatgg aacagcatta  10020
tcatttaggt tattaaggca acatggtttt gaagtatctc aagaagcttt tagtggattt  10080
aaagatcaga atggaaactt tcttgagaat ttaaaggaag acataaaagc aattctttct  10140
ctttatgaag catcattttt agcattagaa ggtgagaata tattagatga ggctaaagta  10200
tttgcaatat ctcatcttaa agaacttagt gaagaaaaga ttggtaaaga attagctgaa  10260
caagtttcac atgctttaga attaccatta catagaagaa cacaaagatt agaagcagtt  10320
tggtcaatag aagcatatag aaagaaagaa gacgcaaatc aagtactttt agaacttgca  10380
atacttgact acaatatgat tcaaagtgta tatcagaggg atttaagaga aacatcaaga  10440
tggtggagaa gagtaggatt agcaactaaa ttacattttg ctagagatag gcttattgaa  10500
agtttttatt gggctgttgg agttgctttt gaaccacaat attctgattg cagaaatagt  10560
gtagcaaaga tgttttcatt tgttactata attgacgata tttacgatgt atatggaact  10620
ttagatgaac ttgaactttt tactgatgca gttgaaagat gggatgtaaa tgctattaat  10680
gatcttcctg attatatgaa gttatgtttt cttgcacttt acaatactat taacgagata  10740
gcttacgata acttaaaaga taaaggtgag aacatacttc cttatttaac aaaagcatgg  10800
gcagatttat gtaatgcatt tcttcaagaa gctaagtggc tttataataa atcaacacct  10860
acatttgatg attattttgg aaatgcatgg aaaagttcta gtggaccttt acagcttatt  10920
tttgcttatt ttgctgtagt acagaacatt aaaaaggaag agattgagaa tcttcagaaa  10980
tatcatgaca taatatcaag acctagtcac atttttaggc tttgtaatga tttagcatct  11040
gcttcagcag aaatagcaag aggtgaaact gctaattctg taagttgtta tatgagaaca  11100
aaaggtatat ctgaagaatt agctactgaa agtgttatga atcttataga cgaaacttgg  11160
aagaaaatga acaaagaaaa acttggtgga tctttatttg caaaaccttt tgttgagact  11220
gctataaatt tagctagaca gtctcattgc acatatcata atggtgatgc acatactagt  11280
ccagatgaat taactaggaa aagagtactt agtgtaataa ctgaaccaat attaccattt  11340
gaaagataag ctagcataaa aataagaagc ctgcatttgc aggcttctta tttttatggc  11400
gcgccgccat tattttttttg aacaattgac aattcatttc ttattttttta ttaagtgata  11460
gtcaaaaggc ataacagtgc tgaatagaaa gaaatttaca gaaaagaaaa ttatagaatt  11520
tagtatgatt aattatactc atttatgaat gtttaattga atacaaaaaa aaatacttgt  11580
tatgtattca attacgggtt aaaatataga caagttgaaa aatttaataa aaaaataagt  11640
cctcagctct tatatattaa gctaccaact tagtatataa gccaaaactt aaatgtgcta  11700
ccaacacatc aagccgttag agaactctat ctatagcaat atttcaaatg taccgacata  11760
caagagaaac attaactata tatattcaat ttatgagatt atcttaacag atataaatgt  11820
aaattgcaat aagtaagatt tagaagttta tagcctttgt gtattggaag cagtacgcaa  11880
aggctttttt atttgataaa aattagaagt atatttattt tttcataatt aatttatgaa  11940
```

```
aatgaaaggg ggtgagcaaa gtgacagagg aaagcagtat cttatcaaat aacaaggtat  12000

tagcaatatc attattgact ttagcagtaa acattatgac ttttatagtg cttgtagcta  12060

agtagtacga aagggggagc tttaaaaagc tccttggaat acatagaatt cataaattaa  12120

tttatgaaaa gaagggcgta tatgaaaact tgtaaaaatt gcaaagagtt tattaaagat  12180

actgaaatat gcaaaataca ttcgttgatg attcatgata aaacagtagc aacctattgc  12240

agtaaataca atgagtcaag atgtttacat aaagggaaag tccaatgtat taattgttca  12300

aagatgaacc gatatggatg gtgtgccata aaaatgagat gttttacaga ggaagaacag  12360

aaaaaagaac gtacatgcat taaatattat gcaaggagct ttaaaaaagc tcatgtaaag  12420

aagagtaaaa agaaaaaata atttatttat taatttaata ttgagagtgc cgacacagta  12480

tgcactaaaa aatatatctg tggtgtagtg agccgataca aaaggatagt cactcgcatt  12540

ttcataatac atcttatgtt atgattatgt gtcggtggga cttcacgacg aaaacccaca  12600

ataaaaaaag agttcggggt agggttaagc atagttgagg caactaaaca atcaagctag  12660

gatatgcagt agcagaccgt aaggtcgttg tttaggtgtg ttgtaataca tacgctatta  12720

agatgtaaaa atacggatac caatgaaggg aaaagtataa tttttggatg tagtttgttt  12780

gttcatctat gggcaaacta cgtccaaagc cgtttccaaa tctgctaaaa agtatatcct  12840

ttctaaaatc aaagtcaagt atgaaatcat aaataaagtt taattttgaa gttattatga  12900

tattatgttt ttctattaaa ataaattaag tatatagaat agtttaataa tagtatatac  12960

ttaatgtgat aagtgtctga cagtgtcaca gaaaggatga ttgttatgga ttataagcgg  13020

ccggccagtg ggcaagttga aaaattcaca aaaatgtggt ataatatctt tgttcattag  13080

agcgataaac ttgaatttga gagggaactt agatggtatt tgaaaaaatt gataaaaata  13140

gttggaacag aaaagagtat tttgaccact actttgcaag tgtaccttgt acctacagca  13200

tgaccgttaa agtggatatc acacaaataa aggaaaaggg aatgaaacta tatcctgcaa  13260

tgctttatta tattgcaatg attgtaaacc gccattcaga gtttaggacg gcaatcaatc  13320

aagatggtga attggggata tatgatgaga tgataccaag ctatacaata tttcacaatg  13380

atactgaaac attttccagc ctttggactg agtgtaagtc tgactttaaa tcatttttag  13440

cagattatga aagtgatacg caacggtatg gaaacaatca tagaatggaa ggaaagccaa  13500

atgctccgga aaacattttt aatgtatcta tgataccgtg gtcaaccttc gatggcttta  13560

atctgaattt gcagaaagga tatgattatt tgattcctat ttttactatg ggaaatatt  13620

ataaagaaga taacaaaatt atacttcctt tggcaattca agttcatcac gcagtatgtg  13680

acggatttca catttgccgt tttgtaaacg aattgcagga attgataaat agttaacttc  13740

aggtttgtct gtaactaaaa acaagtattt aagcaaaaac atcgtagaaa tacggtgttt  13800

tttgttaccc taagttt                                                 13817
```

<210> SEQ ID NO 59
<211> LENGTH: 14709
<212> TYPE: DNA
<213> ORGANISM: Artificial Sequence
<220> FEATURE:
<223> OTHER INFORMATION: plasmid
pMTL8314-Pptaack-thlA-HMGS-Patp-HMGR-Prnf-MK-PMK-PMD-Pfor-idi-isp
A-FS

<400> SEQUENCE: 59

```
aaactccttt ttgataatct catgaccaaa atcccttaac gtgagttttc gttccactga     60

gcgtcagacc ccgtagaaaa gatcaaagga tcttcttgag atcctttttt tctgcgcgta    120
```

-continued atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc cagggggaaa cgcctggtat 600
ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720
ttttgctggc cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggcccccctg caggataaaa 900
aaattgtaga taaattttat aaaatagttt tatctacaat ttttttatca ggaaacagct 960
atgaccgcgg ccgcagatag tcataatagt tccagaatag ttcaatttag aaattagact 1020
aaacttcaaa atgtttgtta aatatatacc aatctagtat agatattttt taaatactgg 1080
acttaaacag tagtaatttg cctaaaaaat tttttcaatt ttttttaaaa aatccttttc 1140
aagttgtaca ttgttatggt aatatgtaat tgaagaagtt atgtagtaat attgtaaacg 1200
tttcttgatt tttttacatc catgtagtgc ttaaaaaacc aaaatatgtc acatgcactt 1260
gtatatttca aataacaata tttattttct cgttaaattc acaaataatt tattaataat 1320
atcaataacc aagattatac ttaaatggat gtttattttt taacactttt atagtaaata 1380
tatttatttt atgtagtaaa aaggttataa ttataattgt atttattaca attaattaaa 1440
ataaaaaata gggttttagg taaaattaag ttattttaag aagtaattac aataaaaatt 1500
gaagttattt ctttaaggag gaaattcata tgaaagaggt tgttattgca tcagctgtta 1560
gaactgcaat aggatcttat ggaaaaagtc ttaaagatgt accagcagta gacttaggtg 1620
caactgcaat aaaggaagca gtaaagaaag caggtataaa acctgaagat gttaatgaag 1680
ttattttagg aaacgtatta caagctggac ttggacagaa tccagctaga caggcatcat 1740
tcaaagcagg attaccagta gagatacctg ctatgactat taataaagtt tgtggttcag 1800
gattaagaac agtttcttta gctgctcaaa ttataaaagc tggtgacgca gatgtaataa 1860
tagcaggtgg tatggaaaat atgtcaagag caccatacct tgctaataat gctagatggg 1920
gttatagaat gggaaacgct aaatttgtag acgaaatgat aactgatgga ctttgggatg 1980
catttaacga ttatcacatg ggaattactg ctgaaaatat agctgagaga tggaatataa 2040
gtagagaaga acaagatgag tttgcacttg catctcagaa aaaggcagaa gaagctatta 2100
aatcaggaca atttaaagat gaaattgttc cagtagtaat taaaggtaga aaaggtgaaa 2160
cagttgtaga cactgatgaa catcctagat ttggatctac aatagaaggt ttagctaaat 2220
taaagcctgc ttttaagaaa gacggaacag taactgctgg aaacgcatca ggtttaaatg 2280
attgtgcagc tgttttagtt attatgtctg ctgaaaaggc aaaggaatta ggtgttaaac 2340
cacttgctaa gatagttagt tatggttcag caggtgtaga tcctgctatt atgggatatg 2400
gacctttttta tgctacaaag gcagctattg aaaaggctgg ttggacagtt gatgaacttg 2460

-continued

```
atcttataga gtcaaatgag gcatttgcag cacaaagtct tgctgttgct aaggatctta   2520
aattcgatat gaataaagta aatgtaaacg gtggtgctat agcacttggt catccaatag   2580
gtgctagtgg tgctagaatt ttagttacat tagttcatgc aatgcaaaag agagacgcta   2640
aaaagggact tgcaacttta tgcataggtg gtggtcaagg aacagcaata cttcttgaaa   2700
aatgttaaga attcgaggct tttactaaaa acaataaaaa caggaggaaa taatatgact   2760
ataggaattg acaaaataaa cttttacgta ccaaaatatt atgtagatat ggcaaaatta   2820
gcagaagcaa gacaagtaga cccaaataaa tttcttattg gaataggaca gactgaaatg   2880
gcagttagtc cagtaaacca agatatagta tcaatgggtg ctaatgctgc taaagatata   2940
ataactgatg aagacaaaaa gaaaatagga atggtaatag tagcaactga gtcagcagta   3000
gatgcagcaa aggcagcagc agtacagatt cataatttat taggtattca accatttgca   3060
agatgtttcg aaatgaaaga agcatgttat gctgctactc ctgcaattca gttagctaag   3120
gattatttag ctacaagacc aaatgagaaa gttttagtta tagctacaga tacagctaga   3180
tatggactta attcaggtgg tgaacctact caaggtgctg gtgctgttgc tatggttata   3240
gctcataatc ctagtatact tgcattaaat gaagacgctg ttgcttatac agaagatgtt   3300
tatgatttct ggagaccaac aggacataag tatccattag tagatggtgc tttatcaaaa   3360
gacgcatata ttagatcttt tcaacaatct tggaatgaat atgctaagag acaaggaaag   3420
agtttagctg attttgctag tctttgcttt catgttcctt ttactaaaat gggtaaaaag   3480
gctttagaat ctataataga taacgcagat gaaacaactc aagagagatt aagatctgga   3540
tatgaagatg cagttgatta caatagatat gttggaaata tatacacagg aagtctttat   3600
ctttctctta taagtcttct tgaaaataga gatttacagg ctggtgaaac tattggatta   3660
ttttcatacg gatcaggttc tgttggtgaa ttttattcag ctacacttgt agaaggatat   3720
aaagatcacc ttgatcaggc agcacacaaa gcacttttaa acaatagaac tgaagtatca   3780
gtagatgcat acgaaacatt tttcaagaga tttgatgatg tagaatttga tgaagagcag   3840
gatgcagttc atgaagatag acatatattc tatctttcaa acatagagaa taatgtaaga   3900
gaatatcata gacctgaata agagctcgtt ataattttca attttcattc tttttaaagg   3960
agattagcat acattttatc ataattatac agacaatata gtaatatatg atgttaaaat   4020
atcaatatat ggttaaaaat ctgtatattt tttcccattt taattatttg tactataata   4080
ttacactgag tgtattgcat atttaaaaaa tatttggtac aattagttag ttaaataaat   4140
tctaaattgt aaattatcag aatccttatt aaggaaatac atagatttaa ggagaaatca   4200
taaaaaggtg taatataaac tggctaaaat tgagcaaaaa ttgagcaatt aagacttttt   4260
gattgtatct ttttatatat ttaaggtata taatcttatt tatattgggg gaaggtacca   4320
tgcaatcatt agacaaaaat ttcagacatt tatcaagaca acaaaagtta caacaattag   4380
ttgataaaca gtggctttca gaagatcagt ttgatatttt acttaatcat cctcttatag   4440
atgaagaagt tgctaatagt cttatagaaa atgtaattgc acagggtgca ttaccagttg   4500
gacttcttcc taatataata gttgatgata aggcttatgt tgtaccaatg atggttgaag   4560
aacctagtgt tgttgcagct gcatcttatg gtgctaaatt agtaaatcag acaggtggat   4620
ttaaaactgt atcatcagaa agaataatga ttggacagat agtatttgat ggtgtagatg   4680
acactgaaaa attaagtgca gatattaaag cattagaaaa acaaatacat aagattgcag   4740
atgaagcata tcctagtata aaagcaagag gtggtggtta tcaaagaata gcaatagata   4800
catttccaga gcaacaactt ttaagtctta aggtatttgt agatacaaaa gatgctatgg   4860
```

```
gtgctaatat gcttaatact atacttgagg caataactgc attccttaaa aatgaatctc   4920
ctcaatcaga tatattaatg tctatacttt caaaccatgc aactgctagt gtagtaaaag   4980
tacaaggtga gatagatgta aaagatcttg ctagaggtga aagaacaggt gaagaagtag   5040
ctaagagaat ggaaagagct tctgtattag ctcaggttga tattcataga gctgcaacac   5100
ataacaaagg tgttatgaat ggaatacatg ctgttgtttt agctacagga aatgatacta   5160
gaggtgctga agcatctgca catgcatacg catcaagaga cggacaatat agaggtatag   5220
caacttggag atatgatcag aagagacaaa gacttattgg aactattgaa gttccaatga   5280
cacttgctat agtaggtggt ggtactaaag tattaccaat agctaaggca tcattagagt   5340
tattaaatgt tgattctgca caagaacttg gacacgtagt tgctgctgtt ggattagcac   5400
aaaactttgc tgcttgtaga gcacttgttt ctgaaggtat tcaacaagga cacatgtcat   5460
tacaatataa aagtttagca atagtagtag gtgcaaaagg tgacgagata gcacaagtag   5520
cagaagctct taaacaggaa ccaagagcta atacacaggt tgctgaaaga attttacagg   5580
aaattagaca gcaataatct agaatatcga tacagataaa aaaatatata atacagaaga   5640
aaaaattata aatttgtggt ataatataaa gtatagtaat ttaagtttaa acctcgtgaa   5700
aacgctaaca aataatagga ggtcaattga tgatagctgt tccatttaac gctggaaaaa   5760
taaaagtttt aattgaggca ttagaatctg gaaattattc atcaataaaa tcagatgtat   5820
atgacggaat gttatatgat gcaccagatc accttaaatc attagtaaac agatttgtag   5880
aacttaataa tataactgag ccattagcag taactataca gacaaatctt cctccttcaa   5940
gaggtcttgg atctagtgca gctgttgctg ttgcttttgt aagagcaagt tatgatttct   6000
taggaaaaag tttaactaaa gaagagctta tagaaaaggc taattgggct gaacaaatag   6060
ctcatggaaa gccatctgga atagatacac aaacaatagt atctggaaag cctgtttggt   6120
ttcaaaaggg acatgcagaa acacttaaaa ctctttcact tgatggatac atggtagtaa   6180
ttgatacagg tgttaaagga agtacaagac aggctgtaga agatgttcat aaactttgcg   6240
aagatcctca atatatgagt cacgtaaaac acataggaaa acttgtactt agagcatctg   6300
atgttattga acatcataac tttgaagcac ttgctgatat attcaatgaa tgtcatgctg   6360
atttaaaggc tcttacagta agtcatgaca aaatagaaca gttaatgaag ataggaaaag   6420
aaaatggtgc tatagctggt aaattaactg gtgctggtag aggtggttca atgttattac   6480
ttgcaaaaga cttaccaact gcaaagaata tagttaaagc agtagagaaa gctggtgcag   6540
cacatacttg gattgaaaat ttaggtggtt aagtcgacaa agacactaaa aaattataaa   6600
agtaaaggag gacattaaat gatacaagta aaggcaccag gaaaattata tatagcaggt   6660
gaatacgctg ttacagaacc aggatataaa tctgttctta tagctcttga tagatttgtt   6720
acagctacta ttgaggaagc tgatcaatac aaaggaacaa tacattcaaa ggcattacat   6780
cacaatccag taacttttag tagagatgaa gattctattg ttatatcaga cccacacgca   6840
gcaaaacaac ttaattatgt agtaactgct atagaaatat ttgagcaata tgcaaaatca   6900
tgtgacatag caatgaagca ttttcattta actatagatt ctaacttaga tgatagtaat   6960
ggacataagt atggacttgg atcttctgct gctgttttag tttcagtaat taaagtactt   7020
aacgaatttt atgatatgaa actttcaaac ctttatatat ataagttagc agtaattgct   7080
aatatgaaat tacagagttt atcttcatgc ggtgatatag cagtaagtgt ttattcaggt   7140
tggttagctt attctacatt tgaccatgaa tgggtaaaac accagataga agatacaaca   7200
```

-continued

```
gttgaagaag tacttattaa aaattggcct ggattacaca tagagccact tcaagctcct   7260
gaaaatatgg aagttcttat aggttggaca ggtagtccag ctagtagtcc tcattttgtt   7320
tctgaagtta aaagacttaa gtcagatcct tcattttacg gtgatttctt agaagattca   7380
catagatgtg tagaaaaatt aattcatgca ttcaaaacta ataatattaa gggtgttcag   7440
aaaatggtaa gacagaatag aactattata caaagaatgg ataaggaagc aacagttgat   7500
atagagactg agaagttaaa atatttatgt gatattgctg aaaaatatca tggtgcaagt   7560
aaaacttcag gtgctggtgg tggtgattgc ggaataacta taataaataa ggatgtagac   7620
aaagagaaaa tatatgatga atggactaaa catggaataa agcctcttaa gtttaatatt   7680
tatcatggac aataaccatg gtcaataatc ttacaataaa taaaagaaag gaggcaaaaa   7740
tatgataaaa tctggaaaag caagagcaca cactaatata gcacttataa aatattgggg   7800
taagaaagat gaggcattaa taataccaat gaataactca atatcagtaa ctttagaaaa   7860
gttttatact gaaacaaaag ttacatttaa cgatcagctt actcaagatc aattttggct   7920
taatggtgaa aaagtttctg gaaaagaatt agaaaagatt tcaaagtata tggatattgt   7980
tagaaataga gctggaatag attggtatgc tgagatagaa tctgataatt ttgttcctac   8040
agctgctggt cttgctagtt ctgctagtgc ttatgcagca ttagctgctg catgtaacca   8100
agcacttgat ttacagttaa gtgataaaga cttaagtaga ttagctagaa ttggatcagg   8160
atcagcatca agatcaatat acggtggttt tgcagaatgg gaaaaaggat ataatgacga   8220
aacttcttat gctgttccat tagaaagtaa tcactttgaa gatgatcttg ctatgatttt   8280
tgtagtaata aaccaacatt ctaaaaaggt tccttcaaga tatggaatgt ctcttacaag   8340
aaatacaagt agattctatc aatattggtt agaccatatt gatgaagatc ttgcagaagc   8400
aaaggcagca atacaagata aggattttaa gagattaggt gaagttattg aagagaatgg   8460
acttagaatg catgctacaa atcttggatc aactccacct tttacttact tagtacaaga   8520
gtcatacgat gtaatggcat tagtacatga gtgtagagaa gcaggatatc catgctattt   8580
cactatggat gctggaccta atgtaaaaat acttgtagag aagaaaaaca aacaacagat   8640
aatagataaa cttttaactc agttcgataa taatcagata atagatagtg atattatagc   8700
tacaggtatt gaaattatag aataaactag ttgtatatta aaatagtaga atacataaga   8760
tacttaattt aattaaagat agttaagtac ttttcaatgt gctttttag atgtttaata   8820
caaatcttta attgtaaaag aaatgctgta ctatttactg ttctagtgac gggattaaac   8880
tgtattaatt ataaataaaa aataagtaca gttgtttaaa attatatttt gtattaaatc   8940
taatagtacg atgtaagtta ttttatacta ttgctagttt aataaaaaga tttaattata   9000
tacttgaaaa ggagaggaac tcgagatggc agagtatata atagcagtag atgagttcga   9060
taacgaaata ggatcaatag aaaagatgga agctcataga aaaggaacac ttcatagagc   9120
attcagtatt ttagttttta actcaaagaa tcaactttta ttacagaaaa gaaatgtaaa   9180
gaaatatcac tctccaggat tatggacaaa cacttgttgt agtcacccaa gatatggtga   9240
atctcttcat gatgctatat acagaagatt aaaagaagag atgggattta cttgcgaact   9300
tgaagaagta ttctcattca tatataaggt aaaacttgaa gataatttat ttgagaatga   9360
atatgaccat gtatttattg gtaaatatga tggtgagata attgttaata aagatgaagt   9420
tgatgatttt aaatgggtag acattaatga agttaaaaag gacataatag aaagacctga   9480
ggcatatact tactggttta agtatcttgt aaataaagct gaaaataaga tatttaaata   9540
aaccggtcag taacgaatag aattagaaaa acaaaggagg caagacaatg gatttcccac   9600
```

aacaattaga agcatgtgta aaacaggcta atcaggcact tagtagattt attgctcctc 9660
ttccttttca aaatacacca gtagtagaaa ctatgcaata cggtgcactt ttaggtggta 9720
aaagattaag accattctta gtatatgcta caggacacat gtttggtgta tcaactaata 9780
ctttagacgc tccagctgct gctgttgaat gtattcatgc ttattcttta atacatgatg 9840
acttaccagc aatggatgac gatgatttaa gaagaggttt acctacatgt catgttaaat 9900
ttggtgaagc taatgcaatt ttagcaggtg acgctttaca aactttagct ttttctatac 9960
tttcagatgc agacatgcct gaagtttcag atagagatag aatttctatg atatcagagc 10020
ttgcatctgc atcaggaata gctggaatgt gcggtggtca agcacttgat ttagatgcag 10080
aaggtaaaca cgtaccactt gatgctttag agagaataca tagacataaa acaggtgctc 10140
ttataagagc agcagtaaga ttaggtgctt taagtgctgg tgacaagggt agaagagcac 10200
ttccagtact tgataagtat gcagaaagta taggattagc ttttcaagtt caagatgaca 10260
tacttgacgt tgttggtgat actgctactt taggaaaaag acagggtgca gatcagcaat 10320
taggaaaatc tacataccct gctttacttg gattagaaca ggctagaaag aaagcaagag 10380
acttaataga tgacgcaaga caaagtctta aacagttagc tgaacaatca cttgacacaa 10440
gtgcacttga agcacttgca gattatatta tacagagaaa caagtaaaag cttttaaagg 10500
aggggaaaaa atggaattta gagtacattt acaggcagac aacgaacaga aaatatttca 10560
aaatcaaatg aaaccagagc cagaagcatc atatcttata aatcaaagaa gaagtgctaa 10620
ttataaacca aacatttgga aaaacgattt tcttgatcag tctttaatat caaaatatga 10680
tggtgatgaa tatagaaaac tttcagaaaa gttaatagaa gaagtaaaga tatacatatc 10740
agcagagact atggatttag ttgctaaatt agaacttata gattctgtta gaaaacttgg 10800
acttgctaat ctttttgaga aagaaataaa ggaagcatta gacagtatag cagcaataga 10860
atcagataat ttaggaacta gagacgatct ttatggaaca gctcttcatt ttaagattct 10920
tagacagcat ggatataagg taagtcaaga tatatttggt agatttatgg atgagaaagg 10980
aacattagaa aatcatcact ttgcacactt aaaaggaatg ttagaattat ttgaggcaag 11040
taatcttgga tttgaaggtg aagacatatt agatgaagct aaagcatctc ttacacttgc 11100
tcttagagat tcaggacata tttgttatcc agactcaaac ttaagtagag atgtagttca 11160
tagtttagaa ttacctagtc atagaagagt tcaatggttc gatgtaaaat ggcagattaa 11220
tgcatacgaa aaagatattt gtagagtaaa tgcaacttta ttagagttag caaagttaaa 11280
ttttaatgtt gttcaagctc agcttcagaa gaatcttaga gaagctagta gatggtgggc 11340
taatcttggt ttcgcagata atttaaagtt tgctagagat agacttgtag agtgtttttc 11400
atgcgcagta ggtgtagcat ttgaaccaga gcattcatct tttagaatat gtttaactaa 11460
ggtaattaat cttgttctta ttatagatga tgtatacgat atatatggat ctgaagaaga 11520
gttaaaacat tttacaaatg ctgttgatag atgggacagt agagaaacag aacagcttcc 11580
tgaatgcatg aaaatgtgtt ttcaagtatt atataacact acttgcgaaa tagcaagaga 11640
gatagaagaa gaaaacggtt ggaatcaagt attacctcaa cttactaagg tttgggctga 11700
tttttgtaag gctcttttag ttgaagcaga gtggtacaat aaatcacata ttccaacatt 11760
agaagaatat cttagaaacg gatgtatatc aagtagtgta tctgtacttt tagttcactc 11820
tttcttttca ataactcatg aaggtacaaa agaaatggct gatttcttac ataaaaatga 11880
agatctttta tacaacataa gtcttatagt aagattaaac aatgatttag gtacatcagc 11940
tgctgaacag gaaagaggtg attctccttc ttctatagtt tgctatatga gagaagttaa 12000
tgcttctgaa gagactgcaa gaaagaatat aaagggaatg attgataatg cttggaaaaa 12060
ggttaatgga aaatgtttca caactaacca agttccattt ctttcatcat tcatgaataa 12120
tgcaactaac atggcaagag tagcacactc attatataaa gacggtgatg gttttggtga 12180
tcaagaaaaa ggacctagaa cacatattct tagtttatta ttccaacctt tagtaaatta 12240
agctagcata aaaataagaa gcctgcattt gcaggcttct tatttttatg gcgcgccgcc 12300
attatttttt tgaacaattg acaattcatt tcttattttt tattaagtga tagtcaaaag 12360
gcataacagt gctgaataga aagaaattta cagaaaagaa aattatagaa tttagtatga 12420
ttaattatac tcatttatga atgtttaatt gaatacaaaa aaaaatactt gttatgtatt 12480
caattacggg ttaaaatata gacaagttga aaaatttaat aaaaaaataa gtcctcagct 12540
cttatatatt aagctaccaa cttagtatat aagccaaaac ttaaatgtgc taccaacaca 12600
tcaagccgtt agagaactct atctatagca atatttcaaa tgtaccgaca tacaagagaa 12660
acattaacta tatatattca atttatgaga ttatcttaac agatataaat gtaaattgca 12720
ataagtaaga tttagaagtt tatagccttt gtgtattgga agcagtacgc aaaggctttt 12780
ttatttgata aaaattagaa gtatatttat tttttcataa ttaatttatg aaaatgaaag 12840
ggggtgagca aagtgacaga ggaaagcagt atcttatcaa ataacaaggt attagcaata 12900
tcattattga ctttagcagt aaacattatg acttttatag tgcttgtagc taagtagtac 12960
gaaaggggga gctttaaaaa gctccttgga atacatagaa ttcataaatt aatttatgaa 13020
aagaagggcg tatatgaaaa cttgtaaaaa ttgcaaagag tttattaaag atactgaaat 13080
atgcaaaata cattcgttga tgattcatga taaaacagta gcaacctatt gcagtaaata 13140
caatgagtca agatgtttac ataaagggaa agtccaatgt attaattgtt caaagatgaa 13200
ccgatatgga tggtgtgcca taaaaatgag atgttttaca gaggaagaac agaaaaaaga 13260
acgtacatgc attaaatatt atgcaaggag ctttaaaaaa gctcatgtaa agaagagtaa 13320
aaagaaaaaa taatttattt attaatttaa tattgagagt gccgacacag tatgcactaa 13380
aaaatatatc tgtggtgtag tgagccgata caaaaggata gtcactcgca ttttcataat 13440
acatcttatg ttatgattat gtgtcggtgg gacttcacga cgaaaaccca caataaaaaa 13500
agagttcggg gtagggttaa gcatagttga ggcaactaaa caatcaagct aggatatgca 13560
gtagcagacc gtaaggtcgt tgtttaggtg tgttgtaata catacgctat taagatgtaa 13620
aaatacggat accaatgaag ggaaaagtat aatttttgga tgtagtttgt ttgttcatct 13680
atgggcaaac tacgtccaaa gccgtttcca aatctgctaa aaagtatatc ctttctaaaa 13740
tcaaagtcaa gtatgaaatc ataaataaag tttaattttg aagttattat gatattatgt 13800
ttttctatta aaataaatta agtatataga atagtttaat aatagtatat acttaatgtg 13860
ataagtgtct gacagtgtca cagaaaggat gattgttatg gattataagc ggccggccag 13920
tgggcaagtt gaaaaattca caaaaatgtg gtataatatc tttgttcatt agagcgataa 13980
acttgaattt gagagggaac ttagatggta tttgaaaaaa ttgataaaaa tagttggaac 14040
agaaaagagt attttgacca ctactttgca agtgtacctt gtacctacag catgaccgtt 14100
aaagtggata tcacacaaat aaaggaaaag ggaatgaaac tatatcctgc aatgctttat 14160
tatattgcaa tgattgtaaa ccgccattca gagtttagga cggcaatcaa tcaagatggt 14220
gaattgggga tatatgatga gatgatacca agctatacaa tatttcacaa tgatactgaa 14280
acattttcca gcctttggac tgagtgtaag tctgacttta aatcattttt agcagattat 14340
gaaagtgata cgcaacggta tggaaacaat catagaatgg aaggaaagcc aaatgctccg 14400
gaaaacattt ttaatgtatc tatgataccg tggtcaacct tcgatggctt taatctgaat 14460
ttgcagaaag gatatgatta tttgattcct atttttacta tggggaaata ttataaagaa 14520
gataacaaaa ttatacttcc tttggcaatt caagttcatc acgcagtatg tgacggattt 14580
cacatttgcc gttttgtaaa cgaattgcag gaattgataa atagttaact tcaggtttgt 14640
ctgtaactaa aaacaagtat ttaagcaaaa acatcgtaga aatacggtgt tttttgttac 14700
cctaagttt 14709

<210> SEQ ID NO 60
<211> LENGTH: 601
<212> TYPE: PRT
<213> ORGANISM: Artificial Sequence
<220> FEATURE:
<223> OTHER INFORMATION: hybrid Type II methyltransferase

<400> SEQUENCE: 60

Met Phe Pro Cys Asn Ala Tyr Ile Glu Tyr Gly Asp Lys Asn Met Asn
1 5 10 15

Ser Phe Ile Glu Asp Val Glu Gln Ile Tyr Asn Phe Ile Lys Lys Asn
20 25 30

Ile Asp Val Glu Glu Lys Met His Phe Ile Glu Thr Tyr Lys Gln Lys
35 40 45

Ser Asn Met Lys Lys Glu Ile Ser Phe Ser Glu Glu Tyr Tyr Lys Gln
50 55 60

Lys Ile Met Asn Gly Lys Asn Gly Val Val Tyr Thr Pro Pro Glu Met
65 70 75 80

Ala Ala Phe Met Val Lys Asn Leu Ile Asn Val Asn Asp Val Ile Gly
85 90 95

Asn Pro Phe Ile Lys Ile Ile Asp Pro Ser Cys Gly Ser Gly Asn Leu
100 105 110

Ile Cys Lys Cys Phe Leu Tyr Leu Asn Arg Ile Phe Ile Lys Asn Ile
115 120 125

Glu Val Ile Asn Ser Lys Asn Asn Leu Asn Leu Lys Leu Glu Asp Ile
130 135 140

Ser Tyr His Ile Val Arg Asn Asn Leu Phe Gly Phe Asp Ile Asp Glu
145 150 155 160

Thr Ala Ile Lys Val Leu Lys Ile Asp Leu Phe Leu Ile Ser Asn Gln
165 170 175

Phe Ser Glu Lys Asn Phe Gln Val Lys Asp Phe Leu Val Glu Asn Ile
180 185 190

Asp Arg Lys Tyr Asp Val Phe Ile Gly Asn Pro Pro Tyr Ile Gly His
195 200 205

Lys Ser Val Asp Ser Ser Tyr Ser Tyr Val Leu Arg Lys Ile Tyr Gly
210 215 220

Ser Ile Tyr Arg Asp Lys Gly Asp Ile Ser Tyr Cys Phe Phe Gln Lys
225 230 235 240

Ser Leu Lys Cys Leu Lys Glu Gly Gly Lys Leu Val Phe Val Thr Ser
245 250 255

Arg Tyr Phe Cys Glu Ser Cys Ser Gly Lys Glu Leu Arg Lys Phe Leu
260 265 270

Ile Glu Asn Thr Ser Ile Tyr Lys Ile Ile Asp Phe Tyr Gly Ile Arg
275 280 285

```
Pro Phe Lys Arg Val Gly Ile Asp Pro Met Ile Ile Phe Leu Val Arg
    290                 295                 300

Thr Lys Asn Trp Asn Asn Asn Ile Glu Ile Ile Arg Pro Asn Lys Ile
305                 310                 315                 320

Glu Lys Asn Glu Lys Asn Lys Phe Leu Asp Ser Leu Phe Leu Asp Lys
                325                 330                 335

Ser Glu Lys Cys Lys Lys Phe Ser Ile Ser Gln Lys Ser Ile Asn Asn
            340                 345                 350

Asp Gly Trp Val Phe Val Asp Glu Val Glu Lys Asn Ile Ile Asp Lys
        355                 360                 365

Ile Lys Glu Lys Ser Lys Phe Ile Leu Lys Asp Ile Cys His Ser Cys
    370                 375                 380

Gln Gly Ile Ile Thr Gly Cys Asp Arg Ala Phe Ile Val Asp Arg Asp
385                 390                 395                 400

Ile Ile Asn Ser Arg Lys Ile Glu Leu Arg Leu Ile Lys Pro Trp Ile
                405                 410                 415

Lys Ser Ser His Ile Arg Lys Asn Glu Val Ile Lys Gly Glu Lys Phe
            420                 425                 430

Ile Ile Tyr Ser Asn Leu Ile Glu Asn Glu Thr Glu Cys Pro Asn Ala
        435                 440                 445

Ile Lys Tyr Ile Glu Gln Tyr Lys Lys Arg Leu Met Glu Arg Arg Glu
    450                 455                 460

Cys Lys Lys Gly Thr Arg Lys Trp Tyr Glu Leu Gln Trp Gly Arg Lys
465                 470                 475                 480

Pro Glu Ile Phe Glu Glu Lys Lys Ile Val Phe Pro Tyr Lys Ser Cys
                485                 490                 495

Asp Asn Arg Phe Ala Leu Asp Lys Gly Ser Tyr Phe Ser Ala Asp Ile
            500                 505                 510

Tyr Ser Leu Val Leu Lys Lys Asn Val Pro Phe Thr Tyr Glu Ile Leu
        515                 520                 525

Leu Asn Ile Leu Asn Ser Pro Leu Tyr Glu Phe Tyr Phe Lys Thr Phe
    530                 535                 540

Ala Lys Lys Leu Gly Glu Asn Leu Tyr Glu Tyr Tyr Pro Asn Asn Leu
545                 550                 555                 560

Met Lys Leu Cys Ile Pro Ser Ile Asp Phe Gly Gly Glu Asn Asn Ile
                565                 570                 575

Glu Lys Lys Leu Tyr Asp Phe Phe Gly Leu Thr Asp Lys Glu Ile Glu
            580                 585                 590

Ile Val Glu Lys Ile Lys Asp Asn Cys
        595                 600
```

<210> SEQ ID NO 61
<211> LENGTH: 419
<212> TYPE: DNA
<213> ORGANISM: Clostridium autoethanogenum

<400> SEQUENCE: 61

```
agaaattttc ctttctaaaa tattttattc catgtcaaga actctgttta tttcattaaa      60

gaactataag tacaaagtat aaggcatttg aaaaaatagg ctagtatatt gattgattat     120

ttattttaaa atgcctaagt gaaatatata catattataa caataaaata agtattagtg     180

taggattttt aaatagagta tctattttca gattaaattt ttgattattt gatttacatt     240

atataatatt gagtaaagta ttgactagca aaattttttg atactttaat ttgtgaaatt     300

tcttatcaaa agttatattt ttgaataatt tttattgaaa aatacaacta aaaaggatta     360
```

tagtataagt gtgtgtaatt ttgtgttaaa tttaaaggga ggaaatgaac atgaaattg 419

<210> SEQ ID NO 62
<211> LENGTH: 567
<212> TYPE: DNA
<213> ORGANISM: Clostridium autoethanogenum

<400> SEQUENCE: 62
ctcctaattt tgaaatctaa tatatctatt aaatcatatt ttcatatgta aataaataag 60
tttttatgca attttgaaaa aggtatttgc ataaaacggc ttgaaatcaa tagttaacgc 120
aatagttatt cttttagcat acattaagtc aacaaaatta gcatgtaata attatgaata 180
attattacat atattcaata ttatattaaa aaaaatactt tgttttaagt ataaagtaaa 240
aaaataggca taaatgtaac aaaaactgtt aattttttgt gtcaataatt tttgttatat 300
tattttaatt aaatttttca catgtataat taaaagtaag atagatattc taatgtactt 360
acttaggtag aaaaacatgt atacaaaatt aaaaaactat tataacacat agtatcaata 420
ttgaaggtaa tactgttcaa tatcgataca gataaaaaaa atatataata cagaagaaaa 480
aattataaat ttgtggtata atataaagta tagtaattta agtttaaacc tcgtgaaaac 540
gctaacaaat aataggaggt gtattat 567

<210> SEQ ID NO 63
<211> LENGTH: 1806
<212> TYPE: DNA
<213> ORGANISM: Artificial Sequence
<220> FEATURE:
<223> OTHER INFORMATION: hybrid Type II methyltransferase

<400> SEQUENCE: 63
atgtttccgt gcaatgccta tatcgaatat ggtgataaaa atatgaacag ctttatcgaa 60
gatgtggaac agatctacaa cttcattaaa aagaacattg atgtggaaga aaagatgcat 120
ttcattgaaa cctataaaca gaaaagcaac atgaagaaag agattagctt tagcgaagaa 180
tactataaac agaagattat gaacggcaaa aatggcgttg tgtacacccc gccggaaatg 240
gcggccttta tggttaaaaa tctgatcaac gttaacgatg ttattggcaa tccgtttatt 300
aaaatcattg acccgagctg cggtagcggc aatctgattt gcaaatgttt tctgtatctg 360
aatcgcatct ttattaagaa cattgaggtg attaacagca aaaataacct gaatctgaaa 420
ctggaagaca tcagctacca catcgttcgc aacaatctgt ttggcttcga tattgacgaa 480
accgcgatca aagtgctgaa aattgatctg tttctgatca gcaaccaatt tagcgagaaa 540
aatttccagg ttaaagactt tctggtggaa aatattgatc gcaaatatga cgtgttcatt 600
ggtaatccgc cgtatatcgg tcacaaaagc gtggacagca gctacagcta cgtgctgcgc 660
aaaatctacg gcagcatcta ccgcgacaaa ggcgatatca gctattgttt ctttcagaag 720
agcctgaaat gtctgaagga aggtggcaaa ctggtgtttg tgaccagccg ctacttctgc 780
gagagctgca gcggtaaaga actgcgtaaa ttcctgatcg aaaacacgag catttacaag 840
atcattgatt tttacggcat ccgccccgttc aaacgcgtgg gtatcgatcc gatgattatt 900
tttctggttc gtacgaagaa ctggaacaat aacattgaaa ttattcgccc gaacaagatt 960
gaaaagaacg aaaagaacaa attcctggat agcctgttcc tggacaaaag cgaaaagtgt 1020
aaaaagttta gcattagcca gaaaagcatt aataacgatg gctgggtttt cgtggacgaa 1080
gtggagaaaa acattatcga caaaatcaaa gagaaaagca agttcattct gaaagatatt 1140
tgccatagct gtcaaggcat tatcaccggt tgtgatcgcg cctttattgt ggaccgtgat 1200
atcatcaata gccgtaagat cgaactgcgt ctgattaaac cgtggattaa aagcagccat 1260
atccgtaaga atgaagttat taagggcgaa aaattcatca tctatagcaa cctgattgag 1320
aatgaaaccg agtgtccgaa tgcgattaaa tatatcgaac agtacaagaa acgtctgatg 1380
gagcgccgcg aatgcaaaaa gggcacgcgt aagtggtatg aactgcaatg gggccgtaaa 1440
ccggaaatct tcgaagaaaa gaaaattgtt ttcccgtata aaagctgtga caatcgtttt 1500
gcactggata agggtagcta ttttagcgca gacatttata gcctggttct gaagaaaaat 1560
gtgccgttca cctatgagat cctgctgaat atcctgaata gcccgctgta cgagttttac 1620
tttaagacct tcgcgaaaaa gctgggcgag aatctgtacg agtactatcc gaacaacctg 1680
atgaagctgt gcatcccgag catcgatttc ggcggtgaga acaatattga gaaaaagctg 1740
tatgatttct ttggtctgac ggataaagaa attgagattg tggagaagat caaagataac 1800
tgctaa 1806

<210> SEQ ID NO 64
<211> LENGTH: 4709
<212> TYPE: DNA
<213> ORGANISM: Artificial Sequence
<220> FEATURE:
<223> OTHER INFORMATION: designed methylation plasmid

<400> SEQUENCE: 64
gtttgccacc tgacgtctaa gaaaaggaat attcagcaat ttgcccgtgc cgaagaaagg 60
cccacccgtg aaggtgagcc agtgagttga ttgctacgta attagttagt tagcccttag 120
tgactcgtaa tacgactcac tatagggctc gaggcggccg cgcaacgcaa ttaatgtgag 180
ttagctcact cattaggcac cccaggcttt acactttatg cttccggctc gtatgttgtg 240
tggaattgtg agcggataac aatttcacac aggaaacaca tatgtttccg tgcaatgcct 300
atatcgaata tggtgataaa aatatgaaca gctttatcga agatgtggaa cagatctaca 360
acttcattaa aaagaacatt gatgtggaag aaaagatgca tttcattgaa acctataaac 420
agaaaagcaa catgaagaaa gagattagct ttagcgaaga atactataaa cagaagatta 480
tgaacggcaa aaatggcgtt gtgtacaccc cgccggaaat ggcggccttt atggttaaaa 540
atctgatcaa cgttaacgat gttattggca atccgtttat taaaatcatt gacccgagct 600
gcggtagcgg caatctgatt tgcaaatgtt ttctgtatct gaatcgcatc tttattaaga 660
acattgaggt gattaacagc aaaaataacc tgaatctgaa actggaagac atcagctacc 720
acatcgttcg caacaatctg tttggcttcg atattgacga aaccgcgatc aaagtgctga 780
aaattgatct gtttctgatc agcaaccaat ttagcgagaa aaatttccag gttaaagact 840
ttctggtgga aaatattgat cgcaaatatg acgtgttcat tggtaatccg ccgtatatcg 900
gtcacaaaag cgtggacagc agctacagct acgtgctgcg caaaatctac ggcagcatct 960
accgcgacaa aggcgatatc agctattgtt tctttcagaa gagcctgaaa tgtctgaagg 1020
aaggtggcaa actggtgttt gtgaccagcc gctacttctg cgagagctgc agcggtaaag 1080
aactgcgtaa attcctgatc gaaaacacga gcatttacaa gatcattgat ttttacggca 1140
tccgcccgtt caaacgcgtg ggtatcgatc cgatgattat ttttctggtt cgtacgaaga 1200
actggaacaa taacattgaa attattcgcc cgaacaagat tgaaaagaac gaaaagaaca 1260
aattcctgga tagcctgttc ctggacaaaa gcgaaaagtg taaaaagttt agcattagcc 1320
agaaaagcat taataacgat ggctgggttt tcgtggacga agtggagaaa aacattatcg 1380

-continued

```
acaaaatcaa agagaaaagc aagttcattc tgaaagatat ttgccatagc tgtcaaggca   1440
ttatcaccgg ttgtgatcgc gcctttattg tggaccgtga tatcatcaat agccgtaaga   1500
tcgaactgcg tctgattaaa ccgtggatta aaagcagcca tatccgtaag aatgaagtta   1560
ttaagggcga aaaattcatc atctatagca acctgattga gaatgaaacc gagtgtccga   1620
atgcgattaa atatatcgaa cagtacaaga aacgtctgat ggagcgccgc gaatgcaaaa   1680
agggcacgcg taagtggtat gaactgcaat ggggccgtaa accggaaatc ttcgaagaaa   1740
agaaaattgt tttcccgtat aaaagctgtg acaatcgttt tgcactggat aagggtagct   1800
attttagcgc agacatttat agcctggttc tgaagaaaaa tgtgccgttc acctatgaga   1860
tcctgctgaa tatcctgaat agcccgctgt acgagtttta ctttaagacc ttcgcgaaaa   1920
agctgggcga gaatctgtac gagtactatc cgaacaacct gatgaagctg tgcatcccga   1980
gcatcgattt cggcggtgag aacaatattg agaaaaagct gtatgatttc tttggtctga   2040
cggataaaga aattgagatt gtggagaaga tcaaagataa ctgctaagaa ttcgatatca   2100
cccgggaact agtctgcagc cctttagtga gggttaattg gagtcactaa gggttagtta   2160
gttagattag cagaaagtca aaagcctccg accggaggct tttgactaaa acttcccttg   2220
gggttatcat tggggctcac tcaaaggcgg taatcagata aaaaaaatcc ttagctttcg   2280
ctaaggatga tttctgctag agatggaata gactggatgg aggcggataa agttgcagga   2340
ccacttctgc gctcggccct tccggctggc tggtttattg ctgataaatc tggagccggt   2400
gagcgtgggt ctcgcggtat cattgcagca ctggggccag atggtaagcc ctcccgtatc   2460
gtagttatct acacgacggg gagtcaggca actatggatg aacgaaatag acagatcgct   2520
gagataggtg cctcactgat taagcattgg taactgtcag accaagttta ctcatatata   2580
ctttagattg atttaaaact tcatttttaa tttaaaagga tctaggtgaa gatccttttt   2640
gataatctca tgaccaaaat cccttaacgt gagttttcgt tccactgagc gtcagacccc   2700
ttaataagat gatcttcttg agatcgtttt ggtctgcgcg taatctcttg ctctgaaaac   2760
gaaaaaaccg ccttgcaggg cggtttttcg aaggttctct gagctaccaa ctctttgaac   2820
cgaggtaact ggcttggagg agcgcagtca ccaaaacttg tcctttcagt ttagccttaa   2880
ccggcgcatg acttcaagac taactcctct aaatcaatta ccagtggctg ctgccagtgg   2940
tgcttttgca tgtctttccg ggttggactc aagacgatag ttaccggata aggcgcagcg   3000
gtcggactga acggggggtt cgtgcataca gtccagcttg gagcgaactg cctacccgga   3060
actgagtgtc aggcgtggaa tgagacaaac gcggccataa cagcggaatg acaccggtaa   3120
accgaaaggc aggaacagga gagcgcacga gggagccgcc aggggaaacg cctggtatct   3180
ttatagtcct gtcgggtttc gccaccactg atttgagcgt cagatttcgt gatgcttgtc   3240
aggggggcgg agcctatgga aaaacggctt tgccgcggcc ctctcacttc cctgttaagt   3300
atcttcctgg catcttccag gaaatctccg ccccgttcgt aagccatttc cgctcgccgc   3360
agtcgaacga ccgagcgtag cgagtcagtg agcgaggaag cggaatatat cctgtatcac   3420
atattctgct gacgcaccgg tgcagccttt tttctcctgc cacatgaagc acttcactga   3480
caccctcatc agtgccaaca tagtaagcca gtatacactc cgctagcgct gaggtctgcc   3540
tcgtgaagaa ggtgttgctg actcatacca ggcctgaatc gccccatcat ccagccagaa   3600
agtgagggag ccacggttga tgagagcttt gttgtaggtg gaccagttgg tgattttgaa   3660
cttttgcttt gccacggaac ggtctgcgtt gtcgggaaga tgcgtgatct gatccttcaa   3720
```

```
ctcagcaaaa gttcgattta ttcaacaaag ccacgttgtg tctcaaaatc tctgatgtta   3780

cattgcacaa gataaaaata tatcatcatg aacaataaaa ctgtctgctt acataaacag   3840

taatacaagg ggtgtttact agaggttgat cgggcacgta agaggttcca actttcacca   3900

taatgaaata agatcactac cgggcgtatt ttttgagtta tcgagatttt caggagctaa   3960

ggaagctaaa atggagaaaa aaatcacggg atataccacc gttgatatat cccaatggca   4020

tcgtaaagaa cattttgagg catttcagtc agttgctcaa tgtacctata accagaccgt   4080

tcagctggat attacggcct ttttaaagac cgtaaagaaa aataagcaca agttttatcc   4140

ggcctttatt cacattcttg cccgcctgat gaacgctcac ccggagtttc gtatggccat   4200

gaaagacggt gagctggtga tctgggatag tgttcaccct tgttacaccg ttttccatga   4260

gcaaactgaa acgttttcgt ccctctggag tgaataccac gacgatttcc ggcagtttct   4320

ccacatatat tcgcaagatg tggcgtgtta cggtgaaaac ctggcctatt tccctaaagg   4380

gtttattgag aatatgtttt ttgtctcagc caatccctgg gtgagtttca ccagttttga   4440

tttaaacgtg gccaatatgg acaacttctt cgcccccgtt ttcacgatgg gcaaatatta   4500

tacgcaaggc gacaaggtgc tgatgccgct ggcgatccag gttcatcatg ccgtttgtga   4560

tggcttccat gtcggccgca tgcttaatga attacaacag tactgtgatg agtggcaggg   4620

cggggcgtaa taatactagc tccggcaaaa aaacgggcaa ggtgtcacca ccctgccctt   4680

tttctttaaa accgaaaaga ttacttcgc                                     4709
```

<210> SEQ ID NO 65
<211> LENGTH: 18
<212> TYPE: DNA
<213> ORGANISM: Artificial Sequence
<220> FEATURE:
<223> OTHER INFORMATION: Oligonucleotide colE1-F

<400> SEQUENCE: 65

```
cgtcagaccc cgtagaaa                                                   18
```

<210> SEQ ID NO 66
<211> LENGTH: 18
<212> TYPE: DNA
<213> ORGANISM: Artificial Sequence
<220> FEATURE:
<223> OTHER INFORMATION: Oligonucleotide colE1-R

<400> SEQUENCE: 66

```
ctctcctgtt ccgaccct                                                   18
```

<210> SEQ ID NO 67
<211> LENGTH: 37
<212> TYPE: DNA
<213> ORGANISM: Artificial Sequence
<220> FEATURE:
<223> OTHER INFORMATION: Oligonucleotide fD1

<400> SEQUENCE: 67

```
ccgaattcgt cgacaacaga gtttgatcct ggctcag                              37
```

<210> SEQ ID NO 68
<211> LENGTH: 37
<212> TYPE: DNA
<213> ORGANISM: Artificial Sequence
<220> FEATURE:
<223> OTHER INFORMATION: Oligonucleotide Rp2

<400> SEQUENCE: 68
cccgggatcc aagcttacgg ctaccttgtt acgactt 37

<210> SEQ ID NO 69
<211> LENGTH: 25
<212> TYPE: DNA
<213> ORGANISM: Artificial Sequence
<220> FEATURE:
<223> OTHER INFORMATION: Oligonucleotide ispS-F

<400> SEQUENCE: 69
aggctgaatt tcttacactt cttga 25

<210> SEQ ID NO 70
<211> LENGTH: 25
<212> TYPE: DNA
<213> ORGANISM: Artificial Sequence
<220> FEATURE:
<223> OTHER INFORMATION: Oligonucleotide ispS-R

<400> SEQUENCE: 70
gtaactccat caaatcctcc actac 25

<210> SEQ ID NO 71
<211> LENGTH: 25
<212> TYPE: DNA
<213> ORGANISM: Artificial Sequence
<220> FEATURE:
<223> OTHER INFORMATION: Oligonucleotide idi-F

<400> SEQUENCE: 71
atacgtgctg tagtcatcca agata 25

<210> SEQ ID NO 72
<211> LENGTH: 25
<212> TYPE: DNA
<213> ORGANISM: Artificial Sequence
<220> FEATURE:
<223> OTHER INFORMATION: Oligonucleotide idiR

<400> SEQUENCE: 72
tcttcaagtt cacatgtaaa accca 25

<210> SEQ ID NO 73
<211> LENGTH: 25
<212> TYPE: DNA
<213> ORGANISM: Artificial Sequence
<220> FEATURE:
<223> OTHER INFORMATION: oligonucleotide dxs-F

<400> SEQUENCE: 73
acaaagtatc taagacagga ggtca 25

<210> SEQ ID NO 74
<211> LENGTH: 25
<212> TYPE: DNA
<213> ORGANISM: Artificial Sequence
<220> FEATURE:
<223> OTHER INFORMATION: oligonucleotide dxs-R

<400> SEQUENCE: 74
gatgtcccac atcccatata agttt 25

<210> SEQ ID NO 75
<211> LENGTH: 6018
<212> TYPE: DNA

<213> ORGANISM: Artificial Sequence
<220> FEATURE:
<223> OTHER INFORMATION: plasmid pMTL85246-IspS-Idi

<400> SEQUENCE: 75

```
ccggggatcc tctagagtcg acgtcacgcg tccatggaga tctcgaggcc tgcagacatg      60

caagcttggc actggccgtc gttttacaac gtcgtgactg ggaaaaccct ggcgttaccc     120

aacttaatcg ccttgcagca catccccctt tcgccagctg gcgtaatagc gaagaggccc     180

gcaccgatcg cccttcccaa cagttgcgca gcctgaatgg cgaatggcgc tagcataaaa     240

ataagaagcc tgcatttgca ggcttcttat ttttatggcg cgccgcattc acttcttttc     300

tatataaata tgagcgaagc gaataagcgt cggaaaagca gcaaaaagtt tcctttttgc     360

tgttggagca tgggggttca gggggtgcag tatctgacgt caatgccgag cgaaagcgag     420

ccgaagggta gcatttacgt tagataaccc cctgatatgc tccgacgctt tatatagaaa     480

agaagattca actaggtaaa atcttaatat aggttgagat gataaggttt ataaggaatt     540

tgtttgttct aatttttcac tcattttgtt ctaatttctt ttaacaaatg ttcttttttt     600

tttagaacag ttatgatata gttagaatag tttaaaataa ggagtgagaa aaagatgaaa     660

gaaagatatg gaacagtcta taaaggctct cagaggctca tagacgaaga aagtggagaa     720

gtcatagagg tagacaagtt ataccgtaaa caaacgtctg gtaacttcgt aaaggcatat     780

atagtgcaat taataagtat gttagatatg attggcggaa aaaaacttaa aatcgttaac     840

tatatcctag ataatgtcca cttaagtaac aatacaatga tagctacaac aagagaaata     900

gcaaaagcta caggaacaag tctacaaaca gtaataacaa cacttaaaat cttagaagaa     960

ggaaatatta taaaaagaaa aactggagta ttaatgttaa accctgaact actaatgaga    1020

ggcgacgacc aaaaacaaaa atacctctta ctcgaatttg ggaactttga gcaagaggca    1080

aatgaaatag attgacctcc caataacacc acgtagttat tgggaggtca atctatgaaa    1140

tgcgattaag ggccggccga agcaaactta agagtgtgtt gatagtgcag tatcttaaaa    1200

ttttgtataa taggaattga agttaaatta gatgctaaaa atttgtaatt aagaaggagt    1260

gattacatga acaaaaatat aaaatattct caaaactttt taacgagtga aaaagtactc    1320

aaccaaataa taaaacaatt gaatttaaaa gaaaccgata ccgtttacga aattggaaca    1380

ggtaaagggc atttaacgac gaaactggct aaaataagta aacaggtaac gtctattgaa    1440

ttagacagtc atctattcaa cttatcgtca gaaaaattaa aactgaatac tcgtgtcact    1500

ttaattcacc aagatattct acagtttcaa ttccctaaca aacagaggta taaaattgtt    1560

gggagtattc cttaccattt aagcacacaa attattaaaa aagtggtttt tgaaagccat    1620

gcgtctgaca tctatctgat tgttgaagaa ggattctaca agcgtacctt ggatattcac    1680

cgaacactag ggttgctctt gcacactcaa gtctcgattc agcaattgct taagctgcca    1740

gcggaatgct ttcatcctaa accaaaagta aacagtgtct taataaaact tacccgccat    1800

accacagatg ttccagataa atattggaag ctatatacgt actttgtttc aaaatgggtc    1860

aatcgagaat atcgtcaact gtttactaaa aatcagtttc atcaagcaat gaaacacgcc    1920

aaagtaaaca atttaagtac cgttacttat gagcaagtat tgtctatttt taatagttat    1980

ctattattta acgggaggaa ataattctat gagtcgcttt tgtaaatttg gaaagttaca    2040

cgttactaaa gggaatgtgt ttaaactcct ttttgataat ctcatgacca aaatccctta    2100

acgtgagttt tcgttccact gagcgtcaga ccccgtagaa aagatcaaag gatcttcttg    2160

agatcctttt tttctgcgcg taatctgctg cttgcaaaca aaaaaaccac cgctaccagc    2220
```

-continued ggtggtttgt ttgccggatc aagagctacc aactcttttt ccgaaggtaa ctggcttcag 2280
cagagcgcag ataccaaata ctgttcttct agtgtagccg tagttaggcc accacttcaa 2340
gaactctgta gcaccgccta catacctcgc tctgctaatc ctgttaccag tggctgctgc 2400
cagtggcgat aagtcgtgtc ttaccgggtt ggactcaaga cgatagttac cggataaggc 2460
gcagcggtcg ggctgaacgg ggggttcgtg cacacagccc agcttggagc gaacgaccta 2520
caccgaactg agatacctac agcgtgagct atgagaaagc gccacgcttc ccgaagggag 2580
aaaggcggac aggtatccgg taagcggcag ggtcggaaca ggagagcgca cgagggagct 2640
tccaggggga aacgcctggt atctttatag tcctgtcggg tttcgccacc tctgacttga 2700
gcgtcgattt ttgtgatgct cgtcaggggg gcggagccta tggaaaaacg ccagcaacgc 2760
ggccttttta cggttcctgg ccttttgctg gccttttgct cacatgttct ttcctgcgtt 2820
atcccctgat tctgtggata accgtattac cgcctttgag tgagctgata ccgctcgccg 2880
cagccgaacg accgagcgca gcgagtcagt gagcgaggaa gcggaagagc gcccaatacg 2940
cagggccccc tgcaggataa aaaaattgta gataaatttt ataaaatagt tttatctaca 3000
atttttttat caggaaacag ctatgaccgc ggccgcggtt aatgttaaaa atttatagta 3060
taactttaaa aaactgtctt aaaaagttgt tatataaaaa atgttgacaa ttaaacagct 3120
atttagtgca aaacaaccat aaaaatttaa aaaataccat aaattacttg aaaaatagtt 3180
gataataatg tagagttata aacaaaggtg aaaagcatta cttgtattct tttttatata 3240
ttattataaa ttaaaatgaa gctgtattag aaaaaataca cacctgtaat ataaaatttt 3300
aaattaattt ttaatttttt caaaatgtat tttacatgtt tagaattttg atgtatatta 3360
aaatagtaga atacataaga tacttaattt aattaaagat agttaagtac ttttcaatgt 3420
gctttttttag atgtttaata caaatcttta attgtaaaag aaatgctgta ctatttactg 3480
tactagtgac gggattaaac tgtattaatt ataaataaaa aataagtaca gttgtttaaa 3540
attatatttt gtattaaatc taatagtacg atgtaagtta ttttatacta ttgctagttt 3600
aataaaaaga tttaattata tacttgaaaa ggagaggaat ttttatgcgt catatggcaa 3660
cagaattatt atgtttacac agacctatat cacttactca caaacttttt aggaatccat 3720
tacctaaagt tattcaagct acacctttaa cattaaaact taggtgtagt gtttctacag 3780
aaaatgtatc atttagtgag acagaaactg aaacaagaag atcagcaaat tatgaaccaa 3840
attcttggga ttatgattat cttctttctt ctgatactga tgagtcaata gaagtacata 3900
aagataaggc taagaaatta gaagctgaag ttaggagaga aataaataat gagaaggctg 3960
aatttcttac acttcttgaa cttattgata atgtacaaag acttggatta ggatatagat 4020
ttgagtctga tataagaaga gcattagata gatttgtaag tagtggagga tttgatggag 4080
ttactaaaac ttcattacat ggaacagcat tatcatttag gttattaagg caacatggtt 4140
ttgaagtatc tcaagaagct tttagtggat ttaaagatca gaatggaaac tttcttgaga 4200
atttaaagga agacataaaa gcaattcttt ctctttatga agcatcattt ttagcattag 4260
aaggtgagaa tatattagat gaggctaaag tatttgcaat atctcatctt aaagaactta 4320
gtgaagaaaa gattggtaaa gaattagctg aacaagtttc acatgcttta gaattaccat 4380
tacatagaag aacacaaaga ttagaagcag tttggtcaat agaagcatat agaaagaaag 4440
aagacgcaaa tcaagtactt ttagaacttg caatacttga ctacaatatg attcaaagtg 4500
tatatcagag ggatttaaga gaaacatcaa gatggtggag aagagtagga ttagcaacta 4560
aattacattt tgctagagat aggcttattg aaagttttta ttgggctgtt ggagttgctt 4620
ttgaaccaca atattctgat tgcagaaata gtgtagcaaa gatgttttca tttgttacta 4680
taattgacga tatttacgat gtatatggaa ctttagatga acttgaactt tttactgatg 4740
cagttgaaag atgggatgta aatgctatta atgatcttcc tgattatatg aagttatgtt 4800
ttcttgcact ttacaatact attaacgaga tagcttacga taacttaaaa gataaaggtg 4860
agaacatact tccttattta acaaaagcat gggcagattt atgtaatgca tttcttcaag 4920
aagctaagtg gctttataat aaatcaacac ctacatttga tgattatttt ggaaatgcat 4980
ggaaaagttc tagtggacct ttacagctta tttttgctta ttttgctgta gtacagaaca 5040
ttaaaaagga agagattgag aatcttcaga aatatcatga cataatatca agacctagtc 5100
acatttttag gctttgtaat gatttagcat ctgcttcagc agaaatagca agaggtgaaa 5160
ctgctaattc tgtaagttgt tatatgagaa caaaaggtat atctgaagaa ttagctactg 5220
aaagtgttat gaatcttata gacgaaactt ggaagaaaat gaacaaagaa aaacttggtg 5280
gatctttatt tgcaaaacct tttgttgaga ctgctataaa tttagctaga cagtctcatt 5340
gcacatatca taatggtgat gcacatacta gtccagatga attaactagg aaaagagtac 5400
ttagtgtaat aactgaacca atattaccat ttgaaagata agaattcgag ctcgaaaggg 5460
gaaattaaat ggcagaatat ataatagctg tagatgaatt tgataacgaa ataggttcaa 5520
ttgaaaaaat ggaggctcac cgtaaaggaa cattacatag agctttttct atattagtat 5580
ttaattctaa aaatcaattg ttattacaga aaagaaatgt aaaaaaatat cattcgcctg 5640
gtctctggac aaatacgtgc tgtagtcatc caagatacgg tgaaagttta catgatgcga 5700
tttatagaag gcttaaggaa gaaatgggtt ttacatgtga acttgaagaa gtatttagtt 5760
ttatttataa agtaaaactt gaagataatc tttttgaaaa tgaatatgat catgtattca 5820
ttgggaaata tgatggagaa ataattgtaa acaaagatga agtagatgat tttaagtggg 5880
ttgatattaa tgaggttaag aaggatatta tagaaaggcc agaagcatac acttattggt 5940
tcaagtattt agttaataag gcagaaaaca aaatatttaa ataagtaaga atttcgtcta 6000
aataaagatt tggggtac 6018

<210> SEQ ID NO 76
<211> LENGTH: 6909
<212> TYPE: DNA
<213> ORGANISM: Artificial Sequence
<220> FEATURE:
<223> OTHER INFORMATION: plasmid pMTL 82151-Patp-HMGR

<400> SEQUENCE: 76
cctgcaggat aaaaaaattg tagataaatt ttataaaata gttttatcta caattttttt 60
atcaggaaac agctatgacc gcggccgctg tatccatatg accatgatta cgaattcgag 120
ctcgttataa ttttcaattt tcattctttt taaaggagat tagcatacat tttatcataa 180
ttatacagac aatatagtaa tatatgatgt taaaatatca atatatggtt aaaaatctgt 240
atattttttc ccattttaat tatttgtact ataatattac actgagtgta ttgcatattt 300
aaaaaatatt tggtacaatt agttagttaa ataaattcta aattgtaaat tatcagaatc 360
cttattaagg aaatacatag atttaaggag aaatcataaa aaggtgtaat ataaactggc 420
taaaattgag caaaaattga gcaattaaga ctttttgatt gtatcttttt atatatttaa 480
ggtatataat cttatttata ttgggggaag gtaccatgca atcattagac aaaaatttca 540
gacatttatc aagacaacaa aagttacaac aattagttga taaacagtgg ctttcagaag 600

```
atcagtttga tattttactt aatcatcctc ttatagatga agaagttgct aatagtctta    660
tagaaaatgt aattgcacag ggtgcattac cagttggact tcttcctaat ataatagttg    720
atgataaggc ttatgttgta ccaatgatgg ttgaagaacc tagtgttgtt gcagctgcat    780
cttatggtgc taaattagta aatcagacag gtggatttaa aactgtatca tcagaaagaa    840
taatgattgg acagatagta tttgatggtg tagatgacac tgaaaaatta agtgcagata    900
ttaaagcatt agaaaaacaa atacataaga ttgcagatga agcatatcct agtataaaag    960
caagaggtgg tggttatcaa agaatagcaa tagatacatt tccagagcaa caacttttaa   1020
gtcttaaggt atttgtagat acaaaagatg ctatgggtgc taatatgctt aatactatac   1080
ttgaggcaat aactgcattc cttaaaaatg aatctcctca atcagatata ttaatgtcta   1140
tactttcaaa ccatgcaact gctagtgtag taaaagtaca aggtgagata gatgtaaaag   1200
atcttgctag aggtgaaaga acaggtgaag aagtagctaa gagaatggaa agagcttctg   1260
tattagctca ggttgatatt catagagctg caacacataa caaaggtgtt atgaatggaa   1320
tacatgctgt tgttttagct acaggaaatg atactagagg tgctgaagca tctgcacatg   1380
catacgcatc aagagacgga caatatagag gtatagcaac ttggagatat gatcagaaga   1440
gacaaagact tattggaact attgaagttc caatgacact tgctatagta ggtggtggta   1500
ctaaagtatt accaatagct aaggcatcat tagagttatt aaatgttgat tctgcacaag   1560
aacttggaca cgtagttgct gctgttggat tagcacaaaa ctttgctgct tgtagagcac   1620
ttgtttctga aggtattcaa caaggacaca tgtcattaca atataaaagt ttagcaatag   1680
tagtaggtgc aaaaggtgac gagatagcac aagtagcaga agctcttaaa caggaaccaa   1740
gagctaatac acaggttgct gaaagaattt tacaggaaat tagacagcaa taatctagag   1800
tcgacgtcac gcgtccatgg agatctcgag gcctgcagac atgcaagctt ggcactggcc   1860
gtcgttttac aacgtcgtga ctgggaaaac cctggcgtta cccaacttaa tcgccttgca   1920
gcacatcccc ctttcgccag ctggcgtaat agcgaagagg cccgcaccga tcgcccttcc   1980
caacagttgc gcagcctgaa tggcgaatgg cgctagcata aaaataagaa gcctgcattt   2040
gcaggcttct tatttttatg gcgcgccgtt ctgaatcctt agctaatggt tcaacaggta   2100
actatgacga agatagcacc ctggataagt ctgtaatgga ttctaaggca tttaatgaag   2160
acgtgtatat aaaatgtgct aatgaaaaag aaaatgcgtt aaaagagcct aaaatgagtt   2220
caaatggttt tgaaattgat tggtagttta atttaatata tttttttctat tggctatctc   2280
gatacctata gaatcttctg ttcacttttg tttttgaaat ataaaaaggg gctttttagc   2340
cccttttttt taaaactccg gaggagtttc ttcattcttg atactatacg taactatttt   2400
cgatttgact tcattgtcaa ttaagctagt aaaatcaatg gttaaaaaac aaaaaacttg   2460
catttttcta cctagtaatt tataatttta agtgtcgagt ttaaaagtat aatttaccag   2520
gaaaggagca agttttttaa taaggaaaaa tttttccttt taaaattcta tttcgttata   2580
tgactaatta taatcaaaaa aatgaaaata aacaagaggt aaaaactgct ttagagaaat   2640
gtactgataa aaaaagaaaa aatcctagat ttacgtcata catagcacct ttaactacta   2700
agaaaaatat tgaaaggact tccacttgtg gagattattt gtttatgttg agtgatgcag   2760
acttagaaca ttttaaatta cataaaggta atttttgcgg taatagattt tgtccaatgt   2820
gtagttggcg acttgcttgt aaggatagtt tagaaatatc tattcttatg gagcatttaa   2880
gaaaagaaga aaataaagag tttatatttt taactcttac aactccaaat gtaaaaagtt   2940
```

-continued

```
atgatcttaa ttattctatt aaacaatata ataaatcttt taaaaaatta atggagcgta   3000
aggaagttaa ggatataact aaaggttata taagaaaatt agaagtaact taccaaaagg   3060
aaaaatacat aacaaaggat ttatggaaaa taaaaaaaga ttattatcaa aaaaaaggac   3120
ttgaaattgg tgatttagaa cctaattttg atacttataa tcctcatttt catgtagtta   3180
ttgcagttaa taaaagttat tttacagata aaaattatta tataaatcga gaaagatggt   3240
tggaattatg gaagtttgct actaaggatg attctataac tcaagttgat gttagaaaag   3300
caaaaattaa tgattataaa gaggtttacg aacttgcgaa atattcagct aaagacactg   3360
attatttaat atcgaggcca gtatttgaaa tttttataa agcattaaaa ggcaagcagg   3420
tattagtttt tagtggattt tttaaagatg cacacaaatt gtacaagcaa ggaaaacttg   3480
atgtttataa aaagaaagat gaaattaaat atgtctatat agtttattat aattggtgca   3540
aaaaacaata tgaaaaaact agaataaggg aacttacgga agatgaaaaa gaagaattaa   3600
atcaagattt aatagatgaa atagaaatag attaaagtgt aactatactt tatatatata   3660
tgattaaaaa aataaaaaac aacagcctat taggttgttg tttttttattt tctttattaa   3720
tttttttaat ttttagtttt tagttctttt ttaaaataag tttcagcctc tttttcaata   3780
ttttttaaag aaggagtatt tgcatgaatt gccttttttc taacagactt aggaaatatt   3840
ttaacagtat cttcttgcgc cggtgatttt ggaacttcat aacttactaa tttataatta   3900
ttattttctt ttttaattgt aacagttgca aaagaagctg aacctgttcc ttcaactagt   3960
ttatcatctt caatataata ttcttgacct atatagtata aatatatttt tattatattt   4020
ttactttttt ctgaatctat tattttataa tcataaaaag ttttaccacc aaaagaaggt   4080
tgtactcctt ctggtccaac atattttttt actatattat ctaaataatt tttgggaact   4140
ggtgttgtaa tttgattaat cgaacaacca gttatactta aaggaattat aactataaaa   4200
atatatagga ttatcttttt aaatttcatt attggcctcc tttttattaa atttatgtta   4260
ccataaaaag gacataacgg gaatatgtag aatattttta atgtagacaa aattttacat   4320
aaatataaag aaaggaagtg tttgtttaaa ttttatagca aactatcaaa aattaggggg   4380
ataaaaattt atgaaaaaaa ggttttcgat gttattttta tgtttaactt taatagtttg   4440
tggtttattt acaaattcgg ccggccagtg ggcaagttga aaaattcaca aaaatgtggt   4500
ataaatatctt tgttcattag agcgataaac ttgaatttga gagggaactt agatggtatt   4560
tgaaaaaatt gataaaaata gttggaacag aaaagagtat tttgaccact actttgcaag   4620
tgtaccttgt acctacagca tgaccgttaa agtggatatc acacaaataa aggaaaaggg   4680
aatgaaacta tatcctgcaa tgctttatta tattgcaatg attgtaaacc gccattcaga   4740
gtttaggacg gcaatcaatc aagatggtga attggggata tatgatgaga tgataccaag   4800
ctatacaata tttcacaatg atactgaaac attttccagc ctttggactg agtgtaagtc   4860
tgactttaaa tcatttttag cagattatga aagtgatacg caacggtatg gaaacaatca   4920
tagaatggaa ggaaagccaa atgctccgga aaacattttt aatgtatcta tgataccgtg   4980
gtcaaccttc gatggcttta atctgaattt gcagaaagga tatgattatt tgattcctat   5040
ttttactatg ggaaatatt ataaagaaga taacaaaatt atacttcctt tggcaattca   5100
agttcatcac gcagtatgtg acggatttca catttgccgt tttgtaaacg aattgcagga   5160
attgataaat agttaacttc aggtttgtct gtaactaaaa acaagtattt aagcaaaaac   5220
atcgtagaaa tacggtgttt tttgttaccc taagtttaaa ctcctttttg ataatctcat   5280
gaccaaaatc ccttaacgtg agttttcgtt ccactgagcg tcagaccccg tagaaaagat   5340
```

caaaggatct tcttgagatc cttttttct gcgcgtaatc tgctgcttgc aaacaaaaaa 5400
accaccgcta ccagcggtgg tttgtttgcc ggatcaagag ctaccaactc tttttccgaa 5460
ggtaactggc ttcagcagag cgcagatacc aaatactgtt cttctagtgt agccgtagtt 5520
aggccaccac ttcaagaact ctgtagcacc gcctacatac ctcgctctgc taatcctgtt 5580
accagtggct gctgccagtg gcgataagtc gtgtcttacc gggttggact caagacgata 5640
gttaccggat aaggcgcagc ggtcgggctg aacggggggt tcgtgcacac agcccagctt 5700
ggagcgaacg acctacaccg aactgagata cctacagcgt gagctatgag aaagcgccac 5760
gcttcccgaa gggagaaagg cggacaggta tccggtaagc ggcagggtcg gaacaggaga 5820
gcgcacgagg gagcttccag ggggaaacgc ctggtatctt tatagtcctg tcgggtttcg 5880
ccacctctga cttgagcgtc gatttttgtg atgctcgtca ggggggcgga gcctatggaa 5940
aaacgccagc aacgcggcct ttttacggtt cctggccttt tgctggcctt ttgctcacat 6000
gttctttcct gcgttatccc ctgattctgt ggataaccgt attaccgcct ttgagtgagc 6060
tgataccgct cgccgcagcc gaacgaccga gcgcagcgag tcagtgagcg aggaagcgga 6120
agagcgccca atacgcaggg cccccctgctt cggggtcatt atagcgattt tttcggtata 6180
tccatccttt ttcgcacgat atacaggatt ttgccaaagg gttcgtgtag actttccttg 6240
gtgtatccaa cggcgtcagc cgggcaggat aggtgaagta ggcccacccg cgagcgggtg 6300
ttccttcttc actgtccctt attcgcacct ggcggtgctc aacgggaatc ctgctctgcg 6360
aggctggccg gctaccgccg gcgtaacaga tgagggcaag cggatggctg atgaaaccaa 6420
gccaaccagg aagggcagcc cacctatcaa ggtgtactgc cttccagacg aacgaagagc 6480
gattgaggaa aaggcggcgg cggccggcat gagcctgtcg gcctacctgc tggccgtcgg 6540
ccagggctac aaaatcacgg gcgtcgtgga ctatgagcac gtccgcgagc tggcccgcat 6600
caatggcgac ctgggccgcc tgggcggcct gctgaaactc tggctcaccg acgacccgcg 6660
cacggcgcgg ttcggtgatg ccacgatcct cgccctgctg gcgaagatcg aagagaagca 6720
ggacgagctt ggcaaggtca tgatgggcgt ggtccgcccg agggcagagc catgactttt 6780
ttagccgcta aaacggccgg ggggtgcgcg tgattgccaa gcacgtcccc atgcgctcca 6840
tcaagaagag cgacttcgcg gagctggtga agtacatcac cgacgagcaa ggcaagaccg 6900
atcgggccc 6909

<210> SEQ ID NO 77
<211> LENGTH: 31
<212> TYPE: DNA
<213> ORGANISM: Artificial Sequence
<220> FEATURE:
<223> OTHER INFORMATION: oligonucleotide EcoRI-HMGS_F

<400> SEQUENCE: 77
agccgtgaat tcgaggcttt tactaaaaac a 31

<210> SEQ ID NO 78
<211> LENGTH: 32
<212> TYPE: DNA
<213> ORGANISM: Artificial Sequence
<220> FEATURE:
<223> OTHER INFORMATION: oligonucleotide EcoRI-HMGS_R

<400> SEQUENCE: 78
aggcgtctag atgttcgtct ctacaaataa tt 32

<210> SEQ ID NO 79
<211> LENGTH: 8116
<212> TYPE: DNA
<213> ORGANISM: Artificial Sequence
<220> FEATURE:
<223> OTHER INFORMATION: plasmid pMTL 82151-HMGS-Patp-HMGR

<400> SEQUENCE: 79
cctgcaggat aaaaaaattg tagataaatt ttataaaata gttttatcta caattttttt 60
atcaggaaac agctatgacc gcggccgctg tatccatatg accatgatta cgaattcgag 120
gcttttacta aaaacaataa aaacaggagg aaataatatg actataggaa ttgacaaaat 180
aaacttttac gtaccaaaat attatgtaga tatggcaaaa ttagcagaag caagacaagt 240
agacccaaat aaatttctta ttggaatagg acagactgaa atggcagtta gtccagtaaa 300
ccaagatata gtatcaatgg gtgctaatgc tgctaaagat ataataactg atgaagacaa 360
aaagaaaata ggaatggtaa tagtagcaac tgagtcagca gtagatgcag caaaggcagc 420
agcagtacag attcataatt tattaggtat tcaaccattt gcaagatgtt tcgaaatgaa 480
agaagcatgt tatgctgcta ctcctgcaat tcagttagct aaggattatt tagctacaag 540
accaaatgag aaagttttag ttatagctac agatacagct agatatggac ttaattcagg 600
tggtgaacct actcaaggtg ctggtgctgt tgctatggtt atagctcata atcctagtat 660
acttgcatta aatgaagacg ctgttgctta tacagaagat gtttatgatt tctggagacc 720
aacaggacat aagtatccat tagtagatgg tgctttatca aaagacgcat atattagatc 780
ttttcaacaa tcttggaatg aatatgctaa gagacaagga aagagtttag ctgattttgc 840
tagtctttgc tttcatgttc cttttactaa aatgggtaaa aaggctttag aatctataat 900
agataacgca gatgaaacaa ctcaagagag attaagatct ggatatgaag atgcagttga 960
ttacaataga tatgttggaa atatatacac aggaagtctt tatctttctc ttataagtct 1020
tcttgaaaat agagatttac aggctggtga aactattgga ttattttcat acggatcagg 1080
ttctgttggt gaattttatt cagctacact tgtagaagga tataaagatc accttgatca 1140
ggcagcacac aaagcacttt taaacaatag aactgaagta tcagtagatg catacgaaac 1200
atttttcaag agatttgatg atgtagaatt tgatgaagag caggatgcag ttcatgaaga 1260
tagacatata ttctatcttt caaacataga gaataatgta agagaatatc atagacctga 1320
ataagagctc gttataattt tcaattttca ttctttttaa aggagattag catacatttt 1380
atcataatta tacagacaat atagtaatat atgatgttaa aatatcaata tatggttaaa 1440
aatctgtata ttttttccca ttttaattat ttgtactata atattacact gagtgtattg 1500
catatttaaa aaatatttgg tacaattagt tagttaaata aattctaaat tgtaaattat 1560
cagaatcctt attaaggaaa tacatagatt taaggagaaa tcataaaaag gtgtaatata 1620
aactggctaa aattgagcaa aaattgagca attaagactt tttgattgta tctttttata 1680
tatttaaggt atataatctt atttatattg ggggaaggta ccatgcaatc attagacaaa 1740
aatttcagac atttatcaag acaacaaaag ttacaacaat tagttgataa acagtggctt 1800
tcagaagatc agtttgatat tttacttaat catcctctta tagatgaaga agttgctaat 1860
agtcttatag aaaatgtaat tgcacagggt gcattaccag ttggacttct tcctaatata 1920
atagttgatg ataaggctta tgttgtacca atgatggttg aagaacctag tgttgttgca 1980
gctgcatctt atggtgctaa attagtaaat cagacaggtg gatttaaaac tgtatcatca 2040
gaaagaataa tgattggaca gatagtattt gatggtgtag atgacactga aaaattaagt 2100
gcagatatta aagcattaga aaaacaaata cataagattg cagatgaagc atatcctagt 2160
ataaaagcaa gaggtggtgg ttatcaaaga atagcaatag atacatttcc agagcaacaa 2220
cttttaagtc ttaaggtatt tgtagataca aaagatgcta tgggtgctaa tatgcttaat 2280
actatacttg aggcaataac tgcattcctt aaaaatgaat ctcctcaatc agatatatta 2340
atgtctatac tttcaaacca tgcaactgct agtgtagtaa aagtacaagg tgagatagat 2400
gtaaaagatc ttgctagagg tgaaagaaca ggtgaagaag tagctaagag aatggaaaga 2460
gcttctgtat tagctcaggt tgatattcat agagctgcaa cacataacaa aggtgttatg 2520
aatggaatac atgctgttgt tttagctaca ggaaatgata ctagaggtgc tgaagcatct 2580
gcacatgcat acgcatcaag agacggacaa tatagaggta tagcaacttg gagatatgat 2640
cagaagagac aaagacttat tggaactatt gaagttccaa tgacacttgc tatagtaggt 2700
ggtggtacta aagtattacc aatagctaag gcatcattag agttattaaa tgttgattct 2760
gcacaagaac ttggacacgt agttgctgct gttggattag cacaaaactt tgctgcttgt 2820
agagcacttg tttctgaagg tattcaacaa ggacacatgt cattacaata taaaagttta 2880
gcaatagtag taggtgcaaa aggtgacgag atagcacaag tagcagaagc tcttaaacag 2940
gaaccaagag ctaatacaca ggttgctgaa agaattttac aggaaattag acagcaataa 3000
tctagagtcg acgtcacgcg tccatggaga tctcgaggcc tgcagacatg caagcttggc 3060
actggccgtc gttttacaac gtcgtgactg ggaaaaccct ggcgttaccc aacttaatcg 3120
ccttgcagca catccccctt tcgccagctg gcgtaatagc gaagaggccc gcaccgatcg 3180
cccttcccaa cagttgcgca gcctgaatgg cgaatggcgc tagcataaaa ataagaagcc 3240
tgcatttgca ggcttcttat ttttatggcg cgccgttctg aatccttagc taatggttca 3300
acaggtaact atgacgaaga tagcaccctg gataagtctg taatggattc taaggcattt 3360
aatgaagacg tgtatataaa atgtgctaat gaaaaagaaa atgcgttaaa agagcctaaa 3420
atgagttcaa atggttttga aattgattgg tagtttaatt taatatattt tttctattgg 3480
ctatctcgat acctatagaa tcttctgttc acttttgttt ttgaaatata aaaaggggct 3540
ttttagcccc tttttttaa aactccggag gagtttcttc attcttgata ctatacgtaa 3600
ctattttcga tttgacttca ttgtcaatta agctagtaaa atcaatggtt aaaaaacaaa 3660
aaacttgcat ttttctacct agtaatttat aattttaagt gtcgagttta aaagtataat 3720
ttaccaggaa aggagcaagt tttttaataa ggaaaaattt ttccttttaa aattctattt 3780
cgttatatga ctaattataa tcaaaaaaat gaaaataaac aagaggtaaa aactgcttta 3840
gagaaatgta ctgataaaaa aagaaaaaat cctagattta cgtcatacat agcaccttta 3900
actactaaga aaaatattga aaggacttcc acttgtggag attatttgtt tatgttgagt 3960
gatgcagact tagaacattt taaattacat aaaggtaatt tttgcggtaa tagattttgt 4020
ccaatgtgta gttggcgact tgcttgtaag gatagtttag aaatatctat tcttatggag 4080
catttaagaa aagaagaaaa taaagagttt atatttttaa ctcttacaac tccaaatgta 4140
aaaagttatg atcttaatta ttctattaaa caatataata aatcttttaa aaaattaatg 4200
gagcgtaagg aagttaagga tataactaaa ggttatataa gaaaattaga agtaacttac 4260
caaaaggaaa aatacataac aaaggattta tggaaaataa aaaaagatta ttatcaaaaa 4320
aaaggacttg aaattggtga tttagaacct aattttgata cttataatcc tcattttcat 4380
gtagttattg cagttaataa aagttatttt acagataaaa attattatat aaatcgagaa 4440
agatggttgg aattatggaa gtttgctact aaggatgatt ctataactca agttgatgtt 4500
agaaaagcaa aaattaatga ttataaagag gtttacgaac ttgcgaaata ttcagctaaa 4560
gacactgatt atttaatatc gaggccagta tttgaaattt tttataaagc attaaaaggc 4620
aagcaggtat tagtttttag tggatttttt aaagatgcac acaaattgta caagcaagga 4680
aaacttgatg tttataaaaa gaaagatgaa attaaatatg tctatatagt ttattataat 4740
tggtgcaaaa aacaatatga aaaaactaga ataagggaac ttacggaaga tgaaaaagaa 4800
gaattaaatc aagatttaat agatgaaata gaaatagatt aaagtgtaac tatactttat 4860
atatatatga ttaaaaaaat aaaaaacaac agcctattag gttgttgttt tttattttct 4920
ttattaattt ttttaatttt tagtttttag ttctttttta aaataagttt cagcctcttt 4980
ttcaatattt tttaaagaag gagtatttgc atgaattgcc ttttttctaa cagacttagg 5040
aaatatttta acagtatctt cttgcgccgg tgattttgga acttcataac ttactaattt 5100
ataattatta ttttcttttt taattgtaac agttgcaaaa gaagctgaac ctgttccttc 5160
aactagttta tcatcttcaa tataatattc ttgacctata tagtataaat atatttttat 5220
tatattttta ctttttttctg aatctattat tttataatca taaaaagttt taccaccaaa 5280
agaaggttgt actccttctg gtccaacata tttttttact atattatcta aataattttt 5340
gggaactggt gttgtaattt gattaatcga acaaccagtt atacttaaag gaattataac 5400
tataaaaata tataggatta tctttttaaa tttcattatt ggcctccttt ttattaaatt 5460
tatgttacca taaaaaggac ataacgggaa tatgtagaat atttttaatg tagacaaaat 5520
tttacataaa tataaagaaa ggaagtgttt gtttaaattt tatagcaaac tatcaaaaat 5580
taggggggata aaaatttatg aaaaaaaggt tttcgatgtt atttttatgt ttaactttaa 5640
tagtttgtgg tttatttaca aattcggccg gccagtgggc aagttgaaaa attcacaaaa 5700
atgtggtata atatctttgt tcattagagc gataaacttg aatttgagag ggaacttaga 5760
tggtatttga aaaaattgat aaaaatagtt ggaacagaaa agagtatttt gaccactact 5820
ttgcaagtgt accttgtacc tacagcatga ccgttaaagt ggatatcaca caaataaagg 5880
aaaagggaat gaaactatat cctgcaatgc tttattatat tgcaatgatt gtaaaccgcc 5940
attcagagtt taggacggca atcaatcaag atggtgaatt ggggatatat gatgagatga 6000
taccaagcta tacaatattt cacaatgata ctgaaacatt ttccagcctt tggactgagt 6060
gtaagtctga ctttaaatca tttttagcag attatgaaag tgatacgcaa cggtatggaa 6120
acaatcatag aatggaagga aagccaaatg ctccggaaaa catttttaat gtatctatga 6180
taccgtggtc aaccttcgat ggctttaatc tgaatttgca gaaaggatat gattatttga 6240
ttcctatttt tactatgggg aaatattata aagaagataa caaaattata cttcctttgg 6300
caattcaagt tcatcacgca gtatgtgacg gatttcacat ttgccgtttt gtaaacgaat 6360
tgcaggaatt gataaatagt taacttcagg tttgtctgta actaaaaaca agtatttaag 6420
caaaaacatc gtagaaatac ggtgtttttt gttaccctaa gtttaaactc ctttttgata 6480
atctcatgac caaaatccct taacgtgagt tttcgttcca ctgagcgtca gaccccgtag 6540
aaaagatcaa aggatcttct tgagatcctt tttttctgcg cgtaatctgc tgcttgcaaa 6600
caaaaaaacc accgctacca gcggtggttt gtttgccgga tcaagagcta ccaactcttt 6660
ttccgaaggt aactggcttc agcagagcgc agataccaaa tactgttctt ctagtgtagc 6720
cgtagttagg ccaccacttc aagaactctg tagcaccgcc tacatacctc gctctgctaa 6780
tcctgttacc agtggctgct gccagtggcg ataagtcgtg tcttaccggg ttggactcaa 6840
gacgatagtt accggataag gcgcagcggt cgggctgaac ggggggttcg tgcacacagc 6900
ccagcttgga gcgaacgacc tacaccgaac tgagatacct acagcgtgag ctatgagaaa 6960
gcgccacgct tcccgaaggg agaaaggcgg acaggtatcc ggtaagcggc agggtcggaa 7020
caggagagcg cacgagggag cttccagggg gaaacgcctg gtatctttat agtcctgtcg 7080
ggtttcgcca cctctgactt gagcgtcgat ttttgtgatg ctcgtcaggg gggcggagcc 7140
tatggaaaaa cgccagcaac gcggcctttt tacggttcct ggccttttgc tggccttttg 7200
ctcacatgtt ctttcctgcg ttatcccctg attctgtgga taaccgtatt accgcctttg 7260
agtgagctga taccgctcgc cgcagccgaa cgaccgagcg cagcgagtca gtgagcgagg 7320
aagcggaaga gcgcccaata cgcagggccc cctgcttcgg ggtcattata gcgatttttt 7380
cggtatatcc atcctttttc gcacgatata caggattttg ccaaagggtt cgtgtagact 7440
ttccttggtg tatccaacgg cgtcagccgg gcaggatagg tgaagtaggc ccacccgcga 7500
gcgggtgttc cttcttcact gtcccttatt cgcacctggc ggtgctcaac gggaatcctg 7560
ctctgcgagg ctggccggct accgccggcg taacagatga gggcaagcgg atggctgatg 7620
aaaccaagcc aaccaggaag ggcagcccac ctatcaaggt gtactgcctt ccagacgaac 7680
gaagagcgat tgaggaaaag gcggcggcgg ccggcatgag cctgtcggcc tacctgctgg 7740
ccgtcggcca gggctacaaa atcacgggcg tcgtggacta tgagcacgtc cgcgagctgg 7800
cccgcatcaa tggcgacctg ggccgcctgg gcggcctgct gaaactctgg ctcaccgacg 7860
acccgcgcac ggcgcggttc ggtgatgcca cgatcctcgc cctgctggcg aagatcgaag 7920
agaagcagga cgagcttggc aaggtcatga tgggcgtggt ccgcccgagg gcagagccat 7980 gacttttta gccgctaaaa cggccggggg gtgcgcgtga ttgccaagca cgtccccatg 8040
cgctccatca agaagagcga cttcgcggag ctggtgaagt acatcaccga cgagcaaggc 8100
aagaccgatc gggccc 8116

<210> SEQ ID NO 80
<211> LENGTH: 55
<212> TYPE: DNA
<213> ORGANISM: Artificial Sequence
<220> FEATURE:
<223> OTHER INFORMATION: Oligonucleotide NotI-XbaI-Prnf-MK_F

<400> SEQUENCE: 80
atgcgcggcc gctaggtcta gaatatcgat acagataaaa aaatatataa tacag 55

<210> SEQ ID NO 81
<211> LENGTH: 27
<212> TYPE: DNA
<213> ORGANISM: Artificial Sequence
<220> FEATURE:
<223> OTHER INFORMATION: Oligonucleotide SalI-Prnf-MK_R

<400> SEQUENCE: 81
tggttctgta acagcgtatt cacctgc 27

<210> SEQ ID NO 82
<211> LENGTH: 4633
<212> TYPE: DNA
<213> ORGANISM: Artificial Sequence
<220> FEATURE:
<223> OTHER INFORMATION: plasmid pMTL8314-Prnf-MK

<400> SEQUENCE: 82

-continued

```
aaactccttt ttgataatct catgaccaaa atcccttaac gtgagttttc gttccactga     60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat   600
ctttatagtc ctgtcgggtt tcgccacctc tgacttgagc gtcgattttt gtgatgctcg    660
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat ttttttatca ggaaacagct    960
atgaccgcgg ccgctaggtc tagaatatcg atacagataa aaaaatatat aatacagaag   1020
aaaaaattat aaatttgtgg tataatataa agtatagtaa tttaagttta aacctcgtga   1080
aaacgctaac aaataatagg aggtcaattg atgatagctg ttccatttaa cgctggaaaa   1140
ataaaagttt taattgaggc attagaatct ggaaattatt catcaataaa atcagatgta   1200
tatgacggaa tgttatatga tgcaccagat caccttaaat cattagtaaa cagatttgta   1260
gaacttaata atataactga gccattagca gtaactatac agacaaatct tcctccttca   1320
agaggtcttg gatctagtgc agctgttgct gttgcttttg taagagcaag ttatgatttc   1380
ttaggaaaaa gtttaactaa agaagagctt atagaaaagg ctaattgggc tgaacaaata   1440
gctcatggaa agccatctgg aatagataca caaacaatag tatctggaaa gcctgtttgg   1500
tttcaaaagg gacatgcaga aacacttaaa actctttcac ttgatggata catggtagta   1560
attgatacag gtgttaaagg aagtacaaga caggctgtag aagatgttca taaactttgc   1620
gaagatcctc aatatatgag tcacgtaaaa cacataggaa aacttgtact tagagcatct   1680
gatgttattg aacatcataa ctttgaagca cttgctgata tattcaatga atgtcatgct   1740
gatttaaagg ctcttacagt aagtcatgac aaaatagaac agttaatgaa gataggaaaa   1800
gaaaatggtg ctatagctgg taaattaact ggtgctggta gaggtggttc aatgttatta   1860
cttgcaaaag acttaccaac tgcaaagaat atagttaaag cagtagagaa agctggtgca   1920
gcacatactt ggattgaaaa tttaggtggt taagtcgacg tcacgcgtcc atggagatct   1980
cgaggcctgc agacatgcaa gcttggcact ggccgtcgtt ttacaacgtc gtgactggga   2040
aaaccctggc gttacccaac ttaatcgcct tgcagcacat ccccctttcg ccagctggcg   2100
taatagcgaa gaggcccgca ccgatcgccc ttcccaacag ttgcgcagcc tgaatggcga   2160
atggcgctag cataaaaata agaagcctgc atttgcaggc ttcttatttt tatggcgcgc   2220
cgccattatt tttttgaaca attgacaatt catttcttat tttttattaa gtgatagtca   2280
aaaggcataa cagtgctgaa tagaaagaaa tttacagaaa agaaaattat agaatttagt   2340
atgattaatt atactcattt atgaatgttt aattgaatac aaaaaaaaat acttgttatg   2400
```

tattcaatta cgggttaaaa tatagacaag ttgaaaaatt taataaaaaa ataagtcctc 2460
agctcttata tattaagcta ccaacttagt atataagcca aaacttaaat gtgctaccaa 2520
cacatcaagc cgttagagaa ctctatctat agcaatattt caaatgtacc gacatacaag 2580
agaaacatta actatatata ttcaatttat gagattatct taacagatat aaatgtaaat 2640
tgcaataagt aagatttaga agtttatagc ctttgtgtat tggaagcagt acgcaaaggc 2700
tttttattt gataaaaatt agaagtatat ttattttttc ataattaatt tatgaaaatg 2760
aaagggggtg agcaaagtga cagaggaaag cagtatctta tcaaataaca aggtattagc 2820
aatatcatta ttgactttag cagtaaacat tatgactttt atagtgcttg tagctaagta 2880
gtacgaaagg gggagcttta aaaagctcct tggaatacat agaattcata aattaattta 2940
tgaaaagaag ggcgtatatg aaaacttgta aaaattgcaa agagtttatt aaagatactg 3000
aaatatgcaa aatacattcg ttgatgattc atgataaaac agtagcaacc tattgcagta 3060
aatacaatga gtcaagatgt ttacataaag ggaaagtcca atgtattaat tgttcaaaga 3120
tgaaccgata tggatggtgt gccataaaaa tgagatgttt tacagaggaa gaacagaaaa 3180
aagaacgtac atgcattaaa tattatgcaa ggagctttaa aaaagctcat gtaaagaaga 3240
gtaaaaagaa aaaataattt atttattaat ttaatattga gagtgccgac acagtatgca 3300
ctaaaaaata tatctgtggt gtagtgagcc gatacaaaag gatagtcact cgcattttca 3360
taatacatct tatgttatga ttatgtgtcg gtgggacttc acgacgaaaa cccacaataa 3420
aaaaagagtt cggggtaggg ttaagcatag ttgaggcaac taaacaatca agctaggata 3480
tgcagtagca gaccgtaagg tcgttgttta ggtgtgttgt aatacatacg ctattaagat 3540
gtaaaaatac ggataccaat gaagggaaaa gtataatttt tggatgtagt ttgtttgttc 3600
atctatgggc aaactacgtc caaagccgtt tccaaatctg ctaaaaagta tatcctttct 3660
aaaatcaaag tcaagtatga aatcataaat aaagtttaat tttgaagtta ttatgatatt 3720
atgtttttct attaaaataa attaagtata tagaatagtt taataatagt atatacttaa 3780
tgtgataagt gtctgacagt gtcacagaaa ggatgattgt tatggattat aagcggccgg 3840
ccagtgggca agttgaaaaa ttcacaaaaa tgtggtataa tatctttgtt cattagagcg 3900
ataaacttga atttgagagg gaacttagat ggtatttgaa aaaattgata aaaatagttg 3960
gaacagaaaa gagtattttg accactactt tgcaagtgta ccttgtacct acagcatgac 4020
cgttaaagtg gatatcacac aaataaagga aaagggaatg aaactatatc ctgcaatgct 4080
ttattatatt gcaatgattg taaaccgcca ttcagagttt aggacggcaa tcaatcaaga 4140
tggtgaattg ggatatatgg atgagatgat accaagctat acaatatttc acaatgatac 4200
tgaaacattt tccagccttt ggactgagtg taagtctgac tttaaatcat ttttagcaga 4260
ttatgaaagt gatacgcaac ggtatggaaa caatcataga atggaaggaa agccaaatgc 4320
tccggaaaac atttttaatg tatctatgat accgtggtca accttcgatg gctttaatct 4380
gaatttgcag aaaggatatg attatttgat tcctattttt actatgggga aatattataa 4440
agaagataac aaaattatac ttcctttggc aattcaagtt catcacgcag tatgtgacgg 4500
atttcacatt tgccgttttg taaacgaatt gcaggaattg ataaatagtt aacttcaggt 4560
ttgtctgtaa ctaaaaacaa gtatttaagc aaaaacatcg tagaaatacg gtgtttttttg 4620
ttaccctaag ttt 4633

<210> SEQ ID NO 83

<211> LENGTH: 6753
<212> TYPE: DNA
<213> ORGANISM: Artificial Sequence
<220> FEATURE:
<223> OTHER INFORMATION: plasmid pMTL 8314-Prnf-MK-PMK-PMD

<400> SEQUENCE: 83
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc caggggggaaa cgcctggtat 600 ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720
ttttgctggc cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggcccccctg caggataaaa 900 aaattgtaga taaattttat aaaatagttt tatctacaat ttttttatca ggaaacagct 960
atgaccgcgg ccgctaggtc tagaatatcg atacagataa aaaaatatat aatacagaag 1020
aaaaaattat aaatttgtgg tataatataa agtatagtaa tttaagttta aacctcgtga 1080
aaacgctaac aaataatagg aggtcaattg atgatagctg ttccatttaa cgctggaaaa 1140
ataaaagttt taattgaggc attagaatct ggaaattatt catcaataaa atcagatgta 1200
tatgacggaa tgttatatga tgcaccagat caccttaaat cattagtaaa cagatttgta 1260
gaacttaata atataactga gccattagca gtaactatac agacaaatct tcctccttca 1320
agaggtcttg gatctagtgc agctgttgct gttgcttttg taagagcaag ttatgatttc 1380
ttaggaaaaa gtttaactaa agaagagctt atagaaaagg ctaattgggc tgaacaaata 1440
gctcatggaa agccatctgg aatagataca caaacaatag tatctggaaa gcctgtttgg 1500
tttcaaaagg gacatgcaga aacacttaaa actctttcac ttgatggata catggtagta 1560
attgatacag gtgttaaagg aagtacaaga caggctgtag aagatgttca taaactttgc 1620
gaagatcctc aatatatgag tcacgtaaaa cacataggaa aacttgtact tagagcatct 1680
gatgttattg aacatcataa ctttgaagca cttgctgata tattcaatga atgtcatgct 1740
gatttaaagg ctcttacagt aagtcatgac aaaatagaac agttaatgaa gataggaaaa 1800
gaaaatggtg ctatagctgg taaattaact ggtgctggta gaggtggttc aatgttatta 1860
cttgcaaaag acttaccaac tgcaaagaat atagttaaag cagtagagaa agctggtgca 1920
gcacatactt ggattgaaaa tttaggtggt taagtcgaca aagacactaa aaaattataa 1980
aagtaaagga ggacattaaa tgatacaagt aaaggcacca ggaaaattat atatagcagg 2040
tgaatacgct gttacagaac caggatataa atctgttctt atagctcttg atagatttgt 2100
tacagctact attgaggaag ctgatcaata caaaggaaca atacattcaa aggcattaca 2160

```
tcacaatcca gtaactttta gtagagatga agattctatt gttatatcag acccacacgc   2220
agcaaaacaa cttaattatg tagtaactgc tatagaaata tttgagcaat atgcaaaatc   2280
atgtgacata gcaatgaagc attttcattt aactatagat tctaacttag atgatagtaa   2340
tggacataag tatggacttg gatcttctgc tgctgtttta gtttcagtaa ttaaagtact   2400
taacgaattt tatgatatga aactttcaaa cctttatata tataagttag cagtaattgc   2460
taatatgaaa ttacagagtt tatcttcatg cggtgatata gcagtaagtg tttattcagg   2520
ttggttagct tattctacat ttgaccatga atgggtaaaa caccagatag aagatacaac   2580
agttgaagaa gtacttatta aaaattggcc tggattacac atagagccac ttcaagctcc   2640
tgaaaatatg gaagttctta taggttggac aggtagtcca gctagtagtc ctcattttgt   2700
ttctgaagtt aaaagactta agtcagatcc ttcattttac ggtgatttct tagaagattc   2760
acatagatgt gtagaaaaat taattcatgc attcaaaact aataatatta agggtgttca   2820
gaaaatggta agacagaata gaactattat acaaagaatg gataaggaag caacagttga   2880
tatagagact gagaagttaa aatatttatg tgatattgct gaaaaatatc atggtgcaag   2940
taaaacttca ggtgctggtg gtggtgattg cggaataact ataataaata aggatgtaga   3000
caaagagaaa atatatgatg aatggactaa acatggaata aagcctctta agtttaatat   3060
ttatcatgga caataaccat ggtcaataat cttacaataa ataaaagaaa ggaggcaaaa   3120
atatgataaa atctggaaaa gcaagagcac acactaatat agcacttata aaatattggg   3180
gtaagaaaga tgaggcatta ataataccaa tgaataactc aatatcagta actttagaaa   3240
agttttatac tgaaacaaaa gttacattta acgatcagct tactcaagat caattttggc   3300
ttaatggtga aaaagtttct ggaaaagaat tagaaaagat ttcaaagtat atggatattg   3360
ttagaaatag agctggaata gattggtatg ctgagataga atctgataat tttgttccta   3420
cagctgctgg tcttgctagt tctgctagtg cttatgcagc attagctgct gcatgtaacc   3480
aagcacttga tttacagtta agtgataaag acttaagtag attagctaga attggatcag   3540
gatcagcatc aagatcaata tacggtggtt ttgcagaatg ggaaaaagga tataatgacg   3600
aaacttctta tgctgttcca ttagaaagta atcactttga agatgatctt gctatgattt   3660
ttgtagtaat aaaccaacat tctaaaaagg ttccttcaag atatggaatg tctcttacaa   3720
gaaatacaag tagattctat caatattggt tagaccatat tgatgaagat cttgcagaag   3780
caaaggcagc aatacaagat aaggatttta agagattagg tgaagttatt gaagagaatg   3840
gacttagaat gcatgctaca aatcttggat caactccacc ttttacttac ttagtacaag   3900
agtcatacga tgtaatggca ttagtacatg agtgtagaga agcaggatat ccatgctatt   3960
tcactatgga tgctggacct aatgtaaaaa tacttgtaga gaagaaaaac aaacaacaga   4020
taatagataa acttttaact cagttcgata ataatcagat aatagatagt gatattatag   4080
ctacaggtat tgaaattata gaataaacta gttccgctaa gcttggcact ggccgtcgtt   4140
ttacaacgtc gtgactggga aaaccctggc gttacccaac ttaatcgcct tgcagcacat   4200
ccccctttcg ccagctggcg taatagcgaa gaggcccgca ccgatcgccc ttcccaacag   4260
ttgcgcagcc tgaatggcga atggcgctag cataaaaata agaagcctgc atttgcaggc   4320
ttcttatttt tatggcgcgc cgccattatt tttttgaaca attgacaatt catttcttat   4380
tttttattaa gtgatagtca aaaggcataa cagtgctgaa tagaaagaaa tttacagaaa   4440
agaaaattat agaatttagt atgattaatt atactcattt atgaatgttt aattgaatac   4500
```

```
aaaaaaaaat acttgttatg tattcaatta cgggttaaaa tatagacaag ttgaaaaatt   4560
taataaaaaa ataagtcctc agctcttata tattaagcta ccaacttagt atataagcca   4620
aaacttaaat gtgctaccaa cacatcaagc cgttagagaa ctctatctat agcaatattt   4680
caaatgtacc gacatacaag agaaacatta actatatata ttcaatttat gagattatct   4740
taacagatat aaatgtaaat tgcaataagt aagatttaga agtttatagc ctttgtgtat   4800
tggaagcagt acgcaaaggc tttttattt gataaaaatt agaagtatat ttattttttc   4860
ataattaatt tatgaaaatg aaagggggtg agcaaagtga cagaggaaag cagtatctta   4920
tcaaataaca aggtattagc aatatcatta ttgactttag cagtaaacat tatgactttt   4980
atagtgcttg tagctaagta gtacgaaagg gggagcttta aaaagctcct tggaatacat   5040
agaattcata aattaattta tgaaaagaag ggcgtatatg aaaacttgta aaaattgcaa   5100
agagtttatt aaagatactg aaatatgcaa aatacattcg ttgatgattc atgataaaac   5160
agtagcaacc tattgcagta aatacaatga gtcaagatgt ttacataaag ggaaagtcca   5220
atgtattaat tgttcaaaga tgaaccgata tggatggtgt gccataaaaa tgagatgttt   5280
tacagaggaa gaacagaaaa aagaacgtac atgcattaaa tattatgcaa ggagctttaa   5340
aaaagctcat gtaaagaaga gtaaaaagaa aaaataattt atttattaat ttaatattga   5400
gagtgccgac acagtatgca ctaaaaaata tatctgtggt gtagtgagcc gatacaaaag   5460
gatagtcact cgcattttca taatacatct tatgttatga ttatgtgtcg gtgggacttc   5520
acgacgaaaa cccacaataa aaaaagagtt cggggtaggg ttaagcatag ttgaggcaac   5580
taaacaatca agctaggata tgcagtagca gaccgtaagg tcgttgttta ggtgtgttgt   5640
aatacatacg ctattaagat gtaaaaatac ggataccaat gaagggaaaa gtataatttt   5700
tggatgtagt ttgtttgttc atctatgggc aaactacgtc caaagccgtt tccaaatctg   5760
ctaaaaagta tatcctttct aaaatcaaag tcaagtatga aatcataaat aaagtttaat   5820
tttgaagtta ttatgatatt atgtttttct attaaaataa attaagtata tagaatagtt   5880
taataatagt atatacttaa tgtgataagt gtctgacagt gtcacagaaa ggatgattgt   5940
tatggattat aagcggccgg ccagtgggca agttgaaaaa ttcacaaaaa tgtggtataa   6000
tatctttgtt cattagagcg ataaacttga atttgagagg gaacttagat ggtatttgaa   6060
aaaattgata aaaatagttg gaacagaaaa gagtattttg accactactt tgcaagtgta   6120
ccttgtacct acagcatgac cgttaaagtg gatatcacac aaataaagga aaagggaatg   6180
aaactatatc ctgcaatgct ttattatatt gcaatgattg taaaccgcca ttcagagttt   6240
aggacggcaa tcaatcaaga tggtgaattg gggatatatg atgagatgat accaagctat   6300
acaatatttc acaatgatac tgaaacattt tccagccttt ggactgagtg taagtctgac   6360
tttaaatcat ttttagcaga ttatgaaagt gatacgcaac ggtatggaaa caatcataga   6420
atggaaggaa agccaaatgc tccggaaaac atttttaatg tatctatgat accgtggtca   6480
accttcgatg gctttaatct gaatttgcag aaaggatatg attatttgat tcctattttt   6540
actatgggga aatattataa agaagataac aaaattatac ttcctttggc aattcaagtt   6600
catcacgcag tatgtgacgg atttcacatt tgccgttttg taaacgaatt gcaggaattg   6660
ataaatagtt aacttcaggt ttgtctgtaa ctaaaaacaa gtatttaagc aaaaacatcg   6720
tagaaatacg gtgtttttg ttaccctaag ttt                                 6753
```

<210> SEQ ID NO 84
<211> LENGTH: 9198

<212> TYPE: DNA
<213> ORGANISM: Artificial Sequence
<220> FEATURE:
<223> OTHER INFORMATION: plasmid pMTL8314-Prnf-MK-PMK-PMD-Pfor-idi-ispS

<400> SEQUENCE: 84

```
aaactccttt ttgataatct catgaccaaa atcccttaac gtgagttttc gttccactga     60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600
ctttatagtc ctgtcgggtt tcgccacctc tgacttgagc gtcgattttt gtgatgctcg    660
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggcccccctg caggataaaa    900
aaattgtaga taaattttat aaaatagttt tatctacaat ttttttatca ggaaacagct    960
atgaccgcgg ccgctaggtc tagaatatcg atacagataa aaaaatatat aatacagaag   1020
aaaaaattat aaatttgtgg tataatataa agtatagtaa tttaagttta aacctcgtga   1080
aaacgctaac aaataatagg aggtcaattg atgatagctg ttccatttaa cgctggaaaa   1140
ataaaagttt taattgaggc attagaatct ggaaattatt catcaataaa atcagatgta   1200
tatgacggaa tgttatatga tgcaccagat caccttaaat cattagtaaa cagatttgta   1260
gaacttaata atataactga gccattagca gtaactatac agacaaatct tcctccttca   1320
agaggtcttg gatctagtgc agctgttgct gttgcttttg taagagcaag ttatgatttc   1380
ttaggaaaaa gtttaactaa agaagagctt atagaaaagg ctaattgggc tgaacaaata   1440
gctcatggaa agccatctgg aatagataca caaacaatag tatctggaaa gcctgtttgg   1500
tttcaaaagg gacatgcaga aacacttaaa actctttcac ttgatggata catggtagta   1560
attgatacag gtgttaaagg aagtacaaga caggctgtag aagatgttca taaactttgc   1620
gaagatcctc aatatatgag tcacgtaaaa cacataggaa aacttgtact tagagcatct   1680
gatgttattg aacatcataa ctttgaagca cttgctgata tattcaatga atgtcatgct   1740
gatttaaagg ctcttacagt aagtcatgac aaaatagaac agttaatgaa gataggaaaa   1800
gaaaatggtg ctatagctgg taaattaact ggtgctggta gaggtggttc aatgttatta   1860
cttgcaaaag acttaccaac tgcaaagaat atagttaaag cagtagagaa agctggtgca   1920
gcacatactt ggattgaaaa tttaggtggt taagtcgaca aagacactaa aaaattataa   1980
aagtaaagga ggacattaaa tgatacaagt aaaggcacca ggaaaattat atatagcagg   2040
tgaatacgct gttacagaac caggatataa atctgttctt atagctcttg atagatttgt   2100
tacagctact attgaggaag ctgatcaata caaaggaaca atacattcaa aggcattaca   2160
```

-continued

```
tcacaatcca gtaactttta gtagagatga agattctatt gttatatcag acccacacgc   2220
agcaaaacaa cttaattatg tagtaactgc tatagaaata tttgagcaat atgcaaaatc   2280
atgtgacata gcaatgaagc attttcattt aactatagat tctaacttag atgatagtaa   2340
tggacataag tatggacttg gatcttctgc tgctgtttta gtttcagtaa ttaaagtact   2400
taacgaattt tatgatatga aactttcaaa cctttatata tataagttag cagtaattgc   2460
taatatgaaa ttacagagtt tatcttcatg cggtgatata gcagtaagtg tttattcagg   2520
ttggttagct tattctacat ttgaccatga atgggtaaaa caccagatag aagatacaac   2580
agttgaagaa gtacttatta aaaattggcc tggattacac atagagccac ttcaagctcc   2640
tgaaaatatg gaagttctta taggttggac aggtagtcca gctagtagtc ctcattttgt   2700
ttctgaagtt aaaagactta agtcagatcc ttcattttac ggtgatttct tagaagattc   2760
acatagatgt gtagaaaaat taattcatgc attcaaaact aataatatta agggtgttca   2820
gaaaatggta agacagaata gaactattat acaaagaatg gataaggaag caacagttga   2880
tatagagact gagaagttaa aatatttatg tgatattgct gaaaaatatc atggtgcaag   2940
taaaacttca ggtgctggtg gtggtgattg cggaataact ataataaata aggatgtaga   3000
caaagagaaa atatatgatg aatggactaa acatggaata aagcctctta agtttaatat   3060
ttatcatgga caataaccat ggtcaataat cttacaataa ataaaagaaa ggaggcaaaa   3120
atatgataaa atctggaaaa gcaagagcac acactaatat agcacttata aaatattggg   3180
gtaagaaaga tgaggcatta ataataccaa tgaataactc aatatcagta actttagaaa   3240
agttttatac tgaaacaaaa gttacattta acgatcagct tactcaagat caattttggc   3300
ttaatggtga aaaagtttct ggaaaagaat tagaaaagat ttcaaagtat atggatattg   3360
ttagaaatag agctggaata gattggtatg ctgagataga atctgataat tttgttccta   3420
cagctgctgg tcttgctagt tctgctagtg cttatgcagc attagctgct gcatgtaacc   3480
aagcacttga tttacagtta agtgataaag acttaagtag attagctaga attggatcag   3540
gatcagcatc aagatcaata tacggtggtt ttgcagaatg ggaaaaagga tataatgacg   3600
aaacttctta tgctgttcca ttagaaagta atcactttga agatgatctt gctatgattt   3660
ttgtagtaat aaaccaacat tctaaaaagg ttccttcaag atatggaatg tctcttacaa   3720
gaaatacaag tagattctat caatattggt tagaccatat tgatgaagat cttgcagaag   3780
caaaggcagc aatacaagat aaggatttta agagattagg tgaagttatt gaagagaatg   3840
gacttagaat gcatgctaca aatcttggat caactccacc ttttacttac ttagtacaag   3900
agtcatacga tgtaatggca ttagtacatg agtgtagaga agcaggatat ccatgctatt   3960
tcactatgga tgctggacct aatgtaaaaa tacttgtaga gaagaaaaac aaacaacaga   4020
taatagataa acttttaact cagttcgata ataatcagat aatagatagt gatattatag   4080
ctacaggtat tgaaattata gaataaacta gttgtatatt aaaatagtag aatacataag   4140
atacttaatt taattaaaga tagttaagta cttttcaatg tgctttttta gatgtttaat   4200
acaaatcttt aattgtaaaa gaaatgctgt actatttact gttctagtga cgggattaaa   4260
ctgtattaat tataaataaa aaataagtac agttgtttaa aattatattt tgtattaaat   4320
ctaatagtac gatgtaagtt attttatact attgctagtt taataaaaag atttaattat   4380
atacttgaaa aggagaggaa ctcgagatgg cagagtatat aatagcagta gatgagttcg   4440
ataacgaaat aggatcaata gaaaagatgg aagctcatag aaaaggaaca cttcatagag   4500
cattcagtat tttagttttt aactcaaaga atcaactttt attacagaaa agaaatgtaa   4560
```

agaaatatca ctctccagga ttatggacaa acacttgttg tagtcaccca agatatggtg 4620
aatctcttca tgatgctata tacagaagat taaaagaaga gatgggattt acttgcgaac 4680
ttgaagaagt attctcattc atatataagg taaaacttga agataattta tttgagaatg 4740
aatatgacca tgtatttatt ggtaaatatg atggtgagat aattgttaat aaagatgaag 4800
ttgatgattt taaatgggta gacattaatg aagttaaaaa ggacataata gaaagacctg 4860
aggcatatac ttactggttt aagtatcttg taaataaagc tgaaaataag atatttaaat 4920
aaaccggtgg gaggaaatga acatggcaac agaattatta tgtttacaca gacctatatc 4980
acttactcac aaacttttta ggaatccatt acctaaagtt attcaagcta cacctttaac 5040
attaaaactt aggtgtagtg tttctacaga aaatgtatca tttagtgaga cagaaactga 5100
aacaagaaga tcagcaaatt atgaaccaaa ttcttgggat tatgattatc ttctttcttc 5160
tgatactgat gagtcaatag aagtacataa agataaggct aagaaattag aagctgaagt 5220
taggagagaa ataaataatg agaaggctga atttcttaca cttcttgaac ttattgataa 5280
tgtacaaaga cttggattag gatatagatt tgagtctgat ataagaagag cattagatag 5340
atttgtaagt agtggaggat ttgatggagt tactaaaact tcattacatg gaacagcatt 5400
atcatttagg ttattaaggc aacatggttt tgaagtatct caagaagctt ttagtggatt 5460
taaagatcag aatggaaact ttcttgagaa tttaaaggaa gacataaaag caattctttc 5520
tctttatgaa gcatcatttt tagcattaga aggtgagaat atattagatg aggctaaagt 5580
atttgcaata tctcatctta aagaacttag tgaagaaaag attggtaaag aattagctga 5640
acaagtttca catgctttag aattaccatt acatagaaga acacaaagat tagaagcagt 5700
ttggtcaata gaagcatata gaaagaaaga agacgcaaat caagtacttt tagaacttgc 5760
aatacttgac tacaatatga ttcaaagtgt atatcagagg gatttaagag aaacatcaag 5820
atggtggaga agagtaggat tagcaactaa attacatttt gctagagata ggcttattga 5880
aagtttttat tgggctgttg gagttgcttt tgaaccacaa tattctgatt gcagaaatag 5940
tgtagcaaag atgttttcat ttgttactat aattgacgat atttacgatg tatatggaac 6000
tttagatgaa cttgaacttt ttactgatgc agttgaaaga tgggatgtaa atgctattaa 6060
tgatcttcct gattatatga agttatgttt tcttgcactt tacaatacta ttaacgagat 6120
agcttacgat aacttaaaag ataaaggtga gaacatactt ccttatttaa caaaagcatg 6180
ggcagattta tgtaatgcat ttcttcaaga agctaagtgg ctttataata aatcaacacc 6240
tacatttgat gattattttg gaaatgcatg gaaaagttct agtggacctt tacagcttat 6300
ttttgcttat tttgctgtag tacagaacat taaaaaggaa gagattgaga atcttcagaa 6360
atatcatgac ataatatcaa gacctagtca catttttagg ctttgtaatg atttagcatc 6420
tgcttcagca gaaatagcaa gaggtgaaac tgctaattct gtaagttgtt atatgagaac 6480
aaaaggtata tctgaagaat tagctactga aagtgttatg aatcttatag acgaaacttg 6540
gaagaaaatg aacaaagaaa aacttggtgg atctttattt gcaaaacctt ttgttgagac 6600
tgctataaat ttagctagac agtctcattg cacatatcat aatggtgatg cacatactag 6660
tccagatgaa ttaactagga aaagagtact tagtgtaata actgaaccaa tattaccatt 6720
tgaaagataa gctagcataa aaataagaag cctgcatttg caggcttctt atttttatgg 6780
cgcgccgcca ttattttttt gaacaattga caattcattt cttatttttt attaagtgat 6840
agtcaaaagg cataacagtg ctgaatagaa agaaatttac agaaaagaaa attatagaat 6900

-continued

```
ttagtatgat taattatact catttatgaa tgtttaattg aatacaaaaa aaaatacttg   6960
ttatgtattc aattacgggt taaaatatag acaagttgaa aaatttaata aaaaaataag   7020
tcctcagctc ttatatatta agctaccaac ttagtatata agccaaaact taaatgtgct   7080
accaacacat caagccgtta gagaactcta tctatagcaa tatttcaaat gtaccgacat   7140
acaagagaaa cattaactat atatattcaa tttatgagat tatcttaaca gatataaatg   7200
taaattgcaa taagtaagat ttagaagttt atagcctttg tgtattggaa gcagtacgca   7260
aaggcttttt tatttgataa aaattagaag tatatttatt ttttcataat taatttatga   7320
aaatgaaagg gggtgagcaa agtgacagag gaaagcagta tcttatcaaa taacaaggta   7380
ttagcaatat cattattgac tttagcagta aacattatga cttttatagt gcttgtagct   7440
aagtagtacg aaagggggag ctttaaaaag ctccttggaa tacatagaat tcataaatta   7500
atttatgaaa agaagggcgt atatgaaaac ttgtaaaaat tgcaaagagt ttattaaaga   7560
tactgaaata tgcaaaatac attcgttgat gattcatgat aaaacagtag caacctattg   7620
cagtaaatac aatgagtcaa gatgtttaca taaagggaaa gtccaatgta ttaattgttc   7680
aaagatgaac cgatatggat ggtgtgccat aaaaatgaga tgttttacag aggaagaaca   7740
gaaaaaagaa cgtacatgca ttaaatatta tgcaaggagc tttaaaaaag ctcatgtaaa   7800
gaagagtaaa aagaaaaaat aatttattta ttaatttaat attgagagtg ccgacacagt   7860
atgcactaaa aaatatatct gtggtgtagt gagccgatac aaaaggatag tcactcgcat   7920
tttcataata catcttatgt tatgattatg tgtcggtggg acttcacgac gaaaacccac   7980
aataaaaaaa gagttcgggg tagggttaag catagttgag gcaactaaac aatcaagcta   8040
ggatatgcag tagcagaccg taaggtcgtt gtttaggtgt gttgtaatac atacgctatt   8100
aagatgtaaa aatacggata ccaatgaagg gaaaagtata atttttggat gtagtttgtt   8160
tgttcatcta tgggcaaact acgtccaaag ccgtttccaa atctgctaaa aagtatatcc   8220
tttctaaaat caaagtcaag tatgaaatca taaataaagt ttaattttga agttattatg   8280
atattatgtt tttctattaa aataaattaa gtatatagaa tagtttaata atagtatata   8340
cttaatgtga taagtgtctg acagtgtcac agaaaggatg attgttatgg attataagcg   8400
gccggccagt gggcaagttg aaaaattcac aaaaatgtgg tataatatct ttgttcatta   8460
gagcgataaa cttgaatttg agagggaact tagatggtat ttgaaaaaat tgataaaaat   8520
agttggaaca gaaaagagta ttttgaccac tactttgcaa gtgtaccttg tacctacagc   8580
atgaccgtta aagtggatat cacacaaata aaggaaaagg gaatgaaact atatcctgca   8640
atgctttatt atattgcaat gattgtaaac cgccattcag agtttaggac ggcaatcaat   8700
caagatggtg aattggggat atatgatgag atgataccaa gctatacaat atttcacaat   8760
gatactgaaa cattttccag cctttggact gagtgtaagt ctgactttaa atcattttta   8820
gcagattatg aaagtgatac gcaacggtat ggaaacaatc atagaatgga aggaaagcca   8880
aatgctccgg aaaacatttt taatgtatct atgataccgt ggtcaacctt cgatggcttt   8940
aatctgaatt tgcagaaagg atatgattat ttgattccta tttttactat ggggaaatat   9000
tataaagaag ataacaaaat tatacttcct ttggcaattc aagttcatca cgcagtatgt   9060
gacggatttc acatttgccg ttttgtaaac gaattgcagg aattgataaa tagttaactt   9120
caggtttgtc tgtaactaaa aacaagtatt taagcaaaaa catcgtagaa atacggtgtt   9180
ttttgttacc ctaagttt                                                 9198
```

<210> SEQ ID NO 85
<211> LENGTH: 6841
<212> TYPE: DNA
<213> ORGANISM: Artificial Sequence
<220> FEATURE:
<223> OTHER INFORMATION: plasmid pMTL83245-Pfor-FS-idi

<400> SEQUENCE: 85

```
aaactccttt ttgataatct catgaccaaa atcccttaac gtgagttttc gttccactga     60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc cagggggaaa cgcctggtat    600
ctttatagtc ctgtcgggtt tcgccacctc tgacttgagc gtcgattttt gtgatgctcg    660
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggcccccctg caggataaaa    900
aaattgtaga taaattttat aaaatagttt tatctacaat ttttttatca ggaaacagct    960
atgaccgcgg ccgcaatatg atatttatgt ccattgtgaa agggattata ttcaactatt   1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattattta ttttaaaatg cctaagtgaa atatatacat attataacaa   1200
taaaataagt attagtgtag gatttttaaa tagagtatct attttcagat taaattttttg   1260
attatttgat ttacattata taatattgag taaagtattg actagcaaaa tttttttgata   1320
ctttaatttg tgaaatttct tatcaaaagt tatatttttg aataattttt attgaaaaat   1380
acaactaaaa aggattatag tataagtgtg tgtaattttg tgttaaattt aaagggagga   1440
aatgaacatg aaacatatgg tgaccatgat tacgaattcg agctcggtac ccggggatcc   1500
tctagttgta tattaaaata gtagaataca taagatactt aatttaatta aagatagtta   1560
agtacttttc aatgtgcttt tttagatgtt taatacaaat ctttaattgt aaaagaaatg   1620
ctgtactatt tactgttcta gtgacgggat taaactgtat taattataaa taaaaaaataa   1680
gtacagttgt ttaaaattat attttgtatt aaatctaata gtacgatgta agttatttta   1740
tactattgct agtttaataa aaagatttaa ttatatactt gaaaaggaga ggaactcgag   1800
atggaattta gagtacattt acaggcagac aacgaacaga aaatatttca aaatcaaatg   1860
aaaccagagc cagaagcatc atatcttata aatcaaagaa gaagtgctaa ttataaacca   1920
aacatttgga aaaacgattt tcttgatcag tctttaatat caaaatatga tggtgatgaa   1980
tatagaaaac tttcagaaaa gttaatagaa gaagtaaaga tatacatatc agcagagact   2040
atggatttag ttgctaaatt agaacttata gattctgtta gaaaacttgg acttgctaat   2100
```

-continued ctttttgaga aagaaataaa ggaagcatta gacagtatag cagcaataga atcagataat 2160
ttaggaacta gagacgatct ttatggaaca gctcttcatt ttaagattct tagacagcat 2220
ggatataagg taagtcaaga tatatttggt agatttatgg atgagaaagg aacattagaa 2280
aatcatcact ttgcacactt aaaaggaatg ttagaattat ttgaggcaag taatcttgga 2340
tttgaaggtg aagacatatt agatgaagct aaagcatctc ttacacttgc tcttagagat 2400
tcaggacata tttgttatcc agactcaaac ttaagtagag atgtagttca tagtttagaa 2460
ttacctagtc atagaagagt tcaatggttc gatgtaaaat ggcagattaa tgcatacgaa 2520
aaagatattt gtagagtaaa tgcaacttta ttagagttag caaagttaaa ttttaatgtt 2580
gttcaagctc agcttcagaa gaatcttaga gaagctagta gatggtgggc taatcttggt 2640
ttcgcagata atttaaagtt tgctagagat agacttgtag agtgtttttc atgcgcagta 2700
ggtgtagcat ttgaaccaga gcattcatct tttagaatat gtttaactaa ggtaattaat 2760
cttgttctta ttatagatga tgtatacgat atatatggat ctgaagaaga gttaaaacat 2820
tttacaaatg ctgttgatag atgggacagt agagaaacag aacagcttcc tgaatgcatg 2880
aaaatgtgtt ttcaagtatt atataacact acttgcgaaa tagcaagaga gatagaagaa 2940
gaaaacggtt ggaatcaagt attacctcaa cttactaagg tttgggctga tttttgtaag 3000
gctcttttag ttgaagcaga gtggtacaat aaatcacata ttccaacatt agaagaatat 3060
cttagaaacg gatgtatatc aagtagtgta tctgtacttt tagttcactc tttcttttca 3120
ataactcatg aaggtacaaa agaaatggct gatttcttac ataaaaatga agatctttta 3180
tacaacataa gtcttatagt aagattaaac aatgatttag gtacatcagc tgctgaacag 3240
gaaagaggtg attctccttc ttctatagtt tgctatatga gagaagttaa tgcttctgaa 3300
gagactgcaa gaaagaatat aaagggaatg attgataatg cttggaaaaa ggttaatgga 3360
aaatgtttca caactaacca agttccattt ctttcatcat tcatgaataa tgcaactaac 3420
atggcaagag tagcacactc attatataaa gacggtgatg gttttggtga tcaagaaaaa 3480
ggacctagaa cacatattct tagtttatta ttccaacctt tagtaaatta actgcagggt 3540
tcaaaacata gattaaaaaa ttaaaggagg ggaaaaaatg gcagagtata taatagcagt 3600
agatgagttc gataacgaaa taggatcaat agaaaagatg gaagctcata gaaaaggaac 3660
acttcataga gcattcagta ttttagtttt taactcaaag aatcaacttt tattacagaa 3720
aagaaatgta aagaaatatc actctccagg attatggaca aacacttgtt gtagtcaccc 3780
aagatatggt gaatctcttc atgatgctat atacagaaga ttaaaagaag agatgggatt 3840
tacttgcgaa cttgaagaag tattctcatt catatataag gtaaaacttg aagataattt 3900
atttgagaat gaatatgacc atgtatttat tggtaaatat gatggtgaga taattgttaa 3960
taaagatgaa gttgatgatt ttaaatgggt agacattaat gaagttaaaa aggacataat 4020
agaaagacct gaggcatata cttactggtt taagtatctt gtaaataaag ctgaaaataa 4080
gatatttaaa taaaagcttg gcactggccg tcgttttaca acgtcgtgac tgggaaaacc 4140
ctggcgttac ccaacttaat cgccttgcag cacatccccc tttcgccagc tggcgtaata 4200
gcgaagaggc ccgcaccgat cgcccttccc aacagttgcg cagcctgaat ggcgaatggc 4260
gctagcataa aaataagaag cctgcatttg caggcttctt atttttatgg cgcgccgcca 4320
ttattttttt gaacaattga caattcattt cttatttttt attaagtgat agtcaaaagg 4380
cataacagtg ctgaatagaa agaaatttac agaaaagaaa attatagaat ttagtatgat 4440
taattatact catttatgaa tgtttaattg aatacaaaaa aaaatacttg ttatgtattc 4500

-continued

```
aattacgggt taaaatatag acaagttgaa aaatttaata aaaaaataag tcctcagctc   4560
ttatatatta agctaccaac ttagtatata agccaaaact taaatgtgct accaacacat   4620
caagccgtta gagaactcta tctatagcaa tatttcaaat gtaccgacat acaagagaaa   4680
cattaactat atatattcaa tttatgagat tatcttaaca gatataaatg taaattgcaa   4740
taagtaagat ttagaagttt atagcctttg tgtattggaa gcagtacgca aaggcttttt   4800
tatttgataa aaattagaag tatatttatt ttttcataat taatttatga aaatgaaagg   4860
gggtgagcaa agtgacagag gaaagcagta tcttatcaaa taacaaggta ttagcaatat   4920
cattattgac tttagcagta aacattatga cttttatagt gcttgtagct aagtagtacg   4980
aaagggggag ctttaaaaag ctccttggaa tacatagaat tcataaatta atttatgaaa   5040
agaagggcgt atatgaaaac ttgtaaaaat tgcaaagagt ttattaaaga tactgaaata   5100
tgcaaaatac attcgttgat gattcatgat aaaacagtag caacctattg cagtaaatac   5160
aatgagtcaa gatgtttaca taaagggaaa gtccaatgta ttaattgttc aaagatgaac   5220
cgatatggat ggtgtgccat aaaaatgaga tgttttacag aggaagaaca gaaaaaagaa   5280
cgtacatgca ttaaatatta tgcaaggagc tttaaaaaag ctcatgtaaa gaagagtaaa   5340
aagaaaaaat aatttattta ttaatttaat attgagagtg ccgacacagt atgcactaaa   5400
aaatatatct gtggtgtagt gagccgatac aaaaggatag tcactcgcat tttcataata   5460
catcttatgt tatgattatg tgtcggtggg acttcacgac gaaaacccac aataaaaaaa   5520
gagttcgggg tagggttaag catagttgag gcaactaaac aatcaagcta ggatatgcag   5580
tagcagaccg taaggtcgtt gtttaggtgt gttgtaatac atacgctatt aagatgtaaa   5640
aatacggata ccaatgaagg gaaaagtata atttttggat gtagtttgtt tgttcatcta   5700
tgggcaaact acgtccaaag ccgtttccaa atctgctaaa aagtatatcc tttctaaaat   5760
caaagtcaag tatgaaatca taaataaagt ttaattttga agttattatg atattatgtt   5820
tttctattaa aataaattaa gtatatagaa tagtttaata atagtatata cttaatgtga   5880
taagtgtctg acagtgtcac agaaaggatg attgttatgg attataagcg gccggccgaa   5940
gcaaacttaa gagtgtgttg atagtgcagt atcttaaaat tttgtataat aggaattgaa   6000
gttaaattag atgctaaaaa tttgtaatta agaaggagtg attacatgaa caaaaatata   6060
aaatattctc aaaacttttt aacgagtgaa aaagtactca accaaataat aaaacaattg   6120
aatttaaaag aaaccgatac cgtttacgaa attggaacag gtaaagggca tttaacgacg   6180
aaactggcta aaataagtaa acaggtaacg tctattgaat tagacagtca tctattcaac   6240
ttatcgtcag aaaaattaaa actgaatact cgtgtcactt taattcacca agatattcta   6300
cagtttcaat tccctaacaa acagaggtat aaaattgttg ggagtattcc ttaccattta   6360
agcacacaaa ttattaaaaa agtggttttt gaaagccatg cgtctgacat ctatctgatt   6420
gttgaagaag gattctacaa gcgtaccttg gatattcacc gaacactagg gttgctcttg   6480
cacactcaag tctcgattca gcaattgctt aagctgccag cggaatgctt tcatcctaaa   6540
ccaaaagtaa acagtgtctt aataaaactt acccgccata ccacagatgt tccagataaa   6600
tattggaagc tatatacgta ctttgtttca aaatgggtca atcgagaata tcgtcaactg   6660
tttactaaaa atcagtttca tcaagcaatg aaacacgcca aagtaaacaa tttaagtacc   6720
gttacttatg agcaagtatt gtctattttt aatagttatc tattatttaa cgggaggaaa   6780
taattctatg agtcgctttt gtaaatttgg aaagttacac gttactaaag ggaatgtgtt   6840
```

t 6841

<210> SEQ ID NO 86
<211> LENGTH: 36
<212> TYPE: DNA
<213> ORGANISM: Artificial Sequence
<220> FEATURE:
<223> OTHER INFORMATION: Oligonucleotide idi_F2

<400> SEQUENCE: 86
aggcactcga gatggcagag tatataatag cagtag 36

<210> SEQ ID NO 87
<211> LENGTH: 47
<212> TYPE: DNA
<213> ORGANISM: Artificial Sequence
<220> FEATURE:
<223> OTHER INFORMATION: Oligonucleotide idi_R2

<400> SEQUENCE: 87
aggcgcaagc ttggcgcacc ggtttattta aatatcttat tttcagc 47

<210> SEQ ID NO 88
<211> LENGTH: 5075
<212> TYPE: DNA
<213> ORGANISM: Artificial Sequence
<220> FEATURE:
<223> OTHER INFORMATION: plasmid pMTL83245-Pfor-idi

<400> SEQUENCE: 88
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc cagggggaaa cgcctggtat 600
ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720
ttttgctggc cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggccccctg caggataaaa 900
aaattgtaga taaattttat aaaatagttt tatctacaat ttttttatca ggaaacagct 960
atgaccgcgg ccgcaatatg atatttatgt ccattgtgaa agggattata ttcaactatt 1020
attccagtta cgttcataga aattttcctt tctaaaatat tttattccat gtcaagaact 1080
ctgtttattt cattaaagaa ctataagtac aaagtataag gcatttgaaa aaataggcta 1140
gtatattgat tgattattta ttttaaaatg cctaagtgaa atatatacat attataacaa 1200
taaaataagt attagtgtag gatttttaaa tagagtatct attttcagat taaattttttg 1260 attatttgat ttacattata taatattgag taaagtattg actagcaaaa ttttttgata 1320
ctttaatttg tgaaatttct tatcaaaagt tatatttttg aataattttt attgaaaaat 1380
acaactaaaa aggattatag tataagtgtg tgtaattttg tgttaaattt aaagggagga 1440
aatgaacatg aaacatatgg tgaccatgat tacgaattcg agctcggtac ccggggatcc 1500
tctagttgta tattaaaata gtagaataca taagatactt aatttaatta aagatagtta 1560
agtacttttc aatgtgcttt tttagatgtt taatacaaat ctttaattgt aaaagaaatg 1620
ctgtactatt tactgttcta gtgacgggat taaactgtat taattataaa taaaaaataa 1680
gtacagttgt ttaaaattat attttgtatt aaatctaata gtacgatgta agttatttta 1740
tactattgct agtttaataa aaagatttaa ttatatactt gaaaaggaga ggaactcgag 1800
atggcagagt atataatagc agtagatgag ttcgataacg aaataggatc aatagaaaag 1860
atggaagctc atagaaaagg aacacttcat agagcattca gtattttagt ttttaactca 1920
aagaatcaac ttttattaca gaaaagaaat gtaaagaaat atcactctcc aggattatgg 1980
acaaacactt gttgtagtca cccaagatat ggtgaatctc ttcatgatgc tatatacaga 2040
agattaaaag aagagatggg atttacttgc gaacttgaag aagtattctc attcatatat 2100
aaggtaaaac ttgaagataa tttatttgag aatgaatatg accatgtatt tattggtaaa 2160
tatgatggtg agataattgt taataaagat gaagttgatg attttaaatg ggtagacatt 2220
aatgaagtta aaaaggacat aatagaaaga cctgaggcat atacttactg gtttaagtat 2280
cttgtaaata aagctgaaaa taagatattt aaataaaccg gtgcgccaag cttggcactg 2340
gccgtcgttt tacaacgtcg tgactgggaa aaccctggcg ttacccaact taatcgcctt 2400
gcagcacatc ccccttttcgc cagctggcgt aatagcgaag aggcccgcac cgatcgccct 2460
tcccaacagt tgcgcagcct gaatggcgaa tggcgctagc ataaaaataa gaagcctgca 2520
tttgcaggct tcttattttt atggcgcgcc gccattattt ttttgaacaa ttgacaattc 2580
atttcttatt ttttattaag tgatagtcaa aaggcataac agtgctgaat agaaagaaat 2640
ttacagaaaa gaaaattata gaatttagta tgattaatta tactcattta tgaatgttta 2700
attgaataca aaaaaaaata cttgttatgt attcaattac gggttaaaat atagacaagt 2760
tgaaaaattt aataaaaaaa taagtcctca gctcttatat attaagctac caacttagta 2820
tataagccaa aacttaaatg tgctaccaac acatcaagcc gttagagaac tctatctata 2880
gcaatatttc aaatgtaccg acatacaaga gaaacattaa ctatatatat tcaatttatg 2940
agattatctt aacagatata aatgtaaatt gcaataagta agatttagaa gtttatagcc 3000
tttgtgtatt ggaagcagta cgcaaaggct tttttatttg ataaaaatta gaagtatatt 3060
tattttttca taattaattt atgaaaatga aagggggtga gcaaagtgac agaggaaagc 3120
agtatcttat caaataacaa ggtattagca atatcattat tgactttagc agtaaacatt 3180
atgactttta tagtgcttgt agctaagtag tacgaaaggg ggagctttaa aaagctcctt 3240
ggaatacata gaattcataa attaatttat gaaaagaagg gcgtatatga aaacttgtaa 3300
aaattgcaaa gagtttatta aagatactga aatatgcaaa atacattcgt tgatgattca 3360
tgataaaaca gtagcaacct attgcagtaa atacaatgag tcaagatgtt tacataaagg 3420
gaaagtccaa tgtattaatt gttcaaagat gaaccgatat ggatggtgtg ccataaaaat 3480
gagatgtttt acagaggaag aacagaaaaa agaacgtaca tgcattaaat attatgcaag 3540
gagctttaaa aaagctcatg taaagaagag taaaaagaaa aaataattta tttattaatt 3600
taatattgag agtgccgaca cagtatgcac taaaaaatat atctgtggtg tagtgagccg 3660
atacaaaagg atagtcactc gcattttcat aatacatctt atgttatgat tatgtgtcgg 3720
tgggacttca cgacgaaaac ccacaataaa aaaagagttc ggggtagggt taagcatagt 3780
tgaggcaact aaacaatcaa gctaggatat gcagtagcag accgtaaggt cgttgtttag 3840
gtgtgttgta atacatacgc tattaagatg taaaaatacg gataccaatg aagggaaaag 3900
tataattttt ggatgtagtt tgtttgttca tctatgggca aactacgtcc aaagccgttt 3960
ccaaatctgc taaaaagtat atcctttcta aaatcaaagt caagtatgaa atcataaata 4020
aagtttaatt ttgaagttat tatgatatta tgtttttcta ttaaaataaa ttaagtatat 4080
agaatagttt aataatagta tatacttaat gtgataagtg tctgacagtg tcacagaaag 4140
gatgattgtt atggattata agcggccggc cgaagcaaac ttaagagtgt gttgatagtg 4200
cagtatctta aaattttgta taataggaat tgaagttaaa ttagatgcta aaaatttgta 4260
attaagaagg agtgattaca tgaacaaaaa tataaaatat tctcaaaact ttttaacgag 4320
tgaaaaagta ctcaaccaaa taataaaaca attgaattta aaagaaaccg ataccgttta 4380
cgaaattgga acaggtaaag ggcatttaac gacgaaactg gctaaaataa gtaaacaggt 4440
aacgtctatt gaattagaca gtcatctatt caacttatcg tcagaaaaat taaaactgaa 4500
tactcgtgtc actttaattc accaagatat tctacagttt caattcccta acaaacagag 4560
gtataaaatt gttgggagta ttccttacca tttaagcaca caaattatta aaaaagtggt 4620
ttttgaaagc catgcgtctg acatctatct gattgttgaa gaaggattct acaagcgtac 4680
cttggatatt caccgaacac tagggttgct cttgcacact caagtctcga ttcagcaatt 4740
gcttaagctg ccagcggaat gctttcatcc taaaccaaaa gtaaacagtg tcttaataaa 4800
acttacccgc cataccacag atgttccaga taaatattgg aagctatata cgtactttgt 4860
ttcaaaatgg gtcaatcgag aatatcgtca actgtttact aaaaatcagt ttcatcaagc 4920
aatgaaacac gccaaagtaa acaatttaag taccgttact tatgagcaag tattgtctat 4980
ttttaatagt tatctattat ttaacgggag gaaataattc tatgagtcgc ttttgtaaat 5040
ttggaaagtt acacgttact aaagggaatg tgttt 5075

<210> SEQ ID NO 89
<211> LENGTH: 6662
<212> TYPE: DNA
<213> ORGANISM: Artificial Sequence
<220> FEATURE:
<223> OTHER INFORMATION: plasmid pMTL83245-Pfor-idi-FS

<400> SEQUENCE: 89
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc cagggggaaa cgcctggtat 600
ctttatagtc ctgtcgggtt tcgccacctc tgacttgagc gtcgattttt gtgatgctcg 660

```
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggcccccctg caggataaaa   900
aaattgtaga taaattttat aaaatagttt tatctacaat ttttttatca ggaaacagct    960
atgaccgcgg ccgcaatatg atatttatgt ccattgtgaa agggattata ttcaactatt   1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattattta ttttaaaatg cctaagtgaa atatatacat attataacaa   1200
taaaataagt attagtgtag gatttttaaa tagagtatct attttcagat taaatttttg   1260
attatttgat ttacattata taatattgag taaagtattg actagcaaaa tttttgata    1320
ctttaatttg tgaaatttct tatcaaaagt tatattttg aataattttt attgaaaaat    1380
acaactaaaa aggattatag tataagtgtg tgtaattttg tgttaaattt aaagggagga   1440
aatgaacatg aaacatatgg tgaccatgat tacgaattcg agctcggtac ccggggatcc   1500
tctagttgta tattaaaata gtagaataca taagatactt aatttaatta aagatagtta   1560
agtacttttc aatgtgcttt tttagatgtt taatacaaat ctttaattgt aaaagaaatg   1620
ctgtactatt tactgttcta gtgacgggat taaactgtat taattataaa taaaaaataa   1680
gtacagttgt ttaaaattat attttgtatt aaatctaata gtacgatgta agttatttta   1740
tactattgct agtttaataa aaagatttaa ttatatactt gaaaaggaga ggaactcgag   1800
atggcagagt atataatagc agtagatgag ttcgataacg aaataggatc aatagaaaag   1860
atggaagctc atagaaaagg aacacttcat agagcattca gtattttagt ttttaactca   1920
aagaatcaac ttttattaca gaaaagaaat gtaaagaaat atcactctcc aggattatgg   1980
acaaacactt gttgtagtca cccaagatat ggtgaatctc ttcatgatgc tatatacaga   2040
agattaaaag aagagatggg atttacttgc gaacttgaag aagtattctc attcatatat   2100
aaggtaaaac ttgaagataa tttatttgag aatgaatatg accatgtatt tattggtaaa   2160
tatgatggtg agataattgt taataaagat gaagttgatg attttaaatg ggtagacatt   2220
aatgaagtta aaaaggacat aatagaaaga cctgaggcat atacttactg gtttaagtat   2280
cttgtaaata aagctgaaaa taagatattt aaataaaccg gtgcgccaag cttttaaagg   2340
aggggaaaaa atggaattta gagtacattt acaggcagac aacgaacaga aaatatttca   2400
aaatcaaatg aaaccagagc cagaagcatc atatcttata aatcaaagaa gaagtgctaa   2460
ttataaacca aacatttgga aaaacgattt tcttgatcag tctttaatat caaaatatga   2520
tggtgatgaa tatagaaaac tttcagaaaa gttaatagaa gaagtaaaga tatacatatc   2580
agcagagact atggatttag ttgctaaatt agaacttata gattctgtta gaaaacttgg   2640
acttgctaat ctttttgaga aagaaataaa ggaagcatta gacagtatag cagcaataga   2700
atcagataat ttaggaacta gagacgatct ttatggaaca gctcttcatt ttaagattct   2760
tagacagcat ggatataagg taagtcaaga tatatttggt agatttatgg atgagaaagg   2820
aacattagaa aatcatcact ttgcacactt aaaaggaatg ttagaattat ttgaggcaag   2880
taatcttgga tttgaaggtg aagacatatt agatgaagct aaagcatctc ttacacttgc   2940
tcttagagat tcaggacata tttgttatcc agactcaaac ttaagtagag atgtagttca   3000
```

-continued

```
tagtttagaa ttacctagtc atagaagagt tcaatggttc gatgtaaaat ggcagattaa   3060
tgcatacgaa aaagatattt gtagagtaaa tgcaacttta ttagagttag caaagttaaa   3120
ttttaatgtt gttcaagctc agcttcagaa gaatcttaga gaagctagta gatggtgggc   3180
taatcttggt ttcgcagata atttaaagtt tgctagagat agacttgtag agtgtttttc   3240
atgcgcagta ggtgtagcat ttgaaccaga gcattcatct tttagaatat gtttaactaa   3300
ggtaattaat cttgttctta ttatagatga tgtatacgat atatatggat ctgaagaaga   3360
gttaaaacat tttacaaatg ctgttgatag atgggacagt agagaaacag aacagcttcc   3420
tgaatgcatg aaaatgtgtt ttcaagtatt atataacact acttgcgaaa tagcaagaga   3480
gatagaagaa gaaaacggtt ggaatcaagt attacctcaa cttactaagg tttgggctga   3540
tttttgtaag gctcttttag ttgaagcaga gtggtacaat aaatcacata ttccaacatt   3600
agaagaatat cttagaaacg gatgtatatc aagtagtgta tctgtacttt tagttcactc   3660
tttcttttca ataactcatg aaggtacaaa agaaatggct gatttcttac ataaaaatga   3720
agatctttta tacaacataa gtcttatagt aagattaaac aatgatttag gtacatcagc   3780
tgctgaacag gaaagaggtg attctccttc ttctatagtt tgctatatga gagaagttaa   3840
tgcttctgaa gagactgcaa gaaagaatat aaagggaatg attgataatg cttggaaaaa   3900
ggttaatgga aaatgtttca caactaacca agttccattt ctttcatcat tcatgaataa   3960
tgcaactaac atggcaagag tagcacactc attatataaa gacggtgatg gttttggtga   4020
tcaagaaaaa ggacctagaa cacatattct tagtttatta ttccaacctt tagtaaatta   4080
agctagcata aaaataagaa gcctgcattt gcaggcttct tatttttatg gcgcgccgcc   4140
attatttttt tgaacaattg acaattcatt tcttattttt tattaagtga tagtcaaaag   4200
gcataacagt gctgaataga aagaaattta cagaaaagaa aattatagaa tttagtatga   4260
ttaattatac tcatttatga atgtttaatt gaatacaaaa aaaaatactt gttatgtatt   4320
caattacggg ttaaaatata gacaagttga aaaatttaat aaaaaaataa gtcctcagct   4380
cttatatatt aagctaccaa cttagtatat aagccaaaac ttaaatgtgc taccaacaca   4440
tcaagccgtt agagaactct atctatagca atatttcaaa tgtaccgaca tacaagagaa   4500
acattaacta tatatattca atttatgaga ttatcttaac agatataaat gtaaattgca   4560
ataagtaaga tttagaagtt tatagccttt gtgtattgga agcagtacgc aaaggctttt   4620
ttatttgata aaaattagaa gtatatttat tttttcataa ttaatttatg aaaatgaaag   4680
ggggtgagca aagtgacaga ggaaagcagt atcttatcaa ataacaaggt attagcaata   4740
tcattattga ctttagcagt aaacattatg acttttatag tgcttgtagc taagtagtac   4800
gaaaggggga gctttaaaaa gctccttgga atacatagaa ttcataaatt aatttatgaa   4860
aagaagggcg tatatgaaaa cttgtaaaaa ttgcaaagag tttattaaag atactgaaat   4920
atgcaaaata cattcgttga tgattcatga taaaacagta gcaacctatt gcagtaaata   4980
caatgagtca agatgtttac ataaagggaa agtccaatgt attaattgtt caaagatgaa   5040
ccgatatgga tggtgtgcca taaaaatgag atgttttaca gaggaagaac agaaaaaaga   5100
acgtacatgc attaaatatt atgcaaggag ctttaaaaaa gctcatgtaa agaagagtaa   5160
aaagaaaaaa taatttattt attaatttaa tattgagagt gccgacacag tatgcactaa   5220
aaaatatatc tgtggtgtag tgagccgata caaaaggata gtcactcgca ttttcataat   5280
acatcttatg ttatgattat gtgtcggtgg gacttcacga cgaaaaccca caataaaaaa   5340
agagttcggg gtagggttaa gcatagttga ggcaactaaa caatcaagct aggatatgca   5400
```

gtagcagacc gtaaggtcgt tgtttaggtg tgttgtaata catacgctat taagatgtaa 5460
aaatacggat accaatgaag ggaaaagtat aatttttgga tgtagtttgt ttgttcatct 5520
atgggcaaac tacgtccaaa gccgtttcca aatctgctaa aaagtatatc ctttctaaaa 5580
tcaaagtcaa gtatgaaatc ataaataaag tttaattttg aagttattat gatattatgt 5640
ttttctatta aaataaatta agtatataga atagtttaat aatagtatat acttaatgtg 5700
ataagtgtct gacagtgtca cagaaaggat gattgttatg gattataagc ggccggccga 5760
agcaaactta agagtgtgtt gatagtgcag tatcttaaaa ttttgtataa taggaattga 5820
agttaaatta gatgctaaaa atttgtaatt aagaaggagt gattacatga acaaaaatat 5880
aaaatattct caaaactttt taacgagtga aaaagtactc aaccaaataa taaaacaatt 5940
gaatttaaaa gaaaccgata ccgtttacga aattggaaca ggtaaagggc atttaacgac 6000
gaaactggct aaaataagta aacaggtaac gtctattgaa ttagacagtc atctattcaa 6060
cttatcgtca gaaaaattaa aactgaatac tcgtgtcact ttaattcacc aagatattct 6120
acagtttcaa ttccctaaca aacagaggta taaaattgtt gggagtattc cttaccattt 6180
aagcacacaa attattaaaa aagtggtttt tgaaagccat gcgtctgaca tctatctgat 6240
tgttgaagaa ggattctaca agcgtacctt ggatattcac cgaacactag ggttgctctt 6300
gcacactcaa gtctcgattc agcaattgct taagctgcca gcggaatgct ttcatcctaa 6360
accaaaagta aacagtgtct taataaaact tacccgccat accacagatg ttccagataa 6420
atattggaag ctatatacgt actttgtttc aaaatgggtc aatcgagaat atcgtcaact 6480
gtttactaaa aatcagtttc atcaagcaat gaaacacgcc aaagtaaaca atttaagtac 6540
cgttacttat gagcaagtat tgtctatttt taatagttat ctattattta acgggaggaa 6600
ataattctat gagtcgcttt tgtaaatttg gaaagttaca cgttactaaa gggaatgtgt 6660
tt 6662

<210> SEQ ID NO 90
<211> LENGTH: 7077
<212> TYPE: DNA
<213> ORGANISM: Artificial Sequence
<220> FEATURE:
<223> OTHER INFORMATION: plasmid pMTL83245-Pfor-idi-ispA-FS

<400> SEQUENCE: 90
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc cagggggaaa cgcctggtat 600
ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720

```
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggcccccctg caggataaaa    900
aaattgtaga taaattttat aaaatagttt tatctacaat ttttttatca ggaaacagct    960
atgaccgcgg ccgcaccgag actagttgta tattaaaata gtagaataca taagatactt   1020
aatttaatta aagatagtta agtacttttc aatgtgcttt tttagatgtt taatacaaat   1080
ctttaattgt aaaagaaatg ctgtactatt tactgttcta gtgacgggat taaactgtat   1140
taattataaa taaaaaataa gtacagttgt ttaaaattat attttgtatt aaatctaata   1200
gtacgatgta agttatttta tactattgct agtttaataa aaagatttaa ttatatactt   1260
gaaaaggaga ggaactcgag atggcagagt atataatagc agtagatgag ttcgataacg   1320
aaataggatc aatagaaaag atggaagctc atagaaaagg aacacttcat agagcattca   1380
gtattttagt ttttaactca aagaatcaac ttttattaca gaaaagaaat gtaaagaaat   1440
atcactctcc aggattatgg acaaacactt gttgtagtca cccaagatat ggtgaatctc   1500
ttcatgatgc tatatacaga agattaaaag aagagatggg atttacttgc gaacttgaag   1560
aagtattctc attcatatat aaggtaaaac ttgaagataa tttatttgag aatgaatatg   1620
accatgtatt tattggtaaa tatgatggtg agataattgt taataaagat gaagttgatg   1680
attttaaatg ggtagacatt aatgaagtta aaaaggacat aatagaaaga cctgaggcat   1740
atacttactg gtttaagtat cttgtaaata aagctgaaaa taagatattt aaataaaccg   1800
gtcagtaacg aatagaatta gaaaaacaaa ggaggcaaga caatggattt cccacaacaa   1860
ttagaagcat gtgtaaaaca ggctaatcag gcacttagta gatttattgc tcctcttcct   1920
tttcaaaata caccagtagt agaaactatg caatacggtg cacttttagg tggtaaaaga   1980
ttaagaccat tcttagtata tgctacagga cacatgtttg gtgtatcaac taatacttta   2040
gacgctccag ctgctgctgt tgaatgtatt catgcttatt ctttaataca tgatgactta   2100
ccagcaatgg atgacgatga tttaagaaga ggtttaccta catgtcatgt taaatttggt   2160
gaagctaatg caattttagc aggtgacgct ttacaaactt tagctttttc tatactttca   2220
gatgcagaca tgcctgaagt ttcagataga gatagaattt ctatgatatc agagcttgca   2280
tctgcatcag gaatagctgg aatgtgcggt ggtcaagcac ttgatttaga tgcagaaggt   2340
aaacacgtac cacttgatgc tttagagaga atacatagac ataaaacagg tgctcttata   2400
agagcagcag taagattagg tgctttaagt gctggtgaca agggtagaag agcacttcca   2460
gtacttgata agtatgcaga aagtatagga ttagcttttc aagttcaaga tgacatactt   2520
gacgttgttg gtgatactgc tactttagga aaaagacagg gtgcagatca gcaattagga   2580
aaatctacat accctgcttt acttggatta gaacaggcta gaaagaaagc aagagactta   2640
atagatgacg caagacaaag tcttaaacag ttagctgaac aatcacttga cacaagtgca   2700
cttgaagcac ttgcagatta tattatacag agaaacaagt aaaagctttt aaaggagggg   2760
aaaaaatgga atttagagta catttacagg cagacaacga acagaaaata tttcaaaatc   2820
aaatgaaacc agagccagaa gcatcatatc ttataaatca aagaagaagt gctaattata   2880
aaccaaacat ttggaaaaac gattttcttg atcagtcttt aatatcaaaa tatgatggtg   2940
atgaatatag aaaactttca gaaaagttaa tagaagaagt aaagatatac atatcagcag   3000
agactatgga tttagttgct aaattagaac ttatagattc tgttagaaaa cttggacttg   3060
ctaatctttt tgagaaagaa ataaaggaag cattagacag tatagcagca atagaatcag   3120
```

-continued

```
ataatttagg aactagagac gatctttatg gaacagctct tcattttaag attcttagac   3180
agcatggata taaggtaagt caagatatat ttggtagatt tatggatgag aaaggaacat   3240
tagaaaatca tcactttgca cacttaaaag gaatgttaga attatttgag gcaagtaatc   3300
ttggatttga aggtgaagac atattagatg aagctaaagc atctcttaca cttgctctta   3360
gagattcagg acatatttgt tatccagact caaacttaag tagagatgta gttcatagtt   3420
tagaattacc tagtcataga agagttcaat ggttcgatgt aaaatggcag attaatgcat   3480
acgaaaaaga tatttgtaga gtaaatgcaa ctttattaga gttagcaaag ttaaatttta   3540
atgttgttca agctcagctt cagaagaatc ttagagaagc tagtagatgg tgggctaatc   3600
ttggtttcgc agataattta aagtttgcta gagatagact tgtagagtgt ttttcatgcg   3660
cagtaggtgt agcatttgaa ccagagcatt catcttttag aatatgttta actaaggtaa   3720
ttaatcttgt tcttattata gatgatgtat acgatatata tggatctgaa gaagagttaa   3780
aacattttac aaatgctgtt gatagatggg acagtagaga aacagaacag cttcctgaat   3840
gcatgaaaat gtgttttcaa gtattatata acactacttg cgaaatagca agagagatag   3900
aagaagaaaa cggttggaat caagtattac ctcaacttac taaggtttgg gctgattttt   3960
gtaaggctct tttagttgaa gcagagtggt acaataaatc acatattcca acattagaag   4020
aatatcttag aaacggatgt atatcaagta gtgtatctgt acttttagtt cactctttct   4080
tttcaataac tcatgaaggt acaaaagaaa tggctgattt cttacataaa aatgaagatc   4140
ttttatacaa cataagtctt atagtaagat taaacaatga tttaggtaca tcagctgctg   4200
aacaggaaag aggtgattct ccttcttcta tagtttgcta tatgagagaa gttaatgctt   4260
ctgaagagac tgcaagaaag aatataaagg gaatgattga taatgcttgg aaaaaggtta   4320
atggaaaatg tttcacaact aaccaagttc catttctttc atcattcatg aataatgcaa   4380
ctaacatggc aagagtagca cactcattat ataaagacgg tgatggtttt ggtgatcaag   4440
aaaaaggacc tagaacacat attcttagtt tattattcca acctttagta aattaagcta   4500
gcataaaaat aagaagcctg catttgcagg cttcttattt ttatggcgcg ccgccattat   4560
tttttgaac aattgacaat tcatttctta tttttatta agtgatagtc aaaaggcata    4620
acagtgctga atagaaagaa atttacagaa aagaaaatta tagaatttag tatgattaat   4680
tatactcatt tatgaatgtt taattgaata caaaaaaaaa tacttgttat gtattcaatt   4740
acgggttaaa atatagacaa gttgaaaaat ttaataaaaa aataagtcct cagctcttat   4800
atattaagct accaacttag tatataagcc aaaacttaaa tgtgctacca acacatcaag   4860
ccgttagaga actctatcta tagcaatatt tcaaatgtac cgacatacaa gagaaacatt   4920
aactatatat attcaattta tgagattatc ttaacagata taaatgtaaa ttgcaataag   4980
taagatttag aagtttatag cctttgtgta ttggaagcag tacgcaaagg ctttttttatt   5040
tgataaaaat tagaagtata tttattttt cataattaat ttatgaaaat gaaagggggt    5100
gagcaaagtg acagaggaaa gcagtatctt atcaaataac aaggtattag caatatcatt   5160
attgacttta gcagtaaaca ttatgacttt tatagtgctt gtagctaagt agtacgaaag   5220
ggggagcttt aaaaagctcc ttggaataca tagaattcat aaattaattt atgaaaagaa   5280
gggcgtatat gaaaacttgt aaaaattgca aagagtttat taaagatact gaaatatgca   5340
aaatacattc gttgatgatt catgataaaa cagtagcaac ctattgcagt aaatacaatg   5400
agtcaagatg tttacataaa gggaaagtcc aatgtattaa ttgttcaaag atgaaccgat   5460
```

-continued atggatggtg tgccataaaa atgagatgtt ttacagagga agaacagaaa aaagaacgta 5520
catgcattaa atattatgca aggagcttta aaaaagctca tgtaaagaag agtaaaaaga 5580
aaaaataatt tatttattaa tttaatattg agagtgccga cacagtatgc actaaaaaat 5640
atatctgtgg tgtagtgagc cgatacaaaa ggatagtcac tcgcattttc ataatacatc 5700
ttatgttatg attatgtgtc ggtgggactt cacgacgaaa acccacaata aaaaaagagt 5760
tcggggtagg gttaagcata gttgaggcaa ctaaacaatc aagctaggat atgcagtagc 5820
agaccgtaag gtcgttgttt aggtgtgttg taatacatac gctattaaga tgtaaaaata 5880
cggataccaa tgaagggaaa agtataattt ttggatgtag tttgtttgtt catctatggg 5940
caaactacgt ccaaagccgt ttccaaatct gctaaaaagt atatcctttc taaaatcaaa 6000
gtcaagtatg aaatcataaa taaagtttaa ttttgaagtt attatgatat tatgtttttc 6060
tattaaaata aattaagtat atagaatagt ttaataatag tatatactta atgtgataag 6120
tgtctgacag tgtcacagaa aggatgattg ttatggatta taagcggccg gccgaagcaa 6180
acttaagagt gtgttgatag tgcagtatct taaaattttg tataatagga attgaagtta 6240
aattagatgc taaaaatttg taattaagaa ggagtgatta catgaacaaa aatataaaat 6300
attctcaaaa ctttttaacg agtgaaaaag tactcaacca aataataaaa caattgaatt 6360
taaaagaaac cgataccgtt tacgaaattg gaacaggtaa agggcattta acgacgaaac 6420
tggctaaaat aagtaaacag gtaacgtcta ttgaattaga cagtcatcta ttcaacttat 6480
cgtcagaaaa attaaaactg aatactcgtg tcactttaat tcaccaagat attctacagt 6540
ttcaattccc taacaaacag aggtataaaa ttgttgggag tattccttac catttaagca 6600
cacaaattat taaaaaagtg gtttttgaaa gccatgcgtc tgacatctat ctgattgttg 6660
aagaaggatt ctacaagcgt accttggata ttcaccgaac actagggttg ctcttgcaca 6720
ctcaagtctc gattcagcaa ttgcttaagc tgccagcgga atgctttcat cctaaaccaa 6780
aagtaaacag tgtcttaata aaacttaccc gccataccac agatgttcca gataaatatt 6840
ggaagctata tacgtacttt gtttcaaaat gggtcaatcg agaatatcgt caactgttta 6900
ctaaaaatca gtttcatcaa gcaatgaaac acgccaaagt aaacaattta agtaccgtta 6960
cttatgagca agtattgtct atttttaata gttatctatt atttaacggg aggaaataat 7020
tctatgagtc gcttttgtaa atttggaaag ttacacgtta ctaaagggaa tgtgttt 7077

<210> SEQ ID NO 91
<211> LENGTH: 10090
<212> TYPE: DNA
<213> ORGANISM: Artificial Sequence
<220> FEATURE:
<223> OTHER INFORMATION:
plasmid pMTL 8314-Prnf-MK-PMK-PMD-Pfor-idi-ispA-FS

<400> SEQUENCE: 91
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc caggggggaaa cgcctggtat 600 ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720
ttttgctggc cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggccccctg caggataaaa 900
aaattgtaga taaattttat aaaatagttt tatctacaat ttttttatca ggaaacagct 960
atgaccgcgg ccgctaggtc tagaatatcg atacagataa aaaaatatat aatacagaag 1020
aaaaaattat aaatttgtgg tataatataa agtatagtaa tttaagttta aacctcgtga 1080
aaacgctaac aaataatagg aggtcaattg atgatagctg ttccatttaa cgctggaaaa 1140
ataaaagttt taattgaggc attagaatct ggaaattatt catcaataaa atcagatgta 1200
tatgacggaa tgttatatga tgcaccagat caccttaaat cattagtaaa cagatttgta 1260
gaacttaata atataactga gccattagca gtaactatac agacaaatct tcctccttca 1320
agaggtcttg gatctagtgc agctgttgct gttgcttttg taagagcaag ttatgatttc 1380
ttaggaaaaa gtttaactaa agaagagctt atagaaaagg ctaattgggc tgaacaaata 1440
gctcatggaa agccatctgg aatagataca caaacaatag tatctggaaa gcctgtttgg 1500
tttcaaaagg gacatgcaga aacacttaaa actctttcac ttgatggata catggtagta 1560
attgatacag gtgttaaagg aagtacaaga caggctgtag aagatgttca taaactttgc 1620
gaagatcctc aatatatgag tcacgtaaaa cacataggaa aacttgtact tagagcatct 1680
gatgttattg aacatcataa ctttgaagca cttgctgata tattcaatga atgtcatgct 1740
gatttaaagg ctcttacagt aagtcatgac aaaatagaac agttaatgaa gataggaaaa 1800
gaaaatggtg ctatagctgg taaattaact ggtgctggta gaggtggttc aatgttatta 1860
cttgcaaaag acttaccaac tgcaaagaat atagttaaag cagtagagaa agctggtgca 1920
gcacatactt ggattgaaaa tttaggtggt taagtcgaca aagacactaa aaaattataa 1980
aagtaaagga ggacattaaa tgatacaagt aaaggcacca ggaaaattat atatagcagg 2040
tgaatacgct gttacagaac caggatataa atctgttctt atagctcttg atagatttgt 2100
tacagctact attgaggaag ctgatcaata caaaggaaca atacattcaa aggcattaca 2160
tcacaatcca gtaactttta gtagagatga agattctatt gttatatcag acccacacgc 2220
agcaaaacaa cttaattatg tagtaactgc tatagaaata tttgagcaat atgcaaaatc 2280
atgtgacata gcaatgaagc attttcattt aactatagat tctaacttag atgatagtaa 2340
tggacataag tatggacttg gatcttctgc tgctgtttta gtttcagtaa ttaaagtact 2400
taacgaattt tatgatatga aactttcaaa cctttatata tataagttag cagtaattgc 2460
taatatgaaa ttacagagtt tatcttcatg cggtgatata gcagtaagtg tttattcagg 2520
ttggttagct tattctacat ttgaccatga atgggtaaaa caccagatag aagatacaac 2580
agttgaagaa gtacttatta aaaattggcc tggattacac atagagccac ttcaagctcc 2640
tgaaaatatg gaagttctta taggttggac aggtagtcca gctagtagtc ctcattttgt 2700
ttctgaagtt aaaagactta agtcagatcc ttcattttac ggtgatttct tagaagattc 2760
acatagatgt gtagaaaaat taattcatgc attcaaaact aataatatta agggtgttca 2820
gaaaatggta agacagaata gaactattat acaaagaatg gataaggaag caacagttga 2880
tatagagact gagaagttaa aatatttatg tgatattgct gaaaaatatc atggtgcaag 2940
taaaacttca ggtgctggtg gtggtgattg cggaataact ataataaata aggatgtaga 3000
caaagagaaa atatatgatg aatggactaa acatggaata aagcctctta agtttaatat 3060
ttatcatgga caataaccat ggtcaataat cttacaataa ataaaagaaa ggaggcaaaa 3120
atatgataaa atctggaaaa gcaagagcac acactaatat agcacttata aaatattggg 3180
gtaagaaaga tgaggcatta ataataccaa tgaataactc aatatcagta actttagaaa 3240
agttttatac tgaaacaaaa gttacattta acgatcagct tactcaagat caattttggc 3300
ttaatggtga aaaagtttct ggaaaagaat tagaaaagat ttcaaagtat atggatattg 3360
ttagaaatag agctggaata gattggtatg ctgagataga atctgataat tttgttccta 3420
cagctgctgg tcttgctagt tctgctagtg cttatgcagc attagctgct gcatgtaacc 3480
aagcacttga tttacagtta agtgataaag acttaagtag attagctaga attggatcag 3540
gatcagcatc aagatcaata tacggtggtt ttgcagaatg ggaaaaagga tataatgacg 3600
aaacttctta tgctgttcca ttagaaagta atcactttga agatgatctt gctatgattt 3660
ttgtagtaat aaaccaacat tctaaaaagg ttccttcaag atatggaatg tctcttacaa 3720
gaaatacaag tagattctat caatattggt tagaccatat tgatgaagat cttgcagaag 3780
caaaggcagc aatacaagat aaggatttta agagattagg tgaagttatt gaagagaatg 3840
gacttagaat gcatgctaca aatcttggat caactccacc ttttacttac ttagtacaag 3900
agtcatacga tgtaatggca ttagtacatg agtgtagaga agcaggatat ccatgctatt 3960
tcactatgga tgctggacct aatgtaaaaa tacttgtaga gaagaaaaac aaacaacaga 4020
taatagataa acttttaact cagttcgata ataatcagat aatagatagt gatattatag 4080
ctacaggtat tgaaattata gaataaacta gttgtatatt aaaatagtag aatacataag 4140
atacttaatt taattaaaga tagttaagta cttttcaatg tgctttttta gatgtttaat 4200
acaaatcttt aattgtaaaa gaaatgctgt actatttact gttctagtga cgggattaaa 4260
ctgtattaat tataaataaa aaataagtac agttgtttaa aattatattt tgtattaaat 4320
ctaatagtac gatgtaagtt attttatact attgctagtt taataaaaag atttaattat 4380
atacttgaaa aggagaggaa ctcgagatgg cagagtatat aatagcagta gatgagttcg 4440
ataacgaaat aggatcaata gaaaagatgg aagctcatag aaaaggaaca cttcatagag 4500
cattcagtat tttagttttt aactcaaaga atcaactttt attacagaaa agaaatgtaa 4560
agaaatatca ctctccagga ttatggacaa acacttgttg tagtcaccca agatatggtg 4620
aatctcttca tgatgctata tacagaagat taaaagaaga gatgggattt acttgcgaac 4680
ttgaagaagt attctcattc atatataagg taaaacttga agataattta tttgagaatg 4740
aatatgacca tgtatttatt ggtaaatatg atggtgagat aattgttaat aaagatgaag 4800
ttgatgattt taaatgggta gacattaatg aagttaaaaa ggacataata gaaagacctg 4860
aggcatatac ttactggttt aagtatcttg taaataaagc tgaaaataag atatttaaat 4920
aaaccggtca gtaacgaata gaattagaaa aacaaaggag gcaagacaat ggatttccca 4980
caacaattag aagcatgtgt aaaacaggct aatcaggcac ttagtagatt tattgctcct 5040
cttccttttc aaaatacacc agtagtagaa actatgcaat acggtgcact tttaggtggt 5100
aaaagattaa gaccattctt agtatatgct acaggacaca tgtttggtgt atcaactaat 5160

-continued

```
actttagacg ctccagctgc tgctgttgaa tgtattcatg cttattcttt aatacatgat   5220
gacttaccag caatggatga cgatgattta agaagaggtt tacctacatg tcatgttaaa   5280
tttggtgaag ctaatgcaat tttagcaggt gacgctttac aaactttagc tttttctata   5340
ctttcagatg cagacatgcc tgaagtttca gatagagata gaatttctat gatatcagag   5400
cttgcatctg catcaggaat agctggaatg tgcggtggtc aagcacttga tttagatgca   5460
gaaggtaaac acgtaccact tgatgcttta gagagaatac atagacataa aacaggtgct   5520
cttataagag cagcagtaag attaggtgct ttaagtgctg gtgacaaggg tagaagagca   5580
cttccagtac ttgataagta tgcagaaagt ataggattag cttttcaagt tcaagatgac   5640
atacttgacg ttgttggtga tactgctact ttaggaaaaa gacagggtgc agatcagcaa   5700
ttaggaaaat ctacataccc tgctttactt ggattagaac aggctagaaa gaaagcaaga   5760
gacttaatag atgacgcaag acaaagtctt aaacagttag ctgaacaatc acttgacaca   5820
agtgcacttg aagcacttgc agattatatt atacagagaa acaagtaaaa gcttttaaag   5880
gaggggaaaa aatggaattt agagtacatt tacaggcaga caacgaacag aaaatatttc   5940
aaaatcaaat gaaaccagag ccagaagcat catatcttat aaatcaaaga agaagtgcta   6000
attataaacc aaacatttgg aaaaacgatt ttcttgatca gtctttaata tcaaaatatg   6060
atggtgatga atatagaaaa ctttcagaaa agttaataga agaagtaaag atatacatat   6120
cagcagagac tatggattta gttgctaaat tagaacttat agattctgtt agaaaacttg   6180
gacttgctaa tctttttgag aaagaaataa aggaagcatt agacagtata gcagcaatag   6240
aatcagataa tttaggaact agagacgatc tttatggaac agctcttcat tttaagattc   6300
ttagacagca tggatataag gtaagtcaag atatatttgg tagatttatg gatgagaaag   6360
gaacattaga aaatcatcac tttgcacact taaaaggaat gttagaatta tttgaggcaa   6420
gtaatcttgg atttgaaggt gaagacatat tagatgaagc taaagcatct cttacacttg   6480
ctcttagaga ttcaggacat atttgttatc cagactcaaa cttaagtaga gatgtagttc   6540
atagtttaga attacctagt catagaagag ttcaatggtt cgatgtaaaa tggcagatta   6600
atgcatacga aaaagatatt tgtagagtaa atgcaacttt attagagtta gcaaagttaa   6660
attttaatgt tgttcaagct cagcttcaga agaatcttag agaagctagt agatggtggg   6720
ctaatcttgg tttcgcagat aatttaaagt ttgctagaga tagacttgta gagtgttttt   6780
catgcgcagt aggtgtagca tttgaaccag agcattcatc ttttagaata tgtttaacta   6840
aggtaattaa tcttgttctt attatagatg atgtatacga tatatatgga tctgaagaag   6900
agttaaaaca ttttacaaat gctgttgata gatgggacag tagagaaaca gaacagcttc   6960
ctgaatgcat gaaaatgtgt tttcaagtat tatataacac tacttgcgaa atagcaagag   7020
agatagaaga agaaaacggt tggaatcaag tattacctca acttactaag gtttgggctg   7080
atttttgtaa ggctctttta gttgaagcag agtggtacaa taaatcacat attccaacat   7140
tagaagaata tcttagaaac ggatgtatat caagtagtgt atctgtactt ttagttcact   7200
ctttcttttc aataactcat gaaggtacaa aagaaatggc tgatttctta cataaaaatg   7260
aagatctttt atacaacata agtcttatag taagattaaa caatgattta ggtacatcag   7320
ctgctgaaca ggaaagaggt gattctcctt cttctatagt ttgctatatg agagaagtta   7380
atgcttctga agagactgca agaaagaata taaagggaat gattgataat gcttggaaaa   7440
aggttaatgg aaaatgtttc acaactaacc aagttccatt tctttcatca ttcatgaata   7500
atgcaactaa catggcaaga gtagcacact cattatataa agacggtgat ggttttggtg   7560
```

-continued atcaagaaaa aggacctaga acacatattc ttagtttatt attccaacct ttagtaaatt 7620
aagctagcat aaaaataaga agcctgcatt tgcaggcttc ttatttttat ggcgcgccgc 7680
cattattttt ttgaacaatt gacaattcat ttcttatttt ttattaagtg atagtcaaaa 7740
ggcataacag tgctgaatag aaagaaattt acagaaaaga aaattataga atttagtatg 7800
attaattata ctcatttatg aatgtttaat tgaatacaaa aaaaaatact tgttatgtat 7860
tcaattacgg gttaaaatat agacaagttg aaaaatttaa taaaaaaata agtcctcagc 7920
tcttatatat taagctacca acttagtata taagccaaaa cttaaatgtg ctaccaacac 7980
atcaagccgt tagagaactc tatctatagc aatatttcaa atgtaccgac atacaagaga 8040
aacattaact atatatattc aatttatgag attatcttaa cagatataaa tgtaaattgc 8100
aataagtaag atttagaagt ttatagcctt tgtgtattgg aagcagtacg caaaggcttt 8160
tttatttgat aaaaattaga agtatattta tttttcata attaatttat gaaaatgaaa 8220
gggggtgagc aaagtgacag aggaaagcag tatcttatca aataacaagg tattagcaat 8280
atcattattg actttagcag taaacattat gacttttata gtgcttgtag ctaagtagta 8340
cgaaaggggg agctttaaaa agctccttgg aatacataga attcataaat taatttatga 8400
aaagaagggc gtatatgaaa acttgtaaaa attgcaaaga gtttattaaa gatactgaaa 8460
tatgcaaaat acattcgttg atgattcatg ataaaacagt agcaacctat tgcagtaaat 8520
acaatgagtc aagatgttta cataaaggga aagtccaatg tattaattgt tcaaagatga 8580
accgatatgg atggtgtgcc ataaaaatga gatgttttac agaggaagaa cagaaaaaag 8640
aacgtacatg cattaaatat tatgcaagga gctttaaaaa agctcatgta aagaagagta 8700
aaaagaaaaa ataatttatt tattaattta atattgagag tgccgacaca gtatgcacta 8760
aaaaatatat ctgtggtgta gtgagccgat acaaaaggat agtcactcgc attttcataa 8820
tacatcttat gttatgatta tgtgtcggtg ggacttcacg acgaaaaccc acaataaaaa 8880
aagagttcgg ggtagggtta agcatagttg aggcaactaa acaatcaagc taggatatgc 8940
agtagcagac cgtaaggtcg ttgtttaggt gtgttgtaat acatacgcta ttaagatgta 9000
aaaatacgga taccaatgaa gggaaaagta taatttttgg atgtagtttg tttgttcatc 9060
tatgggcaaa ctacgtccaa agccgtttcc aaatctgcta aaaagtatat cctttctaaa 9120
atcaaagtca agtatgaaat cataaataaa gtttaatttt gaagttatta tgatattatg 9180
tttttctatt aaaataaatt aagtatatag aatagtttaa taatagtata tacttaatgt 9240
gataagtgtc tgacagtgtc acagaaagga tgattgttat ggattataag cggccggcca 9300
gtgggcaagt tgaaaaattc acaaaaatgt ggtataatat ctttgttcat tagagcgata 9360
aacttgaatt tgagagggaa cttagatggt atttgaaaaa attgataaaa atagttggaa 9420
cagaaaagag tattttgacc actactttgc aagtgtacct tgtacctaca gcatgaccgt 9480
taaagtggat atcacacaaa taaaggaaaa gggaatgaaa ctatatcctg caatgcttta 9540
ttatattgca atgattgtaa accgccattc agagtttagg acggcaatca atcaagatgg 9600
tgaattgggg atatatgatg agatgatacc aagctataca atatttcaca atgatactga 9660
aacattttcc agcctttgga ctgagtgtaa gtctgacttt aaatcatttt tagcagatta 9720
tgaaagtgat acgcaacggt atggaaacaa tcatagaatg gaaggaaagc caaatgctcc 9780
ggaaaacatt tttaatgtat ctatgatacc gtggtcaacc ttcgatggct ttaatctgaa 9840
tttgcagaaa ggatatgatt atttgattcc tatttttact atggggaaat attataaaga 9900
agataacaaa attatacttc ctttggcaat tcaagttcat cacgcagtat gtgacggatt 9960
tcacatttgc cgttttgtaa acgaattgca ggaattgata aatagttaac ttcaggtttg 10020
tctgtaacta aaaacaagta tttaagcaaa aacatcgtag aaatacggtg tttttgtta 10080 ccctaagttt 10090

<210> SEQ ID NO 92
<211> LENGTH: 25
<212> TYPE: DNA
<213> ORGANISM: Artificial Sequence
<220> FEATURE:
<223> OTHER INFORMATION: oligonucleotide repHF

<400> SEQUENCE: 92
aagaagggcg tatatgaaaa cttgt 25

<210> SEQ ID NO 93
<211> LENGTH: 25
<212> TYPE: DNA
<213> ORGANISM: Artificial Sequence
<220> FEATURE:
<223> OTHER INFORMATION: oligonucleotide catR

<400> SEQUENCE: 93
ttcgtttaca aaacggcaaa tgtga 25

<210> SEQ ID NO 94
<211> LENGTH: 20
<212> TYPE: DNA
<213> ORGANISM: Artificial Sequence
<220> FEATURE:
<223> OTHER INFORMATION: oligonucleotide MK-RTPCR-F

<400> SEQUENCE: 94
gtgctggtag aggtggttca 20

<210> SEQ ID NO 95
<211> LENGTH: 20
<212> TYPE: DNA
<213> ORGANISM: Artificial Sequence
<220> FEATURE:
<223> OTHER INFORMATION: oligonucleotide MK-RTPCR-R

<400> SEQUENCE: 95
ccaagtatgt gctgcaccag 20

<210> SEQ ID NO 96
<211> LENGTH: 20
<212> TYPE: DNA
<213> ORGANISM: Artificial Sequence
<220> FEATURE:
<223> OTHER INFORMATION: oligonucleotide PMK-RTPCR-F

<400> SEQUENCE: 96
atatcagacc cacacgcagc 20

<210> SEQ ID NO 97
<211> LENGTH: 24
<212> TYPE: DNA
<213> ORGANISM: Artificial Sequence
<220> FEATURE:
<223> OTHER INFORMATION: oligonucleotide PMK-RTPCR-R

<400> SEQUENCE: 97
aatgcttcat tgctatgtca catg 24

<210> SEQ ID NO 98
<211> LENGTH: 20
<212> TYPE: DNA
<213> ORGANISM: Artificial Sequence
<220> FEATURE:
<223> OTHER INFORMATION: oligonucleotide PMD-RTPCR-F

<400> SEQUENCE: 98
gcagaagcaa aggcagcaat 20

<210> SEQ ID NO 99
<211> LENGTH: 23
<212> TYPE: DNA
<213> ORGANISM: Artificial Sequence
<220> FEATURE:
<223> OTHER INFORMATION: oligonucleotide PMD-RTPCR-R

<400> SEQUENCE: 99
ttgatccaag atttgtagca tgc 23

<210> SEQ ID NO 100
<211> LENGTH: 24
<212> TYPE: DNA
<213> ORGANISM: Artificial Sequence
<220> FEATURE:
<223> OTHER INFORMATION: oligonucleotide idi-RTPCR-F

<400> SEQUENCE: 100
ggacaaacac ttgttgtagt cacc 24

<210> SEQ ID NO 101
<211> LENGTH: 22
<212> TYPE: DNA
<213> ORGANISM: Artificial Sequence
<220> FEATURE:
<223> OTHER INFORMATION: oligonucleotide idi-RTPCR-R

<400> SEQUENCE: 101
tcaagttcgc aagtaaatcc ca 22

<210> SEQ ID NO 102
<211> LENGTH: 20
<212> TYPE: DNA
<213> ORGANISM: Artificial Sequence
<220> FEATURE:
<223> OTHER INFORMATION: oligonucleotide ispA-RTPCR-F

<400> SEQUENCE: 102
accagcaatg gatgacgatg 20

<210> SEQ ID NO 103
<211> LENGTH: 21
<212> TYPE: DNA
<213> ORGANISM: Artificial Sequence
<220> FEATURE:
<223> OTHER INFORMATION: oligonucleotide ispA-RTPCR-R

<400> SEQUENCE: 103
agtttgtaaa gcgtcacctg c 21

<210> SEQ ID NO 104
<211> LENGTH: 20
<212> TYPE: DNA
<213> ORGANISM: Artificial Sequence
<220> FEATURE:

<223> OTHER INFORMATION: oligonucleotide FS-RTPCR-F

<400> SEQUENCE: 104
aagctagtag atggtgggct 20

<210> SEQ ID NO 105
<211> LENGTH: 20
<212> TYPE: DNA
<213> ORGANISM: Artificial Sequence
<220> FEATURE:
<223> OTHER INFORMATION: oligonucleotide FS-RTPCR-R

<400> SEQUENCE: 105
aatgctacac ctactgcgca 20

<210> SEQ ID NO 106
<211> LENGTH: 18
<212> TYPE: DNA
<213> ORGANISM: Artificial Sequence
<220> FEATURE:
<223> OTHER INFORMATION: oligonucleotide ermB-F

<400> SEQUENCE: 106
tttgtaatta agaaggag 18

<210> SEQ ID NO 107
<211> LENGTH: 18
<212> TYPE: DNA
<213> ORGANISM: Artificial Sequence
<220> FEATURE:
<223> OTHER INFORMATION: oligonucleotide ermB-R

<400> SEQUENCE: 107
gtagaatcct tcttcaac 18

<210> SEQ ID NO 108
<211> LENGTH: 20
<212> TYPE: DNA
<213> ORGANISM: Artificial Sequence
<220> FEATURE:
<223> OTHER INFORMATION: oligonucleotide GnK-F

<400> SEQUENCE: 108
tcaggacctt ctggaactgg 20

<210> SEQ ID NO 109
<211> LENGTH: 20
<212> TYPE: DNA
<213> ORGANISM: Artificial Sequence
<220> FEATURE:
<223> OTHER INFORMATION: oligonucleotide GnK-R

<400> SEQUENCE: 109
acctcccctt ttcttggaga 20

<210> SEQ ID NO 110
<211> LENGTH: 20
<212> TYPE: DNA
<213> ORGANISM: Artificial Sequence
<220> FEATURE:
<223> OTHER INFORMATION: oligonucleotide FoT4L-F

<400> SEQUENCE: 110
caggtttcgg tgctgaccta 20

-continued

```
<210> SEQ ID NO 111
<211> LENGTH: 20
<212> TYPE: DNA
<213> ORGANISM: Artificial Sequence
<220> FEATURE:
<223> OTHER INFORMATION: oligonucleotide FoT4L-F

<400> SEQUENCE: 111

aactccgccg ttgtatttca                                               20
```